United States Patent
Heiland

(10) Patent No.: US 12,116,396 B2
(45) Date of Patent: Oct. 15, 2024

(54) LAMP CONSTRUCTS

(71) Applicant: Immunomic Therapeutics, Rockville, MD (US)

(72) Inventor: Teri Heiland, Rockville, MD (US)

(73) Assignee: Immunomic Therapeutics, Inc., Rockville, MD (US)

( * ) Notice: Subject to any disclaimer, the term of this patent is extended or adjusted under 35 U.S.C. 154(b) by 0 days.

(21) Appl. No.: 18/454,526

(22) Filed: Aug. 23, 2023

(65) Prior Publication Data

US 2024/0092864 A1   Mar. 21, 2024

Related U.S. Application Data

(60) Continuation of application No. 17/514,857, filed on Oct. 29, 2021, now Pat. No. 11,773,153, which is a division of application No. 16/607,082, filed as application No. PCT/US2018/028753 on Apr. 22, 2018, now Pat. No. 11,203,629.

(60) Provisional application No. 62/549,119, filed on Aug. 23, 2017, provisional application No. 62/549,033, filed on Aug. 23, 2017, provisional application No. 62/488,741, filed on Apr. 22, 2017.

(51) Int. Cl.
  C07K 14/705   (2006.01)
  A61K 39/00    (2006.01)
  A61P 35/00    (2006.01)

(52) U.S. Cl.
  CPC .. *C07K 14/70596* (2013.01); *A61K 39/00115* (2018.08); *A61P 35/00* (2018.01); *A61K 2039/55522* (2013.01); *A61K 2039/57* (2013.01); *A61K 2039/575* (2013.01); *A61K 2039/6031* (2013.01); *C07K 2319/02* (2013.01); *C07K 2319/03* (2013.01); *C07K 2319/40* (2013.01)

(58) Field of Classification Search
  None
  See application file for complete search history.

(56) References Cited

U.S. PATENT DOCUMENTS

| 2007/0269457 A1 | 11/2007 | Niazi et al. |
| 2012/0294879 A1 | 11/2012 | August et al. |
| 2016/0185831 A1* | 6/2016 | Hearl .................. C07K 14/415 536/23.5 |
| 2016/0271245 A1 | 9/2016 | Hearl et al. |

FOREIGN PATENT DOCUMENTS

| JP | 2012500829 A | 1/2012 |
| JP | 2013503159 A | 1/2013 |
| JP | 2015521467 | 9/2015 |
| WO | 2002080851 A2 | 10/2002 |
| WO | 2010023247 A1 | 3/2010 |
| WO | 2011031298 A1 | 3/2011 |
| WO | 2011046996 A2 | 4/2011 |
| WO | 2013187906 A1 | 12/2013 |
| WO | 2015200357 A2 | 12/2015 |
| WO | 2017020026 A1 | 2/2017 |

OTHER PUBLICATIONS

Nezafat et al. (Comput Biol Chem. Jun. 2016; 62:82-95).*
Arruda et al., "Dendritic Cell-Lysosomal-Associated Membrane Protein (LAMP) and LAMP-1-HIV-1 Gag Chimeras Have Distinct Cellular Trafficking Pathways and Prime T and B Cell Responses to a Diverse Repertoire of Epitopes," J Immunology, 2006, 177: 2265-2275.
Arterburn et al., "The Disulfide Structure of Mouse Lysosome-associated Membrane Protein 1," J. Biol. Chem., 1990, 265:7419-7423.
Carlssons et al., "Structure of Human Lysosomal Membrane Glycoprotein 1, Assignment of Disulfide Bonds and Visualization of its Domain Arrangement," J. Biol. Chem, 1989, 264(34):20526-205311.
De Arruda et al. "DNA vaccine encoding human immunodeficiency virus-1 Gag, targeted to the major histocompatibility complex II compartment by lysosomal-associated membrane protein, elicits enhanced long-term memory response," Immunology, 2004, 112(1):126-33.
Godinho et al., "Regulation of HIV-Gag Expression and Targeting to the Endolysomal /Secretory Pathway by the Luminal Domain of Lysosomal-Associated Membrane Protein (LAMP-1) Enhance Gag-Specific Immune Response," PLOS ONE, 2014, 9(6): e99887.
International Preliminary Report of Patentability mailed Oct. 31, 2019 and received in PCT/US2018/028753.
Nezafat et al., "Designing an efficient multi-epitope peptide vaccine against Vibrio cholerae via combined immunoinformatics and protein interaction based approaches," Comput Biol Chem, 2016, 62:82-95.
Official foreign office action issued for the corresponding EP Patent Application No. 18726576.4 on Nov. 16, 2020.

(Continued)

*Primary Examiner* — Nianxiang Zou
(74) *Attorney, Agent, or Firm* — McNeill PLLC

(57) ABSTRACT

The present invention provides improved LAMP Constructs comprising specific fragments of the LAMP lumenal domain to deliver antigens to immune cells for enhanced processing. These LAMP Constructs can be used for the treatment of disease and in particular, allergies, infectious disease, diabetes, hyperproliferative disorders and/or cancer. The improved LAMP Constructs allow for presentation of properly configured three dimensional epitopes for production of an immune response when administered to a subject. The improved LAMP Constructs can be multivalent molecules, and/or can be provided as part of a multivalent vaccine containing two or more LAMP Constructs. The improved LAMP Constructs as described herein can also be used to generate antibodies when administered to a non-human vertebrate.

28 Claims, 42 Drawing Sheets

Specification includes a Sequence Listing.

(56) References Cited

OTHER PUBLICATIONS

Wilke et al., "Crystal Structure of the conserved domain of the DC lysosomal associated membrane protein: implications for the lysosomal glycocalyx," BMC Biol., 2012, 10:1-15.

Wimer-Mackin et al., "Transmembrane Domain Mutations Influence the Cellular Distribution of Lysosomal Membrane Glycoprotein A," Biochemical and Biophysical Research Comm., 1996, 229(2):472-478.

Written Opinion and International Search Report mailed Jun. 26, 2018 in PCT/US2018/028753.

Zhang et al., "Enhancement of Antitumor Immunity Using a DNA-Based Replicon Vaccine Derived from Semliki Forest Virus," PLoS ONE, 2014, 9(3): e90551.

Zhou et al., "Lamp-2a Facilitates MHC Class II Presentation of Cytoplasmic Antigens," Immunity, 2005, 22(5):571-581.

\* cited by examiner

Figure 2A

| Gene Name Accession No. | Alternative Names | SEQ ID NO. | Orthologs | Signal Sequence | Lumenal Domain ||| Transmembrane Domain | Cytoplasmic Tail |
|---|---|---|---|---|---|---|---|---|---|
| | | | | | First Homologous domain | Hinge Region | Second Homologous Domain | | |
| h. LAMP-1 NP_005552.3 | CD107a; LAMPA; LGP120 | 1 | SEQ ID NO: 6-24 | 1-28 | 29-194 | 195-227 | 228 to 381 or 382 | 382 or 383 to 405 | 406-417 |
| h. LAMP-2 NP_002285.1 | CD107b; LAMPB; LGP110 | 2 | SEQ ID NO:25-43 | 1-28 | 29-192 | 193-228 | 229-375 | 376-399 | 400-410 |
| h. LAMP-3 NP_055213.2 | CD208; DC LAMP; DC-LAMP; DCLAMP; TSC403 | 3 | SEQ ID NO:44-55 | 1-27 | 28-219 | 220-234 | 235-381 | 382-402 | 403-416 |
| LIMP-2 Q14108 | AMRF; EPM4; LGP85; CD36L2; HLGP85; LIMPII; SR-BII; SCARB2 | 4 | SEQ ID NO:56-66 | *5-27 Transmem. *Uncleavable | | 28-433 | | 434-459 | 460-478 |
| h. Endolyn NP_006007.2 | Sialomucin CD164 MUC-24 | 5 | SEQ ID NO:73-79 | 1-23 | | 24-162 | | 163-183 | 184-197 |
| Macrosailin NP_001242.2 | CD68 | 80 | SEQ ID NO: 81-92 | 1-21 | | 22-319 | | 320-344 | 345-354 |

Figure 2A (cont.)

| | | | | | | |
|---|---|---|---|---|---|---|
| LAMP5 NP 036393 | BD-LAMP | 93 | SEQ ID NO: 94-101 | 1-29 | 30-235 | 236-256 | 257-280 |
| h. LIMBIC NP_002329.2 | LSAMP IGLON3 | 67 | SEQ ID NO: 68-72 and 102-113 | 1-28 | 29-315 | 316-338 | No tail |

FIGURE 3: HUMAN LAMP-1 ALIGNMENT WITH ORTHOLOGOUS SEQUENCES

```
                 SIGNAL SEQUENCE         LAMP HOMOLOGY DOMAIN 1
                                                   1
SEQIDNO:1    MAAPGSARRPLL LLLLLLLAGLAH-CASA AMFMVKNGN--GTACIMANFSAAFSVNYDTKS    58
SEQIDNO:6    MAAPGAR-RPLL-----LLLLAGLAH--GASALFEVK-NN--GTTCIMASFSASFLTTYETAN    52
SEQIDNO:7    --------MARAAG-VCWTLLMGCVFA--AHAVTFEVTDGN---STCIKGELNASFSISYNTTN    50
SEQIDNO:8    -MSWRQVKMPVYWMAVMLLIGVVQ-VATAVQFEVKDGKTNITCILADLSINFSVSYNVSS       58
SEQIDNO:9    MAAPGSARRPLLLLLLLLLLGLVH-CASAAMFMVKNGN-GTACIMANFSASFSVNYDTKS       58
SEQIDNO:10   MAAPGSARRSLLL-LLLLLLGLTH-CASAAMFIVKNGN-GTACIMANFSAAFSVNYDTKS       57
SEQIDNO:11   MAAFGGARPRPL--LLLLLAGLVH--GAAAVFVVKDAN-GTACIMANFSAAFLASYETRS       55
SEQIDNO:12   MEAPGGARRPLLLL----LLLGLVH--GASAVFVVRNSN-GTACIMANFSAVFSVIYESKS     54
SEQIDNO:13   MAAPGGARRRPLLL---LLFAGLVH--GASAVFVVKNGN-GTACIMADFSATFLTSYDTRS     55
SEQIDNO:14   MAAPGAR-RPLL---LLLLAGLAH--SAPALFEVKDNN-GTACIMASFSASFLTTYDAGH       53
SEQIDNO:15   --------MGGAA--RAVLLGFL----QASSSFDVRDST-GKVCIIANLTVAFSVEYKSSG    46
SEQIDNO:16   MAAPGGAWRRPLLLL-LLLLGLAR--GASAVFVVSDGN-GTACIMADFAAAFEISYDSPS      56
SEQIDNO:17   MAEPGGARTPQRLL--LLLLGLIH--VASSIFVVKNGT-GTACIMANFSATFSMNYTTKS      55
SEQIDNO:18   --------MARALL--AAVLLGFL---QASSSFDVRDST-GKVCIIANLTVAFSVEYKSNG    47
SEQIDNO:19   --------MARGLLA--AAALLGFL---QASSSFEVKDSS-GKVCILADLTVAFSVEYKTNV   48
SEQIDNO:20   MVSSSSCRRGLLL---AAVLLGFL----QASSTFEVRDKT-GKICILANFSAEFTVDYSTKA   54
SEQIDNO:21   MKSFPSFVALFI-VCSAVLADT-----QAVVTLEVKEGN---STCIKAEFSAVFSITYNTTN    53
SEQIDNO:22   MKRSHALVVL--I-IAWFSLSGC-----IQAVSLEVKEGN---STCIKANLSAYFSITYNTSS   52
SEQIDNO:23   MTRTCPFVVG-I-AC-FAILGCVTVVQSQVTLEVTEGN--STCIKAELSASFSITYDTAN      55
SEQIDNO:24   ---------------------------------------------------------         0
```

```
                              LAMP HOMOLOGY DOMAIN 1
                                       2
SEQIDNO:1    GPKNMTFDLPSDATVVLNRSSCKENTSLSLNYVIAFGRGH--TLTLNFTRNATRYSVQLM    116
SEQIDNO:6    GSQIVNISLPASAEVLKNGSSCGKENVSDPSLTITFGRGY--LLTLNFTKNTTRYSVQHM    110
SEQIDNO:7    GTSVSVFALPASASVSE-RSSCGS-AAVPPELALVFGDTHTHTLSLLFSRDQRLYRVSNI    108
SEQIDNO:8    KMELATFVLPSEAVTNINKSSCGVENTTAPVLAIQFGSNH---SLSIHFARNNTRYEVAEL  116
SEQIDNO:9    GPKNMTFDLPSDATVVLNRSSCGKENTSDPSLVIAFGRGH--TLTLNFTRNATRYSVQLM    116
SEQIDNO:10   GPKNMTFDLPSDAKVVLNSSSCGKENTSDPSLVIAFGRGQ--TLTLNFTRNATRYSVQLM    115
SEQIDNO:11   GPKNVTFDLPSDA-VVLNSSSCGKENTSDPSLMIAFGKGH---GLTLNFTRNATRYSVQLM   112
SEQIDNO:12   GYKNASFELPATA-EVQNTSSCGRENTSNPSLQIAFGRGH--VLALNFTRNATLYSVPLL    111
SEQIDNO:13   GPQNKSFELPAGA-EVSNSSCGKENASDSSLVITFGRGH---TLTLIFTRNATRYEVQLM    112
SEQIDNO:14   VSKVSNMTLPASAEVLKNSSSCGEKNASEPTLAITFGEGY---LLKLTFTKNTTRYSVQHM   111
SEQIDNO:15   QKQFAHFFLPQNATSQ-SHSSCGEGNTSHPILALSFGAGH--LISLNFSKTLDKYQVEEL    103
SEQIDNO:16   GAKNTTFSLPASA-QVLNSSSCGKENTSDSSLVIAFGRGH--TLTLSFTRNATRYSVQLM    113
SEQIDNO:17   GLESTTFRLPQNA-SVMNSSSCGKENTSNPILEIGFGGGH--TLTMNFSSTTQSYQVELL    112
SEQIDNO:18   QKQFAHFFLPQNATSQ-SHSSCGEGNTSHPILALSFGAGH--LLSLNFSKTLDKYQVEEL    104
SEQIDNO:19   QKEFVHFFLPQNASVD-SQSSCGKDNASHPILVLDFGGGH--SLSLNFSESADKYQVEEL    105
SEQIDNO:20   KVERKTFQLPSSAHINKESSSCGKEKETSQVLVVEFGTGN--SLTFTFEKSNDFYHVSNL    112
SEQIDNO:21   DTRTVSVFLPNSTTVDSANSSCGS-NGSTPGLMAKFGPGH--YFGMNFSTNGSLYSVDTL    110
SEQIDNO:22   STRTAQFILPDSATVDPDSSTCGG-NGSSPWLVAVFGAGH---ALGLFSTNGSFYSVANL    109
SEQIDNO:23   GTRTVMVPLPGSAVVGV-ASSCGG-DGRSPWLVALFGDGH---ALGLFSSNDSLYSVAKL    111
SEQIDNO:24   ---------------------------------------------------------         0
```

FIGURE 3 (cont.)

LAMP HOMOLOGY DOMAIN 1

```
                                        3
SEQIDNO:1   SFVYNLSDTHLFPNASSK-EIKT-VESITD-PASIDKKYR-VSGTQVHMNN--VATLHDA  173
SEQIDNO:6   YFTYNLSDTEHFPNAISK-EIYT-MDSTTDIKADINKAYRCVSDIRVYMKN--VTVVLRDA  167
SEQIDNO:7   SLQYNLSDGDIFPQSSSAGVQSVMASVSELMSARLNSTYRCVSSSSISLSAAVNLTLSGV  168
SEQIDNO:8   VMSYNLSDKIIFPNASENGTKTV-STNKTAVLAENDTVYKCMNPHLIRMDN--ANATFHDI  174
SEQIDNO:9   SFVYNLSDTHLFPNASSK-EIKT-VESITDIRADIDKKYRCVSGTQVHMNN--VTVTLHDA  173
SEQIDNO:10  SFVYNLSDTHLFPNASSK-EIKT-VESITDIRADIDKKYRCVSGTQVHMNN--VTVTLHDA  172
SEQIDNO:11  SFIYNLSDQIFPNASSK-ETKT-VESATDIRADINKKYRCVSNTQIHMHN--VTVTFHDV  169
SEQIDNO:12  SFVYNLSDSDLFPNASSK-DIKT-VGSTTDIKADIDKRYRCVSDSKVPMGN--VTVTLQDA  168
SEQIDNO:13  RFAYNLSDTDTFPNSSST-GVKT-VESATDIKADINKTYRCVSETQVNMDN--VTVTLRDA  169
SEQIDNO:14  YFTYNLSDTQFFPNASSK-GPDT-VDSTTDIKADINKTYRCVSDIRVYMKN--VTIVLWDA  168
SEQIDNO:15  TFHYNLSDETLFPNATEG-KVMV-ATQKSVIQARIGTEYRCINSKYVRMKH--VNITFSNV  160
SEQIDNO:16  TLVYNLSDAEFFPSASSK-GTKT-VAASTDIRADLNTKYPCVSNSQVHLLN--VTVTLGNA  170
SEQIDNO:17  SFSYNLSDATLFPNASKGSEESS--VKSRTDIQADIHKKYRCVSSNRITMSN--VTIVLSDV  170
SEQIDNO:18  TFHYNLSDETLFPNASEG-KVME-VTQKSVIQARIGTEYRCINSKYIYIRH--VNITFSNV  161
SEQIDNO:19  VFHYNLSDATLFPNSSTG-GMKT-VSHKSIIQAHMGTQYPCINSKHINMKN--VNVTFSNV  162
SEQIDNO:20  TFSYNLSDSSFFPNSSG--GQRE-VSRAGDIQANINTTYRCRSNHRVNMTN--VTVLFSNV  168
SEQIDNO:21  FLRYNLSDASLFPEANSSGPVDFELSASVGIWAPTNTTYRCLSPTTITITR-PSVTFSEM  169
SEQIDNO:22  TLQYNLSDASVFPDANSSGVVTV--VSSSVGIWAAVNTTYRCLSSVLFQVGG--ATVTFSDM  167
SEQIDNO:23  TLQYNLSDVSNFPEANSTDVVTVE-TTSVGMVARVNTTYRCISASPVIVGG--ATVTFSNV  169
SEQIDNO:24  ------------------------------------------------------------    0
```

LAMP HOMOLOGY DOMAIN 1                    Hinge Region

```
                      4
SEQIDNO:1   TIQAYLSNSSFSRGETRCEQDRPSPTTAPPAP------------PSP-SP---SPVPKSPS  218
SEQIDNO:6   TIQAYLSSGNFSKEETHCTQDGFSPTTGP---------------PSP-SP---PLVPTNPT  209
SEQIDNO:7   QMEAYMSSANLSADESVCSADQPSTTVAPPPSTT------------------TSPPPIPPVPE  213
SEQIDNO:8   RLEAYLKQSNFSQKVSTCSEDITPTSAPA-PV----T-------T-------TAPVPAP-VPDPP  219
SEQIDNO:9   TIQAYLSNSSFSRGETRCEQDRPSPTTAPPAP------------PSP-SP---SPVPESPS  218
SEQIDNO:10  TIQAYLSNSSFSREETRCEQDRPSPTTAPPAP------------PSP-SP---SPVPESPS  217
SEQIDNO:11  TIQAYLANSNFSKEETRCEQDGPFPTTAPPPP--------------PHP-SP---SPAPESPS  214
SEQIDNO:12  TIQAYLWNNSFSQAESRCRQDMPSPTTAPPAPPVP------PSPPSP-SP---PFKPESPS  219
SEQIDNO:13  AIQAYLSSSNFSREETRCEQDLPT-----------P------TPPQP-AP---TPAPASPA  210
SEQIDNO:14  TIQAYLPSSNFSKEETRCPQDQPSPTTGP---------------PSP-SP---PLVPTNPS  210
SEQIDNO:15  TLEAYPTNDTFSANKTECREDMVSTTTVAPTTPKH-----ATSQVPTTSPAPTAAPSSPA  215
SEQIDNO:16  TIQAYLANNSFSQQETRCEQDKPSP--------PTP------TAPPTP-TP---TPAPTSPV  214
SEQIDNO:17  TIQAYLSNNTFSKEETRCSQDTPSPSPVPTTHPTT-----IPVPTP-TPTRPPTPAEIPP  224
SEQIDNO:18  TLEAYPTNGTFSTNKTECSEDMVSTTTVAPTTPKH-----ITSQVPATSPAPTAAPSNPA  216
SEQIDNO:19  TLEAYLTNGTLSVNKTECAEDRVSTTTMVPTTPKQ-----TTSQSPTTGPAPTS-PPNPT  216
SEQIDNO:20  TLEAYLPNNAFSKNDSVCAEDKTSTVA---PPITTH-----IPTTTSLAPPT-PPPTDTPK  220
SEQIDNO:21  KLEAYMPGNDFSPAERVCAADQTTTGAPTTTT-----------SAATP-TT-PSPTPAGTPE  218
SEQIDNO:22  RLEAYMPGNDLSPRESFCAADQTTTAPPTTTAAP----TTTAATTM-AP-PAPTPPGTPV  221
SEQIDNO:23  TMEAFMTGEDLSPNESVCTADQSFTTAPPPPPS---------TTTAA-PA-PVPTPPGTPS  219
SEQIDNO:24  ----------------MVQICRVQSWFVGVTPLLIFATVLHQGFATVAP-PTPAPHKEPGRPE   46
                             *    :                                *
```

FIGURE 3 (cont.)

```
            Hinge              LAMP HOMOLOGY DOMAIN 2
                    1                                    2
SEQIDNO:1   VDKYNVSGTNGT-CLLASMGLQLNLTYE--RKDNTTVTRLLNINPNKTSASGSCGAHLVTL  276
SEQIDNO:6   VSKYNVTGNNGT-CLLASMALQLNITYL--KKDNKEVTRAFNISPNDT-SSGSCGINLVTL  266
SEQIDNO:7   RGNYSVTDGNGTVCVLALMGLQLNITHT-TTQNQSVSELMNLQPNQTTVSGSCGVTESSL   272
SEQIDNO:8   VVQYSVNRSSEP-CLLAKVGLQMNITYT-TKDGKNGSYVFNIESKGVTVDGNCTNTTAYL   277
SEQIDNO:9   VDKYNVSGTNGT-CLLASMGLQLNLTYE--RKDNTTVTRLLNINPNKFSASGSCGAHLVTL  276
SEQIDNO:10  VDKYNVSGTNGT-CLLASMGLQLNLTYE--RKDNTTVTRLLNINPNKTLASGSCGAHLVTL  275
SEQIDNO:11  VHKYNVSGANGT-CLLASMGLQLNVTYK--KKDNTTVVKVVSINPNKTTAGGSCGAQLVTL  272
SEQIDNO:12  VSRYNVSDGNAT-CLLASMGLQLNLTYV--HRDNATVTRVFNINPNKTKPSGHCGAQQVTL  277
SEQIDNO:13  VFPYNVSGSNGT-CLLASMGLQLNVTYP--RVDNKTVTREFNVNPNKTTFGGNCSATLATL  268
SEQIDNO:14  VSKYNVTGDNGT-CLLASMALQLNITYM--KKDNTTVTRAFNINPSDK--YSGTCGAQLVTL 267
SEQIDNO:15  VGKYNVTGANGT-CVLASMGLQLNITYV--KKDEKMGLDLLNFIPHNTSASGMCESTSAFL  273
SEQIDNO:16  VSPYNVSGANGT-CLLASMGLQLNVTYR--TKDNTTVTRGLNINPNKTTFGGSCSAQLVTL  272
SEQIDNO:17  IFKYNVSDANGT-CLLASMGLQLNITYA--KKDNSSARIIWNINPNKTVAGGSCSPQVAIL  282
SEQIDNO:18  VGKYNVTGANGT-CVLASMGLQLNITYL--KKDGKTGLDLLNFVPHNTNASGTCENTSAFL  274
SEQIDNO:19  VGKYNVTGPNGT-CVLAYMGLQLNITYQ--QKDEKMGLDLLNFVPHNTTSSGRCDNTSALL  274
SEQIDNO:20  IGRYNVTGLHGI-CLLATMGLQVNVTYS--TKNKTSKSELLNLPP-TAEVSGTCENSSITL  277
SEQIDNO:21  QGSYSVKNASGTVCLMAKMGVQLNVSYFSQSQNKTVQELLNLTPNLTSSSGLCGGTNATL   278
SEQIDNO:22  RGTYSVVNGNDTTCLLAQMGLQLNVSYFSRSQNKTVQSLVNLTPNLTNSTGSCEKGSATL   281
SEQIDNO:23  QGSYSVSNSNGTVCLLAPMALQLNISHFSASQNKTIQEVVNLLPNQTTSSGSCDPTSATL   279
SEQIDNO:24  RGYYNVTNHNGTICLMAYMGLQLNISYNSTSQKKVVQDVMNLQPNLTKHSGLCDSDIASL   106
              *.*       *::*  :.:*:*::                *        * *       *
```

```
                          LAMP HOMOLOGY DOMAIN 2
SEQIDNO:1   ELHS-EGTVLLTQFGMNASSRFFLQGIQLNTTLP--DARDPAFKAANGSLRALQATVGN  334
SEQIDNO:6   KVEN-K-NRALELQFGMNASSSLFFLQGVRLNMTLP--DALVPTFSISNHSLKALQATVGN 323
SEQIDNO:7   RLSD---ETTNLTFSFTMNSTTQKYYLSAVSVSALWP--DMS-VVFEAGNTSLSALQCSVGR 328
SEQIDNO:8   SLST-GS-IDLRFNFTLNSSLEVFYLDGVSLSTGLPADANDTHFEAANSSLNYMQTNVHK  335
SEQIDNO:9   ELHS-EGSTVLLFLFGMNASSSRFFLQGIQLNTTLP--DARDPAFKAANGSLRALQATVGN 334
SEQIDNO:10  ELHS-EGSTVLLFQFGMNASSSRFFLQGIQLNTTLP--DARDPAFKAANSSLRALQATVGN 333
SEQIDNO:11  ELRS-ESVTLLAFQFGMNASTSRFFLQGIQLNMTLP--DAPDPTFKAGNNSLPALQATIGN 330
SEQIDNO:12  ELQS-ERSTVLVFQFGMNASSGQYFLQGVLLNTTLP--DAREPAFSASNSSLRALQATLGN 335
SEQIDNO:13  ELHS-ENLLLLALQFVMNESSSPVFLQGVQLNLTLP--DAKEGSFTATNSSLRALQATAGN 326
SEQIDNO:14  KVGN-K-SRVLELQFGMNATSSLFFLQGVQLNMTLP--DAIEPTFSTSNYSLKALQASVGN 324
SEQIDNO:15  NLAF-EK-TKITFHFVLNASSEKFFLQGVNVSTTLPSEAKAPTFEASNDSMSESRATVGN  331
SEQIDNO:16  ELQG-ESLRLLALQFALNTSSSPVFLQGVQLNMTLP--DARDPSFSAANSSLRALQATAGN 330
SEQIDNO:17  ELQT-EN-STLAFSFGMNATTSKFFLPEIRFHKFFP--DAKDPAFGAVNSSLKELQATVGN 339
SEQIDNO:18  NLAF-EK-TKITFHFVLNASSEKFFLQGVNVSTTLPSEAKAPMFEASNDSMSELRATVGN  332
SEQIDNO:19  NLTF-EK-TRVIFQFALNATAEKFFLQGVSVSTTLPSEAKNPKFEATNNSMSELRASVGN  332
SEQIDNO:20  NLTS-ES-TSLSFQFSQNTSTEKYFLQGIIVTANLPPEATEKNISYSNHTLNALKTSVGK  335
SEQIDNO:21  VLAQ--EETTVLSFLFTVNSTSNKYHLSGITLQANWT-DMM-SPFSASNTSLDYLRSSLGH 335
SEQIDNO:22  ILTQ-Q-TTILIFTFSLNSTSSKYHLSGLSLQANWS-DMA-AAFSASNASLSYLRSTFGH  337
SEQIDNO:23  VLTQ-ANATNLSFLFTLNSTSNRYHLTGLSVVAAWS-DMT-APFNTSNSSLDYQRGSLGR  336
SEQIDNO:24  NLTVDAVKTNLTFVFTMNSTSNKYHLSEVTVSAAWP--EMK-EPVSVHNSSLDYLRGTVGY 164
              :         :  * *  :     .*  :  .     :    .  * ::   :  ,
```

FIGURE 3 (cont.)

```
                    LAMP HOMOLOGY DOMAIN 2              Trans. Domain
                    3                              4
SEQIDNO:1   SYKCNAEEHVRVTKAFSVNIFKVWVQAFKVEGGQFGSVEECLDENSMLIPIAVGGALAG   394
SEQIDNO:6   SYKCNTEEHIFVSKMLSLNVFSVQVQAFKVDSDRFGSVEECVQDGNNMLIPIAVGGALAG   383
SEQIDNO:7   SYVCSAQQMLSVTPVFSINTFRLQLQPFNITANPFSTAEECRVDQENMLIPIIVGAALAG   388
SEQIDNO:8   SFKCNSKQTLQITDFFTVNTYHLQVQAFNSD-NTFASAVECSLDENGMLVPIVVGAALAG   394
SEQIDNO:9   SYKCNAEEHVRVTKAFSVNIFKVWVQAFKVEGGQFGSVEECVLDENNMLIPIAVGGALAG   394
SEQIDNO:10  SYKCNAEEHVRVTKAFSVNIFKVWVQAFKVEGGQFGSVEECLLDENNMLIPIAVGGALAG   393
SEQIDNO:11  SYKCNAGEHVQVTEAFSVNIIKVWVQAFQVQGDKFGSVEECQLDENSMLIPIAVGGALAG   390
SEQIDNO:12  SYKCNSEEHVRVTEAFSLSIFKVWVQAFQVKGDKFGSVEECLLDQDSMLIPIAVGGALAG   395
SEQIDNO:13  SYKCNAEQRLRVTSSFSLNMFRVWLQAFRVDGDKFGPVEECQLDENSMLIPIAVGGALAG   386
SEQIDNO:14  SYKCNSEEHIFVSKALALNVFSVQVQAFRVESDRFGSVEECVQDGNNMLIPIAVGGALAG   384
SEQIDNO:15  SYKCSAEENFQVTDKALVNVFNVQVQAFKVDGDKFGAMEECQLDENNMLIPIIVGAALAG   391
SEQIDNO:16  SYKCRSEQPLQVTEAFALNVFQVRVQAFRVDGDKFGPAEECQLDENSMLIPIAVGGALAG   390
SEQIDNO:17  SYKCNAEENVHVTDGFSVNIFRVRVQAFKVEGDKFGSVEECLLDENNMLIPIAVGGALAG   399
SEQIDNO:18  SYKCSAEENLQVTDKALVNVFNVQVQAFKVDGDKFGAVEECQLDENNMLIPIIVGAALAG   392
SEQIDNO:19  SYKCSSEENLQVTDQALVNVFNVQVQIFKIDGDKFGPVEECQLDENNMLIPIIVGAALAG   392
SEQIDNO:20  SYKCIAEESIWISGKAAVNIFNIQLQAFKIPGDKFGAVEECQLDENNMLIPIIVGAALAG   395
SEQIDNO:21  SYMCNAEQTLFVVSTFSINMFELQVQPFGVTSTQFASAEVCQIDQDQMLIPIIVGAALAG   395
SEQIDNO:22  SYMCNAEQILAVTPVFSLNTFSLQIQPFGVTTNQFAAAEECQMDQDQMLIPIIVGASLAG   397
SEQIDNO:23  SYMCISEQTLVVDQNFSLNTFQLQVQPFGITRGQFAQAEECQLDQDNMLIPIVVGAALAG   396
SEQIDNO:24  SYFCRDEQTLNVAQNLSINTFQLQVQPFAVKGDQFGAAEECQLDEDDMLIPIVVGAALAG   224
            *:*     :  :      :.    : :* *    *.    *  * : **:** **.:***

Cytoplasmic Tail
SEQIDNO:1   LVLIVLIAYLVGRKRSHAGYQTI   417
SEQIDNO:6   LVLIVLIAYLIGRKRSHAGYQTI   406
SEQIDNO:7   LVLIVLVAYLIGRKRTHAGYQTI   411
SEQIDNO:8   LVLIVLIAYLIGRKRSHAGYQTI   417
SEQIDNO:9   LVLIVLIAYLVGRKRSHAGYQTI   417
SEQIDNO:10  LVLIVLIAYLVGRKRSHAGYQT-   415
SEQIDNO:11  LVLIVLIAYLIGRKRSHAGYQTI   413
SEQIDNO:12  LVLVVLIAYLIGRKRSHAGYQT-   417
SEQIDNO:13  LVLIVLLAYLIGRKRSHAGYQTI   409
SEQIDNO:14  LVLIVLIAYLIGRKRSHAGYQTI   407
SEQIDNO:15  LVLIVLIAYLIGRKRSHAGYQTI   414
SEQIDNO:16  LVLVVLMAYLVGRKRSHAGYQTI   413
SEQIDNO:17  LVLIVLIAYLIGRKRSHAGYQTI   422
SEQIDNO:18  LVLIVLIAYLIGRKRSHAGYQTI   415
SEQIDNO:19  LVLIVLIAYLIGRKRSHAGYQTI   415
SEQIDNO:20  LVLIVLIAYLIGRKRSHAGYQTI   418
SEQIDNO:21  LVLIVLIAYLIGRKRSHAGYQTI   418
SEQIDNO:22  LVLIVLIAYLIGRKKSHAGYQTI   420
SEQIDNO:23  LVLIVLIAYLIGRKRSHAGYQTI   419
SEQIDNO:24  LVVIVLLAYLIGRKRSHAGYQSI   247
            **:;**;***;***;;******;
```

FIGURE 3 (cont.)

LAMP-1

| Accession No. | Species | SEQ ID NO: | Accession No. | Species | SEQ ID NO: |
|---|---|---|---|---|---|
| NP_005552.3 | H. sapiens | 1 | NP_990614.1 | G. gallus | 15 |
| NP_034814.2 | M. musculus | 6 | NP_001011507.1 | S. scrofa | 16 |
| NP_955996.1 | D. rerio | 7 | XP_001374132.1 | M. domestica | 17 |
| NP_001087042.1 | X. laevis | 8 | XP_003203252.1 | M. gallopavo | 18 |
| NP_001233491.1 | P. troglodytes | 9 | XP_002191607.2 | T. guttate | 19 |
| XP_001087801.1 | M. mulatta | 10 | XP_003218797.1 | A. carolinensis | 20 |
| XP_534193.2 | C. lupus familiaris | 11 | XP_004067118.1 | O. latipes | 21 |
| XP_002723509.1 | O. cuniculus | 12 | XP_003969941.1 | T. rubripes | 22 |
| NP_001068592.1 | B. taurus | 13 | NP_001158846.1 | S. salar | 23 |
| NP_036989.1 | R. novegicus | 14 | XP_003452974.1 | O. niloticus | 24 |

FIGURE 4: HUMAN LAMP-2 ALIGNMENT WITH ORTHOLOGOUS SEQUENCES

| | | |
|---|---|---|
| SEQIDNO:2 | ---------------------------------------------------------- | 0 |
| SEQIDNO:25 | ---------------------------------------------------------- | 0 |
| SEQIDNO:26 | ---------------------------------------------------------- | 0 |
| SEQIDNO:27 | ---------------------------------------------------------- | 0 |
| SEQIDNO:28 | ---------------------------------------------------------- | 0 |
| SEQIDNO:29 | ---------------------------------------------------------- | 0 |
| SEQIDNO:30 | ---------------------------------------------------------- | 0 |
| SEQIDNO:31 | ---------------------------------------------------------- | 0 |
| SEQIDNO:32 | ---------------------------------------------------------- | 0 |
| SEQIDNO:33 | ---------------------------------------------------------- | 0 |
| SEQIDNO:34 | ---------------------------------------------------------- | 0 |
| SEQIDNO:35 | ---------------------------------------------------------- | 0 |
| SEQIDNO:36 | ---------------------------------------------------------- | 0 |
| SEQIDNO:37 | MAMKNFTLQQERDTSVALIIRTYVRAFLKVYTKVPKPQRCHNQW---QSLNIEGIEGIEI | 57 |
| SEQIDNO:38 | ---------------------------------------------------------- | 0 |
| SEQIDNO:39 | --------------------------MECREGEVTPCKQKNNLFSGIN-DDISGAKQ | 30 |
| SEQIDNO:40 | ---------------------------------------------------------- | 0 |
| SEQIDNO:41 | ---------------------------------------------------------- | 0 |
| SEQIDNO:42 | ---------------------------------------------------------- | 0 |
| SEQIDNO:43 | ---------------------------------------------------------- | 0 |

| | | |
|---|---|---|
| SEQIDNO:2 | ---------------------------------------------------------- | 0 |
| SEQIDNO:25 | ---------------------------------------------------------- | 0 |
| SEQIDNO:26 | ---------------------------------------------------------- | 0 |
| SEQIDNO:27 | ---------------------------------------------------------- | 0 |
| SEQIDNO:28 | ---------------------------------------------------------- | 0 |
| SEQIDNO:29 | ---------------------------------------------------------- | 0 |
| SEQIDNO:30 | ---------------------------------------------------------- | 0 |
| SEQIDNO:31 | ---------------------------------------------------------- | 0 |
| SEQIDNO:32 | ---------------------------------------------------------- | 0 |
| SEQIDNO:33 | ---------------------------------------------------------- | 0 |
| SEQIDNO:34 | ---------------------------------------------------------- | 0 |
| SEQIDNO:35 | ---------------------------------------------------------- | 0 |
| SEQIDNO:36 | ---------------------------------------------------------- | 0 |
| SEQIDNO:37 | VKGSKWR---SALETIITIQVKRK----------------SQVQKYHPFSLHSECQKTNQE | 99 |
| SEQIDNO:38 | ---------------------------------------------------------- | 0 |
| SEQIDNO:39 | AKQRQCTPQKPPKRATATLPLQRPPRGIPGPAPAAVAAAVAADRITPSGSHQTRPPEAAR | 90 |
| SEQIDNO:40 | ---------------------------------------------------------- | 0 |
| SEQIDNO:41 | ---------------------------------------------------------- | 0 |
| SEQIDNO:42 | ---------------------------------------------------------- | 0 |
| SEQIDNO:43 | ---------------------------------------------------------- | 0 |

FIGURE 4 (cont.)

```
SEQIDNO:2   ----------------------------------------------------------MV-     4
SEQIDNO:25  -----------------------------------------------------------M      1
SEQIDNO:26  --------------------------------------------------------MGDT      4
SEQIDNO:27  ----------------------------------------------------------MG      0
SEQIDNO:28  --------------------------------------------------------MVCF      4
SEQIDNO:29  --------------------------------------------------------MVCF      4
SEQIDNO:30  --------------------------------------------------------MVCF      4
SEQIDNO:31  --------------------------------------------------------MVCF      4
SEQIDNO:32  --------------------------------------------------------MVCF      4
SEQIDNO:33  --------------------------------------------------------MVCF      4
SEQIDNO:34  --------------------------------------------------------MVCF      4
SEQIDNO:35  --------------------------------------------------------MVCF      4
SEQIDNO:36  ----------------------------------------------------------MP      2
SEQIDNO:37  G----TGGVATVIADECLLWPSIPFSTLAQKVNLGSCEAFSIIGYSVFALFIYLKPNMLDF    156
SEQIDNO:38  ------------------------------------------------------------      0
SEQIDNO:39  DERPVRDPRNRAAAPSGHWRRAGGPQPHR--------HHR--------------HRPHGPAPLRR  133
SEQIDNO:40  ------------------------------------------------------------      0
SEQIDNO:41  ------------------------------------------------------------      0
SEQIDNO:42  ------------------------------------------------------------      0
SEQIDNO:43  ------------------------------------------------------------      0
```

```
                    SIGNAL SEQUENCE           LAMP HOMOLOGY DOMAIN 1
                                                        1
SEQIDNO:2   -RL-----FPVPGSGLVLVCLVLGAVR--SYALELNLTDSENATCLYAKWQMNFTVRYETT    57
SEQIDNO:25  -CL-----SPVKGAKLILIFLFLGAVQ--SNALIVNLTDS-KGTCLYAEWEMNFTITYETT    53
SEQIDNO:26  GAM--ERCACPAAVLLLSLVL---MG--ATAFEVEIKDDKNATCIYAKLSVNITVQYETD    57
SEQIDNO:27  --------MAVRGFLPLLFILLSGIVHADDMMTSPLPS--------------TAELK       35
SEQIDNO:28  -RL-----FPVPGSGLVLVCLVLGAVQ--SYALELNLTDSGKATCLYAKWQMNFTVRYETT    57
SEQIDNO:29  -RL-----FPVPGSGLVLVCLVLGAVQ--SYALELNLTDSGKATCLYAKWQMNFTVRYETT    57
SEQIDNO:30  -RL-----FPVPGSGLVLVCLVLGAVR--SHALELNEADSAIN---------------       39
SEQIDNO:31  -RL-----SPAPGSGLVLLCLVLGAVS--SYALEVNVTDSEKATCLYAKWQMNFTIQYNTT    57
SEQIDNO:32  -RL------SPVPGSGLVLLCLVLGAVS--SYALELNLTDSEKALCLYAKWQMNFTIPYETT   57
SEQIDNO:33  -RL-----APVPGSGFLLLCLVLGAVS--SYALELNLTDSSNATCLYAKWQMNFTIRYETT    57
SEQIDNO:34  -RL-----SPVPGSGLLMLCLVLGAVS--SYALELNLTNSEKATCLYAKWQMNFTIRYETT    57
SEQIDNO:35  -RL-----APVPGCGFLLFCIVLGTVS--SYALELNLTDSSKATCLYAKWQMNFTIRYETT    57
SEQIDNO:36  -LL-----SPVTGSKLVLLFLFLGAVR--SDALKLNLTDS-KGTCLYAEWEMNFTITYEAL    54
SEQIDNO:37  IELAELMLSTETQLLEPTRVCCGICQ--SYALEINLTDSKNATCLYSKWQMTFTINYETT    214
SEQIDNO:38  ---MAPPRCPAGLALLLLLLGACGFFQ--SYAVEVDVKDASNFTCLYAQWMMKFLIKYETN    56
SEQIDNO:39  LLLRPPP-PAA------AAARFLGFFQ--SYAVEVDIKDASNATCLYADWMMRFLIKYESN   185
SEQIDNO:40  ---M---ERCACPAALLLLSLVL---MG--AMAFDVEIKDDKNATCIYAKLSVNVTVQYETN   51
SEQIDNO:41  ---------MF-RCAFLILFLALGNELHLSHGTEVSVNNTENKLCYANLMVNFSVTYEVG    51
SEQIDNO:42  -----MKVSHATAGLVVWFVVLGCIDAVT----L-EVKESNTTCIKADLSASFSIIYNTT    50
SEQIDNO:43  ------------------------------------------------------------     0
```

FIGURE 4 (cont.)

LAMP HOMOLOGY DOMAIN 1
                              2
```
SEQIDNO:2   NKTYKTVTISDH---GTVTYNGSICGDDQNGPKIAVQFGPGFS-WIANFTKAA----STYSI 111
SEQIDNO:25  NQTNKTITIAVP--DKATHDGSSCGDDRNSAKIMIQFGFAVS-WAVNFTKEA---SHYSI  107
SEQIDNO:26  TSSSKNITFFVP--SDVTTNGSSCGSDGKAPLLVINFGNSQS-WSLNFTRNN----STYSG 111
SEQIDNO:27  ---T----ANLP--LVIQTTSSTTSTTTT-SRP--SSTSTHSTLTTEPAA----------  73
SEQIDNO:28  NKTYKTVTISDR---GTVTYNGSICGDDQNGPKIAVQFGPGFS-WIANFSKAA---STYSI 111
SEQIDNO:29  NKTYKTVTISDR---GTVTYNGSICGDDQNGPKIAVQFGPGFS-WIANFSKAA---STYSI 111
SEQIDNO:30  CSKCKTVTISDH---GTVTYNGSICGDDQNGPKIAVQFGPGFS-WIANFTKAA---STYSI  93
SEQIDNO:31  SKNFKTATISDF---STATYNGSVCGNDQNNPKIVVQFGSGFS-WIVNFTKKE---SAYLI 111
SEQIDNO:32  SKSYKTVTISNF---GTPTYNGSICGDNQNGSRIAVQFGSGFS-WIVNFTKSV---SVYSI 111
SEQIDNO:33  DKHNKTVPISDL---GAATYNGSFCGDDQNGPKIAVQFGSGFS-WIVNFTKEAASPSTYLV 114
SEQIDNO:34  NNSHKTVSISDF---GAATYNGSFCGDDHNDPQIVMQFGSGFS-WIVNFAKES---SSYLI 111
SEQIDNO:35  DKHNKTVTISDF---DAAAYNGSVCGDDQNGPKIAVQFGSGFS-WIVNFTKEASSTSTYLV 114
SEQIDNO:36  K-VNETVTITVP--DKVTYNGSSCGDDKNGAKIMIQYGSTLS-WAVNFTKEA---SQYFI 107
SEQIDNO:37  GNETKNVTVTVP--ENVTYDGSSCGDNQTVPQIAVQFGLGYS-WHLNFTKKEN--NSYSF 269
SEQIDNO:38  SSDYKNASLDLT--STVTHNGSICGSDTQAALLAVQFGDGHS-WSINFTKNN----ETYRA 110
SEQIDNO:39  SGDYKFTTLNLS--SSVTHNGSVCGNDTQAALVAVQFGEGHS-WSINITKNN----ETYQG 239
SEQIDNO:40  TSSTKNVTFSVP--SEVTTNGSSCGSNGKAPILVINFGNGHS-WSLNFTRND---SMYSG  105
SEQIDNO:41  VNKNETVIFVLP--ENVTTEGSTCDNTTSTLKL--SFGHGHS-WTVEFTKKN----KTYQV 103
SEQIDNO:42  HAEP-TVQVLLPNSTTVDTANSTCGKDGSSPRLVAVFGSGY-TLGLNFSTNG----TLYQV 105
SEQIDNO:43  ------------------------------------------------------------   0
```

LAMP HOMOLOGY DOMAIN 1
                              3
```
SEQIDNO:2   DSVSFSYNTGDTTFPDAEDKGI-LTVDELLAIKIPNDLFRCNSLSTLEKNDVVQNYWD 170
SEQIDNO:25  HDIVLSYNTSDSTVFPGAVAKGV-HTVKNPENFKVPLDVIFKCNSVLTYNLTPVVQKYWG 166
SEQIDNO:26  SALIFTYNTNDTILFPDALRKGLIS-STAMFLGPVPLNSTYKCISREVVVSENVTQIIYD 170
SEQIDNO:27  --------------KTTTARTTVTTSA---PTSTQSTSSSSTSATVTTLAP 107
SEQIDNO:28  DSISFSYNTGDNTTFPDAEDKGI-ITVDELLAIKIPLNDLFRCNSLSTLEKNDVVQNYWD 170
SEQIDNO:29  DSISFSYNTGDNTTFPDAEDKGI-ITVDELLAIKIPLNDLFRCNSLSTLEKNDVVQNYWD 170
SEQIDNO:30  DSISFSYNTGDNTTFPDAEDKGI-LTVDELLAIKIPLNDLFRCNSLSTLEKNDVVQHYWD 152
SEQIDNO:31  DSISFSYNLSDNATFPDAKEKGI-LTVHDLVGFRIPLNNIFRCNSLSTLEKNGVVQYYWD 170
SEQIDNO:32  DSISFSYNTGDNTTFPDAKDKGI-LTVNESVAFKIPLNDIFRCNSLSSLVKNGVVQNYWD 170
SEQIDNO:33  DTISFSYNTNDNKTFPDAKEKEV-FTVNNRVALKIPLNDIFRCNSLSTLENRDVVQHYWD 173
SEQIDNO:34  NSISFSYNTSDTTTFPDAKKKGV-LTVNDSVGFQVPLNDIFRCNSLSTLEKDNVVQHYWD 170
SEQIDNO:35  DSISFSYNTNDNATFPDAKEKGV-FTVNNRVALKIPLNDIFRCNSLSTLEKSDVVQHYWD 173
SEQIDNO:36  NNITLSYNTNDTKTFPGAVPKGI-LTVLIPVGSQLPLGVIFKCSSVLTFNLSPVVQRYWG 166
SEQIDNO:37  DTIVFTYNTSDNETFPEAKEKGQVLSVFEFRYARIPLNKIFRCHSEESLIGDKATHHYWE 329
SEQIDNO:38  EFITFTYNTNDTAVFPDARRQGPVTIVVKDAMEPIQLNNVFVCHHTTSLEAENVTQIFWN 170
SEQIDNO:39  DFITLTYNTNDTAVFPDAKPKGPITVLVRDPSRFIQLNTVFVCHNSFVIEAENTTQIFWN 299
SEQIDNO:40  GALIFTYNTNDSTLFPDALKEGLIS-STAAFLGPIPLNSTYKCISSEVVVSENVTQIISD 164
SEQIDNO:41  DTIVFSYNLNDSSVFPNSTSKETKFVTVKSIITNVSVDTYYSCKSENVLTVESVIQTLYD 163
SEQIDNO:42  SSLTLQYNLSDTSVFPNATISGVVTLVSASVGIEANVNTTYKCASPTVIDVATAKVNFTD 165
SEQIDNO:43  ------------------------------------------MTQIGGVQPVFLA  13
```

FIGURE 4 (cont.)

```
                    LAMP HOMOLOGY DOMAIN 1        Hinge Region
                                4
SEQIDNO:2     VLVQAFVQNGTVSTNEFLCKKTS----TVAPTIHTTVPS-------PTTTPT--PKEKPE  219
SEQIDNO:25    IHLQAFVQNGTVSKNEQVCEEDQTP--TTVAPIIHTTAPSTTTTLTPTSTPTPTPTPT  224
SEQIDNO:26    VKLEAFMANGTLGK-EIICDADKPS--PVPSPTQPST-----TASTAIPAPTSKPLDKPT  222
SEQIDNO:27    TTTGHNTTNSTTEPFTTTGHNTTNS--TTDAPTTTHTNAT----VAPTPPPTPSVPKPT  161
SEQIDNO:28    VLVQAFVQNGTVSTNEFLCDEDKTS----TVAPTIHTTVPS-------PTTTPT--PKEKPE  219
SEQIDNO:29    VLVQAFVQNGTVSTNEFLCDEDKTS---TVAPTIHTTVPS-------PTTTPT--PKEKPE  219
SEQIDNO:30    VLVQAFVQNGTVSTNEFLCDKDKTS---TVAPTVHTTVPS-------PTTTPT--RIP---  198
SEQIDNO:31    VHVQAFVQNGTVSTKEFLCEKDKTS--TTVVPTISTTTPS-------PTTTPT--PKEKPE  220
SEQIDNO:32    VHVQAFVQNGTVSTNEYLCEKDNTT--TTVAPIVPTTVPSPTTTSSPTTTPS--PKEKPD  226
SEQIDNO:33    VHVQAFVQNGTVSTTEFLCDKDKTV---TTAVPIVPTTLPS-------PT--------KPV  216
SEQIDNO:34    VHVQAFVQNGTVSTKEFLCDKDKTL--TTTVPVIPTSVPS-------PTTTPT--PKEKPE  220
SEQIDNO:35    VHVQAFVQNGTVSTTEFLCDKDKTV--TTAMPIVPTTAPS-------PT--------KPV  216
SEQIDNO:36    IHLQAFVQNGTVSKHEQVCKEDKTA---TTVAPIIHTTVPSPTTTLTPTSI-----PVPTPT  220
SEQIDNO:37    TVVQAFIQNGTISKEEFICSKDRAS--TTVAPVTTQVVPS---------TTATPVPQDKPY  379
SEQIDNO:38    VTMQPFVQNGTISKKESRCYADTPTAAPTVLPTVANVTTAS--TTISPAPTTAPKPAENPV  229
SEQIDNO:39    VTMQAFVQNGTVSKKESRCPADTPTSEPTVPPTIANVTTASTTTLSPAPTTAPKPVENPV  359
SEQIDNO:40    VKLEAFMQNGTLGK-EVSCDADKPS--PTPT-TNPST-----TASTTTPTPTSKPLDNPT  215
SEQIDNO:41    VALQAFVINGSKSDTDTVCSADMTS----TTVAPTT-----TV-----TSTAAPTSTPLPTPT  213
SEQIDNO:42    MRLEAYMPGNELSPNETVCFADQTS--TTPSPTTVSTTAV----PTQT----P--PGTPQ  213
SEQIDNO:43    VTVHLIL---------ATV--LHQTF--AT----VTPPVTTA-----VPHK----E--PGRPD  48

Hinge             LAMP HOMOLOGY DOMAIN 2
                        1                          2
SEQIDNO:2     AGTYSVNNG--NDTCLLATMGLQLNITQ------DKVASVININPNTTHSTGSCRSHTAL  271
SEQIDNO:25    VGNYSIRNG--NTTCLLATMGLQLNITE------EKVPFIFNINPATTNFTGSCQPQSAQ  276
SEQIDNO:26    MGNYTVSDA--SGICLLASMGLQINTSLL--SEGKNIWRPFNIDPLGIKTNGTCTNQTGT  278
SEQIDNO:27    VGNYSVKTD-NVSDCLLAKMGLQFSFKIS-----GNASLQTVNLDPNVTKVNGTCGSGGSD  216
SEQIDNO:28    AGTYSVNNG--NDTCLLATMGLQLNITQ------DKVASVININPNTTHSTGSCRSHTAL  271
SEQIDNO:29    AGTYSVNNG--NETCLLATMGLQLNITQ------DKVASVININPNTTHSTGSCRSHTAL  271
SEQIDNO:30    ------------------------------PXVASVININPNTTHSTGSCRSHTAL  224
SEQIDNO:31    VGSYSVNNS--NGTCLLATMGLQLNITH------NKVASVININPNTTDFTGSCQPQTAL  272
SEQIDNO:32    VGSYLVKNG--SDTCLLATMGLQLNVTH------DKVASVININPNVTGYSGSCHPQTAL  279
SEQIDNO:33    VGSYSVVNS--NGTCLLATMGLQLNITH------DKVASVFNINPNTTNATGSCQPQTAL  268
SEQIDNO:34    TGSYSVTSS--NGTCLLANMGLQLNITQ------DKVASVININPNTTNATGNCHSKTAL  272
SEQIDNO:35    VGSYSVVNS--NGTCLLATMGLQLNITH------DKVASVFNINPNTTNATGSCQPQTAL  268
SEQIDNO:36    VGNYTISNG--NATCLLATMGLQLNITE------EKVPFIFNINPATTNFTGSCQPQTAQ  272
SEQIDNO:37    PGKYAVKNG--NDTCLLATMGLQLNVTQ------NKVNSVININPNVTDFTGSCSNETAE  431
SEQIDNO:38    TGNYSLKTG---NKTCLLATVGLQLNISQ------DK-PLLINIDPKTTHADGTCGNTSAT  280
SEQIDNO:39    TGNYSLKSG--NKTCFLATVGLQLNVSQ------EK-PLLININPKTTVADGACGNTTAT  410
SEQIDNO:40    TGNYSVSDV--NGTCLLASMGLQINTSLL--SEGKNIWTAFNIDPTAMSKNGTCSNQTGT  271
SEQIDNO:41    TGKYSIAPDVNSTACLMATFGLQIGYKQG----D--KEETINLVPNITEVGGACGANSS-  266
SEQIDNO:42    QGNYTVKDA-NDTICLLAKMGLQLNVSYT--SQNKTVQDVLNLNPNVTNSTGSCGASSAT  270
SEQIDNO:43    QGDYQVTSS-NGTVCFLASMGLQLNITFNSTSQNKTLQEVINIQPNRTKSSGSCDTSSAL  107
                                                  .*: *     *  *
```

FIGURE 4 (cont.)

LAMP HOMOLOGY DOMAIN 2

```
SEQIDNO:2   RLNS--STIKYLDFVFAVKNE-----NRFYLKEVNISMY-LNGSV-FSIANNNLSYWDAP 324
SEQIDNO:25  LRLNN--SQIKYLDFIFAVKNE-----KRFYLKEVNVYMY-LANGSA-FNISNKNLSFWDAP 329
SEQIDNO:26  LILTE--NRTIIEFTFALKNK-----NHFYLEEVNITLI---NGSAFSSRQNQNLSTWEAS 329
SEQIDNO:27  SSLFLTS--KDITVHFVFTNDS---QKFRLHALTLTVD-LGNG-NIFNDSNTNLSLWEAS 269
SEQIDNO:28  LRLNS--STIKYLDFVFAVKNE-----NRFYLKEVNVSMY-LVNGSV-FSIANNNLSYWDAP 324
SEQIDNO:29  LRLNS--STIKYLDFVFAVKNE-----NRFYLKEVNVSMY-LVNGSV-FSIANNNLSYWDAP 324
SEQIDNO:30  LRLNS--STIKYLDFVFAVKNE-----NRFYLKEVNISMY-LVNGSV-FSIANNNLSYWDAP 277
SEQIDNO:31  LRLNS--SNIKYLDFVFAVKNE-----NRFYLKEVNVSMY-LVNGSV-FSIANNNLSYWDAP 325
SEQIDNO:32  LRLNS--SNIKYLDFVFAVKNE-----NRFYLKEVNVSMY-LANGSV-FSFANNNLSYWDAP 331
SEQIDNO:33  LRLSS--SNIKYLDFVFAVKNE-----NRFYLKEVNVSMI-LVNGSV-YSISNTNLSYWDAP 321
SEQIDNO:34  LRLSG--SNIKYLDFVFAVKND-----NRFYLKEVNVSVY-LVNGSV-FSIANNNLSYWDAP 325
SEQIDNO:35  LRLSS--SNIKYLDFVFAVKNE-----NRFYLKEVNVSMI-LVNGSV-YSISNTNLSYWDAP 321
SEQIDNO:36  LRLNN--SQIKYLDFIFAVKNE-----KRFYLKEVNVNMY-LANGSA-FHVSNNNLSFWDAP 325
SEQIDNO:37  LRLSG--SNVKYIDFIFAVKNG-----NRFYLKEVNVSIS--FVNASD-LNVANNNLSYWDAP 484
SEQIDNO:38  LKLND--GNPTLIDFTFIV--NASASVQKFYLREVNVTLLNYQNGSVILSADMNNLSKWDAS 338
SEQIDNO:39  LKLND--GNSTLIGFTFAVKNTSASVQKFYLREVNVTLLNRLNGSVISSADNSNLSKWDAF 469
SEQIDNO:40  LILTD----NSTVIEFTLALKNK-----NHFYLKEVNVALI----NGSASSTRQNQNLSAWEAS 322
SEQIDNO:41  -DLILTS--DTITIMFTFSNDG---KKFHLHALKVTVK--PATG-DPVIAVNNNMSIWAAA 318
SEQIDNO:42  LVLTQ-TQSTILTFNFTLNSTT---NKYHLSGVTLIAN-WFDS-AHFSMSNMSLNYLRST 324
SEQIDNO:43  LTLTTDAEKTNLTFVFALNTTS---NKYHLSEVSLSAA-LSDMKETFVAQNHSLDYLRGT 163
                 *       : . : . .        ::: *  :.:          *  .:.     .
```

LAMP HOMOLOGY DOMAIN 2                                    Trans. Domain
                            3                            4

```
SEQIDNO:2   LGSSYMCNKEQTVSVSGAFQINTFDLRVQPFNVTGKYSTAQDCSADD-DNFLVPIAVGA 383
SEQIDNO:25  LGSSYMCNKEQVLSVSRAFQINTFNLKVQPFNVTKGQYSTAQECSLDDD-TILIPIIVGA 388
SEQIDNO:26  VDSSYMCHKEQQIKVSEDLFINAFDVRVQPFGVNNGTFATAEDCFAD-Q-NFIVPVVGA 387
SEQIDNO:27  VGSSYMCRKEQSYNISDKLTLNTFELQVQPFDVKKNSFSTAHECSLDDT-SLLIPTIVGA 328
SEQIDNO:28  LGSSYMCNKEQTVSVSGAFQINTFDLRVQPFNVTQGKYSTAEECSADSDLNFLIPVAVGV 384
SEQIDNO:29  LGSSYMCNKEQTVSVSGAFQINTFDLRVQPFNVTQGKYSTAQDCSADD-DNFLVPIAVGA 383
SEQIDNO:30  LGSSYMCNKEQTVSVSGAFQINTFDLRVQPFNVTQGKYSTAEECSADSDLNFLIPVAVGV 337
SEQIDNO:31  LGSSYMCNKEQTVSVSGAFQINTFDLRVQPFNVMEGKYSTAQECSLDDD-TILIPTIVGA 384
SEQIDNO:32  LGSSYMCNKEQTVSVSGEFQINTFDLRVQPFNVKDGKYSTAQDCRADD-DNFLVPIAVGA 390
SEQIDNO:33  LGSSYMCNKEQTVSVSGAFQINTFDLRVQPFSVTEGKYSTAQECSLDDD-TILIPIIVGA 380
SEQIDNO:34  LGSSYMCNKEQTVSVSGAFQINTFNLRVQPFSVMEGKYSTAQDCSADD-DNFIVPIAVGA 384
SEQIDNO:35  LGSSYMCNKEQTVSVSGALQINTFDLRVQPFSVTEGKYSTAEECSADSDLNFLIPVAVGV 381
SEQIDNO:36  LGSSYMCNKEQVVSVSRTFQINTFNLKVQPFNVTKGEYSTAQDCSADEP-NFLVPIAVGA 384
SEQIDNO:37  LGSSYMCNKEQTLALADSLQINTFNLRVQPFSVVAGKYSTAEDCSADDD-NFIVPIAVGA 543
SEQIDNO:38  LGNSYMCRKEQTLEINENLQVHTFNLWVQPFLVKENKFSIAEECFADSDLNFLIPVAVGM 398
SEQIDNO:39  LGSSYMCRKEQTLQINENVQVHTFNLWIQPFLVEANKFATAEECIADSDLNFLIPIAVGV 529
SEQIDNO:40  VGSSYMCHKEQQIKVSEDLVINSFDVRVQLFGVKNETFATAQQCSLDDD-SIVIPIVVGA 381
SEQIDNO:41  VGSSYMCNKEQTLNVTDTLTLYTFELRVQPFEVNKGEFATAHECSLDDT-SILIPIIVGA 377
SEQIDNO:42  LGYSYMCNAEQTLFVTPSFSLNTFDLQVQPFGVKSGRFATAEEECQMDQN-QMIIPIIVGA 383
SEQIDNO:43  LGFSYMCRERQTLGVTPDFAINTFQVQVQPFGVTGKQFAAAEECQLDKD-DMLIPIIVGA 222
                :. ****. .*    :   . : :*::  :* *  *    ::  *.:*   *    :::*: **
```

FIGURE 4 (cont.)

```
                             Cytoplasmic Tail
SEQ ID NO:2     KHHAGYEQF-LKHHH-AGYEQF     410
SEQ ID NO:25    GLSGLIIVIVIAVLIGRRHTY-AGYQTL  415
SEQ ID NO:26    ALGVIVVLVMVAYFIGPPKQSSAGIEQM  415
SEQ ID NO:27    ALAGLIFIVVIAVLIGRRRTY-VGYQTL  355
SEQ ID NO:28    ALGFLIIVVFISMIGPRKSP-TGYQSV   411
SEQ ID NO:29    ALAGVLLVLLAYFIGLKRHH-AGYEQF   410
SEQ ID NO:30    ALGFLIIVVFISMIGRRKSR-TGYQSV   364
SEQ ID NO:31    GLSGLIIVIVIAVLIGRRKSY-AGYQTL  411
SEQ ID NO:32    ALAGVLIIVLLAYFIGLKRHH-AGYEQF  417
SEQ ID NO:33    GLSGLIVIVIAVLIGRRKSI-AGYQTL   407
SEQ ID NO:34    ALAGVLILIVLLAYFIGLKRHH-AGYEQF 411
SEQ ID NO:35    ALGFLIIVVFISMIGRRKSP-TGYQSV   408
SEQ ID NO:36    ALGGVLILVLLAYFIGLKRHH-TGYEQF  411
SEQ ID NO:37    ALGFLIIVFTSYIIGRRKSR-TGYQSV   570
SEQ ID NO:38    ALGFLIIVFTSYIIGRRKSR-TGYQSV   425
SEQ ID NO:39    ALGFLIIVFISIIIGPRKSR-TGYQSV   556
SEQ ID NO:40    ALAGLIVTIVIAVLIGRRKGY-SGYQTL  408
SEQ ID NO:41    ALAGLIVIAVTGPRKTY-VGYQTL      404
SEQ ID NO:42    ALAGLIVTLIAVLIGRRSH-AGYQAI    410
SEQ ID NO:43    ALAAMLIVLSAYLIGPKRSH-AGYQSI   249
```

| Accession No. | Species | SEQ ID NO | LAMP-2 Accession No. | Species | SEQ ID NO |
|---|---|---|---|---|---|
| NP_002285.1 | H. sapiens | 2 | NP_001231184.1 | S. scrofa | 34 |
| NP_034815.2 | M. musculus | 25 | XP_004022401.1 | O. aries | 35 |
| NP_001087881.1 | X. laevis | 26 | NP_058764.2 | R. norvegicus | 36 |
| NP_001013551.1 | D. rerio | 27 | XP_001510101.2 | O. anatinus | 37 |
| XP_003918270.1 | P. Anubis | 28 | NP_001001749.1 | G. gallus | 38 |
| XP_003918270.1 | M. mulatta | 29 | XP_002191794.1 | T. guttata | 39 |
| XP_003317709.1 | P. troglodytes | 30 | NP_001161192.2 | X. tropicalis | 40 |
| XP_005641822.1 | C. lupus familiaris | 31 | NP_001133282.1 | S. salar | 41 |
| XP_001493687.3 | E. caballus | 32 | XP_003445330.1 | O. niloticus | 42 |
| NP_001029742.1 | B. Taurus | 33 | XP_003961835.1 | T. rubripes | 43 |

FIGURE 5: HUMAN LAMP-3 ALIGNMENT WITH ORTHOLOGOUS SEQUENCES

SIGNAL SEQUENCE          LAMP HOMOLOGY DOMAIN 1

```
SEQIDNO:3   MPRQLSAAALFASLAVILHD-----GSQMRAKAFPETRDYSQPTAAATVQDIKKPV-QQP  55
SEQIDNO:44  MPRQLSAAAALFASLAVILHD-----GSQMRAKAFPETRDYSQPSAAATVQDIKKPV-QQP  55
SEQIDNO:45  MPRQLSAAAVLFASLAVILHD-----GSQMRAKAFPKTRDYSQPTAAATGQDIAKPV-QQP  55
SEQIDNO:46  MPRQLSAAAVLFASLAVILHD-----GSQMRAKAFPKTRDYSQPTAAATGQDIAKPV-QQP  55
SEQIDNO:47  MSWQLSAAVALFVSLALILHY-----GSQIRAKMFPETVDFQ-PTTAATVRATAKPFL-HL  54
SEQIDNO:48  MSWRLSAVLVSFVSLAVFLHY-----GHHMKAKVFPEITDSSSPTTAATVQATAEPSLWKP  56
SEQIDNO:49  ------------------------------------------------------------   0
SEQIDNO:50  MAWQLSAVVVLFVSLAVILYY-----GSHVPANVFPEITDYSQPTTAATIQTRAQPSLSQP  56
SEQIDNO:51  MSWQIPAVVMSFMALVAIWYYDSNYNSHMQAKVFPEITGYSSPTTG---QATVKPSLLQP   57
SEQIDNO:52  MSWQISAVVLFFVSLAVIWYYDS-----HMKANVFPEITGYSSPTTG---QATVKPSLLQP  53
SEQIDNO:53  MPGQTSAVAVL-LCLAVILH-----GYQIREKEFPEARGYLQYTATTTEQITAKPPL-PL   53
SEQIDNO:54  MPGQISAVAVLFLSLTVILH-----GYQIREKEFPKARGYLQYTATSAEQITTKPLL-QL   54
SEQIDNO:55  ------------------------------------------------------------   0
```

LAMP HOMOLOGY DOMAIN 1

```
SEQIDNO:3   AKQAPHQTLAARFMDGHITFQTAATVKTP--------------TTTPATTKNTATTSPITY  102
SEQIDNO:44  AKQAPHQTLAARFMDGHITFQTAATVKTP--------------TTTPATTKNTATTSPITY  102
SEQIDNO:45  ANQAPHQTLAARLMDGHITFQTAATIKTP--------------TTTPVTTKNTPTTSPIIY  102
SEQIDNO:46  ANQAPHQTLAAPLMDGHITFQTAATIKTP--------------TTTPVTTKNTPTTSPIIY  102
SEQIDNO:47  TNQVPSQTLAARSMDGHIASQPAATTSSSEPPTTHTTVKTLVTTSLVTANSTPSSSPIIY   114
SEQIDNO:48  TNHTPHKTLAAKSTDGHVTSQIATTVTDSETLTTHTTITTLAATSLAATNSTPSTSPTTH   116
SEQIDNO:49  ------------------------------------------------------------   0
SEQIDNO:50  TNQVPHKTLATRSMDGQVTSQTAATTVNPETPVTHTTIKTAAATSLVTTNSTLSTSPITN   116
SEQIDNO:51  TNYVPHKTAAARSTDGHVTSQTVAKTSSSETLTTNTTIDVLAFTSFVTTKSTLPTTPTTH   117
SEQIDNO:52  TNHVPCNTAAAKSTDGHVTSQTVAKTSSPETLTTNTTIEVLVTTSPVTTQSTLPTTPTTH   113
SEQIDNO:53  TNQTSHATLASRSKDDYIQTAAETS--TFE-----DTAHITMKTAIPVTTKSLLPISSTSY  107
SEQIDNO:54  INQRSHITLASPFKDDYIQMAAETS---AIE-----NTAHITMKTVTPVTTKSLPPISSASY 108
SEQIDNO:55  ----------------------------------------MDRVSLLSTILLY          14
```

LAMP HOMOLOGY DOMAIN 1

```
SEQIDNO:3   TLVT----------TQATPNNSHTAPPVTEVTVGPSLAPYSLPPTI--TPPAHTTGTSSSTV  152
SEQIDNO:44  TLVT----------TQATPNNSHTAPPVTEVTVGPSLVPYSLPPTI--TPPAHTTGTSSSTV  152
SEQIDNO:45  TLVT----------TQATSNNSHTAPPLTKVTVGPSLAPYSLPPTI---TPPAHTTGTSSSTV 152
SEQIDNO:46  TLVT----------TQATSNNSHTAPPLTKVTVGPSLAPYSLPPTI--TPPAHTTGTSSSTV  152
SEQIDNO:47  TLVT----------TIVTPNNSNTAAPVTEATIGPSADPGSLPTTS--TPLAHTTRINPSTL  164
SEQIDNO:48  TLFT----------TLATPNTSHMAAPVTEAAISPSAGLSSLLPTI--IPPAHTTGRSSTL   166
SEQIDNO:49  ------------------------------------------------------------   0
SEQIDNO:50  TLLT----------TLATPDNTHTTTPVTEATIGPSAGPGSPPTITTTSSAYTTGTRSSTV   168
SEQIDNO:51  TLVT----------TLATPNKSHVTFPVTEAKVGLSVGPSSPFVTV--NPTAHTTGNRPSTA  167
SEQIDNO:52  TLVT----------TLATPSKSHVTFPVTEAKAGLSIGPSSPPVTI--NPAAHTTGNRPSTA  163
SEQIDNO:53  TFV-------------RTNNSHMTASSTEDTIGSGSITHL---------PFPTTRASLAAV  146
SEQIDNO:54  TFV-------------RSNNAHMTASSTDDTIGSGSIAHL---------PVPTTRASLAIV  147
SEQIDNO:55  GLLYINDAYSENTFAQPSNTTTPAPNTTTTHVTSNTTTLAP-----------------NTTT  59
```

FIGURE 5 (cont.)

```
                       LAMP HOMOLOGY DOMAIN 1
SEQIDNO:3    SHTTGNTTQPSNQTTLPATLSIALHKSTTGQKPVQP---THAPGTTAAAHNTTRTAAPAS  209
SEQIDNO:44   SHTTGNTTQPSNQTTLPATLSIALHKSTTGQKPVQP---THAPGTTAAAHNTTRTAAPAS  209
SEQIDNO:45   NHTTGNATQPSNQTTLPATLSIALHKSTTGQKPVQP---THAPGTTAAAHNTTRTAAPAS  209
SEQIDNO:46   NHTTGNATQPSNQTTLPATLSIAPHKSTTGQKPVQP---THAPGTTAAAHNTTRTAAPAS  209
SEQIDNO:47   SHKTRKTTHFGNQTTLPATLSTSTHKSTSSHKSAQS---THAPGPTTAAHNTTQTASPAT  221
SEQIDNO:48   SPTAGKTTQPSNQTTLPATLSTSPHNSTASQKPTHP---NHTPGPTTGAHNTTQTASPAT  223
SEQIDNO:49   ------MTQSSRSVLLLMLSSLHCLGSSLESNPKDPSVLAEAPGQN------KRDSDISL  48
SEQIDNO:50   SHTTGKTTQLSNQTTLPATLSTSPHNSTTSQNPAHS---THTPGPTTGCNTTQTASPTT  225
SEQIDNO:51   SHTTGKTTQLSNQTTLPATLSTSPHNITTSQKPTQP---THTPGPTTATYNTTQTASPAT  224
SEQIDNO:52   SHTTGKTTQLSNQTTLPATLSTSPHNITTSQKPTQP---THTPGPTTAANNTTHTASPAT  220
SEQIDNO:53   NHITGRSTQLGGQTTLPKALFTPSHESTTTQRPTLS---TI-VSELTPTGKDRSTTSSVP  202
SEQIDNO:54   NYITGRATQLGGQTTLPKTFFTASHKSTTNQRPTLS---TNVLGTSTPTHKDRSTTSPVP  204
SEQIDNO:55   THVTSNTTTLA-----PNTTTTHITSNTTTLAPNTT---TTLAPNTTTTHSVTTTKTAST  111
                *   .                :

Hinge       LAMP HOMOLOGY DOMAIN 2
                          1
SEQIDNO:3    TVPGPTLAPQPSSVKTGIYQVLN-GSRLCIKAEMGIQLIVQDKESVFSPRRYFNIDPNAT  268
SEQIDNO:44   TVPGPTLAPQPSSVKTGIYQVLN-GSRLCIKAEMGIQLIVQDKESVSWGHRTITLSS---K  266
SEQIDNO:45   TVPGSTLAPQPSSVKTGIYQVLN-GSRLCIKAEMGIQLIVQDKESVFSPRRYFNLDPNAT  268
SEQIDNO:46   TVPGSTLAPQPSSIKTGIYQVLN-GSRLCIKAEMGIQLIVQDKESVFSPRRYFNLDPNAT  268
SEQIDNO:47   PASGPTLAPQPSSPKTGIYQVLN-GSRLCIKAEMGIELMVQDTKSVFSPQRYFNIDPNAT  280
SEQIDNO:48   IAPGPTLAPQPSSAKTGIYQVLN-GSKLCIKAEMGIELTVQDTQSVFSPQRYFNIDPNTT  282
SEQIDNO:49   VPQMPVLQPKETAPPIVTYTIRNPQGKVCVRASFGVEFVVREN-----KKKYYFNLTPNSA  104
SEQIDNO:50   TAPGPTLAPQPSSAKTGMYQILN-GSKLCIKAEMGIQLTVQDTKSASPPQGYFNIDPNTT  284
SEQIDNO:51   IAPRPTLAPQPLSPKTGIYQVHN-GSRLCIKAEMGIQLTVQDSVSVFSPQKYFNIDPNAT  283
SEQIDNO:52   IAPRPTLAPQPLSPKTGIYQVLN-GSKLCIKAEMGIQLTVQDSVSVFSPQKYFNIDPNAT  279
SEQIDNO:53   LVPRPTFVTWSSPAKIGTYEVLN-GSRLCIKAEMGIALIVQEKGLDSATQRHFNIDPSLT  261
SEQIDNO:54   LVPRPTLVTWSSPAKIGTYEVLN-GSRLCIKAEMGIALIVQEKDLDSATQRYFNIDPSLT  263
SEQIDNO:55   TTPTPTLEPKPSPPETGNYTVKI-KNEFCIEALMGLELELTNS----TKTQQYFNIVPSQI  167
              .:         *  :   ...*:.* :*: :  :.     :  :.:

LAMP HOMOLOGY DOMAIN 2
                            2
SEQIDNO:3    QASGNCGTRK-----SNLLLNFQGGFVNLTFTKDEESYYISEVGAYLTVS-----DPETIY  319
SEQIDNO:44   SLSGGCLARNEHSPHPLFLFFEKGPPSVTQAEDEESYYISEVGAYLTVS-----DPETIY  321
SEQIDNO:45   QASGNCGTRN-----SNLLLNFQGGFVNLTFTKDEGSYYISEVGACLTVS-----DPETIY  319
SEQIDNO:46   QASGNCGTRN-----SNLLLNFQGGFVNLTFTKDEGSYYISEVGACLTVS-----DPETIY  319
SEQIDNO:47   QTSGNCGSQK-----SNLLLNFQGGFVNLTFLKDENSYYINEVGAYLAVS-----NPEKIY  331
SEQIDNO:48   QASGNCGSPK-----SKLLINFQGGFVNLTFTKDENSYYVSGVGAYLTVS-----NPEKVY  333
SEQIDNO:49   RATGYCANQK-----TVLSLEFSGGNLEFTFIKDGDQSYVKTVKGSLRAAPPCKNCPSKIY  160
SEQIDNO:50   QVSGICGSRK-----SNLLLNFWGGFVNLTFTKDENSYYISEVGAYLTVS-----NPEKTY  335
SEQIDNO:51   QASGNCGSRK-----SNLLLNFQGGFVNLTFTKGEKSYYISEVEAYLTVS-----NPAKVY  334
SEQIDNO:52   QASGNCGSRK-----SNLLLNFQGGFVNLTFIKDENSYYISEVEAYLTVS-----NPAKVY  330
SEQIDNO:53   HASGKCGSQN-----SNLFLNFQGGSVNVTFTKEENLYYVSEVGAYLTIS-----NTEKTY  312
SEQIDNO:54   HASGKCDSQK-----SNLFLNFQGGSVNITFTKEENLYYISEVGAYLTIS-----NTEKTY  314
SEQIDNO:55   NSNGTCEKSK-----ANLNLTFANSYINFVFAQDDNSYYLDNVTVYFNLT-----RSESWY  218
              . *  *   :    *  * *   .   ,..   :    *:,.*  :    :   . *
```

FIGURE 5 (cont.)

```
                            LAMP HOMOLOGY DOMAIN 2
                                3                                    4
SEQIDNO:3   QGIKHAVVMFQTAVGHSFKCVSEQSLQLSAHLQVTTIVQLQAFDFEDDHFGNVDECSSD  379
SEQIDNO:44  QGIKHAVVMFQTAVGHSFKCVSEQSLQLSAHLQLKTTDVQLQAFDFEDDHFGNVDECSSD 381
SEQIDNO:45  QGMKHAVVMFQTAVGHSFKCVSEQSLQLSAHLQLKTTNVQLQAFDFEDDHFGNVDECSSD 379
SEQIDNO:46  QGMKHAVVMFQTAVGHSFKCVSEQSLQLSAHLQLKTTNVQLQAFDFEDDHFGNVDECSSD 379
SEQIDNO:47  QGMKSSVVMFETGVGHSFKCVSEQSIQLSTHLQLKTMNVQFQAFDFEDDHFGNVDECSSD 391
SEQIDNO:48  QGMKNAVVMFETMIGHSFKCVSEQSIQLSPHLQLNTMNVQLQAFDFEDDHFGNVDECSSD 393
SEQIDNO:49  VGLVDNEKLFKAKNGLSFNCKSETMLILADYFRLKLVPLQIQAFDLVNGAFGKEVECWAD 220
SEQIDNO:50  QGMKSPVVMFETVIGHSFKCVSEQSLELSTQLHLKTTNVQLQAFDFEDDNFGNVDECSSD 395
SEQIDNO:51  QGLKHAMMMFETVVGHSFKCVSEQSIQLSTYLQLKTMNVQLQAFDFEDDHFGNADECISD 394
SEQIDNO:52  QGMKYAMMMFETVVGHSFKCVSEQSIQLSNHLQLKTVNVQLQAFDFEDDRFGNADECISD 390
SEQIDNO:53  QGKS-TMMMFETVVGHSFKCVSEQSIQLSAQLQMKTMNIHLQAFDFEGDSFGIVDECLSD 371
SEQIDNO:54  QGKKNTLMMFETVVGHSFKCVSEQSIQLSAQLQMKTMNIHLQAFDFEGDSFGNVNECLSD 374
SEQIDNO:55  GNAT-NQKLLKTENGYSVKCKNTPKIQLGDTMNLVMTNVKLQVFNFKDNSFGKETTCKYD 277
             .   :::  * *.:*  .   : *.  :.:   :::*.*::  .. **    *  *

Trns Memb.      Cyto. Tail
SEQIDNO:3   YTIV-LPV-IGAIVVGLCLMGMGVYKIRLRCQSSGYQRI  416
SEQIDNO:44  YTIV-LPV-IGAIVVGLCLMGMGVYKIRLRCQSSGYQRI  418
SEQIDNO:45  YTIV-LPV-IGAIVVGLCLVGIGVYKIRLRCQSSGYQRI  416
SEQIDNO:46  YTIV-LPV-IGAIVVGLCLVGMGVYKIRLRCQSSGYQRI  416
SEQIDNO:47  YTVV-LPV-IGAIVLGLCAVGLIVYGIHLRRESSGYQRI  428
SEQIDNO:48  YTIV-LPV-IGAIVLGLCAVGLIVYGIPLKRESSEYQRI  430
SEQIDNO:49  YNKPMIPIILGAVAAAICLIAILTYVLVREIRNQGYEQL  259
SEQIDNO:50  YTVV-LPV-IGAIVLGLFAVGLIVYGVRVRREASGYQRI  432
SEQIDNO:51  RNRREIPVAVGLSIAVLLAVLLTACLVTRKRPSRGYERM  433
SEQIDNO:52  RNPREIPVAVGLSIAVLLAVLLTACLVTRKRPSRGYERM  429
SEQIDNO:53  YTVV-LPV-VGIIVVVLCVVGLGIYKIRQRRQSSAYQRI  408
SEQIDNO:54  YTVV-LPM-VAIIVVVICVVGLSVYKIPQRHQSSAYQRI  411
SEQIDNO:55  HNFG-LMI-AGIVIVVIVVLGVIIYFIWHKRKSSGYQRI  314
             .   : :  .    : : :     :  .    *:::
```

| | LAMP-3 | | | | |
|---|---|---|---|---|---|
| Accession No. | Species | SEQ ID NO: | Accession No. | Species | SEQ ID NO: |
| NP_055213.2 | H. sapiens | 3 | XP_001496333.1 | E. caballus | 50 |
| XP_001155195.3 | P. troglodytes | 44 | NP_001095605.1 | B. Taurus | 51 |
| XP_003894825.1 | P. Anubis | 45 | XP_004003158.1 | O. aries | 52 |
| NP_001028044.1 | M. mulatta | 46 | NP_001012015.1 | R. norvegicus | 53 |
| XP_848889.2 | C. lupus familiaris | 47 | NP_796330.2 | M. musculus | 54 |
| XP_003358746.1 | S. scrofa | 48 | XP_002936919.2 | X. tropicalis | 55 |
| XP_001342688.2 | D. rerio | 49 | | | |

FIGURE 6: HUMAN LIMP-2 ALIGNMENT WITH ORTHOLOGOUS SEQUENCES

```
                                                                    SIGNAL SEQUENCE
SEQIDNO:4   ----------------------------------------------MKRCCFYTAGTLS 13
SEQIDNO:56  ----------------------------------------------MGRCCFYTAGTLS 13
SEQIDNO:57  ----------------------------------------------MGRCCFYTAGTLS 13
SEQIDNO:58  ----------------------------------------------MGRCCFYTVGTLS 13
SEQIDNO:59  ----------------------------------------------MGRCCFYAVGTLS 13
SEQIDNO:60  ----------------------------------------------MGRCCFYTAGTLS 13
SEQIDNO:61  --------------------------------------------MTPRSCTIYAFGIVC 15
SEQIDNO:62  ----------------------------------------------MARCCFYTAGTLS 13
SEQIDNO:63  ----------------------------------------------MRSLCLVFVGVLA 13
SEQIDNO:64  ----------------------------------------------MVKWAVFGTAAVS 13
SEQIDNO:65  MQLDDILHINNCKADCSSLSTTPNPKTDLVNMNGPKHKFCTKLSSTYLRKWWITIV---VA 58
SEQIDNO:66  -------------------------------MYGRSNRLCAKLSSAFLRKWWFVIA---FA 27

LAMP HOMOLOGY DOMAIN
SEQIDNO:4   LLLLVTSVTLLVAIVFQKAVDQSIEKKIVLRNGTEAFDSWEKPPLPVYTQFYFFNVTNPE 73
SEQIDNO:56  LLLLVTSVTLLVARVFQKAVDQSIEKKIVLRNGTEAFDSWEKPPLPVYTQFYFFNVTNPE 73
SEQIDNO:57  LLLLVTSVTLLVARVFQKAVDQSIEKKIVLRNGTEAFDSWEKPPLPVYTQFYFFNVTNPE 73
SEQIDNO:58  LLLLVTSIALLVARVFQKAVDQTIEKNIVLRNGSETFDSWKKPPLPVYAQFYFFNVTNPE 73
SEQIDNO:59  LLLLVTSITLLVARVFQKAVDQTIEKNIVLRNGSETFDSWKKPPLPVYTQFYFFNVTNPE 73
SEQIDNO:60  LLLLVTSVTLLVARVFQKAVDQTIEKNMVLQNGTKVFNSWEKPPLPVYIQFYFFNVTNPE 73
SEQIDNO:61  AHLLILGIALLLAQVFQTMIQERIKKEITLAENSRVLDGWINPPPPVYMQYFFFNVTNPD 75
SEQIDNO:62  LLLLVTSVTLLVARVFQKAVDQTIEKNMVLQNGTKVFDSWEKPPLPVYIQFYFFNVTNPE 73
SEQIDNO:63  LTLLIASISLLVAHVFQTVVDLQVKQGTVLKNGTETFEAWEDPPPPVYMQFYFFNVTNPL 73
SEQIDNO:64  VTLLIVSIVLLLTHTFMDIVEGQVKQAIVLKNESEVFEDWANPPPPVYMQFYFFNVTNPL 73
SEQIDNO:65  AALIIG--GIVVACEFTVLIDAVVDRMVALRPGAKTFGWWAKPPVEPRISLYIYNVTNAD 116
SEQIDNO:66  LSLLVL--GALVTFGFTAFIRTIIDHQVALRVGGQSFGWWSRPPVEPIIRIFVYNVTNAD 85
              *::    ::: *    :   :.:  .*    .: *  **     :.:****

LAMP HOMOLOGY DOMAIN
SEQIDNO:4   EILRGE-TPRVEEVGPYTYRELRNKANIQFGDNGTTISAVSNKAYVFERDQSVGDPKIDL 132
SEQIDNO:56  EILRGE-TPRVEEVGPYTYRELPNKANIQFGDNGTTISAVSNKAYVFERDQSVGDPKIDL 132
SEQIDNO:57  EILRGE-TPRVEEVGPYTYRELRNKANVQFGDNGTTISAVSNKAYVFERDQSVGDPKIDL 132
SEQIDNO:58  EILRGE-IPRLEEVGPYTYRELRDKADIQFGDNGTTISAVSNKAYVFERNQSVGDPKTDL 132
SEQIDNO:59  EILNGE-TPRLEEVGPYTYPELRNKDDIQFGDNGTTISAVSNKAYVFERDKSVGDPKIDL 132
SEQIDNO:60  EILQGE-IPLLEEVGPYTYRELRNKANIQFGENGTTISAVTNKAYVFERNQSVGDPNVDL 132
SEQIDNO:61  EFLAGKEKAKVTQMGPYTYREYRPRENVTYLENGTKIFATNPKSFVFLRNMSAGDPEVDR 135
SEQIDNO:62  EILQGE-IPLLEEVGPYTYRELRNKANVQFGENGTTISAVTNKAYIFERNQSVGDPTVDL 132
SEQIDNO:63  EVLQGA-TPLVEEKGPYTYREYRPRVHVQFLDNGTKVSALNPKTYVFEPEKSVGNPEVDL 132
SEQIDNO:64  EVLSGE-KPFVDEIGPYTYREYRPRENITFSVNGTEVSAVTPKTYVFEPEKSIGDPKVDL 132
SEQIDNO:65  DFLSNGSKAIVDEVGPYVYSETWEKVNIVENDNGTL-SYNLRKIYSFREDLSVG-PEDDV 174
SEQIDNO:66  EFLNNGTKPILDELGPYVYVQTWEKVNIKENPNGTI-SYNQKRVYIFNEDLSGG-LEDDV 143
              :.*    . :  :: ***.* :    ..:   ***       :: *  :*  *   *
```

FIGURE 6 (cont.)

LAMP HOMOLOGY DOMAIN

```
SEQIDNO:4   IRTLNIPVLTVIEWSQ-V-HFLREIIEAMLKAYQQKLFVTHTVDELLWGYKDEILSLIHV 190
SEQIDNO:56  IRTLNIPVLTVIEWSQ-V-RFLREIIEAMLKAYQQKLFVTHTVDELLWGYKDEILSLIHV 190
SEQIDNO:57  IRTLNIPVLTVIEWSQ-V-HFLREIIEAMLKAYQQKLFVTHTVDELLWGYKDEILSLIHV 190
SEQIDNO:58  IRTLNIPAVTAMEWAH-L-HFFRELIEALLKAYQQTLFVTHTVDELLWGYKDEILSLINV 190
SEQIDNO:59  LRTLNIPALTAMEWTQ-L-PLLRDIIEALLKAYRQKLFVTHTVDELLWGYKDEILSLINT 190
SEQIDNO:60  IRTINIPLLTVVDLAQ-L-TLLRELIEAMLKAYQQKLFVIHTVHELLWGYKDEILSLVHI 190
SEQIDNO:61  VTTVNIPMIAVMNELNSYSFFVRTAVSMYMGSMGMGLFMNRTVHEILWGFKDPLLTKLHA 195
SEQIDNO:62  IRTINIPLLTVVEMAQ-Q-PFLREIIEAMLKAYQQTLFVTHTVHELLWGYKDEVLSLVHI 190
SEQIDNO:63  IRTINVPAVTAMEWTR-A-TSLQFATEVLLLLYQESLFTVRTVHELLWGYKDKLLSTIHV 190
SEQIDNO:64  IRTVNIPLVTILEMTK-DSSLLRPFIIAALKTYKEGMFVTRTVDELLWGYKDAVLSILHP 191
SEQIDNO:65  VIVPNIPMLSATSQSKHAARFLRLAMASIMDILKIKPFVQVSVGQLLWGYEDPLLKLAKD 234
SEQIDNO:66  VIVPNIPMLSATSQSKHAARFLRLAMASIMDILKIKPFVEVSVGQLLWGYEDPLLKLAKD 203
              : . *:* ::  , .  .:      :       *   :* ::***::* :*. :
```

LAMP HOMOLOGY DOMAIN
                                                                            1
```
SEQIDNO:4   FRPDI-----SPYFGLFYEKNGTNDGDYVFLTGEDSYLNFTKIVEWNGKTSLDWWITDKCN 246
SEQIDNO:56  FRPDI-----SPYFGLFYEKNGTNDGDYVFLTGEDSYLNFTKIVEWNGKTSLDWWITDKCN 246
SEQIDNO:57  FRPDI-----SPYFGLFYEKNGTNDGDYVFLTGEDNYLNFTKIVEWNGKTSLDWWITDKCN 246
SEQIDNO:58  FKPEI-----SPYFGLYYGKNGTNDGDYVFLTGEDNYLNFSKIVEWNGKTSLDWWTTDKCN 246
SEQIDNO:59  FKHDV-----SPYFGLFYGKNGTNDGDYVFLTGEDNYLNFSKIVEWNGKTSLDWWTADECN 246
SEQIDNO:60  FKPDV-----SPNFGLFYERNGTNDGEYVFLTGEDNYLNFSKIVEWNGKTSLDWWTTDTCN 246
SEQIDNO:61  MRPEV-----DEHFGLMYNKNGTHEGEFVFHTGEKNYMNYGKIDTWNGISQMNWWSSNQSN 251
SEQIDNO:62  FRPDV-----SPNFGLFYERNGTNDGEYVFLTGEDNYLNFTKIVEWNGKTSLDWWTTDTCN 246
SEQIDNO:63  LHPEI-----DPVFGFFNKMNGTDDGEYVFLSGEMNYLNFSRIVEWKGKESLNWWTTKTCN 246
SEQIDNO:64  FKKNI-----SDTFGLFYKMNTTDDGEYIFLSGEKDYLEFTQIAEWKGQKALNWWTTETCN 247
SEQIDNO:65  VVPKEQKLPYEEFGLLYGKNGTSSDRVTVNTGVDDIRRYGIIDNFNGRTHLPHWTTDACN 294
SEQIDNO:66  VVPKEQKLPYEEFGLMYGKNSTSKDTVTVWTGVDDITQYGIIDKYNGRSHQTHWLSEQCN 263
              .  .        **:    *  *  ,, .  :*  .  .:   ::*       *  :..*
```

LAMP HOMOLOGY DOMAIN
                                2
```
SEQIDNO:4   MINGTDGDSFHPLITKDEVLYVFPSDFCRSVYITFSDYES-VQGLPAFRYKVPAEILANT 305
SEQIDNO:56  MINGTDGDSFHPLITKDEVLYVFPSDFCRSVYITFSDYES-VQGLPAFRYKVPAEILANT 305
SEQIDNO:57  MINGTDGDSFHPLITKDEVLYVFPSDFCRSVYITFSDYES-VQGLPAFRYKVPAEILANT 305
SEQIDNO:58  MINGTDGDSFHPLIDKDEILYVFPSEFCRSVYITFSDFKS-VQGIPAFRYKVPGEVLANT 305
SEQIDNO:59  MINGTDGDPTFHPLITRDEVLYVFPSDFCRSVYITFSDFES-VQGLPALRYKVPAEILANT 305
SEQIDNO:60  MINGTDGDSFHPLISKDEVLYLFPSDLCRSVHITFSSFEN-VEGLPAFRYKVPAEILANT 305
SEQIDNO:61  MINGTDGSVFHTFLSRKELLYIFAADLCRSIHLGYVRDME-VKGIPAFRFAPPSDVLAPP 310
SEQIDNO:62  MINGTDGDSFHPLISKDETLYIFPSDFCRSVYITFSSFEN-VEGLPAFRYKVPAEILANS 305
SEQIDNO:63  MINGTDGTSFHPLISKDENIYIFSSDFCRSLYLVYDSSGS-VAGVPTYRFVPSPMVFANT 305
SEQIDNO:64  MINGTDGTSFHPLLNKDDTIYMFSSDLCRSIYAVYESSEN-IKDISVFRFSPPASVFANV 306
SEQIDNO:65  TLAGTDGSIFPPHIDHDPILHVYDKDLCRLLPLVFEKEVMTSNEVPGYRFTPPEWVFADV 354
SEQIDNO:66  RLNGTDGSIFPPPRITKNSTLHVYEKDLCRLLPLSFEKEVTVRGGVKGYRFTPSPDVFASV 323
              :****  *   :  ,  ::::   ::**  :       :   :      *:   ::*
```

FIGURE 6 (cont.)

```
                              LAMP HOMOLOGY DOMAIN
                        3         4         5
SEQIDNO:4   ---SDNAGFCIPE-GNCLGSGVLNVSICKNGAPIIMSFPHFYQADEREVSAIEGMHP-NQ 360
SEQIDNO:56  ---SDNAGFCIPE-GNCLGSGVLNVSICKNGAPIIMSFPHFYQADEREVSAIEGMHP-NK 360
SEQIDNO:57  ---SDNAGFCIPE-GNCLGSGVLNVSICKNGAPIIMSFPHFYQADERFVSAIEGMHP-NK 360
SEQIDNO:58  ---SDNAGFCVPK-GNCLGSGVLNISICKNGAPIIISFPHFYEADKKFVSAIDGMRP-NK 360
SEQIDNO:59  ---SDNAGFCIPK-GNCLGSGVLNVSVCKNGAPIIMSFPHFYQADEKFVSAIGGMHP-NK 360
SEQIDNO:60  ---SENAGFCIPE-GNCMDSGVLNISICKNGAPIIMSFPHFYQADEKFVSAIKGMHP-NK 360
SEQIDNO:61  DENPANAGFCVPA-GDCLGKGVLKVSVCPQGAPIVVSFPHFYQADERYINAIEGMNP-NE 368
SEQIDNO:62  ---SENAGFCIPE-GNCMDAGVLNVSICKNGAPIIMSFPHFYQADEKFVSAIKGMRP-NK 360
SEQIDNO:63  TVNPDNAGFCVPP-GNCPGAGVLNVSICKQGAPIFLSAPHFYQADQKFVSDIEGMHP-TK 363
SEQIDNO:64  SVNPQNKGFCVPE-GNCLPSGLLNVSICKEGAPIVLSSPHFYQADENVINSIRGMKP-VK 364
SEQIDNO:65  DSHPDNMCFCPAGKPSCSPNGLFNVSLCQYDSPIMLSFPHFYLADESLRTQVEGISPPMK 414
SEQIDNO:66  DKNPNNMCYCPAG--PPCAPHGLFNVSLCQYDSPILLSFPHFYMADQTLRTAVEGISPPEK 382
                *  :*        *   *::::*:*: .:**.:* **** **:    . : *: *   :

LAMP HOMOLOGY DOMAIN

SEQIDNO:4   EDHETFVDINPLTGIILKAAKRFQINIYVKKLDDFVETGDIRTMVFPVMYLNESVHIDKE 420
SEQIDNO:56  EDHETFVDINPLTGIILKAAKRFQINIYVKKLDDFVETGDIRTMVFPVMYLNESVHIDKE 420
SEQIDNO:57  EDHETFVDINPLTGIILKAAKRFQINIYVKKLDDFVETGDIPTMVFPVMYLNESVLIDKE 420
SEQIDNO:58  DYHETFVDINPLTGIILRAAKRFQINVYVKKLDDFIETGNIRTMVFPVMYINESVLIDKD 420
SEQIDNO:59  EYHETFVDINPLTGIILRAAKRFQINVYVRKLDDFVETGNIQTLVFPVMYINESVLIDKE 420
SEQIDNO:60  EEHESFVDINPLTGIILRGAKRFQINTYVRKLDDFVETGDIRTMVFPVMYLNESVLIDKE 420
SEQIDNO:61  EEHETYLDINPTTGVPIRACKRAQLNIILKRVRGFPNTKFLNETIFPIMYVNETATIDDE 428
SEQIDNO:62  EEHESFVDINPLTGIILRGAKRFQINTYVKKLDDFVETGNIRTMVFPVMYLNESVLIDKE 420
SEQIDNO:63  EYHETFVDINPLTGLVLQAAKRMQINIHVRKLPEFFETGNIPTLIFPVMYINESVLIDEA 423
SEQIDNO:64  EHHMTFLDINPLTGTLIQAAKRIQVNVYVPKINVYLITQDIQTLFFPVMHLNESVLIDDK 424
SEQIDNO:65  EKHQFFFDVQPKMGTTLRVRARIQINLAVSQVFDIKQVANFPDIIFPILWFEEGIDNLPD 474
SEQIDNO:66  DKHQLFIDVQPDMGTALRARARIQINLAVSQVVDIKQVANFPDIVFPILWFEEGIDSLPD 442
               :  *  : .*::*   *   ::    *  *:*   : ::     .  : ,**::  .:*

Trans. Domain        Cytoplasmic Tail

SEQIDNO:4   TASRLKSMINTTLIITNI-----PYIIMALGVFFGLVFTWLACKGQGSMDEGTADERAPLI 476
SEQIDNO:56  TASRLKSMINTTLIITNI-----PYIIMALGVFFGLVFTWLACKGQGSMDEGTADEPAPLI 476
SEQIDNO:57  TASRLKSVINTTLIITNI-----PYIIMALGVFFGFVFTWLACKGQGSMDEGTADERAPLI 476
SEQIDNO:58  TASRLKSVINTTLIITNI-----PYIVMALGVFFGLIFTWLACRGQGSMDEGTPDERAPLI 476
SEQIDNO:59  TASRLKSVINTTLIVTNI-----PYIIMALGVFFGLIFTWLACRGQGSTDEGTADERAPLI 476
SEQIDNO:60  TANQLKSVTNTTLVVTNI-----PYTIMALGVFFGLVFTWLACRGQGSMDEGTADERAPLI 476
SEQIDNO:61  SAAQMPMLLLIVTVVSNF-----PVITLALGVILLVVLIFLVCPNPQRKNEVKRIDFTEAF 484
SEQIDNO:62  TASQLKSVINTTLIVTNI-----PYIIMALGVFFGLIFTWLACRGQGSTDEGTADERAPLI 476
SEQIDNO:63  SANKLKHVLLEASVVTGI-----PFVIMAIGIVFGIVFSVLVCRAQGAREESTEEERSPLI 479
SEQIDNO:64  SAGRLRSILFQGPVVANI-----PFIIMGLGIILAFLFTTLSCLQKRSRDEGTEEEPGPLI 480
SEQIDNO:65  EVTDL---MRPFAEQVPPKIPVALIVGLCALGVILLLLSTF---CLIPNSHRQSTLHLEGSNY 530
SEQIDNO:66  EILDL----MKVATNIPPRAKFILTIALFGLGGFLVVAVI---CLVRKSHRQSTLHLEGSNY 498
               :   :           :    :  .:*  .: .:      *    :  .
```

FIGURE 6 (cont.)

```
SEQIDNO:4   RT--------------------------------------------------  478
SEQIDNO:56  RT--------------------------------------------------  478
SEQIDNO:57  RT--------------------------------------------------  478
SEQIDNO:58  RT--------------------------------------------------  478
SEQIDNO:59  RT--------------------------------------------------  478
SEQIDNO:60  RT--------------------------------------------------  478
SEQIDNO:61  HSFATTKDETAYTQVSNQAELSPENPNNQPLRNGSYIAMSPVEAQKC        531
SEQIDNO:62  RT--------------------------------------------------  478
SEQIDNO:63  RT--------------------------------------------------  481
SEQIDNO:64  RAS-------------------------------------------------  483
SEQIDNO:65  LATA------QVDMNKRQNKDNQPARY-------------------------  551
SEQIDNO:66  LATA------SVDQAKKKARMDNGMSSKSN----------------------  522
            *
```

LIMP-2

| Accession No. | Species | SEQ ID NO: | Accession No. | Species | SEQ ID NO: |
|---|---|---|---|---|---|
| NP_005497.1 | H. sapiens | 4 | NP_775366.1 | D. rerio | 61 |
| XP_517214.2 | P. troglodytes | 56 | NP_446453.1 | R. norvegicus | 62 |
| XP_001096458.1 | M. mulatta | 57 | XP_420593.1 | G. gallus | 63 |
| XP_005639134.1 | C. lupus familiaris | 58 | NP_001016557.1 | X. tropicalis | 64 |
| NP_001095623.1 | B. Taurus | 59 | NP_726504.2 | D. Melanogaster | 65 |
| NP_031670.1 | M. musculus | 60 | XP_314345.2 | A. gambiae | 66 |

FIGURE 7: HUMAN LIMBIC/SLAMP ALIGNMENT WITH ORTHOLOGOUS SEQUENCES

```
                 SIGNAL SEQUENCE            LAMP HOMOLOGY DOMAIN
                                                       1
SEQIDNO:67   -MVKRVQPDRKQLPLV-LLRLLCL-LPTGLPVRSVDFNRGTDNITVRQGDTAILRCVVED   57
SEQIDNO:68   -MVRRVQPDRKQLPLV-LLRLLCL-LPTGLPVRSVDFNRGTDNITVRQGDTAILRCVVED   57
SEQIDNO:69   -MGARVQPDRKQLPLV-LLRLLCL-LPTGLPVRSVDFNRGTDNITVRQGDTAILRCVVED   57
SEQIDNO:70   -MVGRVQPDRKQLPLV-LLRLLCL-LPTGLPVRSVDFNRGTDNITVRQGDTAILRCVVED   57
SEQIDNO:71   -MVGRSQSDRNQLPLF-LLRLLCL-LPTGLPVRSGDFNRSTDNMTVRQGDTAILRCFVED   57
SEQIDNO:72   ----MSCLWIHSVFIPGFF---LLF-GFEGFPVISVESQRSTDNITIRQGDTTVIRCYVDD   53
SEQIDNO:102  -MVGRVQPDRKQLPLV-LLRLLCL-LPTGLPVRSVDFNRGTDNITVRQGDTAILRCVVED   57
SEQIDNO:103  -MVGPVQPDRKQLPLV-LLRLLCL-LPTGLPVRSVDFNRGTDNITVRQGDTAILRCVVED   57
SEQIDNO:104  -MVARVQPDRKQLPLV-LLRLLCL-LPTGLPVRSVDFNRGTDNITVRQGDTAILRCVVED   57
SEQIDNO:105  -MVARVQPDRKQLPLV-LLRLLCL-LPTGLPVRSVDFNRGTDNITVRQGDTAILRCVVED   57
SEQIDNO:106  -------------MSFAGEAA--------SQILNKAEPLFISRSEAFKFAVGDTITLPCEVAS   42
SEQIDNO:107  ------MRPCLLHSIWMLGFVLCLLSLQGLPVRSGDFNRSTDNITVRQGDTAILRCFVED   54
SEQIDNO:108  -MLGARRPPRSQLPLV-LLRLLCL-LPTGLPVRSVDFNRGTDNITVRQGDTAILRCVVED   57
SEQIDNO:109  -MVGRVHPDRKQLPLV-LLRLLCL-LPTGLPVRGVDFTRGTDNITVRQGDTAILRCYVED   57
SEQIDNO:110  -MVARAQPDRKQLPLV-LLRLLCL-LPTGLPVRSVDFTRGTDNITVRQGDTAILRCFVED   57
SEQIDNO:111  -----MPTYW-LHSIWVL-GFFLSLF-SLQGLPVRSVDFTRGTDNITVRQGDTAILRCYVED   54
SEQIDNO:112  -------MRPCLLHSIWMLGFVLCLLSLQGLPVRSGDFNRSTDNITVRQGDTAILRCFVED   54
SEQIDNO:113  MQVGRKSCWRQ---LQASFFRLLCL-IPTGFPVRSVDMQRATDNITIRQGDTAIIRCYVDD   57
                                :  :..  ***  :  *  * .

LAMP HOMOLOGY DOMAIN
                                           2
SEQIDNO:67   KN-SKVAWLNRSGIIFAGHDKWSLDPRVELEKRHSLEYSLRIQKVDVDEGSYTCSVQTQ   116
SEQIDNO:68   KN-SKVAWLNRSGIIFAGHDKWSLDPRVELEKRHSLEYSLRIQKVDVYDEGSYTCSVQTQ   116
SEQIDNO:69   KN-SKVAWLNRSGIIFAGHDKWSLDPRVELEKRHSLEYSLRIQKVDVYDEGSYTCSVQTQ   116
SEQIDNO:70   KN-SKVAWLNRSGIIFAGHDKWSLDPRVELEKRHALEYSLRIQKVDVYDEGSYTCSVQTQ   116
SEQIDNO:71   KS-SKVAWLNRSGIIFAVDDKWSLDPRVELEKRSPFEYSLRIQKVDVSDEGPYICSVQTN   116
SEQIDNO:72   KV-SKVAWLNRSNIIFAGEDKWSLDPRVELVTQGQLEYSLRIQKVDVFDEGPYTCSIQTK   112
SEQIDNO:102  KN-SKVAWLNRSGIIFAGHDKWSLDPRVELEKRHALEYSLRIQKVDVYDEGSYTCSVQTQ   116
SEQIDNO:103  KN-SKVAWLNRSGIIFAGHDKWSLDPRVELEKRHSLEYSLRIQKVDVYDEGSYTCSVQTQ   116
SEQIDNO:104  KN-SKVAWLNRSGIIFAGHDKWSLDPRVELEKRHSLEYSLRIQKVDVYDEGSYTCSVQTQ   116
SEQIDNO:105  KN-SKVAWLNRSGIIFAGHDKWSLDPRVELEKRHSLEYSLRIQKVDVYDEGSYTCSVQTQ   116
SEQIDNO:106  PGTYVLAWKRGIAILTAGSVKVTPDPRVRLVN----GYSLQIRDAVPQDAGDYICQIAML   98
SEQIDNO:107  RS-SRVAWLNRSGIIFAGDDKWSLDPRVELEKRSLLEYSLRIQKVDVSDEGPYTCSVQTK   113
SEQIDNO:108  KN-SKVAWLNRSGIIFAGHDKWSLDPRVELEKRHSLEYSLRIQKVDVYDEGSYTCSVQTQ   116
SEQIDNO:109  KS-SKVAWLNRSGIIFAGHDKWSLDPRVELEKRTALEYSLRIQKVDVYDEGSYTCSVQTQ   116
SEQIDNO:110  RS-SKVAWLNRSGIIFAGEDKWSLDPRVELEKRSPLEYSLRIQKVDVYDEGSYTCSVQTQ   116
SEQIDNO:111  RS-SKVAWLNRSGIIFAGEDKWSLDPRVELEKRNPLEYSLRIQKVDVYDEGSYTCSVQTQ   113
SEQIDNO:112  RS-SRVAWLNRSGIIFAGDDKWSLDPRVELEKRSLLEYSLRIQKVDVSDEGPYTCSVQTK   113
SEQIDNO:113  KV-SKVAWLNRSNIIFAGQDKWSLDPRVDLVTKGQLEYSLRIQKVDVYDEGSYTCSIQTK   116
              :** .  *: *      *:****  * .       ***:*:..   *  *  *.:
```

FIGURE 7 (cont.)

```
                       LAMP HOMOLOGY DOMAIN
                                3
SEQIDNO:67    HEPKTSQVYLIVQVPPKISNISS---DVTVNEGSNVTLVCMANGRPEPVITWRHLTP---T   171
SEQIDNO:68    HEPKTSQVYLIVQVPPKISNISS---DVTVNEGSNVTLVCMANGRPEPVITWRHLTP---T   171
SEQIDNO:69    HEPKTSQVYLIVQVPPKISNISS---DVTVNEGSNVTLVCMANGRPEPVITWRHLTP---T   171
SEQIDNO:70    HEPKTSQVYLIVQVPPKISNISS---DVTVNEGSNVTLVCMANGRPEPVITWRHLTP---L   171
SEQIDNO:71    QHTKTMQVYLIVQVPPKISNISA---DITVNEGSNVTLMCIAYGRPEPMITWRHLTP---T   171
SEQIDNO:72    QQSKTSQVYLIVQVPAIIYKVSE---DITVNEGSNVALTCLANGRPDPAITWRLLNP---S   167
SEQIDNO:102   HEPKTSQVYLIVQVPPKISNISS---DVTVNEGSNVTLVCMANGRPEPVITWRHLTP---L   171
SEQIDNO:103   HEPKTSQVYLIVQVPPKISNISS---DVTVNEGSNVTLVCMANGRPEPVITWRHLTP---T   171
SEQIDNO:104   HEPKTSQVYLIVQVPPKISNISS---DVTVNEGSNVTLVCMANGRPEPVITWRHLTP---T   171
SEQIDNO:105   HEPKTSQVYLIVQVPPKISNISS---DVTVNEGSNVTLVCMANGRPEPVITWRHLTP---T   171
SEQIDNO:106   DPR-EITHSVEILVPPKITHVTSGGHLQVRKGSPVRLECSATGNPMPNITWTRKNNLLPN   157
SEQIDNO:107   QHTKTTQVYLIVQVPPKISNISA---DITVNEGSNVTLMCIAYGRPEPMITWRHLTP---T   168
SEQIDNO:108   HEPKTSQVYLIVQVPPKISNISS---DVTVNEGSNVTLVCMANGRPEPVITWRHLTP---T   171
SEQIDNO:109   HQPKTSQVYLIVQVPPKISNISS---DVTVNEGSNVTLVCMANGRPEPVITWRHLTP---T   171
SEQIDNO:110   HHPKTSQVYLIVQVPPKISNISS---DITVNEGSNVTLVCMANGRPEPVITWRHLTP---T   171
SEQIDNO:111   HHPKTSQVYLIVQVPPKISNISS---DITVNEGSNVTLVCMANGRPEPVITWRHLTP---T   168
SEQIDNO:112   QHTKTTQVYLIVQVPPKISNISA---DITVNEGSNVTLMCIAYGRPEPMITWRHLTP---T   168
SEQIDNO:113   QQPKTSQVYLIVQVPASIYQVSN---DITVNEGSNVTLSCLANGRPDPAITWRLLNP---S   171
                .  : :**  * :::   .: *.:** * * * *.* * ***  .

LAMP HOMOLOGY DOMAIN
                                4
SEQIDNO:67    GREFEGEEEYLEILGITREQSGKYECKAANEVSSADVKQVKVTVNYPPTITESKS         230
SEQIDNO:68    GREFEGEEEYLEILGITREQSGKYECKAANEVSSADVKQVKVTVNYPPTITESKS-NEAT   230
SEQIDNO:69    GREFEGEEEYLEILGITREQSGKYECKAANEVSSADVKQVKVTVNYPPTITESKS-NEAT   230
SEQIDNO:70    GREFEGEEEYLEILGITREQSGKYECKAANEVSSADVKQVKVTVNYPPTITESKS-NEAT   230
SEQIDNO:71    ARDFEGEEEFLEIQGITREQSGRYECKAANEVASADVKQVRVTVNYPPIITESNS-NEAT   230
SEQIDNO:72    AEALDV--GEYLEISGVVRSQAGRYECKASNDVSTPDVKYVNVVVNYPPYIKDVRS-SETA  225
SEQIDNO:102   GREFEGEEEYLEILGITREQSGKYECKAANEVSSADVKQVKVTVNYPPTITESKS-NEAT   230
SEQIDNO:103   GREFEGEEEYLEILGITREQSGKYECKAANEVSSADVKQVKVTVNYPPTITESKS-NEAT   230
SEQIDNO:104   GRELEGEEEYLEILGITREQSGKYECKAANEVSSADVKQVKVTVNYPPTITESKS-NEAT   230
SEQIDNO:105   GREFEGEEEYLEILGITREQSGKYECKAANEVSSADVKQVKVTVNYPPTITESKS-NEAT   230
SEQIDNO:106   GEEQFT--NPVYVIENMDRHKGGTYICTANNGVGQVATSQIILHVLYPPEISVENPTVYSG  216
SEQIDNO:107   ARDFEGEEEFLEIQGITREQSGRYECKAANEVASADVKQVRVTVNYPPIITESKS-NEAT   227
SEQIDNO:108   GREFEGEEEYLEILGITREQSGKYECKAANEVSSADVRQVKVTVNYPPTITESKS-NEAT   230
SEQIDNO:109   GREFEGEEEYLEILGITREQSGKYECKAANEVSSADVKQVKVTVNYPPTITESKS-NEAT   230
SEQIDNO:110   GKEFEGEEEYLEILGITREQSGKYECKAANEVASADVKQVRVTVNYPPTITESKS-NEAA   230
SEQIDNO:111   GKEFEGEEEYLEILGITREQSGKYECKAANEVASADVKQVRVTVNYPPTITESKS-NEAA   227
SEQIDNO:112   ARDFEGEEEFLEIQGITREQSGRYECKAANEVASADVKQVRVTVNYPPIITESKS-NEAT   227
SEQIDNO:113   AEPLDG--EEYLDIIGIMRTQAGRYECKASNDVATPDVKYVNVIVNYPPTIKKTQS-SETP  229
                ..       * .: *  :,* * *,* * *,   . :  : * ***  *.  .   :
```

FIGURE 7 (cont.)

LAMP HOMOLOGY DOMAIN

```
              5                                                  6
SEQIDNO:67    TGRQASLKCEASAVPAPDFEWYRDDTRINSANGLEIKSTEGQSSLTVTNVTEEHYGNYTC   290
SEQIDNO:68    TGRQASLKCEASAVPAPDFEWYRDDTRINSANGLEIKSTEGQSSLTVTNVTEEHYGNYTC   290
SEQIDNO:69    TGRQASLKCEASAVPAPDFEWYRDDTRINSANGLEIKSTEGQSSLTVTNVTEEHYGNYTC   290
SEQIDNO:70    TGRQASLKCEASAVPAPDFEWYRDDTRINSANGLEIKSTEGQSSLTVTNVTEEHYGNYTC   290
SEQIDNO:71    TGKQAILRCEASAVPAPDFEWYKDDTRINSAQGLEIRNTGSRSVLMVANVTEEHYGNYTC   290
SEQIDNO:72    VGQAGVLHCEASAVPQPEFEWYRDERRLSSQSLTIQVSGSRTVLVVANVTEEDYGNYTC   285
SEQIDNO:102   TGRQASLKCEASAVPAPDFEWYRDDTRINSANGLEIKSTEGQSSLTVTNVTEEHYGNYTC   290
SEQIDNO:103   TGRQASLKCEASAVPAPDFEWYRDDTRITSANGLEIKSTEGQSSLTVANVTEEHYGNYTC   290
SEQIDNO:104   TGRKASLKCEASAVPAPDFEWYRDDTRINSANGLEIKSTEGQSSLTVTNVTEEHYGNYTC   290
SEQIDNO:105   TGRKASLKCEASAVPAPDFEWYRDDTRINSANGLEIKSTEGQSSLTVTNVTEEHYGNYTC   290
SEQIDNO:106   EGQEAMLVCIVHGESQPEVLWHKDTMQIDQTERHVIENRGAPHTLIIRKVHPQDFGNYSC   276
SEQIDNO:107   TGKQAILRCEASAVPAPDFEWYKDDTRINSAQGLEIRNTGSRSVLMVANVTEEHYGNYTC   287
SEQIDNO:108   TGRKASLKCEASAVPAPDFEWYRDDTRINSANGLEIKSTEGQSSLTVTNVTEEHYGNYTC   290
SEQIDNO:109   TGRQASLKCEASAVPAPDFEWYRDDTRINSANGLEIKSIEGQSLLMVTNVTEEHYGNYTC   290
SEQIDNO:110   TGRQALLRCEASAVPTPDFEWYRDDTRINSANGLEIKSTGSQSLLMVANVTEEHYGNYTC   290
SEQIDNO:111   TGRQALLRCEASAVPTPDFEWYRDDTRINSANGLEIKSTGSQSLLMVANVTEEHYGNYTC   287
SEQIDNO:112   TGKQAILRCEASAVPAPDFEWYKDDTRINSAQGLEIPNTGSRSVLMVANVTEEHYGNYTC   287
SEQIDNO:113   VGRNGTLRCEVTAVPTPEFEWYRDDKRLANTQSITIQTSGTTTSLTIANITEEDYGNYTC   289
              *:  . *  *  . .     *:.  *::*    :: .::   *.       *  :  :: :.:****:*
```

Trns Memb.

```
SEQIDNO:67    VAANKLGVTNASLVLFRPGSVRGINGSISLAVPLWLLAASLLCLL-SKC------------   338
SEQIDNO:68    VAANKLGVTNASLVLFRPGSVRGINGSISLAVPLWLLAASLLCLL-SKC------------   338
SEQIDNO:69    VAANKLGVTNASLVLFRPGSVRGINGSISLAVPLWLLAASLLCLL-SKC------------   338
SEQIDNO:70    VAANKLGVTNASLVLFSKYAKTEPDSMQVIE-FLHIDLKSIRHPL-KVNPIQK-------   341
SEQIDNO:71    VAANKLGITNTSLYLYI-GPGTPIDNATSLAASLWLMANILLCLF-CTC------------   337
SEQIDNO:72    VATNRLGVHNASVFLYKPGMGRDINSAGCICQSLWLLLLCVSSAL-LQC------------   333
SEQIDNO:102   VAANKLGVTNASLVLFRPGSVRGINGSISLAVPLWLLAASLFCLL-SKC------------   338
SEQIDNO:103   VAANNLGVTNASLVLFRPGSVRGINGSISLAVPLWLLAASLLCLL-SKC------------   338
SEQIDNO:104   VAANNLGVTNASLVLFRPGSVRGINGSISLAVPLWLLAASLLCLL-SKC------------   338
SEQIDNO:105   VAANNLGMTNASLVLFRPGSVRGINGSISLAVPLWLLAASLLCLL-SKC------------   338
SEQIDNO:106   IADNQLGKTRKTVTLTGKPKTAVF----RSVPNSQWKDKYNISWIVDSHSPIEEFKLYYRQ   333
SEQIDNO:107   VAANKLGITNTSLYLYI-GPGTPIDSATSLAASLWLMANLLFCLF-CTC------------   334
SEQIDNO:108   VAANNLGVTNASLVLFRPGSVRGINGSISLAVPLWLLAASLLCLL-SKC------------   338
SEQIDNO:109   VAANKLGVTNASLILFRPGSVRGINGSISLAVPLWLLAASLFCLL-SKC------------   338
SEQIDNO:110   VAANKLGVTNASLYLYRPGTGRVDNGSVSLAVPLWLLAASLLCLL-SKC------------   338
SEQIDNO:111   VAANKLGVTNASLYLYRPGTGRVDNGSMSLAVPLWLLAASLLCLL-SKC------------   335
SEQIDNO:112   VAANKLGITNTSLYLYI-GPGTPIDSATSLAASLWLMANLLFCLF-CTC------------   334
SEQIDNO:113   VASNRLGVQNASLFLYRPGTGRDINGSACVSQSLWLLLASFACLF-LKC------------   337
              :*  *.**   . :: *                            :      .   .
```

FIGURE 7 (cont.)

```
SEQIDNO:67                                                                                           338
SEQIDNO:68                                                                                           338
SEQIDNO:69                                                                                           338
SEQIDNO:70                                                                                           341
SEQIDNO:71                                                                                           337
SEQIDNO:72                                                                                           333
SEQIDNO:102                                                                                          338
SEQIDNO:103                                                                                          338
SEQIDNO:104                                                                                          338
SEQIDNO:105                                                                                          338
SEQIDNO:106   MTFSIGQLQPLQTDWRDIVLPAFPYSHHYTQGMSYLIRGLEFDQQYEARVQSRNRYGWSD                            393
SEQIDNO:107                                                                                          334
SEQIDNO:108                                                                                          338
SEQIDNO:109                                                                                          338
SEQIDNO:110                                                                                          338
SEQIDNO:111                                                                                          335
SEQIDNO:112                                                                                          334
SEQIDNO:113                                                                                          337

SEQIDNO:67                                            338
SEQIDNO:68                                            338
SEQIDNO:69                                            338
SEQIDNO:70                                            341
SEQIDNO:71                                            337
SEQIDNO:72                                            333
SEQIDNO:102                                           338
SEQIDNO:103                                           338
SEQIDNO:104                                           338
SEQIDNO:105                                           338
SEQIDNO:106   FSESFLFTTSNTGKWMGQCCTNPG                417
SEQIDNO:107                                           334
SEQIDNO:108                                           338
SEQIDNO:109                                           338
SEQIDNO:110                                           338
SEQIDNO:111                                           335
SEQIDNO:112                                           334
SEQIDNO:113                                           337
```

| LIMBIC/LSAMP ||||||
|---|---|---|---|---|---|
| Accession No. | Species | SEQ ID NO: | Accession No. | Species | SEQ ID NO: |
| NP_002329.2 | H. sapiens | 67 | NP_001192297.1 | B. Taurus | 105 |
| XP_516662.2 | P. troglodytes | 68 | XP_312298.5 | A. gambiae | 106 |
| XP_002716722.1 | O. cuniculus | 69 | NP_001096385.1 | X. tropicalis | 107 |
| NP_780757.1 | M. musculus | 70 | XP_003434117.1 | C. lupus familiaris | 108 |
| NP_001086181.1 | X. laevis | 71 | XP_001362972.1 | M. domestica | 109 |
| NP_001034921.1 | D. rerio | 72 | NP_990205.1 | G. gallus | 110 |
| NP_058938.1 | R. norvegicus | 102 | XP_002190582.1 | T. guttate | 111 |
| XP_001502710.1 | E. caballus | 103 | NP_001096385.1 | X. tropicalis | 112 |
| NP_001231626.1 | S. scrofa | 104 | XP_003449349.1 | O. niloticus | 113 |

FIGURE 8: HUMAN ENDOLYN ALIGNMENT WITH ORTHOLOGOUS SEQUENCES

```
                SIGNAL SEQUENCE                 LAMP HOMOLOGY DOMAIN
SEQIDNO:5   MSRLSRSLLWAATCLGVLCVLSADKNTTQH-PNVTTLAPISNVTSAP-----V-TSLPLV 53
SEQIDNO:73  MSGSSRPLLWAATCLAVLCVSAAQPNITTLAPNVTEVFT-----TT-----TKVVPTTQM 50
SEQIDNO:74  MSRLSRSLLWAVTCLAVLCVLSAEENPTPH-TNVTSLAPTSNITSAP-----V-TSLPLV 53
SEQIDNO:75  MLGLSRQLLWAVGCLAALCVLTAAKNSTIL-PPSTTTPWLSPPTTQT-----TSAPPKTL 54
SEQIDNO:76  MSGLSRPLLLAVGCLAALCVITAAGNTTLA-PNVTTASS-PPPTTTTVPVSPTTLSPLPV 58
SEQIDNO:77  MSGLSRPLLLAVGYLAALCVITAARNTTVT-PNVTTPSS-PPPTTATVPVSPTTLTPPPV 58
SEQIDNO:78  MSGLSRQLCWAAACLAALCALTAAQSFSSD-PNGTTTTTQATTDAAT-----TPVTTAAPA 55
SEQIDNO:79  MSGASRGLFWAATCLAALCLSAAQSNS-SASPNVTDPPT-----TT-----SKVVPTTLT 49
                *    **  * *, *, **  *       *

LAMP HOMOLOGY DOMAIN
                    1       2   3         4       5        6         7        8
SEQIDNO:5   TTPAPETCEGRNSCVSCFNVSVV-NTTCFWIECKD--ESYCSHNSTVSDCQVGNTTDFCS 110
SEQIDNO:73  PTVLPETCASFNSCVSCVNATFTNNITCFWLHCQEANKTYCAN-EPLSNCSQVNRTDLCS 109
SEQIDNO:74  TTPAPETCEGRNSCVSCFNASTV-NTTCFWIECKD---ESYCSHNSTVSDCQVGNTTDFCS 110
SEQIDNO:75  PTPAPEICENPNSCISCFDA-----NNTCFWIECKG--KSYCSDNSTVSDCHVVNGTDFCS 108
SEQIDNO:76  TTPAPDICGSRNSCVSCVDG-----NATCFWIECKG--KSYCSDNSTAGDCKVVNTTGFCS 112
SEQIDNO:77  TTPAPDICGSRNSCISCVDG-----NATCFWIECKG--KSYCSDNSTVSDCKVVNTTGFCA 112
SEQIDNO:78  TTPAPDPCDNRNSCVSCVNTSVD-ATACSWIECKE---KSYCSHNTTVSDCQVVNSTQLCS 112
SEQIDNO:79  TTKPPETCESFNSCVSCVNATLTNNITCWWLDCHEANKTYCSS-ELVSNCTQKTSTDSCS 108
              *  *;  *  ,  ***;** ,;     ;*  *; *;   ;;** ;     ,;*    ,   *   *;

LAMP HOMOLOGY DOMAIN
SEQIDNO:5   VST--ATPVPTANSTAKPTVQPSPSTT--SKTVTTSGTTNNTVTPTSQPVRKSTFDAASFIG 168
SEQIDNO:73  VIPPTTPVPT-NSTAKPTTRPSSPTFTPSVVTTSAGTTNTTLTPTSQPERKSTFDAASFIG 168
SEQIDNO:74  VPT--ATLVPTANSTAKPTVQPSPSTT--SKTVTTSGTTNTTVTPTSQPVRKSTFDAASFIG 168
SEQIDNO:75  GPT--VTPLPT-NSTAKTTTLPSPSSA-STTATTSGTTNTTLAPTTQPMRKSTFDAASFIG 165
SEQIDNO:76  VPT--TTPTPT-NSTAKTTTLPSTTTT-STTATTSGTTNTTLSPTIQPTRKSTFDAASFIG 169
SEQIDNO:77  VPT--TTPTPT-NSTAKTTTLPSTTTT-STTATTSGTANTTLTPTIQPMRKSTFDAASFIG 169
SEQIDNO:78  APE--PTMMPT-NSTAKTTTQPSSSTA-TTTATTSGTTNITLSPTSQPGPKSTFDAASFIG 169
SEQIDNO:79  VIP--TTPVPT-NSTAKPTTRPSSPTPTPSVVTSAGATNTTVTPTSQPERKSTFDAASFIG 166
               *    ** ***** *,  **    ;     ,,,*;,*;;* *;,** **  ************

Trns Memb.  Cytoplasmic Tail
SEQIDNO:5   GIVLVLGVQAVIFFLYKFCKSKERNYHTL 197
SEQIDNO:73  GIVLVLGVQAVIFFLYKFCKSKERNYHTL 197
SEQIDNO:74  GIVLVLGVQAVIFFLYKFCKSKERNYHTL 197
SEQIDNO:75  GIVLVLGVQAVIFFLYKFCKSKERNYHTL 194
SEQIDNO:76  GIVLVLGVQAVIFFLYKFCKSKERNYHTL 198
SEQIDNO:77  GIVLVLGVQAVIFFLYKFCKSKERNYHTL 198
SEQIDNO:78  GIVLILGVQAVIFFLYKFCKSKERNYHTL 198
SEQIDNO:79  GIVLVLGVQAVIFFLYKFCKSKERNYHTL 195
            ****;************************
```

FIGURE 8 (cont.)

| Accession No. | Species | SEQ ID NO. | Accession No. | Species | SEQ ID NO. |
|---|---|---|---|---|---|
| | | | Endolyn | | |
| NP_006007.2 | H. sapiens | 5 | NP_001039506.1 | B. taurus | 76 |
| NP_058594.1 | M. musculus | 73 | XP_004011265.1 | O. aries | 77 |
| XP_001091286.1 | M. mulatta | 74 | XP_532256.2 | C. lupus familiaris | 78 |
| XP_001924661.2 | S. scrofa | 75 | NP_114000.1 | R. norvegicus | 79 |

FIGURE 9: HUMAN MACROSAILIN ALIGNMENT WITH ORTHOLOGOUS SEQUENCES

```
              SIGNAL SEQUENCE           LAMP HOMOLOGY DOMAIN 1
                                1
SEQIDNO:80    MRLAVLFSGALLGL LAAQGTGNDCPHKKSATLLPSFTVTPTVTEST----GTTSHRTTK 55
SEQIDNO:81    MRLAVLFSGALLGL-LAAQGTGNDCPHKKSATLLPSFTVTPTVTEST----GTTSHRTTK 55
SEQIDNO:82    MRLAVFFSGALLGL-LAAQGTGNDCPHKKSATLLPSFTVTPTATESTPS-PGTTSHRTTK 58
SEQIDNO:83    MRLPVCL--ILLGP-LIAQGTEEDCPHKKAVTLLPSFTMTPTATESTAS-PTTSHRPTTT 56
SEQIDNO:84    MRLAVLFLGALLGL-LAAQGTGNDCPHKKSATLLPSFTVTPTATEST----GTTSHRTTK 55
SEQIDNO:85    MRFPVCL--TLLVL-LVAQGTGKDCPHKKAATLLPSFTETPTTTGSTAS-PTTTHRPTTT 56
SEQIDNO:86    MRPAVFFLGALVGL-LAAQGTRSDCPHKKSATLLPSFTVTPTATESTGS-PGTTSHSTTT 58
SEQIDNO:87    MRLAVLFSGALLGL-LAAQETGNDCPHKKSATLLPSFTVTPTATESTAS-PGTTSHQTTQ 58
SEQIDNO:88    MRLPVLFLA-LLGL-HAA-----------------------------S-SGTTSHRTTK 27
SEQIDNO:89    MTLAVLFLGALLGL-LAESTTSH-------------------------------- 22
SEQIDNO:90    MRLAVLFSGALLGL-LAAQGTGNDCPHKKSATLLPSFTVTPTATEST----GTTSHRTTK 55
SEQIDNO:91    MRLSLLLSGILLGL-LAEQGAGDKCPQEKSVTLVPSFTVTTIATERSTTSPETTTSSGS- 58
SEQIDNO:92    --------MGLTLPLPAQGSQCRANCPHKKSATLVPSFTVTPTATSG----PTTTAHQTTT 49

LAMP HOMOLOGY DOMAIN 1

SEQIDNO:80    SHKTTTHRTTT        TGTTSHGPTTATHNPTTTSHGNVTVHPTSNSTATSQGPSTA  108
SEQIDNO:81    SHKTTTHRTTT--------TGTASHGPTTATHNPTTTSHGNVTVHPTSNSTATSQGPSTAT 108
SEQIDNO:82    SHRTTTWRISTTTHTTNTTGTTSSESPTATHSPA--------------------------- 92
SEQIDNO:83    SHGNVTVH---------T------SSGPTTVTHNPA------------------------- 77
SEQIDNO:84    SHKTTTHRTTT--------TGTTSHRPTTATHNPTTTSHRNATVHPTSNSTATSQGPSTAT 108
SEQIDNO:85    SHRPTTTS-----------HRPTTTSHRPTTTSHRPT-----------------TTS 85
SEQIDNO:86    AETT---------------SHAPNTTTHQ---------------------------- 72
SEQIDNO:87    SHRTTTT------------GTTSDHPTTATHNP------------------------ 79
SEQIDNO:88    NPHTT--------SHSTATPGTTSHRPTTAT-------------------------- 50
SEQIDNO:89    --RTTTPR---------TTTTGTTSHGPTTVTHNPA--------------------- 47
SEQIDNO:90    SHKTTTHRTTT--------TGTTSHRPTTATHNPNTTSHRNATVHPTSNSTATSQGPSTAT 108
SEQIDNO:91    --TATTYRTS----------TAATTPHS------------------NSTATS------- 80
SEQIDNO:92    DHGTTTSHETTTSQGTSTHGTSTPHTTTTGHGTT-TGHQN------TSH----------- 91

LAMP HOMOLOGY DOMAIN 1

SEQIDNO:80    HSPATTSHGNATVHPT-SNSTATSPG----------F-T---SSAHPEPPPPSPSPSPTSK 154
SEQIDNO:81    HSPATTSHGNATVHPT-SNSTATSPG----------F-T---SSAHPEPPPPSPSPSPTSK 154
SEQIDNO:82    ---TTTSHQNTTVHPT-SNITATSPG----------PST---RSPHPEP-PPSPSPSPGSK 135
SEQIDNO:83    ---TTTSHGNATISHATVSPTT------NG-TATSPRSST--VGPHPGPPPPSP--SPRSK 124
SEQIDNO:84    HRPATTSHGNATVHPT-SNSTATSPG----------L-T---SSAHPGPPPPSPSPSPASK 154
SEQIDNO:85    HRPTTTSHGNATV-----SP-----------TTNSPGFST--VGPHPGPPPPSPSPSPSST 128
SEQIDNO:86    -APTTPGHRNTTIHPTTSNSTSNTTGTTGTGKPHTSTSY--TQPGPGPRPPPSPGPGPQ 129
SEQIDNO:87    ---TTTSHGNTTVHPTTSNSTVTSPG----------SAS---SSPHPRPPPSPSPSPGSK 124
SEQIDNO:88    ----PTTGHGNVTVHPTTSNTTSNTTTTTGTS----PGFST--STPHPGPPPPPSPSPGSR 102
SEQIDNO:89    ----TTTSHGNATVHPT-SSSTATSPG-----------SST--RPPHPGPPPPSPSPSPGSQ 91
SEQIDNO:90    HRPATTSHGNATVHPT-SNSTATSPG----------L-T---SSAHPGPPPPSPSPSPASK 154
SEQIDNO:91    --YSTTSEGTAVTHGTTTSPRN-------------TSTT--STSQSVPVPPSPQPTSSPS 123
SEQIDNO:92    --STTTSHGTSTPHKTTTRHPTTSHGTTTSHGTSTGHWTARPTIRPGPPPPPP----SPG 145
                      *  ..  . .                              *  ** *
```

FIGURE 9 (cont.)

LAMP HOMOLOGY DOMAIN

```
                     2
SEQIDNO:80  ETIGDYTWTNGSQPCVHLQAQIQIRVMYTTQGGG---------EAWGISVLNPNK-TKVQ 204
SEQIDNO:81  ETIGDYTWTNGSQPCVHLQAQIQIRVMYTTQGGG---------EAWGISVLNPNK-TKVQ 204
SEQIDNO:82  EAIGDYTWSNGSQPCVRLQAQIQIRVLYPTQGGG---------EAWGISVLNPNR-TKAQ 185
SEQIDNO:83  GALGNYTWANGSQPCVQLQAQIQIRILYPIQGGPKVKLKWGLKRAWGISVLNPNK-TKVQ 183
SEQIDNO:84  ETIGDYMWTNGSQPCVHLQAQIQIRVMYTTQGGG---------EAWGISVLNPNK-TKVQ 204
SEQIDNO:85  GALGNYTWTNGSQPCVQLQAQIQIRILYLTQGGK-----------KAWGLSVLNPNK-TKVQ 178
SEQIDNO:86  DAIGDYTWTTGSQPCARLQARIQIGVVYPTQAGG---------QAWGISVLNPNS-TKPW 179
SEQIDNO:87  EAIGDYIWTNGSQPCVRLQAQIQIRVLYPTLGGG---------KAWGISVLNPNK-TKAQ 174
SEQIDNO:88  EAVGNYTWTNGSQPCVQLQAQIQIRVLYPTQGGG---------QAWGMSVLNPNR-TKAQ 152
SEQIDNO:89  EAIGDYTWTNGSQPCVQLQAQIQIRVLYPTQGGG---------EAWGISVLNPNK-TKAL 141
SEQIDNO:90  ETIGDYMWTNGSQPCVHLQAQIQIRVMYTTQGGG---------EAWGISVLNPNK-TKVQ 204
SEQIDNO:91  GAVGDYIGANGSQLCVHLRAQIQMRVLYQASGGG---------KLWGIFVLNPNR-TMAQ 173
SEQIDNO:92  KAVGNYTVFNGSQPCLRLRAEIRLWVLYQAQEEGEAPPVSG------AASFPPPRPRPVA 199
             :.*:*   .*** * :*:*.*:: ::*              : *
```

LAMP HOMOLOGY DOMAIN

```
                3
SEQIDNO:80  GSCEGAHPHLLLSF----PYGHLSFGFMQDLQQ--KVVYLSYMAVEYNVSFPHAAQWTFS 258
SEQIDNO:81  GSCEGAHPHLLLSF----PYGHLSFGFMQDLQQ--KAVYLSYMAVEYNVSFPHAAQWTFS 258
SEQIDNO:82  GGCEGTHSHLLLSF----PSGQLSFGFKQDPLQ--SAVYLNYMAVEYNVSFPQAVQWTFS 239
SEQIDNO:83  GGCDGTHPHLSLSF----PYGQLTFGFKQDLHQSPSTVYLDYMAVEYNVSFPQAAQWTFM 239
SEQIDNO:84  GSCEGAHPHLLLSF----PYGHLSFGFMQDLQQ--RVVYLSYMAVEYNVSFPHAAQWTFS 258
SEQIDNO:85  GGCDSAHPHLALSF----PYGQLTFGFKQDRHQSHSTVYLNYMAVEYNVSFPQAAQWTFS 234
SEQIDNO:86  GDCDGARPHLLLSF----PFGQLSFGFTQEPQQ--GSVYLDYLALQYNVSFPQAAQWTFS 233
SEQIDNO:87  GGCA--HPHLLLSF----PYGQLSFGFKQEPLQ--STVYLNYIAVEYNVSFPQAAQWTFL 226
SEQIDNO:88  GGCEGPRPHLLLSF----PYGQLSFGFKQDPGQGQSAVYLSYLAVEYNVSFPQAARWTFS 208
SEQIDNO:89  GGCEGAHPHVRLSF----PYGQLTFGFKQQPQE--STVYLNYMAVEYNVSFPRAAQWTFS 195
SEQIDNO:90  GSCEGAHPHLLLSF----PYGHLSFGFMQDLQQ--RVVYLSYMAVEYNVSFPHAAQWTFS 258
SEQIDNO:91  GNCEANHSSLILSF----PNGKLIFGFKQDSIK--KIVYLSHLATEFNVSFPSATRWIFS 227
SEQIDNO:92  GEGDGERSRVTPVASAMTVEGGSPAGFAM------------------------------ 228
             *   : :             *    **
```

LAMP HOMOLOGY DOMAIN

```
                       4                                   5
SEQIDNO:80  AQNASLRDLQAPLGQSFSCSNSSIILSPAVHLDLLSLRLQAAQLPHTGVFGQSFSCPSDR 318
SEQIDNO:81  AQNASLRDLQAPLGRSFSCSNSSIILSPAVHLDLLSLRLQAAQLPHTGVFGQSFSCPSDR 318
SEQIDNO:82  VQNSSLRDLQTPLGHSFSCRNASIIVSPALHLDLLSLKLQAAQLPSGAFGPSFSCPNDK 299
SEQIDNO:83  AQNSSLRELQAPLGQSFCCGNASIVLSPAVHLDLLSRLQAAQLPDKGHFGPCFSCNRDQ 299
SEQIDNO:84  AQNASLRDLQAPLGQSFSCSNSSIILSPAVHLDLLSLRLQAAQLPHTGVFGQSFSCPSDR 318
SEQIDNO:85  AQNSSLQELQAPLGQSFCCGNTSIVLSPAIHLDLLSRLQAAQLPDKGHFGPCFSCASDQ 294
SEQIDNO:86  GQNASLRALQAPLGQSFSCRNASILLTPALRLDLLHLKLQAAQLPPSGAFGPSFSCPSEH 293
SEQIDNO:87  VQNSSLRDLQAPLGRFSCRNASIALSPAFHLDLLSLKLQAAQLTPTGAFGPSFSCPSDQ 286
SEQIDNO:88  AQNASLPDLQAPLGQSFSCRNASIAVSPALHLDLLSRVQAAQLPRTGIFGPSFSCPADH 268
SEQIDNO:89  VQNSSLRDLQTPVGRSYSCRNASIIILSTAFHLDLLSLKLQAAQLPPTGNFGPSFSCPSDQ 255
SEQIDNO:90  AQNASLRDLQAPLGQSFSCSNSSIILSPAVHLDLLSLRLQAAQLPHTGVFGQSFSCPSDR 318
SEQIDNO:91  VENSSLQDLQTPLGHSFSCRNRSIALSPDIHLDLLSLQLQAAQLSSSGAFGAAFSCSADL 287
SEQIDNO:92  -LGAEVRSRAPSLGRAGKTRL--RIHQPVVVLQ-------HTYYV-------------- 263
             .:.:::    :*:        `*:         :
```

FIGURE 9 (cont.)

```
              Trans. Domain       Cyto Tail
SEQIDNO:80  -SLLPLIIGLIIIGLIIIGLLAIVLIAFCIIRRRPSAYQAL 354
SEQIDNO:81  -SILLPLIIGLIIIGLIILGLIILGLITIVLIAFCIIRRRPSAYQAL 354
SEQIDNO:82  -SILLPLIIGLIILGLIILGLVILGLITIVLIAFCITRRQPTYQPL 335
SEQIDNO:83  -SLLPLIIGIVLIGLIIIGLLAIVLIAFCIVRRQSTYQPL 335
SEQIDNO:84  -SILLPLIIGLVLIGLVLIGLLAIVLIAFCVTRRQSTYQPL 354
SEQIDNO:85  -SILLPLIIGLVLIGLVLIGLLALALVTFCIIRRRPTYQPL 330
SEQIDNO:86  -FNLLPLIVGVISLGLLALAIVTFCIIRRRPTYQAL 329
SEQIDNO:87  -SILLPLIIGLIIIGLIVGLLAIVLVAFCIARRRPSAYQAL 322
SEQIDNO:88  PSILVPLIIGLIIVGLIIVLVFFCIIRRRPAYQPL 305
SEQIDNO:89  -TILLPLIIGLIIFLGLIIVLVLVFFCIIRRRPAYQPL 291
SEQIDNO:90  -SILLPLIIGIVLIGLLAIVLIAFCIVRRRPSAYQPL 354
SEQIDNO:91  -NILVPLIVGLVLTLILIVLSAFCISRRRPPAYQPL 323
SEQIDNO:92  ---------------------------------------- 263
```

| Accession No. | Species | SEQ ID NO: | Accession No. | Species | SEQ ID NO: |
|---|---|---|---|---|---|
| NP_001242.2 | H. sapiens | 80 | XP_849733.1 | C. lupus familiaris | 86 |
| XP_003315403.1 | P. troglodytes | 81 | NP_001093232.1 | E. caballus | 87 |
| NP_001039367.1 | B. taurus | 82 | XP_002719034.1 | O. aries | 88 |
| BAA23738.1 | M. musculus | 83 | XP_003131995.1 | S. scrofa | 89 |
| XP_014974003.1 | M. mulatta | 84 | XP_003912313.1 | P. anubis | 90 |
| NP_001026808.1 | R. norvegicus | 85 | XP_001369761.1 | M. domestica | 91 |
|  |  |  | XP_001517723.2 | O. anatinus | 92 |

Macrosailin

FIGURE 10: HUMAN LAMP5 ALIGNMENT WITH ORTHOLOGOUS SEQUENCES

SIGNAL SEQUENCE — LAMP HOMOLOGY DOMAIN

```
                                                          1
SEQIDNO:93   MDLQGRGVPSIDRLRVLLMLFHTMAQIMAEQEVENLSGLSTNPEKDIFVVRENGTTCLMA  60
SEQIDNO:94   MDLRGRAVPSIDRLRVLLMLFHTMAQIMAEQEVENLSGLSTNPEKDIFVVRENGTTCLMA  60
SEQIDNO:95   MDLQGRAVPSVDRLRVLLMLFHTMAQIMAEQEVENLSGLSTNPEKDIFVVRENGTTCLMA  60
SEQIDNO:96   MDLRGRAFPSVYRLRVLLMLFYTMARITAEQEVENLSGLSTNPEKDIFVVRENGTTCLMA  60
SEQIDNO:97   MDLRRRALLGVDGLRVLLMLFHTVTRIMAEQEVENLSGLSTNPEKDIFVVRENGTTCLMA  60
SEQIDNO:98   MDLRVRTLLGGDRLRILLMFFHVMVQTVAEQEVENLSGLSTNPEKDIFVVRENGTTCLMA  60
SEQIDNO:99   MDLRGRALLGGDRLRILLMFFHAMAQTVAEQEVENLSGLSTNPEKDIFVVRENGTTCLMA  60
SEQIDNO:100  --------MAAGRLPGLLFLLHAAARLAAEQEVENLSGLSPNPEKDIFVVRENRTTCLMA  52
SEQIDNO:101  --MDYRACTSALRMPVLLLLLCTFSCNLAEQEVENLSGLSSNPDKNIFAIRENGTTCLMA  58
                     . : **:;;  .      ***********:**:;**.;:*** ******
```

LAMP HOMOLOGY DOMAIN

```
                                 2
SEQIDNO:93   EFAAKFIVPYDVWASNYVDLITEQADIALTRGAEVKGRCGHSQSELQVFWVDRAYALKML  120
SEQIDNO:94   EFAAKFIVPYDVWASNYVDLITEQADIALTRGAEVKGRCGHSESELQVFWVDRAYALKML  120
SEQIDNO:95   EFAAKFIVPYDVWASNYVDLITEQADIALTRGAEVKGRCGHSESELQVFWVDRAYALKML  120
SEQIDNO:96   EFAAKFIVPYDVWASNYVDLITEQADISLTRGAEVKGHCGHNESELQVFWVDRAYALKML  120
SEQIDNO:97   EFAAKFIVPYDVWASNYVDLITEQADISLTRGAEVKGHCGHDESELQVFWVDRAYALKML  120
SEQIDNO:98   EFAAKFIVPYDVWASNYVDLITEQAEISLTRGAEVKGHCGHNESELEVFWVDHAYTLRML  120
SEQIDNO:99   EFAAKFIVPYDVWASNYVDLITEQAEISLTRGAEVKGRCGHNESELQVFWVDRAYTLKML  120
SEQIDNO:100  EFAAKFVVPYDVWASNYVDLITEQADIPLSRGAEMKGKCGTNESELEISWLERAYTLKLF  112
SEQIDNO:101  EFSARILVPYEVPSSNEVDWDLEEASIQLPRDTEIRGKCWNNESELHLSWLDKAYTLKLF  118
             **:*:;;:***;* ;** **    *;*.*  *  *.;*;;*;*  .;***.:  *;::**:*:::
```

LAMP HOMOLOGY DOMAIN

```
SEQIDNO:93   FVK--------------------------ESHNMSKGPEATWRLSKVQFVYDSSEKTHF  153
SEQIDNO:94   FVK--------------------------ESHNMSKGPEATWRLSKVQFVYDSSEKTHF  153
SEQIDNO:95   FVK--------------------------ESHNTSKGPEATWRLSKVQFVYDSSEKTHF  153
SEQIDNO:96   FVK--------------------------ESRNASKGPEATWRLSKVQFVYDSSEKTHF  153
SEQIDNO:97   FLK--------------------------ESHNTPKGPEATWKLSKVQFVYDSSEKTHF  153
SEQIDNO:98   FVK--------------------------ESHNTSKGPEATWNLNKVHFVYDSSEKTHF  153
SEQIDNO:99   FVK--------------------------ESHNTSKGLEATWKLSKVQFVYDSSEKTHF  153
SEQIDNO:100  FLKVRGCPRRLGRGRCAAALPGFDQPCPPQEGHNTSRGPEAFWRLSRIQFSYDTSERTYF  172
SEQIDNO:101  FSK--------------------------EGQDA---SKSRSWKMSKIQFLYDPSEHTIF  149
             * *                           *.;;   . , *.;.;;:* ** **;* *
```

FIGURE 10 (cont.)

```
                                   LAMP HOMOLOGY DOMAIN
                                       3
SEQIDNO:93    KDAVSAGKHTANSHHLSALVTPAGKSYECQAQQTISLASSDPQKTVTMILSAVHIQPFDI 213
SEQIDNO:94    KDAVSAGKHTANSHHLSALVTPAGKSYECQAQQTISLASSDLQKTVTMILSAVHIQPFDI 213
SEQIDNO:95    KDAVSAGKHTANSHHLSALVTPAGKSYECQAQQTISLASSDPQKMVTMILSAVHIQPFDI 213
SEQIDNO:96    KDAVSAGKHTANSHRLSALVTPAGKSYECQAQQSISLASSDPQKTVTMILSAVHIQPFDI 213
SEQIDNO:97    KDAVSAGKHTANSHHLSALVTPAGKSYECQAQQTISLASSDPQKTVTMILSAVHIQPFDI 213
SEQIDNO:98    KAPVKVNKYIASSHHLSALVTPAGMSYECQAQQTISLASSDPQKTVTMILSAVHIQPFDI 213
SEQIDNO:99    KDAVSAGKHTANSHHLSALVTPAGMSYECQAQQTISLASSDPQKTVTMILSAVHIQPFDI 213
SEQIDNO:100   KDAVSPGKHTASSHRLSALVTPAGKSYECQAQQTISLISSDHQKSVQLLLSEVRIQPFDI 232
SEQIDNO:101   KSGARPGRHTANSHHLSLMVTPAGMSYECEATQRISLTSTDHQKIVVLYLSEVHLQPFDI 209
                *  .  .:: *,**;** ;***** ****;* * *** *;* ** * ; ** *;;*****

Trans. Domain        Cyto Tail
                                 4
SEQIDNO:93    ISDFVFSEEHKCPVDEREQLEETLPLILGLILGLVIMVTLAIYHVHHKMTANQVQIPRDR 273
SEQIDNO:94    ISDFVFSEEHKCPVDEREQLEETLPLILGLILGLVIMVTLAIYHVHHKMTANQVQIPRDR 273
SEQIDNO:95    ISDFVFSEEHKCPVDEREQLEETLPLILGLILGLVIVVTLTIYHVHHKMTANQVQIPRDR 273
SEQIDNO:96    ISDFVFSEEHKCPVDEREQLEETLPLILGLILGLVIVVTLAIYHIHHKMTANQVQIPRDR 273
SEQIDNO:97    ISDFVFSEEHKCPVDEREQLEETLPLILGLILGLVIVVTLVIYHIHHKMTANQVQIPRDR 273
SEQIDNO:98    ISDFVFSEEHKCPVDEQEQLEETLPLILGLILGLVIVITLVIYHIHHKMTANQVQIPRDR 273
SEQIDNO:99    ISDFVFSEEHKCPVDEREQLEETLPLILGLILGLVIVITLVIYHIHHKMTANQVQIPRDR 273
SEQIDNO:100   TADFVFSEEHKCPVDQREQLEETLPLILGLILGLVIVITLCVYHIHHKLTANQVQIPRDR 292
SEQIDNO:101   KSDFVYSEEYKCFTDQRKQLEETLPLILGLTLGVAILIIVAVYHIHHKMTANQVQIPRDR 269
                 ;***;***,***.*;;;********** **;,*;; ; ;**;***;**********

SEQIDNO:93    SQYKHMG 280
SEQIDNO:94    SQYKHMG 280
SEQIDNO:95    SQYKHMG 280
SEQIDNO:96    SQYKHMG 280
SEQIDNO:97    SQYKHMG 280
SEQIDNO:98    SQYKHMG 280
SEQIDNO:99    SQYKHMG 280
SEQIDNO:100   SQYKHMG 299
SEQIDNO:101   SLYKHMG 276
                *  *****
```

| LAMP5 | | | | | |
|---|---|---|---|---|---|
| Accession No. | *Species* | SEQ ID NO: | Accession No. | *Species* | SEQ ID NO: |
| NP_036393.1 | *H. sapiens* | 93 | NP_001076887.1 | *B. taurus* | 97 |
| XP_514512.3 | *P. troglodytes* | 94 | NP_083806.2 | *M. musculus* | 98 |
| NP_001181627.1 | *M. mulatta* | 95 | NP_001014205.1 | *R. norvegicus* | 99 |
| XP_850634.1 | *C. lupus familiaris* | 96 | XP_004935300.1 | *G. gallus* | 100 |
| | | | NP_001090781.1 | *X. tropicalis* | 101 |

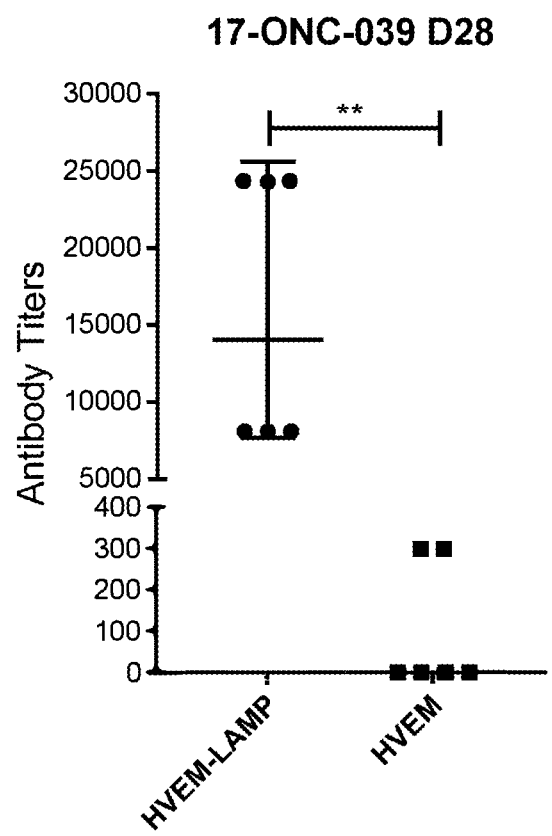
Figure 11    HVEM specific IgG antibody (day 28)

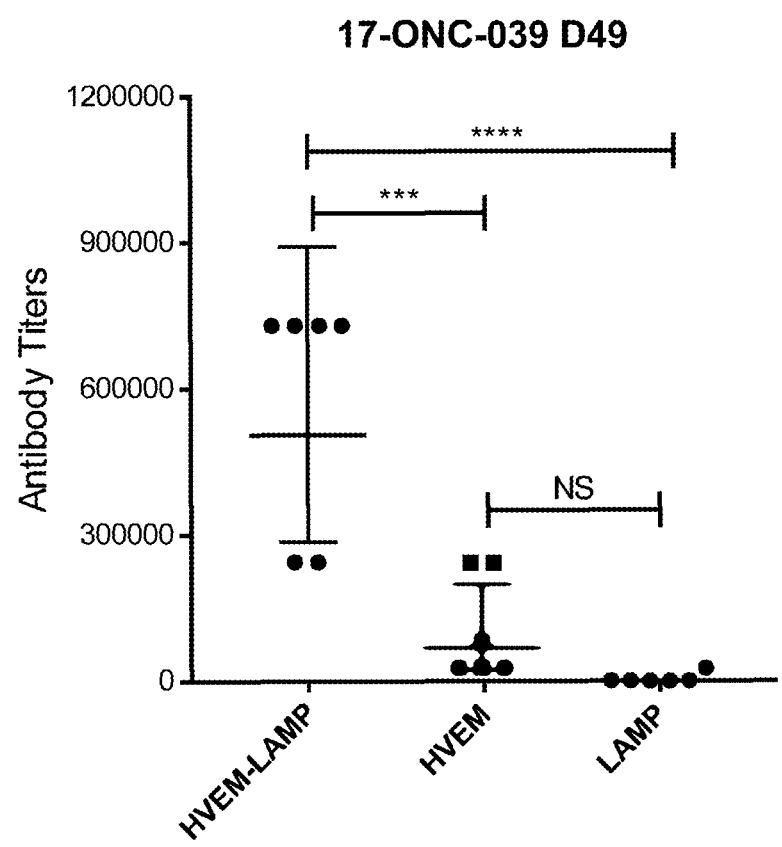
Figure 12    HVEM specific IgG antibody (day 49)

Figure 19

Survivin – Example of a Complete LAMP Construct (SEQ ID NO:115)

maprsarrplllllllllllglmhcasaaMFMVKNGNGTACIMANFSAAFSVNYDTKSGPKNMTLDLPSDATVVLNRSSCGKENTSDP
SLVIAFGRGHTLTLNFTRNATRYSVQLMSFVYNLSDTHLFPNASSKEIKTVESITDIRADIDKKYRCVSGTQVHMNNVTVTLH
DATIQAYLSNSSFSRGETRCEQDRPSPTTAPPAPPSPSPSPVPKSPSVDKYNVSGTNGTCLLASMGLQLNLTYERKDNTTVTR
LLNINPNKTSASGSCGAHLVTLELHSEGTTVLLFQFGMNASSSRFFLQGIQLNTILPDARDPAFKAANGSLRALQATVGNSYK
CNAEEHVRVTKAFSVNIFKVWVQAFKVEGGQFGSVEECLLDENSLEMGAPTLPPAWQPFLKDHRISTFKNWPFLEGCAC
TPERMAEAGFIHCPTENEPDLAQCFFCFKELEGWEPDDDPIEEHKKHSSGCAFLSVKKQFEELTLGEFLKLDRERAKNKIA
KETNNKKKEFEETAKKVRRAIEQLAAMDEFTLIPIAVGGALAGLVLIVLIAYLVGRKRSHAGYQTI

Survivin – Example of a ILC-1 Construct (SEQ ID NO:116)

maprsarrplllllllllllglmhcasaMGAPTLPPAWQPFLKDHRISTFKNWPFLEGCACTPERMAEAGFIHCPTENEPDLAQCFFC
FKELEGWEPDDDPIEEHKKHSSGCAFLSVKKQFEELTLGEFLKLDRERAKNKIAKETNNKKKEFEETAKKVRRAIEQLAAM
DAMFMVKNGNGTACIMANFSAAFSVNYDTKSGPKNMTLDLPSDATVVLNRSSCGKENTSDPSLVIAFGRGHTLTLNFTRN
ATRYSVQLMSFVYNLSDTHLFPNASSKEIKTVESITDIRADIDKKYRCVSGTQVHMNNVTVTLHDATIQAYLSNSSFSRGETR
CEQDRPSPTTAPPAPPSPSPSPVPKSPSVDKYNVSGTNGTCLLASMGLQLNLTYERKDNTTVTRLLNINPNKTSASGSCGAH
LVTLELHSEGTTVLLFQFGMNASSSRFFLQGIQLNTILPDARDPAFKAANGSLRALQATVGNSYKCNAEEHVRVTKAFSVNIF
KVWVQAFKVEGGQFGSVEECLLDENSMLIPIAVGGALAGLVLIVLIAYLVGRKRSHAGYQTI

Survivin – Example of a ILC-2 Construct (SEQ ID NO:117)

maprsarrplllllllllllglmhcasaMGAPTLPPAWQPFLKDHRISTFKNWPFLEGCACTPERMAEAGFIHCPTENEPDLAQCFFCF
KELEGWEPDDDPIEEHKKHSSGCAFLSVKKQFEELTLGEFLKLDRERAKNKIAKETNNKKKEFEETAKKVRRAIEQLAAMDA
MFMVKNGNGTACIMANFSAAFSVNYDTKSGPKNMTLDLPSDATVVLNRSSCGKENTSDPSLVIAFGRGHTLTLNFTRNAT
RYSVQLMSFVYNLSDTHLFPNASSKEIKTVESITDIRADIDKKYRCVSGTQVHMNNVTVTLHDATIQAYLSNSSFSRGETRCE
QDLIPIAVGGALAGLVLIVLIAYLVGRKRSHAGYQTI

Survivin – Example of a ILC-3 Construct (SEQ ID NO:118)

maprsarrplllllllllllglmhcasaAMFMVKNGNGTACIMANFSAAFSVNYDTKSGPKNMTLDLPSDATVVLNRSSCGKENTSDP
SLVIAFGRGHTLTLNFTRNATRYSVQLMSFVYNLSDTHLFPNASSKEIKTVESITDIRADIDKKYRCVSGTQVHMNNVTVTLH
DATIQAYLSNSSFSRGETRCEQDLEMGAPTLPPAWQPFLKDHRISTFKNWPFLEGCACTPERMAEAGFIHCPTENEPDLAQ
CFFCFKELEGWEPDDDPIEEHKKHSSGCAFLSVKKQFEELTLGEFLKLDRERAKNKIAKETNNKKKEFEETAKKVRRAIEQLAA
MDEFTLIPIAVGGALAGLVLIVLIAYLVGRKRSHAGYQTI

Survivin – Example of a ILC-4 Construct (SEQ ID NO:119)

maprsarrplllllllllllglmhcasaAMFMVKNGNGTACIMANFSAAFSVNYDTKSGPKNMTLDLPSDATVVLNRSSCGKENTSDP
SLVIAFGRGHTLTLNFTRNATRYSVQLMSFVYNLSDTHLFPNASSKEIKTVESITDIRADIDKKYRCVSGTQVHMNNVTVTLH
DATIQAYLSNSSFSRGETRCEQDLEMGAPTLPPAWQPFLKDHRISTFKNWPFLEGCACTPERMAEAGFIHCPTENEPDLA
QCFFCFKELEGWEPDDDPIEEHKKHSSGCAFLSVKKQFEELTLGEFLKLDRERAKNKIAKETNNKKKEFEETAKKVRRAIEQ
LAAMDEFTCLLASMGLQLNLTYERKDNTTVTRLLNINPNKTSASGSCGAHLVTLELHSEGTTVLLFQFGMNASSSRFFLQG
IQLNTILPDARDPAFKAANGSLRALQATVGNSYKCNAEEHVRVTKAFSVNIFKVWVQAFKVEGGQFGSVEECLLDENSM
LIPIAVGGALAGLVLIVLIAYLVGRKRSHAGYQTI

```
                           SEQUENCE LISTING

Sequence total quantity: 119
SEQ ID NO: 1              moltype = AA  length = 417
FEATURE                   Location/Qualifiers
source                    1..417
                          mol_type = protein
                          organism = Homo sapiens
SEQUENCE: 1
MAAPGSARRP LLLLLLLLLL GLMHCASAAM FMVKNGNGTA CIMANFSAAF SVNYDTKSGP    60
KNMTFDLPSD ATVVLNRSSC GKENTSDPSL VIAFGRGHTL TLNFTRNATR YSVQLMSFVY   120
NLSDTHLFPN ASSKEIKTVE SITDIRADID KKYRCVSGTQ VHMNNVTVTL HDATIQAYLS   180
NSSFSRGETR CEQDRPSPTT APPAPPSPSP SPVPKSPSVD KYNVSGTNGT CLLASMGLQL   240
NLTYERKDNT TVTRLLNINP NKTSASGSCG AHLVTLELHS EGTTVLLFQF GMNASSSRFF   300
LQGIQLNTIL PDARDPAFKA ANGSLRALQA TVGNSYKCNA EEHVRVTKAF SVNIFKVWVQ   360
AFKVEGGQFG SVEECLLDEN SMLIPIAVGG ALAGLVLIVL IAYLVGRKRS HAGYQTI     417

SEQ ID NO: 2              moltype = AA  length = 410
FEATURE                   Location/Qualifiers
source                    1..410
                          mol_type = protein
                          organism = Homo sapiens
SEQUENCE: 2
MVCFRLFPVP GSGLVLVCLV LGAVRSYALE LNLTDSENAT CLYAKWQMNF TVRYETTNKT    60
YKTVTISDHG TVTYNGSICG DDQNGPKIAV QFGPGFSWIA NFTKAASTYS IDSVSFSYNT   120
GDNTTFPDAE DKGILTVDEL LAIRIPLNDL FRCNSLSTLE KNDVVQHYWD VLVQAFVQNG   180
TVSTNEFLCD KDKTSTVAPT IHTTVPSPTT TPTPKEKPEA GTYSVNNGND TCLLATMGLQ   240
LNITQDKVAS VININPNTTH STGSCRSHTA LLRLNSSTIK YLDFVFAVKN ENRFYLKEVN   300
ISMYLVNGSV FSIANNNLSY WDAPLGSSYM CNKEQTVSVS GAFQINTFDL RVQPFNVTQG   360
KYSTAQDCSA DDDNFLVPIA VGAALAGVLI LVLLAYFIGL KHHHAGYEQF             410

SEQ ID NO: 3              moltype = AA  length = 416
FEATURE                   Location/Qualifiers
source                    1..416
                          mol_type = protein
                          organism = Homo sapiens
SEQUENCE: 3
MPRQLSAAAA LFASLAVILH DGSQMRAKAF PETRDYSQPT AAATVQDIKK PVQQPAKQAP    60
HQTLAARFMD GHITFQTAAT VKIPTTTPAT TKNTATTSPI TYTLVTTQAT PNNSHTAPPV   120
TEVTVGPSLA PYSLPPTITP PAHTTGTSSS TVSHTTGNTT QPSNQTTLPA TLSIALHKST   180
TGQKPVQPTH APGTTAAAHN TTRTAAPAST VPGPTLAPQP SSVKTGIYQV LNGSRLCIKA   240
EMGIQLIVQD KESVFSPRRY FNIDPNATQA SGNCGTRKSN LLLNFQGGFV NLTFTKDEES   300
YYISEVGAYL TVSDPETIYQ GIKHAVVMFQ TAVGHSFKCV SEQSLQLSAH LQVKTTDVQL   360
QAFDFEDDHF GNVDECSSDY TIVLPVIGAI VVGLCLMGMG VYKIRLRCQS SGYQRI       416

SEQ ID NO: 4              moltype = AA  length = 478
FEATURE                   Location/Qualifiers
source                    1..478
                          mol_type = protein
                          organism = Homo sapiens
SEQUENCE: 4
MGRCCFYTAG TLSLLLLVTS VTLLVARVFQ KAVDQSIEKK IVLRNGTEAF DSWEKPPLPV    60
YTQFYFFNVT NPEEILRGET PRVEEVGPYT YRELRNKANI QFGDNGTTIS AVSNKAYVFE   120
```

```
RDQSVGDPKI DLIRTLNIPV LTVIEWSQVH FLREIIEAML KAYQQKLFVT HTVDELLWGY    180
KDEILSLIHV FRPDISPYFG LFYEKNGTND GDYVFLTGED SYLNFTKIVE WNGKTSLDWW    240
ITDKCNMING TDGDSFHPLI TKDEVLYVFP SDFCRSVYIT FSDYESVQGL PAFRYKVPAE    300
ILANTSDNAG FCIPEGNCLG SGVLNVSICK NGAPIIMSFP HFYQADERFV SAIEGMHPNQ    360
EDHETFVDIN PLTGIILKAA KRFQINIYVK KLDDFVETGD IRTMVFPVMY LNESVHIDKE    420
TASRLKSMIN TTLIITNIPY IIMALGVFFG LVFTWLACKG QGSMDEGTAD ERAPLIRT     478

SEQ ID NO: 5               moltype = AA   length = 197
FEATURE                    Location/Qualifiers
source                     1..197
                           mol_type = protein
                           organism = Homo sapiens
SEQUENCE: 5
MSRLSRSLLW AATCLGVLCV LSADKNTTQH PNVTTLAPIS NVTSAPVTSL PLVTTPAPET     60
CEGRNSCVSC FNVSVVNTTC FWIECKDESY CSHNSTVSDC QVGNTTDFCS VSTATPVPTA    120
NSTAKPTVQP SPSTTSKTVT TSGTTNNTVT PTSQPVRKST FDAASFIGGI VLVLGVQAVI    180
FFLYKFCKSK ERNYHTL                                                   197

SEQ ID NO: 6               moltype = AA   length = 406
FEATURE                    Location/Qualifiers
source                     1..406
                           mol_type = protein
                           organism = Mus musculus
SEQUENCE: 6
MAAPGARRPL LLLLLAGLAH GASALFEVKN NGTTCIMASF SASFLTTYET ANGSQIVNIS     60
LPASAEVLKN GSSCGKENVS DPSLTITFGR GYLLTLNFTK NTTRYSVQHM YFTYNLSDTE    120
HFPNAISKEI YTMDSTTDIK ADINKAYRCV SDIRVYMKNV TVVLRDATIQ AYLSSGNFSK    180
EETHCTQDGP SPTTGPPSPS PPLVPTNPTV SKYNVTGNNG TCLLASMALQ LNITYLKKDN    240
KTVTRAFNIS PNDTSSGSCG INLVTLKVEN KNRALELQFG MNASSSLFFL QGVRLNMTLP    300
DALVPTFSIS NHSLKALQAT VGNSYKCNTE EHIFVSKMLS LNVFSVQVQA FKVDSDRFGS    360
VEECVQDGNN MLIPIAVGGA LAGLVLIVLI AYLIGRKRSH AGYQTI                   406

SEQ ID NO: 7               moltype = AA   length = 411
FEATURE                    Location/Qualifiers
source                     1..411
                           mol_type = protein
                           organism = Danio rerio
SEQUENCE: 7
MARAAGVCWT LLMGCVFAAH AVTFEVTDGN STCIKGELNA SFSISYNTTN GTSVSVFALP     60
ASASVSERSS CGSAAVPPEL ALVFGDTHTH TLSLLFSRDQ RLYRVSNISL QYNLSDGDIF    120
PQSSSAGVQS VMASVSELMS ARLNSTYRCV SSSSISLSAA VNLTLSGVQM EAYMSSANLS    180
ADESVCSADQ PSTTVAPPPS TTTSPPPIPP VPERGNYSVT DGNGTVCVLA LMGLQLNITH    240
TTTQNQSVSE LMNLQPNQTT VSGSCGVTES SLRLSDETTN LTFSFTMNST TQKYYLSAVS    300
VSALWPDMSV VFEAGNTSLS ALQCSVGRSY VCSAQQMLSV TPVFSINTFR LQLQPFNITA    360
NRFSTAEECR VDQENMLIPI IVGAALAGLV LIVLVAYLIG RKRTHAGYQT I             411

SEQ ID NO: 8               moltype = AA   length = 417
FEATURE                    Location/Qualifiers
source                     1..417
                           mol_type = protein
                           organism = Xenopus laevis
SEQUENCE: 8
MSWRQVKMPV YWMAVMLLIG VVQVATAVQF EVKDGKTNIT CILADLSINF SVSYNVSSKM     60
ELATFVLPSE AVTNINKSSC GVENTTAPVL AIQFGSNHSL SIHFARNNTR YEVAELVMSY    120
NLSDKIIFPN ASENGTKTVS TNKTAVLAEN DTVYKCMNPH LIRMDNANAT FHDIRLEAYL    180
KQSNFSQKVS TCSEDITPTS APAPVTTTAP VPAPVPDPPV VQYSVNRSSE PCLLAKVGLQ    240
MNITYTTKDG KNGSYVFNIE SKGVTVDGNC TNTTAYLSLS TGSIDLRFNF TLNSSLEVFY    300
LDGVSLSTGL PADANDTHFE AANSSLNYMQ TNVHKSFKCN SKQTLQITDP FTVNTYHLQV    360
QAFNSDNTFA SAVECSLDEN GMLVPIVVGA ALAGLVLIVL IAYLIGRKRS HAGYQTI       417

SEQ ID NO: 9               moltype = AA   length = 417
FEATURE                    Location/Qualifiers
source                     1..417
                           mol_type = protein
                           organism = Pan troglodytes
SEQUENCE: 9
MAAPGSARRP LLLLLLLLLL GLVHCASAAM FMVKNGNGTA CIMANFSASF SVNYDTKSGP     60
KNMTFDLPSD ATVVLNRSSC GKENTSDPSL VIAFGRGHTL TLNFTRNATR YSVQLMSFVY    120
NLSDTHLFPN ASSKEIKTVE SITDIRADID KKYRCVSGTQ VHMNNVVTTL HDATIQAYLS    180
NSSFSRGETR CEQDRPSPTT APPAPPSPSP SPVPESPSVD KYNVSGTNGT CLLASMGLQL    240
NLTYERKDNT TVTRLLNINP NKTSASGSCG AHLVTLELHS EGSTVLLFLF GMNASSSRFF    300
LQGIQLNTTL PDARDPAFKA ANGSLRALQA TVGNSYKCNA EEHVRVTKAF SVNIFKVWVQ    360
AFKVEGGQFG SVEECVLDEN NMLIPIAVGG ALAGLVLIVL IAYLVGRKRS HAGYQTI       417

SEQ ID NO: 10              moltype = AA   length = 415
FEATURE                    Location/Qualifiers
source                     1..415
                           mol_type = protein
                           organism = Macaca mulatta
```

```
SEQUENCE: 10
MAAPGSARRS LLLLLLLLLG LTHCASAAMF IVKNGNGTAC IMANFSAAFS VNYDTKSGPK    60
NMTFDLPSDA KVVLNSSSCG KENTSDPSLV IAFGRGQTLT LNFTRNATRY SVQLMSFVYN   120
LSDTHLFPNA SSKEIKTVES ITDIRADIDK KYRCVSGTQV HMNNVTVTLH DATIQAYLSN   180
SSFSREETRC EQDRPSPTTA PPAPPSPSPS PVPESPSVDK YNVSGTNGTC LLASMGLQLN   240
LTYERKDNTT VTRLLNINPN KTLASGSCGA HLVTLELHSE GSTVLLFQFG MNASSSRFFL   300
QGIQLNTTLP DARDPAFKAA NSSLRALQAT VGNSYKCNAE EHVRVTKAFS VNIFKVWVQA   360
FKVEGGQFGS VEECLLDENN MLIPIAVGGA LAGLVLIVLI AYLVGRKRSH AGYQT        415

SEQ ID NO: 11           moltype = AA   length = 413
FEATURE                 Location/Qualifiers
source                  1..413
                        mol_type = protein
                        organism = Canis lupus
SEQUENCE: 11
MAAFGGARPR PLLLLLLAGL VHGAAAVFVV KDANGTACIM ANFSAAFLAS YETRSGPKNV    60
TFDLPSDAVV LNSSSCGKEN TSDPSLMIAF GKGHGLTLNF TRNATRYSVQ LMSFIYNLSD   120
TQIFPNASSK ETKTVESATD IRADINKKYR CVSNTQIHMH NVTVTFHDVT IQAYLANSNF   180
SKEETRCEQD GPFPTTAPPP PPHPSPSPAP ESPSVHKYNV SGANGTCLLA SMGLQLNVTY   240
KKKDNTTVVK VVSINPNKTT AGGSCGAQLV TLELRSESVT LLAFQFGMNA STSRFFLQGI   300
QLNMTLPDAR DPTFKAGNNS LRALQATIGN SYKCNAGEHV QVTEAFSVNI IKVWVQAFQV   360
QGDKFGSVEE CQLDENSMLI PIAVGGALAG LVLIVLIAYL IGRKRSHAGY QTI          413

SEQ ID NO: 12           moltype = AA   length = 417
FEATURE                 Location/Qualifiers
source                  1..417
                        mol_type = protein
                        organism = Oryctolagus cuniculus
SEQUENCE: 12
MEAPGGARRP LLLLLLLGLV HGASAVFVVR NSNGTACIMA NFSAVFSVIY ESKSGYKNAS    60
FELPATAEVQ NTSSCGRENT SNPSLQIAFG RGHVLALNFT RNATLYSVPL LSFVYNLSDS   120
DLFPNASSKD IKTVGSTTDI KADIDKRYRC VSDSKVPMGN VTVTLQDATI QAYLWNNSFS   180
QAESRCRQDM PSPTTAPPAP PVPPSPPSPS PPPKPESPSV SRYNVSDGNA TCLLASMGLQ   240
LNLTYVHRDN ATVTRVFNIN PNKTKPSGHC GAQQVTLELQ SERSTVLVFQ FGMNASSGQY   300
FLQGVLLNTT LPDAREPAFS ASNSSLRALQ ATLGNSYKCN SEEHVRVTPA FSLSIFKVWV   360
QAFQVKGDKF GSVEECLLDQ DSMLIPIAVG GALAGLVLVV LIAYLIGRKR SHAGYQT      417

SEQ ID NO: 13           moltype = AA   length = 409
FEATURE                 Location/Qualifiers
source                  1..409
                        mol_type = protein
                        organism = Bos taurus
SEQUENCE: 13
MAAPGGARRR PLLLLLLFAGL VHGASAVFVV KNGNGTACIM ADFSATFLTS YDTRSGPQNK   60
SFELPAGAEV SNSSSCGKEN ASDSSLVITF GRGHTLTLIF TRNATRYEVQ LMRFAYNLSD   120
TDTFPNSSST GVKTVESATD IKADINKTYR CVSETQVNMD NVTVTLRDAA IQAYLSSSNF   180
SREETRCEQD LPTPTPPPQP APTPAPASPA VFRYNVSGSN GTCLLASMGL QLNVTYREFN   240
NKTVTREFNV NPNKTTFGGN CSATLATLEL HSENLLLLAL QFVMNESSSR VFLQGVQLNL   300
TLPDAKEGSF TATNSSLRAL QATAGNSYKC NAEQRLRVTS SFSLNMFRVW LQAFRVDGDK   360
FGPVEECQLD ENSMLIPIAV GGALAGLVLI VLLAYLIGRK RSHAGYQTI               409

SEQ ID NO: 14           moltype = AA   length = 407
FEATURE                 Location/Qualifiers
source                  1..407
                        mol_type = protein
                        organism = Rattus norvegicus
SEQUENCE: 14
MAAPGARRPL LLLLLAGLAH SAPALFEVKD NNGTACIMAS FSASFLTTYD AGHVSKVSNM    60
TLPASAEVLK NSSSCGEKNA SEPTLAITFG EGYLLKLTFT KNTTRYSVQH MYFTYNLSDT   120
QFFPNASSKG PDTVDSTTDI KADINKTYRC VSDIRVYMKN VTIVLWDATI QAYLPSSNFS   180
KEETRCPQDQ PSPTTGPPSP SPPLVPTNPS VSKYNVTGDN GTCLLASMAL QLNITYMKKD   240
NTTVTRAFNI NPSDKYSGTC GAQLVTLKVG NKSRVLELQF GMNATSSLFF LQGVQLNMTL   300
PDAIEPTFST SNYSLKALQA SVGNSYKCNS EEHIFVSKAL ALNVFSVQVQ AFRVESDRFG   360
SVEECVQDGN NMLIPIAVGG ALAGLVLIVL IAYLIGRKRS HAGYQTI                 407

SEQ ID NO: 15           moltype = AA   length = 414
FEATURE                 Location/Qualifiers
source                  1..414
                        mol_type = protein
                        organism = Gallus gallus
SEQUENCE: 15
MGGAARAVLL GFLQASSSFD VRDSTGKVCI IANLTVAFSV EYKSSGQKQF AHFFLPQNAT    60
SQSHSSCGEG NTSHPILALS FGAGHLISLN FSKTLDKYQV EELTFHYNLS DETLFPNATE   120
GKVMVATQKS VIQARIGTEY RCINSKYVRM KHVNITFSNV TLEAYPTNDT FSANKTECRE   180
DMVSTTTVAP TTPKHATSQV PTTSPAPTAA PSSPAVGKYN VTGANGTCVL ASMGLQLNIT   240
YVKKDEKMGL DLLNFIPHNT SASGMCESTS AFLNLAFEKT KITFHFVLNA SSEKFFLQGV   300
NVSTTLPSEA KAPTFEASND SMSESRATVG NSYKCSAEEN FQVTDKALVN VFNVQVQAFK   360
VDGDKFGAME ECQLDENNML IPIIVGAALA GLVLIVLIAY LIGRKRSHAG YQTI         414
```

```
SEQ ID NO: 16               moltype = AA  length = 413
FEATURE                     Location/Qualifiers
source                      1..413
                            mol_type = protein
                            organism = Sus scrofa
SEQUENCE: 16
MAAPGGAWRR PLLLLLLLLG LARGASAVFV VSDGNGTACI MADFAAAFEI SYDSRSGAKN    60
TTFSLPASAQ VLNSSSCGKE NTSDSSLVIA FGRGHTLTLS FTRNATRYSV QLMTLVYNLS   120
DAEFFPSASS KGTKTVAAST DIRADLNTKY RCVSNSQVHL LNVTVTLGNA TIQAYLANNS   180
FSQQETRCEQ DKPSPPTPTA PPTPTPTPAP TSPVVSRYNV SGANGTCLLA SMGLQLNVTY   240
RTKDNTTVTR GLNINPNKTT FGGSCSAQLV TLELQGESLR LLALQFALNT SSSRVFLQGV   300
QLNMTLPDAR DPSFSAANSS LRALQATAGN SYKCRSEQRL QVTEAFALNV FQVRVQAFRV   360
DGDKFGPAEE CQLDENSMLI PIAVGGALAG LVLVVLMAYL VGRKRSHAGY QTI          413

SEQ ID NO: 17               moltype = AA  length = 422
FEATURE                     Location/Qualifiers
source                      1..422
                            mol_type = protein
                            organism = Monodelphis domestica
SEQUENCE: 17
MAEPGGARTP QRLLLLLLGL IHVASSIFVV KNGTGTACIM ANFSATFSMN YTTKSGLEST    60
TFRLPQNASV MNSSSCGKEN TSNPILEIGF GGGHTLTMF SSTTQSYQVE LLSFSYNLSD   120
ATLFPNASKG SEESSVKSKT DIQADIHKKY RCVSSNRITM SNVTIVLSDV TIQAYLSNNT   180
FSKEETRCSQ DTPSPSPVPT THPTTIPVPT PTPTRPPTPA EIPPIFKYNV SDANGTCLLA   240
SMGLQLNITY AKKDNSSARI IWNINPNKTV AGGSCSPQVA ILELQTENST LAFSFGMNAT   300
TSKFFLREIR FHKFFPDAKD PAFGAVNSSL KELQATVGNS YKCNAEENVH VTDGFSVNIF   360
RVRVQAFKVE GDKFGSVEEC LLDENNMLIP IAVGGALAGL VLIVLIAYLI GRKRSHAGYQ   420
TI                                                                 422

SEQ ID NO: 18               moltype = AA  length = 415
FEATURE                     Location/Qualifiers
source                      1..415
                            mol_type = protein
                            organism = Meleagris gallopavo
SEQUENCE: 18
MARALLAAVL LGFLQASSSF DVRDSTGKVC IIANLTVAFS VEYKSNGQKQ FAHFFLPQNA    60
TSQSHSSCGE GNTSHPILAL SFGAGHLLSL NFSKTLDKYQ VEELTPHYNL SDETLFPNAS   120
EGKVMEVTQK SVIQARIGTE YRCINSKYIY IRHVNITFSN VTLEAYPTNG TFSTNKTECS   180
EDMVSTTTVA PTTPKHITSQ VPATSPAPTA APSNPAVGKY NVTGANGTCV LASMGLQLNI   240
TYLKKDGKTG LDLLNFVPHN TNASGTCENT SAFLNLAFEK TKITFHFVLN ASSEKFFLQG   300
VNVSTTLPSE AKAPMFEASN DSMSELRATV GNSYKCSAEE NLQVTDKALV NVFNVQQAF   360
KVDGDKFGAV EECQLDENNM LIPIIVGAAL AGLVLIVLIA YLIGRKRSHA GYQTI        415

SEQ ID NO: 19               moltype = AA  length = 415
FEATURE                     Location/Qualifiers
source                      1..415
                            mol_type = protein
                            organism = Taeniopygia guttata
SEQUENCE: 19
MARGLLAAAA LLGFLQASSS FEVKDSSGKV CILADLTVAF SVEYKTNVQK EFVHFFLPQN    60
ASVDSQSSCG KDNASHPILV LDFGGGHSLS LNFSESADKY QVEELVPHYN LSDATLFPNS   120
STGGMKTVSH KSIIQAHMGT QYRCINSKHI NMKNVNVTFS NVTLEAYLTN GTLSVNKTEC   180
AEDRVSTTTM VPTTPKQTTS QSPTTGPAPT SPPNPTVGKY NVTGPNGTCV LAYMGLQLNI   240
TYQQKDEKMG LDLLNFVPHN TTSSGRCDNT SALLNLTFEK TRVIFQFALN ATAEKFFLQG   300
VSVSTTLPSE AKNPKFEATN NSMSELRASV GNSYKCSSEE NLQVTDQALV NVFNVQVQIF   360
KIDGDKFGPV EECQLDENNM LIPIIVGAAL AGLVLIVLIA YLIGRKRSHA GYQTI        415

SEQ ID NO: 20               moltype = AA  length = 418
FEATURE                     Location/Qualifiers
source                      1..418
                            mol_type = protein
                            organism = Anolis carolinensis
SEQUENCE: 20
MVSSSSCRRG LLLAAVLLGF LQASSTFEVR DKTGKICILA NFSAEFTVDY STKAKVERKT    60
FQLPSSAHIN KESSSCGKEK ETSQVLVVEF GTGNSLTFTF EKSNDFYHVS NLTFSYNLSD   120
SSFFPNSSGG QREVSRAGDI QANINTTYRC RSNHRVNMTN VTVLFSNVTL EAYLPNNAFS   180
KNDSVCAEDK TSTVAPPITT HIPTTTSLAP PTPPPTDTPK IGRYNVTGLH GICLLATMGL   240
QVNVTYSTKN KTSKSELLNL PPTAEVSGTC ENSSITLNLT SESTSLSFQF SQNTSTEKYF   300
LQGIIVTANL PPEATEKNIS YSNHTLNALK TSVGKSYKCI AEEESIWISGK AAVNIFNIQL   360
QAFKIPGDKF GAVEECQLDE NNMLIPIIVG AALAGLVLIV LIAYLIGRKR SHAGYQTI     418

SEQ ID NO: 21               moltype = AA  length = 418
FEATURE                     Location/Qualifiers
source                      1..418
                            mol_type = protein
                            organism = Oryzias latipes
SEQUENCE: 21
MKSFPSFVAL FIVCSAVLAD TQAVVTLEVK EGNSTCIKAE FSAVFSITYN TTNDTRTVSV    60
FLPNSTTVDS ANSSCGSNGS TPGLMAKFGP GHYFGMNFST NGSLYSVDTL FLRYNLSDAS   120
```

```
LFPEANSSGP VDFELSASVG IWAPTNTTYR CLSPTTITIT RPSVTFSEMK LEAYMPGNDF   180
SPAERVCAAD QTTTGAPTTT TSAATPTTPS PTPAGTPEQG SYSVKNASGT VCLMAKMGVQ   240
LNVSYFSQSQ NKTVQELLNL TPNLTSSSGL CGGTNATLVL AQEETTVLSF LFTVNSTSNK   300
YHLSGITLQA NWTDMMSPFS ASNTSLDYLR SSLGHSYMCN AEQTLFVVST FSINMFELQV   360
QPFGVTSTQF ASAEVCQIDQ DQMLIPIIVG AALAGLVLIV LIAYLIGRKR SHAGYQTI    418

SEQ ID NO: 22          moltype = AA  length = 420
FEATURE                Location/Qualifiers
source                 1..420
                       mol_type = protein
                       organism = Takifugu rubripes
SEQUENCE: 22
MKRSHALVVL IIAWFSLSGC IQAVSLEVKE GNSTCIKANL SAYFSITYNT SSSTRTAQFI   60
LPDSATVDPD SSTCGGNGSS PWLVAVFGAG HALGLGFSTN GSFYSVANLT LQYNLSDASV  120
FPDANSSGVV TVVSSSVGIW AAVNTTYRCL SSVLFQVGGA TVTFSDMRLE AYMPGNDLSP  180
RESFCAADQT TTAPPTTTAA PTTTAATTMA PPAPTPPGTP VRGTYSVVNG NDTTCLLAQM  240
GLQLNVSYFS RSQNKTVQSL VNLTPNLTNS TGSCEKGSAT LILTQQTTIL IPTFSLNSTS  300
SKYHLSGLSL QANWSDMAAA FSASNASLSY LRSTFGHSYM CNAEQILAVT PVFSLNTFSL  360
QIQPFGVTTN QFAAAEECQM DQDQMLIPII VGASLAGLVL IVLIAYLIGR KKSHAGYQTI  420

SEQ ID NO: 23          moltype = AA  length = 419
FEATURE                Location/Qualifiers
source                 1..419
                       mol_type = protein
                       organism = Salmo salar
SEQUENCE: 23
MTRTCPFVVG IACFAILGCV TVVQSQVTLE VTEGNSTCIK AELSASFSIT YDTANGTRTV   60
MVPLPGSAVV GVASSCGGDG RSPWLVALFG DGHALGLGFS SNDSLYSVAK LTLQYNLSDV  120
SNFPEANSTD VVTVETTSVG MVARVNTTYR CISASPVIVG GATVTFSNVT MEAFMTGEDL  180
SPNESVCTAD QSFTTAPPPP PSTTTAAPAP VPTPPGTPSQ GSYSVSNSNG TVCLLARMAL  240
QLNISHFSAS QNKTIQEVVN LLPNQTTSSG SCDPTSATLV LTQANATNLS FLFTLNSTSN  300
RYHLTGLSVV AAWSDMTAPF NTSNSSLDYQ RGSLGRSYMC ISEQTLVVDQ NFSLNTFQLQ  360
VQPFGITRGQ FAQAEEECQLD QDNMLIPIVV GAALAGLVLI VLIAYLIGRK RSHAGYQTI  419

SEQ ID NO: 24          moltype = AA  length = 247
FEATURE                Location/Qualifiers
source                 1..247
                       mol_type = protein
                       organism = Oreochromis niloticus
SEQUENCE: 24
MVQICRVQSW FVGVTPLLIF ATVLHQGFAT VAPPTPAPHK EPGRPERGYY NVTNHNGTIC   60
LMAYMGLQLN ISYNSTSQKK VVQDVMNLQP NLTKHSGLCD SDIASLNLTV DAVKTNLTFV  120
FTMNSTSNKY HLSEVTVSAA WPEMKEPVSV HNSSLDYLRG TVGYSYFCRD EQTLNVAQNL  180
SINTFQLQVQ PFAVKGDQFG AAEECQLDED DMLIPIVVGA ALAGLVVIVL LAYLIGRKRS  240
HAGYQSI                                                            247

SEQ ID NO: 25          moltype = AA  length = 415
FEATURE                Location/Qualifiers
source                 1..415
                       mol_type = protein
                       organism = Mus musculus
SEQUENCE: 25
MCLSPVKGAK LILIFLFLGA VQSNALIVNL TDSKGTCLYA EWEMNFTITY ETTNQTNKTI   60
TIAVPDKATH DGSSCGDDRN SAKIMIQFGF AVSWAVNFTK EASHYSIHDI VLSYNTSDST  120
VFPGKAKGV HTVKNPENFK VPLDVIFKCN SVLTYNLTPV VQKYWGIHLQ AFVQNGTVSK  180
NEQVCEEDQT PTTVAPIIHT TAPSTTTLT PTSTPTPTPT PTPTVGNYSI RNGNTTCLLA  240
TMGLQLNITE EKVPFIFNIN PATTNFTGSC QPQSAQLRLN NSQIKYLDFI FAVKNEKRFY  300
LKEVNVYMYL ANGSAFNISN KNLSFWDAPL GSSYMCNKEQ VLSVSRAFQI NTFNLKVQPF  360
NVTKGQYSTA QECSLDDDTI LIPIIVGAGL SGLIIVIVIA YLIGRRKTYA GYQTL       415

SEQ ID NO: 26          moltype = AA  length = 415
FEATURE                Location/Qualifiers
source                 1..415
                       mol_type = protein
                       organism = Xenopus laevis
SEQUENCE: 26
MGDTGAMERC ACPAAVLLLS LVLMGATAFE VEIKDDKNAT CIYAKLSVNI TVQYETDTSS   60
SKNITPVPS DVTTNGSSCG SDGKAPLLVI NFGNSQSWSN NPTRNNSTYS GSALIFTYNT  120
NDTILFPDAL RKGLISSTAM FLGPVPLNST YKCISREVVV SENVTQIIYD VKLEAFMANG  180
TLGKEIICDA DKPSPVPSPT QPSTTASTAI PAPTSKPLDK PTMGNYTVSD ASGICLLASM  240
GLQINTSLLS EGKNIWRPFN IDPLGIKTNG TCTNQTGTLI LTENRTIIEF TFALKNKNHF  300
YLEEVNITLI NGSAFSSRQN QNLSTWEASV DSSYMCHKEQ QIKVSEDLFI NAFDVRVQPF  360
GVNNGTFATA EDCFADQNFI VPIVVGAALG VLVVLVMVAY FIGRRKQSSA GYEQM       415

SEQ ID NO: 27          moltype = AA  length = 355
FEATURE                Location/Qualifiers
source                 1..355
                       mol_type = protein
                       organism = Danio rerio
```

```
SEQUENCE: 27
MAVRGFLPLL FILLSGIVHA DDMMTSPLPS TAELKTANLP LVIQTTSSTT STTTTSRPSS    60
TSTHSTLTTE PAAKTTTART TVTTSAPTST QSTSSSSTSA TVTTLAPTTT GHNTTNSTTE   120
PPTTTGHNTT NSTTDAPTTT HTNATVAPTP PPTTPSVPKP TVGNYSVKTD NVSDCLLAKM   180
GLQFSFKISG NASLQTVNLD PNVTKVNGTC GSGGSDSSLF LTSKDITVHF VFTNDSQKFR   240
LHALTLTVDL GNGNIFNDSN TNLSLWEASV GSSYMCRKEQ SYNISDKLTL NTFELQVPF    300
DVKKNSFSTA HECSLDDTSL LIPIIVGAAL AGLIFIVVIA YVIGRRRTYV GYQTL        355

SEQ ID NO: 28           moltype = AA   length = 411
FEATURE                 Location/Qualifiers
source                  1..411
                        mol_type = protein
                        organism = Papio anubis
SEQUENCE: 28
MVCFRLFPVP GSGLVLVCLV LGAVQSYALE LNLTDSGKAT CLYAKWQMNF TVRYETTNKT    60
YKTVTISDRG TVTYNGSICG DDQNGPKIAV QFGPGFSWIA NFSKAASTYS IDSISFSYNT   120
GDNTTFPDAE DKGIITVDEL LAIKIPLNDL FRCNSLSTLE KNDVVQNYWD VLVQAFVQNG   180
TVSTNEFLCD EDKTSTVAPT IHTTVPSPTT TPTPKEKPEA GTYSVNNGND TCLLATMGLQ   240
LNITQDKVAS VININPNTTH STGSCRSHTA LLRLNSSTIK YLDFVFAVKN ENRFYLKEVN   300
VSMYLVNGSV FSIANNNLSY WDAPLGSSYM CNKEQTVSVS GAFQINTFDL RVQPFNVTQG   360
KYSTAEECSA DSDLNFLIPV AVGVALGFLI IVVFISYMIG RRKSRTGYQS V            411

SEQ ID NO: 29           moltype = AA   length = 410
FEATURE                 Location/Qualifiers
source                  1..410
                        mol_type = protein
                        organism = Macaca mulatta
SEQUENCE: 29
MVCFRLFPVP GSGLVLVCLV LGAVQSYALE LNLTDSGKAT CLYAKWQMNF TVRYETTNKT    60
YKTVTISDRG TVTYNGSICG DDQNGPKIAV QFGPGFSWIA NFSKAASTYS IDSISFSYNT   120
GDNTTFPDAE DKGIITVDEL LAIKIPLNDL FRCNSLSTLE KNDVVQNYWD VLVQAFVQNG   180
TVSTNEFLCD EDKTSTVAPT IHTTVPSPTT TPTPKEKPEA GTYSVNNGNE TCLLATMGLQ   240
LNITQDKVAS VININPNTTH STGSCRSHTA LLRLNSSTIK YLDFVFAVKN ENRFYLKEVN   300
VSMYLVNGSV FSIANNNLSY WDAPLGSSYM CNKEQTVSVS GAFQINTFDL RVQPFNVTQG   360
KYSTAQDCSA DDDNFLVPIA VGAALAGVLI LVLLAYFIGL KRHHAGYEQF              410

SEQ ID NO: 30           moltype = AA   length = 364
FEATURE                 Location/Qualifiers
SITE                    200
                        note = Xaa can be any naturally occurring amino acid
source                  1..364
                        mol_type = protein
                        organism = Pan troglodytes
SEQUENCE: 30
MVCFRLFPVP GSGLVLVCLV LGAVRSHALE LNEADSAINC SKCKTVTISD HGTVTYNGSI    60
CGDDQNGPKI AVQFGPGFSW IANFTKAAST YSIDSISFSY NTGDNTTFPD AEDKGILTVD   120
ELLAIKIPLN DLFRCNSLST LEKNDVVQHY WDVLVQAFVQ NGTVSTNEFL CDKDKTSTVA   180
PTVHTTVPSP TTTPTRIPPX VASVININPN TTHSTGSCRS HTALLRLNSS TIKYLDFVFA   240
VKNENRFYLK EVNISMYLVN GSVFSIANNN LSYWDAPLGS SYMCNKEQTV SVSGAFQINT   300
FDLRVQPFNV TQGKYSTAEE CSADSDLNFL IPVAVGVALG FLIIVVFISY MIGRRKSRTG   360
YQSV                                                               364

SEQ ID NO: 31           moltype = AA   length = 411
FEATURE                 Location/Qualifiers
source                  1..411
                        mol_type = protein
                        organism = Canis lupus
SEQUENCE: 31
MVCFRLSPAP GSGLVLLCLV LGAVSSYALE VNVTDSEKAT CLYAKWQMNF TIQYNTTSKN    60
FKTATISDFS TATYNGSVCG NDQNNPKIVV QFGSGFSWIV NFTKKESAYL IDSISFSYNL   120
SDNATFPDAK EKGILTVHDL VGFRIPLNNI FRCNSLSTLE KNGVVQYYWD VHVQAFVQNG   180
TVSTKEFLCE KDKTSTTVVP TISTTTPSPT TTPTPKEKPE VGSYSVNNSN GTCLLATMGL   240
QLNITHNKVA SVININPNTT DFTGSCQPQT ALLRLNSSNI KYLDFVFAVK NENRFYLKEV   300
NVSMYLVNGS VFSIANNNLS YWDAPLGSSY MCNKEQTVSV SGAFQINTFD LRVQPFNVME   360
GKYSTAQECS LDDDTILIPI IVGAGLSGLI IVIVIAYLIG RRKSYAGYQT L            411

SEQ ID NO: 32           moltype = AA   length = 417
FEATURE                 Location/Qualifiers
source                  1..417
                        mol_type = protein
                        organism = Equus caballus
SEQUENCE: 32
MVCFRLSPVP GSGLVLLCLV LGAVSSYALE LNLTDSEKAL CLYAKWQMNF TIPYETTSKS    60
YKTVTISNFG TPTYNGSICG DNQNGSRIAV QFGSGFSWIV NFTKSVSVYS IDSISFSYNT   120
GDNTTFPDAK DKGILTVNES VAFKIPLNDI FRCNSLSSLV KNGVVQNYWD VHVQAFVQNG   180
TVSTNEYLCE KDNTTTVAP IVPTTVPSPT TTSSPTTTPS PKEKPDVGSY LVKNGSDTCL   240
LATMGLQLNV THDKVASVIN INPNVTGYSG SCHPQTALLR LNSSNIKYLD FVFAVKNENR   300
FYLKEVNVSM YLANGSVFSF ANNNLSYWDA PLGSSYMCNK EQTVSVSGEF QINTFDLRVQ   360
PFNVKDGKYS TAQDCRADDD NFLVPIAVGA ALAGVLILVL LAYFIGLKRH HAGYEQF      417
```

```
SEQ ID NO: 33             moltype = AA  length = 407
FEATURE                   Location/Qualifiers
source                    1..407
                          mol_type = protein
                          organism = Bos taurus
SEQUENCE: 33
MVCFRLAPVP GSGFLLLCLV LGAVSSYALE LNLTDSSNAT CLYAKWQMNF TIRYETTDKH   60
NKTVPISDLG AATYNGSFCG DDQNGPKIAV QFGSGFSWIV NFTKEAASPS TYLVDTISFS  120
YNTNDNKTFP DAKEKEVFTV NNRVALKIPL NDIFRCNSLS TLENRDVVQH YWDVHVQAFV  180
QNGTVSTTEF LCDKDKTVTT AVPIVPTTLP SPTKPVVGSY SVVNSNGTCL LATMGLQLNI  240
THDKVASVFN INPNTTNATG SCQPQTALLR LSSSNIKYLD FVFAVKNENR FYLKEVNVSM  300
ILVNGSVYSI SNTNLSYWDA PLGSSYMCNK EQTVSVSGAF QINTFDLRVQ PFSVTEGKYS  360
TAQECSLDDD TILIPIIVGA GLSGLIIVIV IAYLIGRRKS YAGYQTL                407

SEQ ID NO: 34             moltype = AA  length = 411
FEATURE                   Location/Qualifiers
source                    1..411
                          mol_type = protein
                          organism = Sus scrofa
SEQUENCE: 34
MVCFRLSPVP GSGLLMLCLV LGAVSSYALE LNLTNSEKAT CLYAKWQMNF TIRYETTNNS   60
HKTVSISDFG AATYNGSFCG DDHNDPQIVM QFGSGFSWIV NFAKESSSYL INSISFSYNT  120
SDTTTFPDAK KKGVLTVNDS VGFQVPLNDI FRCNSLSTLE KDNVVQHYWD VHVQAFVQNG  180
TVSTKEFLCD KDKTLTTTVP VIPTSVPSPT TTPTPKEKPE TGSYSVTSSN GTCLLANMGL  240
QLNITQDKVA SVININPNTT NATGNCHSKT ALLRLSGSNI KYLDFVFAVK NDNRFYLKEV  300
NVSVYLVNGS VFSIANNNLS YWDAPLGSSY MCNKEQTVSV SGAFQINTFN LRVQPFSVME  360
GKYSTAQDCS ADDDNFIVPI AVGAALAGVL ILVLLAYFIG LKRHHAGYEQ F           411

SEQ ID NO: 35             moltype = AA  length = 408
FEATURE                   Location/Qualifiers
source                    1..408
                          mol_type = protein
                          organism = Ovis aries
SEQUENCE: 35
MVCFRLAPVP GCGFLLFCLV LGTVSSYALE LNLTDSSKAT CLYAKWQMNF TIRYETTDKH   60
NKTVTISDFD AAAYNGSVCG DDQNGPKIAV QFGSGFSWIV NFTKEASSTS TYLVDSISFS  120
YNTNDNATFP DAKEKGVFTV NNRVALKIPL NDIFRCNSLS TLEKSDVVQH YWDVHVQAFV  180
QNGTVSTTEF LCDKDKTVTT AMPIVPTTAP SPTKPVVGSY SVVNSNGTCL LATMGLQLNI  240
THDKVASVFN INPNTTNATG SCQPQTALLR LSSSNIKYLD FVFAVKNENR FYLKEVNVSM  300
ILVNGSVYSI SNTNLSYWDA PLGSSYMCNK EQTVSVSGAL QINTFDLRVQ PFSVTEGKYS  360
TAEECSADSD LNFLIPVAVG VALGFLIIVV FISYMIGRRK SRTGYQSV                408

SEQ ID NO: 36             moltype = AA  length = 411
FEATURE                   Location/Qualifiers
source                    1..411
                          mol_type = protein
                          organism = Rattus norvegicus
SEQUENCE: 36
MRLLSPVTGS KLVLLFLFLG AVRSDALKLN LTDSKGTCLY AEWEMNFTIT YEALKVNETV   60
TITVPDKVTY NGSSCGDDKN GAKIMIQYGS TLSWAVNFTK EASQYFINNI TLSYNTNDTK  120
TFPGAVPKGI LTVIIPVGSQ LPLGVIFKCS SVLTFNLSPV VQHYWGIHLQ AFVQNGTVSK  180
HEQVCKEDKT ATTVAPIIHT TVPSPTTTLT PTSIPVPTPT VGNYTISNGN ATCLLATMGL  240
QLNITEEKVP FIFNINPATT NFTGSCQPQT AQLRLNNSQI KYLDFIFAVK NEKRFYLKEV  300
NVNMYLANGS AFHVSNNNLS FWDAPLGSSY MCNKEQVVSV SRTFQINTFN LKVQPFNVTK  360
GEYSTAQDCS ADEDNFLVPI AVGAALGGVL ILVLLAYFIG LKRHHTGYEQ F           411

SEQ ID NO: 37             moltype = AA  length = 570
FEATURE                   Location/Qualifiers
source                    1..570
                          mol_type = protein
                          organism = Ornithorhynchus anatinus
SEQUENCE: 37
MAMKNFTLQQ ERDTSVALII RTYVRAFLKV YTKVPKPQRC HNQWQSLNIE GIEGIEIVKG   60
SKWRSALETI ITIQVKRKSQ VQKYHPFSLH SECQKTNQEG TGGVATVIAD ECLLWPSIPF  120
STLAQKVNLG SCEAFSIIGY SVFALFIYLK PNMLDFIELA ELMLSTETQL LEPTRVCCGI  180
CQSYALEINL TDSKNATCLY SKWQMTFTIN YETTGNETKN VTVTVPENVT YDGSSCGDNQ  240
TVPIAVQFG LGYSWHLNFT KKENNSYSFD TIVFTYNTSD NETFPEAKEK GQVLSVPEFR  300
YARIPLNKIF RCHSEESLIG DKATHHYWET VVQAFIQNGT ISKEEFICSK DRASTTVAPV  360
TTQVVPSTTA TPVPQDKPYP GKYAVKNGND TCLLATMGLQ LNVTQNKVNS VININPNVTD  420
FTGSCSNETA ELRLSGSNVK YIDFIFAVKN GNRFYLKEVN VSISFVNASD LNVANNNLSY  480
WDAPLGSSYM CNKEQTLALA DSLQINTFNL RVQPFSVVAG KYSTAEDCSA DDDNFIVPIA  540
VGAALGGLVI LVLMAYFVGR KRRATGYEQF                                   570

SEQ ID NO: 38             moltype = AA  length = 425
FEATURE                   Location/Qualifiers
source                    1..425
                          mol_type = protein
                          organism = Gallus gallus
```

```
SEQUENCE: 38
MAPPRCPAGL ALLLLLLGAC GFFQSYAVEV DVKDASNFTC LYAQWMMKFL IKYETNSSDY    60
KNASLDLTST VTHNGSICGS DTQAALLAVQ FGDGHSWSIN FTKNNETYRA EFITFTYNTN   120
DTAVFPDARR QGPVTIVVKD AMHPIQLNNV FVCHHTTSLE AENVTQIFWN VTMQPFVQNG   180
TISKKESRCY ADTPTAAPTV LPTVANVTTA STTISPAPTT APKPAENPVT GNYSLKTGNK   240
TCLLATVGLQ LNISQDKPLL INIDPKTTHA DGTCGNTSAT LKLNDGNRTL IDFTFIVNAS   300
ASVQKFYLRE VNVTLLNYQN GSVILSADNN NLSKWDASLG NSYMCRKEQT LEINENLQVH   360
TFNLWVQPFL VKENKFSIAE ECFADSDLNF LIPVAVGMAL GFLIILVFIS YIIGRRKSRT   420
GYQSV                                                              425

SEQ ID NO: 39          moltype = AA   length = 556
FEATURE                Location/Qualifiers
source                 1..556
                       mol_type = protein
                       organism = Taeniopygia guttata
SEQUENCE: 39
MECREGEVTR CKQKNNLFSG INDDISGAKQ AKQRQCTPQK PPKRATATLP LQRPPRGIPG    60
PAPAAVAAAV AADRITPSGS HQTRPPEAAR DERPVRDPRN RAAAPSGHWR RAGGPQRHRH   120
HRHRRHGPAP LRRLLLRPPP PAAAAARFLG FFQSYAVEVD IKDASNATCL YADWMMRFLI   180
KYESNSGDYK TTTLNLSSSV THNGSVCGND TQAALVAVQF GEGHSWSINI TKNNETYQGD   240
FITLTYNTND TAVFPDAKRK GPITVLVRDP SRPIQLNTVF VCHNSFVIEA ENTTQIFWNV   300
TMQAFVQNGT VSKKESRCPA DTPTSEPTVP PTIANVTTAS TTTLSPAPTT APKPVANPVT   360
GNYSLKSGNK TCFLATVGLQ LNVSQEKPLL ININPKTTVA DGACGNTTAT LKLNDGNSTL   420
IGFTFAVKNT SASVQKFYLR EVNVTLLNRL NGSVISSADN SNLSKWDAFL GSSYMCRKEQ   480
TLQINENVQV HTFNLWIQPF LVEANKFATA EECIADSDLN FLIPIAVGVA LGFLIILVFI   540
SYIIGRRKSR TGYQSV                                                  556

SEQ ID NO: 40          moltype = AA   length = 408
FEATURE                Location/Qualifiers
source                 1..408
                       mol_type = protein
                       organism = Xenopus tropicalis
SEQUENCE: 40
MERCACPAAL LLLSLVLMGA MAFDVEIKDD KNATCIYAKL SVNVTVQYET NTSSTKNVTF    60
SVPSEVTTNG SSCGSNGKAP ILVINFGNGH SWSLNFTRND SMYSGGALIF TYNTNDSTLF   120
PDALKEGLIS STAAFLGPIP LNSTYKCISS EVVVSENVTQ IISDVKLEAF MQNGTLGKEV   180
SCDADKPSPT PTTNPSTTAS TTTPTPTSKP LDNPTTGNYS VSDVNGTCLL ASMGLQINTS   240
LLSEGKNIWT AFNIDPTAMS KNGTCSNQTG TLILTDNSTV IEFTLALKNK NHFYLKEVNV   300
ALINGSASST RQNQNLSAWE ASVGSSYMCH KEQQIKVSED LVINSFDVRV QLFGVKNETF   360
ATAQQCSLDD DSIVIPIVVG AALAGLIVII VIAYLIGRRK GYSGYQTL                408

SEQ ID NO: 41          moltype = AA   length = 404
FEATURE                Location/Qualifiers
source                 1..404
                       mol_type = protein
                       organism = Salmo salar
SEQUENCE: 41
MFRCAFLILF LALGNELHLS HGTEVSVNNT ENKLCLYANL MVNFSVTYEV GVNKNETVIF    60
VLPENVTTEG STCDNTTSTL KLSFGHGHSW TVEFTKKNKT YQDTIVFSY NLNDSSVFPN    120
STSKETKFVT VKSIITNVSV DTYYSCKSEN VLTVESVIQT LYDVALQAFV INGSKSDTDT   180
VCSADMTSTT VAPTTTVTST AAPTSTPTLP TPTTGKYSIA PDVNSTACLM ATFGLQIGYK   240
QGDKEETINL VPNITEVGGA CGANSSDLIL TSDTITIMFT FSNDGKKFHL HALKVTVKPA   300
TGDPVIAVNN NMSIWAAAVG SSYMCNKEQT LNVTDTLTLY TFELRVQPFE VNKGEFATAH   360
ECSLDDTSIL IPIIVGAALA GLILIVVIAY VIGRRKTYVG YQTL                    404

SEQ ID NO: 42          moltype = AA   length = 410
FEATURE                Location/Qualifiers
source                 1..410
                       mol_type = protein
                       organism = Oreochromis niloticus
SEQUENCE: 42
MKVSHATAGL VVWFVVLGCI DAVTLEVKES NTTCIKADLS ASFSIIYNTT HAERTVQVLL    60
PNSTTVDTAN STCGKDGSSP RLVAVFGSGY TLGLNFSTNG TLYQVSSLTL QYNLSDTSVF   120
PNATISGVVT LVSASVGIEA NVNTTYKCAS PTVIDVATAK VNFTDMRLEA YMPGNELSPN   180
ETVCFADQTS TTPSPTTVST TAVPTQTPPG TPQQGNYTVK DANDTICLLA KMGLQLNVSY   240
TSQNKTVQDV LNLNPNVTNS TGCGASSAT LVLTQTQSTI LTFNFTLNST TNKYHLSGVT    300
LIANWFDSAH FSMSNNSLNY LRSTLGYSYM CNAEQTLFVT PSFSLNTFDL QVQPFGVKSG   360
RFATAEECQM DQNQMIIPII VGAALAGLVL ITLIAYLIGK RRSHAGYQAI              410

SEQ ID NO: 43          moltype = AA   length = 249
FEATURE                Location/Qualifiers
source                 1..249
                       mol_type = protein
                       organism = Takifugu rubripes
SEQUENCE: 43
MTQIGGVQPV FLAVTVHLIL ATVLHQTFAT VTPPVTTAVP HKEPGRPDQG DYQVTSSNGT    60
VCFLASMGLQ LNITFNSTSQ NKTLQEVINI QPNRTKSSGS CDTSSALLTL TTDAEKTNLT   120
FVFALNTTSN KYHLSEVSLS AALSDMKETF VAQNHSLDYL RGTLGFSYMC RERQTLGVTP   180
DFAINTFQVQ VQPFGVTGKQ FAAAEECQLD KDDMLIPIII GAALAALVLI VLSAYLIGRK   240
```

```
RSHAGYQSI                                                                             249

SEQ ID NO: 44            moltype = AA  length = 418
FEATURE                  Location/Qualifiers
source                   1..418
                         mol_type = protein
                         organism = Pan troglodytes
SEQUENCE: 44
MPRQLSAAAA LFASLAVILH DGSQMRAKAF PETRDYSQPS AAATVQDIKK PVQQPAKQAP    60
HQTLAARFMD GHITFQTAAT VKTPTTTPAT TKNTATTSPI TYTLVTTQAT PNNSHTAPPV   120
TEVTVGPSLV PYSLPPTITP PAHTTGTSSS TVSHTTGNTT QPSNQTTLPA TLSIALHKST   180
TGQKPVQPTH APGTTAAAHN TTRTAAPAST VPGPTLAPQP SSVKTGIYQV LNGSRLCIKA   240
EMGIQLIVQD KESVSWGHRT ITLSSKSLSG GCLARNEHSP HPLFLFFEKG PPSVTQAEDE   300
ESYYISEVGA YLTVSDPETI YQGIKHAVVM FQTAVGHSFK CVSEQSLQLS AHLQLKTTDV   360
QLQAFDFEDD HFGNVDECSS DYTIVLPVIG AIVVGLCLMG MGVYKIRLRC QSSGYQRI     418

SEQ ID NO: 45            moltype = AA  length = 416
FEATURE                  Location/Qualifiers
source                   1..416
                         mol_type = protein
                         organism = Papio anubis
SEQUENCE: 45
MPRQLSAAAV LFASLAVILH DGSQMRAKAF PKTRDYSQPT AAATGQDIAK PVQQPANQAP    60
HQTLAARLMD GHITFQTAAT IKTPTTTPVT TKNTPTTSPI IYTLVTTQAT SNNSHTAPPL   120
TKVTVGPSLA PYSLPPTITP PAHTTGTSSS TVNHTTGNAT QPSNQTTLPA TLSIALHKST   180
TGQKPVQPTH APGTTAAAHN TTRTAAPAST VPGSTLAPQP SSVKTGIYQV LNGSRLCIKA   240
EMGIQLIVQD KESVFSPRRY FNLDPNATQA SGNCGTRNSN LLLLNFQGGFV NLTFTKDEGS  300
YYISEVGACL TVSDPETIYQ GMKHAVVMFQ TAVGHSFKCV SEQSLQLSAH LQLKTTNVQL  360
QAFDFEDDHF GNVDECSSDY TIVLPVIGAI VVGLCLVGIG VYKIRLRCQS SGYQRI       416

SEQ ID NO: 46            moltype = AA  length = 416
FEATURE                  Location/Qualifiers
source                   1..416
                         mol_type = protein
                         organism = Macaca mulatta
SEQUENCE: 46
MPRQLSAAAV LFASLAVILH DGSQMRAKAF PKTRDYSQPT AAATGQDIAK PVQQPANQAP    60
HQTLAARLMD GHITFQTAAT IKTPTTTPVT TKNTPTTSPI IYTLVTTQAT SNNSHTAPPL   120
TKVTVGPSLA PYSLPPTITP PAHTTGTSSS TVNHTTGNAT QPSNQTTLPA TLSIAPHKST   180
TGQKPVQPTH APGTTAAAHN TTRTAAPAST VPGSTLAPQP SSIKTGIYQV LNGSRLCIKA   240
EMGIQLIVQD KESVFSPRRY FNLDPNATQA SGNCGTRNSN LLLLNFQGGFV NLTFTKDEGS  300
YYISEVGACL TVSDPETIYQ GMKHAVVMFQ TVVGHSFKCV SEQSLQLSAH LQLKTTNVQL  360
QAFDFEDDHF GNVDECSSDY TIVLPVIGAI VVGLCLVGMG VYKIRLRCQS SGYQRI       416

SEQ ID NO: 47            moltype = AA  length = 428
FEATURE                  Location/Qualifiers
source                   1..428
                         mol_type = protein
                         organism = Canis lupus
SEQUENCE: 47
MSWQLSAAVA LFVSLALILH YGSQIRAKMF PETVDFQPTT AATVRATAKP FLHLTNQVPS    60
QTLAARSMDG HIASQRAATT SSSEPPTTHT TVKTLVTTSL VTANSTPSSS PIIYTLVTTI   120
VTPNNSNTAA PVTEATIGPS ADPGSLPTTS TPLAHTTRTN PSTLSHKTRK TTHFGNQTTL   180
PATLSTSTHK STSSHKSAQS THAPGPTTAA HNTTQTASPA TPASGPTLAP QPSSPKTGIY   240
QVLNGSRLCI KAEMGIELMV QDTKSVFSPQ RYFNIDPNAT QTSGNCGSQK SNLLLNFQGG   300
FVNLTFLKDE NSYYINEVGA YLAVSNPEKI YQGMKSSVVM FETGVGHSFK CVSEQSIQLS   360
THLQLKTMNV QFQAFDFEDD HFGNVDECSS DYTVVLPVIG AIVLGLCAVG LIVYGIHLRR  420
ESSGYQRI                                                            428

SEQ ID NO: 48            moltype = AA  length = 430
FEATURE                  Location/Qualifiers
source                   1..430
                         mol_type = protein
                         organism = Sus scrofa
SEQUENCE: 48
MSWRLSAVLV SFVSLAVFLH YGHHMKAKVF PEITDSSSPT TAATVQATAE PSLWKPTNHT    60
PHKTLAAKST DGHVTSQIAT TVTDSETLTT HTTITTLAAT SLAATNSTPS TSPTTHTLFT   120
TLATPNTSHM AAPVTEAAIS PSAGLSSLLP TIIPPAHTTG TRSSTLSPTA GKTTQPSNQT   180
TLPATLSTSP HNSTASQKPT HPNHTPGPTT GAHNTTQTAS PATIAPGPTL APQPSSAKTG   240
IYQVLNGSKL CIKAEMGIEL TVQDTQSVFS PQRYFNIDPN TTQASGNCGS RKSKLLLNFQ   300
GGFVNLTFTK DENSYYVSGV GAYLTVSNPE KVYQGMKNAV VMFETMIGHS FKCVSEQSIQ   360
LSPHLQLNTM NVQLQAFDFE DDHFGNVDEC SSDYTIVLPV IGAIVLGLCA VGLIVYGIRL   420
KRESSEYQRI                                                          430

SEQ ID NO: 49            moltype = AA  length = 259
FEATURE                  Location/Qualifiers
source                   1..259
                         mol_type = protein
                         organism = Danio rerio
```

```
SEQUENCE: 49
MTQSSRSVLL LMLSSLHCLG SSLESNPKDP SVLAEAPGQN KRDSDISLVP QMPVLQPKET    60
APPLVTYTIR NPQGKVCVRA SFGVEFVVRE NKKKYYFNLT PNSARATGYC ANQKTVLSLE   120
FSGGNLEFTF IKDGDQSYVK TVKGSLRAAP PCKNCPSKIY VGLVDNEKLF KAKNGLSFNC   180
KSETMLILAD YFRLKLVPLQ IQAFDLVNGA FGKEVECWAD YNKRMIPIIL GAVAAAICLI   240
AILTYVLVRE HRNQGYEQL                                                259

SEQ ID NO: 50           moltype = AA  length = 432
FEATURE                 Location/Qualifiers
source                  1..432
                        mol_type = protein
                        organism = Equus caballus
SEQUENCE: 50
MAWQLSAVVV LFVSLAVILY YGSHVRANVF PEITDYSQPT TAATIQTRAQ PSLSQPTNQV    60
PHKTLATRSM DGQVTSQTAA TTVNPETPVT HTTIKTAAAT SLVTTNSTLS TSPITNTLLT   120
TLATPDNTHT TTPVTEATIG PSAGPGSPPT TITTTSSAYT TGTRSSTVSH TTGKTTQLSN   180
QTTLPATLST SPHNSTTSQN PAHSTHTPGP TTGTCNTTQT ASPTTTAPGP TLAPQPSSAK   240
TGMYQILNGS KLCIKAEMGI QLTVQDTKSA SPPQGYFNID PNTTQVSGIC GSRKSNLLLN   300
FWGGFVNLTF TKDENSYYIS EVGAYLTVSN PEKTYQGMKS PVVMFETVIG HSFKCVSEQS   360
LELSTQLHLK TTNVQLQAFD FEDDNFGNVD ECSSDYTVVL PVIGAIVLGL FAVGLIVYGV   420
RVRREASGYQ RI                                                       432

SEQ ID NO: 51           moltype = AA  length = 433
FEATURE                 Location/Qualifiers
source                  1..433
                        mol_type = protein
                        organism = Bos taurus
SEQUENCE: 51
MSWQIPAVVM SFMALVAIWY YDSHYNSHMQ AKVFPEITGY SSPTTGQATV KPSLLQPTNY    60
VPHKTAAARS TDGHVTSQTV AKTSSSETLT TNTTIDVLTT TSPVTTKSTL PTTPTTHTLV   120
TTLATPNKSH VTFPVTEAKV GLSVGPSSPP VTVNPTAHTT GNRPSTASHT TGKTTQLSNQ   180
TTLPATLSTS PHNITTSQKP TQPTHTPGPT TATYNTTQTA SPATIAPRPT LAPQPLSPKT   240
GIYQVHNGSK LCIKAEMGIQ LTVQDSVSVF SPQKYFNIDP NATQASGNCG SRKSNLLLNF   300
QGGFVNLTFT KGEKSYYISE VEAYLTVSNP AKVYQGLKHA MMMFETVVGH SFKCVSEQSI   360
QLSTYLQLKT MNVQLQAFDF EDDHFGNADE CISDRNRREI PVAVGLSIAV LLAVLLTACL   420
VTRKRPSRGY ERM                                                      433

SEQ ID NO: 52           moltype = AA  length = 429
FEATURE                 Location/Qualifiers
source                  1..429
                        mol_type = protein
                        organism = Ovis aries
SEQUENCE: 52
MSWQISAVVL FFVSLAVIWY YDSHMKANVF PEITGYSSPT TGQATVKPSL LQPTNHVPCN    60
TAAAKSTDGH VTSQTVAKTS SPETLTTNTT IEVLTTTSPV TTQSTLPTTP TTHTLVTTLA   120
TPSKSHVTFP VTEAKAGLSI GPSSPPVTIN PAAHTTGNRP STASHTTGKT TQLSNQTTLP   180
ATLSTSPHNI TTSQKPTQPT HTPGPTTAAN NTTHTASPAT IAPRPTLAPQ PLSPKTGLYQ   240
VLNGSKLCIK AEMGIQLTVQ DSVSVFSPQK YFNIDPNATQ ASGNCGSRKS NLLLNFQGGF   300
VNLTFIKDEN SYYISEVEAY LTVSNPAKVY QGMKYAMMMF ETVVGHSFKC VSEQSIQLSN   360
HLQLKTVNVQ LQAFDFEDDR FGNADECISD RNRREIPVAV GLSIAVLLAV LLTACLVTRK   420
RPSRGYERM                                                           429

SEQ ID NO: 53           moltype = AA  length = 408
FEATURE                 Location/Qualifiers
source                  1..408
                        mol_type = protein
                        organism = Rattus norvegicus
SEQUENCE: 53
MPGQTSAVAV LLCLAVILHG YQIREKEFPE ARGYLQYTAT TTEQITAKPP LPLTNQTSHA    60
TLASRSKDDY IQTAAETSTF EDTAHITMKT AIPVTTKSLL PISSSYTFV RTNNSHMTAS    120
STEDTIGSGS ITHLPFPTTR ASLAAVNHIT GRSTQLGGQT TLPKALFTPS HESTTTQRPT   180
LSTIVSELTP TGKDRSTTSS VPLVPRPTFV TWSSPAKIGT YEVLNGSRLC IKAEMGIALI   240
VQEKGLDSAT QRHFNIDPSL THASGKCGSQ NSNLFLNFQG GSVNVTFTKE ENLYYVSEVG   300
AYLTISNTEK TYQGKSTMMM FETVVGHSFK CVSEQSIQLS AQLQMKTMNI HLQAFDFEGD   360
SFGIVDECLS DYTVVLPVVG IIVVVLCVVG LGIYKIRQRR QSSAYQRI                408

SEQ ID NO: 54           moltype = AA  length = 411
FEATURE                 Location/Qualifiers
source                  1..411
                        mol_type = protein
                        organism = Mus musculus
SEQUENCE: 54
MPGQISAVAV LFLSLTVILH GYQIREKEFP KARGYLQYTA TSAEQITTKP LLQLINQRSH    60
ITLASRFKDD YIQMAAETSA IENTAHITMK TVTPVTTKSL PPISSASYTF VRSNNAHMTA   120
SSTDDTIGSG SIAHLPVPTT RASLAIVNYI TGRATQLGGQ TTLPKTFFTA SHKSTTNQRP   180
TLSTNVLGTS TPTHKDRSTT SPVLVPRPT LVTWSSPAKI GTYEVLNGSR LCIKAEMGLA   240
LIVQEKDLDS ATQRYFNIDP SLTHASGKCD SQKSNLFLNF QGGSVNITFT KEENLYYISE   300
VGAYLTISNT EKTYQGKKNT LMMFETVVGH SFKCVSEQSI QLSAQLQMKT MNIHLQAFDF   360
EGDSFGNVNE CLSDYTVVLP MVAIIVVVIC VVGLSVYKIR QRHQSSAYQR I             411
```

```
SEQ ID NO: 55              moltype = AA  length = 314
FEATURE                    Location/Qualifiers
source                     1..314
                           mol_type = protein
                           organism = Xenopus tropicalis
SEQUENCE: 55
MDRVSLLSTI LLLYGLLYIN DAYSENTFAQ PSNTTTPAPN TTTTHVTSNT TTLAPNTTTT    60
HVTSNTTTLA PNTTTTHITS NTTTLAPNTT TTLAPNTTTT HSVTTTTKTAS TTTPTPTLEP   120
KPSPPETGNY TVKIKNEFCI EALMGLELEL TNSTKTQQYF NIVPSQINSN GTCEKSKANL   180
NLTFANSYIN FVFAQDDNSY YLDNVTVYFN LTRSESWYGN ATNQKLLKTE NGYSVKCKNT   240
PKIQLGDTMN LVMTNVKLQV FNFKDNSFGK ETTCKYDHNF GLMIAGIVIV VIVVLGVIIY   300
FIWHKRKSSG YQRI                                                     314

SEQ ID NO: 56              moltype = AA  length = 478
FEATURE                    Location/Qualifiers
source                     1..478
                           mol_type = protein
                           organism = Pan troglodytes
SEQUENCE: 56
MGRCCFYTAG TLSLLLLVTS VTLLVARVFQ KAVDQSIEKK IVLRNGTEAF DSWEKPPLPV    60
YTQFYFFNVT NPEEILRGET PRVEEVGPYT YRELRNKANI QFGDNGTTIS AVSNKAYVFE   120
RDQSVGDPKI DLIRTLNIPV LTVIEWSQVR FLREIIEAML KAYQQKLFVT HTVDELLWGY   180
KDEILSLIHV FRPDISPYFG LFYEKNGTND GDYVFLTGED SYLNFTKIVE WNGKTSLDWW   240
ITDKCNMING TDGDSFHPLI TKDEVLYVFP SDFCRSVYIT FSDYESVQGL PAFRYKVPAE   300
ILANTSDNAG FCIPEGNCLG SGVLNVSICK NGAPIIMSFP HFYQADERFV SAIEGMHPNK   360
EDHETFVDIN PLTGIILKAA KRFQINIYVK KLDDFVETGD IRTMVFPVMY LNESVHIDKE   420
TASRLKSMIN TTLIITNIPY IIMALGVFFG LVFTWLACKG QGSMDEGTAD ERAPLIRT     478

SEQ ID NO: 57              moltype = AA  length = 478
FEATURE                    Location/Qualifiers
source                     1..478
                           mol_type = protein
                           organism = Macaca mulatta
SEQUENCE: 57
MGRCCFYTAG TLSLLLLVTS VTLLVARVFQ KAVDQSIEKK IVLRNGTEAF DSWEKPPLPV    60
YTQFYFFNVT NPEEILRGET PRVEEVGPYT YRELRNKANV QFGDNGTTIS AVSNKAYVFE   120
RDQSVGDPKI DLIRTLNIPV LTVIEWSQVH FLREIIEAML KAYQQKLFVT HTVDELLWGY   180
KDEILSLIHV FRPDISPYFG LFYEKNGTND GDYVFLTGED NYLNFTKIVE WNGKTSLDWW   240
ITDKCNMING TDGDSFHPLI TKDEVLYVFP SDFCRSVYIT FSDYESVQGL PAFRYKVPAE   300
ILANTSDNAG FCIPEGNCLG SGVLNVSICK NGAPIIMSFP HFYQADERFV SAIEGMHPNK   360
EDHETFVDIN PLTGIILKAA KRFQINIYVK KLDDFVETGD IRTMVFPVMY LNESVLIDKE   420
TASRLKSVIN TTLIITNIPY IIMALGVFFG FVFTWLACKG QGSMDEGTAD ERAPLIRT     478

SEQ ID NO: 58              moltype = AA  length = 478
FEATURE                    Location/Qualifiers
source                     1..478
                           mol_type = protein
                           organism = Canis lupus
SEQUENCE: 58
MGRCCFYTVG TLSLLLLVTS IALLVARVFQ KAVDQTIEKN IVLRNGSETF DSWKKPPLPV    60
YAQFYFFNVT NPEEILRGEI PRLEEVGPYT YRELRDKADI QFGDNGTTIS AVSNKAYVFE   120
RNQSVGDPKT DLIRTLNIPA VTAMEWAHLH FFRELIEALL KAYQQTLFVT HTVDELLWGY   180
KDEILSLINV FKPEISPYFG LYYGKNGTND GDYVFLTGED NYLNFSKIVE WNGKTSLDWW   240
TTDKCNMING TDGDSFHPLI DKDEILYVFP SEFCRSVYIT FSDFKSVQGL PAFRYKVPGE   300
VLANTSDNAG FCVPKGNCLG SGVLNISICK NGAPIIISFP HFYEADKKFV SAIDGMRPNK   360
DYHETFVDIN PLTGIILRAA KRFQINVYVK KLDDFIETGN IRTMVFPVMY INESVLIDKD   420
TASRLKSVIN TTLIITNIPY IVMALGVFFG LIFTWLACRG QGSMDEGTPD ERAPLIRT     478

SEQ ID NO: 59              moltype = AA  length = 478
FEATURE                    Location/Qualifiers
source                     1..478
                           mol_type = protein
                           organism = Bos taurus
SEQUENCE: 59
MGRCCFYAVG TLSLLLLVTS ITLLVARVFQ KAVDQTIEKN IVLRNGSETF DSWKKPPLPV    60
YTQFYFFNVT NPEEILNGET PRLEEVGPYT YRELRNKDDI QFGDNGTTIS AVSNKAYVFE   120
RDKSVGDPKI DLLRTLNIPA LTAMEWTQLP LLRDIIEALL KAYRQKLFVT HTVDELLWGY   180
KDEILSLINT FKHDVSPYFG LFYGKNGTND GDYVFLTGED NYLNFSKIVE WNGKTSLDWW   240
TADECNMING TDGDTFHPLI TRDEVLYVFP SDFCRSVYIT FSDFESVQGL PALRYKVPAE   300
ILANTSDNAG FCIPKGNCLG SGVLNVSVCK NGAPIIMSFP HFYQADEKFV SAIGGMHPNK   360
EYHETFVDIN PLTGIILRAA KRFQINVYVR KLDDFVETGN IQTLVFPVMY INESVLIDKE   420
TASRLKSVIN TTLIVTNIPY IIMALGVFFG LIFTWLACRG QGSTDEGTAD ERAPLIRT     478

SEQ ID NO: 60              moltype = AA  length = 478
FEATURE                    Location/Qualifiers
source                     1..478
                           mol_type = protein
                           organism = Mus musculus
```

```
SEQUENCE: 60
MGRCCFYTAG TLSLLLLVTS VTLLVARVFQ KAVDQTIEKN MVLQNGTKVF NSWEKPPLPV      60
YIQFYFFNVT NPEEILQGEI PLLEEVGPYT YRELRNKANI QFGENGTTIS AVTNKAYVFE     120
RNQSVGDPNV DLIRTINIPL LTVVDLAQLT LLRELIEAML KAYQQKLFVI HTVHELLWGY     180
KDEILSLVHI FKPDVSPNFG LFYERNGTND GEYVFLTGED NYLNFSKIVE WNGKTSLDNW     240
TTDTCNMING TDGDSFHPLI SKDEVLYLFP SDLCRSVHIT FSSFENVEGL PAFRYKVPAE     300
ILANTSENAG FCIPEGNCMD SGVLNISICK NGAPIIMSFP HFYQADEKFV SAIKGMHPNK     360
EEHESFVDIN PLTGIILRGA KRFQINTYVR KLDDFVETGD IRTMVFPVMY LNESVLIDKE     420
TANQLKSVIN TTLVVTNIPY IIMALGVFFG LVFTWLACRG QGSMDEGTAD ERAPLIRT      478

SEQ ID NO: 61           moltype = AA   length = 531
FEATURE                 Location/Qualifiers
source                  1..531
                        mol_type = protein
                        organism = Danio rerio
SEQUENCE: 61
MTRRSCTIYA TGIVCAHLLI LGIALLLAQV FQTMIQERIK KEITLAENSR VLDGWINPPP      60
PVYMQYFFFN VTNPDEFLAG KEKAKVTQMG PYTYREYRPR ENVTYLENGT KIFATNPKSF     120
VFLRNMSAGD PEVDRVTTVN IPMIAVMNEL NSYSFFVRTA VSMYMGSMGM GLFMNRTVHE     180
ILWGFKDPLL TKLHAMRPEV DEHFGLMYNK NGTHEGEFVF HTGEKNYMNY GKIDTWNGIS     240
QMNWWSSNQS NMINGTDGSV FHTFLSRKEL LYIFAADLCR SIHLGYVRDM EVKGIPAFRF     300
APPSDVLAPP DENPANAGFC VPAGDCLGKG VLKVSVCRQG APIVVSFPHF YQADERYINA     360
IEGMNPNEEE HETYLDINPT TGVPIRACKR AQLNIILKRV RGFPNTKFLN ETIFPIMYVN     420
ETATIDDESA AQMRMLLLIV TVVSNFPVII LALGVILLVV LIFLVCRNRQ RKNEVKRIDF     480
TEAFHSFATT KDETAYTQVS NQAEDSPENR NNQPLRNGSY IAMSPVEAQK C              531

SEQ ID NO: 62           moltype = AA   length = 478
FEATURE                 Location/Qualifiers
source                  1..478
                        mol_type = protein
                        organism = Rattus norvegicus
SEQUENCE: 62
MARCCFYTAG TLSLLLLVTS VTLLVARVFQ KAVDQTIEKN MVLQNGTKVF DSWEKPPLPV      60
YIQFYFFNVT NPEEILQGEI PLLEEVGPYT YRELRNKANV QFGENGTTIS AVTNKAYIFE     120
RNQSVGDPTV DLIRTINIPL LTVVEMAQQG FLREIIEAML KAYQQTLFVT HTVHELLWGY     180
KDEVLSLVHI FRPDVSPNFG LFYERNGTND GEYVFLTGED NYLNFTKIVE WNGKTSLDWW     240
TTDTCNMING TDGDSFHPLI SKDETLYIFP SDFCRSVYIT FSSFENVEGL PAFRYKVPAE     300
ILANSSENAG FCIPEGNCMD AGVLNVSICK NGAPIIMSFP HFYQADEKFV SAIKGMRPNK     360
EEHESFVDIN PLTGIILRGA KRFQINTYVK KLDDFVETGN IRTMVFPVMY LNESVLIDKE     420
TASQLKSVIN TTLIVTNIPY IIMALGVFFG LIFTWLACRG QGSTDEGTAD ERAPLIRT      478

SEQ ID NO: 63           moltype = AA   length = 481
FEATURE                 Location/Qualifiers
source                  1..481
                        mol_type = protein
                        organism = Gallus gallus
SEQUENCE: 63
MRSLCLVTVG VLALTLLIAS ISLLVAHVFQ TVVDLQVKQG TVLKNGTETF EAWEDPPPPV      60
YMQFYFFNVT NPLEVLQGAT PLVEEKGPYT YREYRPRVHV QFLDNGTKVS ALNPKTYVFE     120
PEKSVGNPEV DLIRTINVPA VTAMEWTRAT SLQFATEVLL LLYQESLFTV RTVHELLWGY     180
KDKLLSTIHV LHPEIDPVFG FFNKMGTDD GEYVFLSGEN NYLNFSRIVE WKGKESLNWW     240
TTKTCNMING TDGTSFHPLI SKDENIYIFS SDFCRSLYLV YDSSGSVAGV PTYRFVPSPM     300
VFANTTVNPD NAGFCVPPGN CPGAGVLNVS ICKQGAPIFL SAPHFYQADQ KFVSDIEGMH     360
PTKEYHETFV DINPLTGLVL QAAKRMQINI HVRKLPEFFE TGNIRTLIFP VMYINESVLI     420
DEASANKLKH VLLEASVVTG IPFVIMAIGI VFGIVFSVLV CRAQGAREES TEEERSPLIR     480
T                                                                    481

SEQ ID NO: 64           moltype = AA   length = 483
FEATURE                 Location/Qualifiers
source                  1..483
                        mol_type = protein
                        organism = Xenopus tropicalis
SEQUENCE: 64
MVKWAVFGTA AVSVTLLIVS IVLLLTHTFM DIVEGQVKQA IVLKNESEVF EDWANPPPPV      60
YMQFYFFNVT NPLEVLSGEK PFVDEIGPYT YREYRPRENI TFSVNGTEVS AVTPKTYVFE     120
PEKSIGDPKV DLIRTVNIPL VTILEMTKDS SLLRPFIIAA LKTYKEGMFV TRTVDELLWG     180
YKDAVLSILH PFKKNISDTF GLFYKMNTTD DGEYIFLSGE KDYLEFTQIA EWKGQKALNW     240
WTTETCNMIN GTDGTSFHPL LNKDDTIYMF SSDLCRSIYA VYESSENIKD ISVFRFSPPA     300
SVFANVSVNP QNKGFCVPEG NCLPSGLLNV SICKEGAPIV LSSPHFYQAD ENVINSIRGM     360
KPVKEHHMTF LDLNPLTGTL IQAAKRIQVN VYVRKINVYL ITQDIQTLFF PVMHLNESVL     420
IDDKSAGRLR SILFQGRVVA NIPFIIMGLG IILAFLFTTL SCLQKRSRDE GTEEERGPLI     480
RAS                                                                  483

SEQ ID NO: 65           moltype = AA   length = 551
FEATURE                 Location/Qualifiers
source                  1..551
                        mol_type = protein
                        organism = Drosophila melanogaster
SEQUENCE: 65
```

```
MQLDDILHIN NCKADCSSLS TTPNPKTDLV NMNGPKHKFC TKLSSTYLRK WWITIVVAAA    60
LIIGGIVVAC EFTVLIDAVV DRMVALRPGA KTFGWWAKPP VEPRISLYIY NVTNADDFLS   120
NGSKAIVDEV GPYVYSETWE KVNIVENDNG TLSYNLRKIY SFREDLSGVP EDDVVIVPNI   180
PMLSATSQSK HAARFLRLAM ASIMDILKIK PFVQVSVGQL LWGYEDPLLK LAKDVVPKEQ   240
KLPYEEFGLL YGKNGTSSDR VTVNTGVDDI RRYGIIDNFN GRTHLPHWTT DACNTLAGTD   300
GSIFPPHIDH DRILHVYDKD LCRLLPLVFE KEVMTSNEVP GYRFTPPEWV FADVDSHPDN   360
MCFCPAGKPS CSPNGLFNVS LCQYDSPIML SFPHFYLADE SLRTQVEGIS PPMKEKHQFF   420
FDVQPKMGTT LRVRARIQIN LAVSQVFDIK QVANFPDIIF PILWFEEGID NLPDEVTDLM   480
RFAEQVPPKI RVALIVGLCA LGVILLLLST FCLIRNSHRQ STLHLEGSNY LATAQVDMNK   540
KQNKDNQPAR Y                                                      551

SEQ ID NO: 66           moltype = AA  length = 522
FEATURE                 Location/Qualifiers
REGION                  1..522
                        note = str. PEST
source                  1..522
                        mol_type = protein
                        organism = Anopheles gambiae
SEQUENCE: 66
MYGRSNRLCA KLSSAFLRKW WFVIAFALSL LVLGALVTFG FTAFIRTIID HQVALRVGGQ    60
SFGWWSRPPV EPIIRIFVYN VTNADEFLNN GTKPILDELG PYVYVQTWEK VNIKENPNGT   120
ISYNQKRVYI FNEDLSGGLE DDVVIVPNIP MLSATSQKH AARFLRLAMA SIMDILKIKP   180
FVEVSVGQLL WGYEDPLLKL AKDVVPKEQK LPYEEFGLMY GKNSTSKDTV TVWTGVDDIT   240
QYGIIDKYNG RSHQTHWLSE QCNRLNGTDG SIFPPRITKN STLHVYEKDL CRLLPLSFEK   300
EVTVRGGVKG YRFTPSPDVF ASVDKNPNNM CYCPAGPPCA PHGLFNVSLC QYDSPILLSF   360
PHFYMADQTL RTAVEGISPP EKDKHQLFID VQPDMGTALR ARARIQINLA VSQVVDIKQV   420
ANFPDIVFPI LWFEEGIDSL PDEILDLMKV ATNIPPRAKF ILTIALFGLG GFLFVVAVIC   480
LVRKSHRQST LHLEGSNYLA TASVDQAKKK AKMDNGMSSK SN                     522

SEQ ID NO: 67           moltype = AA  length = 338
FEATURE                 Location/Qualifiers
source                  1..338
                        mol_type = protein
                        organism = Homo sapiens
SEQUENCE: 67
MVRRVQPDRK QLPLVLLRLL CLLPTGLPVR SVDFNRGTDN ITVRQGDTAI LRCVVEDKNS    60
KVAWLNRSGI IFAGHDKWSL DPRVELEKRH SLEYSLRIQK VDVYDEGSYT CSVQTQHEPK   120
TSQVYLIVQV PPKISNISSD VTVNEGSNVT LVCMANGRPE PVITWRHLTP TGREFEGEEE   180
YLEILGITRE QSGKYECKAA NEVSSADVKQ VKVTVNYPPT ITESKSNEAT TGRQASLKCE   240
ASAVPAPDFE WYRDDTRINS ANGLEIKSTE GQSSLTVTNV TEEHYGNYTC VAANKLGVTN   300
ASLVLFRPGS VRGINGSISL AVPLWLLAAS LLCLLSKC                          338

SEQ ID NO: 68           moltype = AA  length = 338
FEATURE                 Location/Qualifiers
source                  1..338
                        mol_type = protein
                        organism = Pan troglodytes
SEQUENCE: 68
MVRRVQPDRK QLPLVLLRLL CLLPTGLPVR SVDFNRGTDN ITVRQGDTAI LRCVVEDKNS    60
KVAWLNRSGI IFAGHDKWSL DPRVELEKRH SLEYSLRIQK VDVYDEGSYT CSVQTQHEPK   120
TSQVYLIVQV PPKISNISSD VTVNEGSNVT LVCMANGRPE PVITWRHLTP TGREFEGEEE   180
YLEILGITRE QSGKYECKAA NEVSSADVKQ VKVTVNYPPT ITESKSNEAT TGRQASLKCE   240
ASAVPAPDFE WYRDDTRINS ANGLEIKSTE GQSSLTVTNV TEEHYGNYTC VAANKLGVTN   300
ASLVLFRPGS VRGINGSISL AVPLWLLAAS LLCLLSKC                          338

SEQ ID NO: 69           moltype = AA  length = 338
FEATURE                 Location/Qualifiers
source                  1..338
                        mol_type = protein
                        organism = Oryctolagus cuniculus
SEQUENCE: 69
MGARVQPDRK QLPLVLLRLL CLLPTGLPVR SVDFNRGTDN ITVRQGDTAI LRCVVEDKNS    60
KVAWLNRSGI IFAGHDKWSL DPRVELEKRH SLEYSLRIQK VDVYDEGSYT CSVQTQHEPK   120
TSQVYLIVQV PPKISNISSD VTVNEGSNVT LVCMANGRPE PVITWRHLTP TGREFEGEEE   180
YLEILGITRE QSGKYECKAA NEVSSADVKQ VKVTVNYPPT ITESKSNEAT TGRQASLKCE   240
ASAVPAPDFE WYRDDTRINS ANGLEIKSTE GQSSLTVTNV TEEHYGNYTC VAANKLGVTN   300
ASLVLFRPGS VRGINGSISL AVPLWLLAAS LLCLLSKC                          338

SEQ ID NO: 70           moltype = AA  length = 341
FEATURE                 Location/Qualifiers
source                  1..341
                        mol_type = protein
                        organism = Mus musculus
SEQUENCE: 70
MVGRVQPDRK QLPLVLLRLL CLLPTGLPVR SVDFNRGTDN ITVRQGDTAI LRCVVEDKNS    60
KVAWLNRSGI IFAGHDKWSL DPRVELEKRH ALEYSLRIQK VDVYDEGSYT CSVQTQHEPK   120
TSQVYLIVQV PPKISNISSD VTVNEGSNVT LVCMANGRPE PVITWRHLTP LGREFEGEEE   180
YLEILGITRE QSGKYECKAA NEVSSADVKQ VKVTVNYPPT ITESKSNEAT TGRQASLKCE   240
ASAVPAPDFE WYRDDTRINS ANGLEIKSTE GQSSLTVTNV TEEHYGNYTC VAANKLGVTN   300
```

```
ASLVLFSKYA KTEPDSMQVI EFLHIDLKSI RHPLKVNPIQ K                341

SEQ ID NO: 71           moltype = AA   length = 337
FEATURE                 Location/Qualifiers
source                  1..337
                        mol_type = protein
                        organism = Xenopus laevis
SEQUENCE: 71
MVGRSQSDRN QLPLFLLRLL CLLPTGLPVR SGDFNRSTDN MTVRQGDTAI LRCFVEDKSS    60
KVAWLNRSGI IFAVDDKWSL DPRVELEKRS PFEYSLRIQK VDVSDEGPYI CSVQTNQHTK   120
TMQVYLIVQV PPKISNISAD ITVNEGSNVT LMCIAYGRPE PMITWRHLTP TARDFEGEEE   180
FLEIQGITRE QSGRYECKAA NEVASADVKQ VRVTVNYPPI ITESNSNEAT TGKQAILRCE   240
ASAVPAPDFE WYKDDTRINS AQGLEIRNTG SRSVLMVANV TEEHYGNYTC VAANKLGITN   300
TSLYLYIGPG TPIDNATSLA ASLWLMANIL LCLFCTC                            337

SEQ ID NO: 72           moltype = AA   length = 333
FEATURE                 Location/Qualifiers
source                  1..333
                        mol_type = protein
                        organism = Danio rerio
SEQUENCE: 72
MSCLWIHSVF IPGFFLLFGF EGFPVISVES QRSTDNITIR QGDTTVIRCY VDDKVSKVAW    60
LNRSNIIFAG EDKWSLDPRV ELVTQGQLEY SLRIQKVDVF DEGPYTCSIQ TKQQSKTSQV   120
YLIVQVPAII YKVSEDITVN EGSNVALTCL ANGRPDPAIT WRLLNPSAEA LDVGEYLEIS   180
GVVRSQAGRY ECKASNDVST PDVKYVNVVV NYPPYIKDVR SSETAVGQAG VLHCEASAVP   240
QPEFEWYRDE RRLSSSQSLT IQVSGSRTVL VVANVTEEDY GNYTCVATNR LGVHNASVFL   300
YKPGMGRDIN SAGCICQSLW LLLLCVSSAL LQC                                333

SEQ ID NO: 73           moltype = AA   length = 197
FEATURE                 Location/Qualifiers
source                  1..197
                        mol_type = protein
                        organism = Mus musculus
SEQUENCE: 73
MSGSSRRLLW AATCLAVLCV SAAQPNITTL APNVTEVPTT TTKVVPTTQM PTVLPETCAS    60
FNSCVSCVNA TFTNNITCFW LHCQEANKTY CANEPLSNCS QVNRTDLCSV IPPTTPVPTN   120
STAKPTTRPS SPTPTPSVVT SAGTTNTTLT PTSQPERKST FDAASFIGGI VLVLGVQAVI   180
FFLYKFCKSK ERNYHTL                                                  197

SEQ ID NO: 74           moltype = AA   length = 197
FEATURE                 Location/Qualifiers
source                  1..197
                        mol_type = protein
                        organism = Macaca mulatta
SEQUENCE: 74
MSRLSRSLLW AVTCLAVLCV LSAEENPTPH TNVTSLAPTS NITSAPVTSL PLVTTPAPET    60
CEGRNSCVSC FNASTVNTTC FWIECKDESY CSHNSTVSDC QVGNTTDFCS VPTATLVPTA   120
NSTAKPTVQP SPSTTSKTVT TSGTTNTTVT PTSQPVRKST FDAASFIGGI VLVLGVQAVI   180
FFLYKFCKSK ERNYHTL                                                  197

SEQ ID NO: 75           moltype = AA   length = 194
FEATURE                 Location/Qualifiers
source                  1..194
                        mol_type = protein
                        organism = Sus scrofa
SEQUENCE: 75
MLGLSRQLLW AVGCLAALCV LTAAKNSTIL PPSTTTPWLS PPTTQTTSAP PKTLPTPAPE    60
ICENRNSCIS CFDANNTCFW IECKGKSYCS DNSTVSDCHV VNGTDFCSGP TVTPLPTNST   120
AKTTTLPSPS SASTTATTSG TTNTTLAPTT QPMRKSTFDA ASFIGGIVLV LGVQAVIFFL   180
YKFCKSKERN YHTL                                                     194

SEQ ID NO: 76           moltype = AA   length = 198
FEATURE                 Location/Qualifiers
source                  1..198
                        mol_type = protein
                        organism = Bos taurus
SEQUENCE: 76
MSGLSRPLLL AVGCLAALCV ITAAGNTTLA PNVTTASSPP PTTTTVPVSP TTLSPLPVTT    60
PAPDICGSRN SCVSCVDGNA TCFWIECKGK SYCSDNSTAG DCKVVNTTGF CSVPTTTPTP   120
TNSTAKTTTL PSTTTTSTTA TTSGTTNTTL SPTIQPTRKS TFDAASFIGG IVLVLGVQAV   180
IFFLYKFCKS KERNYHTL                                                 198

SEQ ID NO: 77           moltype = AA   length = 198
FEATURE                 Location/Qualifiers
source                  1..198
                        mol_type = protein
                        organism = Ovis aries
SEQUENCE: 77
MSGLSRPLLL AVGYLAALCV ITAARNTTVT PNVTTPSSPP PTTATVPVSP TTLTPPPVTT    60
```

```
PAPDICGSRN SCISCVDGNA TCFWIECKGK SYCSDNSTVS DCKVVNTTGF CAVPTTTPTP  120
TNSTAKTTTL PSTTTTSTTA TTSGTANTTL TPTIQPMRKS TFDAASFIGG IVLVLGVQAV  180
IFFLYKFCKS KERNYHTL                                                198

SEQ ID NO: 78           moltype = AA   length = 198
FEATURE                 Location/Qualifiers
source                  1..198
                        mol_type = protein
                        organism = Canis lupus
SEQUENCE: 78
MSGLSRQLCW AAACLAALCA LTAAQSFSSD PNGTTTTTQA TTDAATTRVT TAAPATTPAP   60
DPCDNRNSCV SCVNTSVDAT ACSWIECKEK SYCSHNTTVS DCQVVNSTQL CSAPEPTMMP  120
TNSTAKTTTQ PSSSTATTTA TTSGTTNITL SPTSQPGRKS TFDAASFIGG IVLILGVQAV  180
IFFLYKFCKS KERNYHTL                                                198

SEQ ID NO: 79           moltype = AA   length = 195
FEATURE                 Location/Qualifiers
source                  1..195
                        mol_type = protein
                        organism = Rattus norvegicus
SEQUENCE: 79
MSGASRGLFW AATCLAALCL SAAQSNSSAS PNVTDPPTTT SKVVPTTLTT TKPPETCESF   60
NSCVSCVNAT LTNNITCVWL DCHEANKTYC SSELVSNCTQ KTSTDSCSVI PTTPVPTNST  120
AKPTTRPSSP TPTPSVVTSA GATNTTVTPT SQPERKSTFD AASFIGGIVL VLGVQAVIFF  180
LYKFCKSKER NYHTL                                                   195

SEQ ID NO: 80           moltype = AA   length = 354
FEATURE                 Location/Qualifiers
source                  1..354
                        mol_type = protein
                        organism = Homo sapiens
SEQUENCE: 80
MRLAVLFSGA LLGLLAAQGT GNDCPHKKSA TLLPSFTVTP TVTESTGTTS HRTTKSHKTT   60
THRTTTTGTT SHGPTTATHN PTTTSHGNVT VHPTSNSTAT SQGPSTATHS PATTSHGNAT  120
VHPTSNSTAT SPGFTSSAHP EPPPPSPSPS PTSKETIGDY TWTNGSQPCV HLQAQIQIRV  180
MYTTQGGGEA WGISVLNPNK TKVQGSCEGA HPHLLLSFPY GHLSFGFMQD LQQKVVYLSY  240
MAVEYNVSFP HAAQWTFSAQ NASLRDLQAP LGQSFSCSNS SIILSPAVHL DLLSLRLQAA  300
QLPHTGVFGQ SFSCPSDRSI LLPLIIGLIL LGLLALVLIA FCIIRRRPSA YQAL        354

SEQ ID NO: 81           moltype = AA   length = 354
FEATURE                 Location/Qualifiers
source                  1..354
                        mol_type = protein
                        organism = Pan troglodytes
SEQUENCE: 81
MRLAVLFSGA LLGLLAAQGT GNDCPHKKSA TLLPSFTVTP TVTESTGTTS HRTTKSHKTT   60
THRTTTTGTA SHGPTTATHN PTTTSHGNVT VHPTSNSTAT SQGPSTATHS PATTSHGNAT  120
VHPTSNSTAT SPGFTSSAHP EPPPPSPSPS PTSKETIGDY TWTNGSQPCV HLQAQIQIRV  180
MYTTQGGGEA WGISVLNPNK TKVQGSCEGA HPHLLLSFPY GHLSFGFMQD LQQKAVYLSY  240
MAVEYNVSFP HAAQWTFSAQ NASLRDLQAP LGRSFSCSNS SIILSPAVHL DLLSLRLQAA  300
QLPHTGVFGQ SFSCPSDRSI LLPLIIGLIL LGLLALVLIA FCIIRRRPSA YQAL        354

SEQ ID NO: 82           moltype = AA   length = 335
FEATURE                 Location/Qualifiers
source                  1..335
                        mol_type = protein
                        organism = Bos taurus
SEQUENCE: 82
MRLAVFFSGA LLGLLAAQGT GNDCPHKKSA TLLPSFTVTP TATESTPSPG TTSHRTTKSH   60
RTTTWRISTT THTTNTTGTT SSESPTATHS PATTTSHQNT TVHPTSNITA TSPGPSTRSP  120
HPEPPPSPSP SPGSKEAIGD YTWSNGSQPC VRLQAQIQIR VLYPTQGGGE AWGISVLNPN  180
RTKAQGGCEG THSHLLLSFP SGQLSFGFKQ DPLQSAVYLN YMAVEYNVSF PQAVQWTFSV  240
QNSSLRDLQT PLGHSFSCRN ASIIVSPALH LDLLSLKLQA AQLSPSGAFG PSFSCPNDKS  300
ILLPLIIGLI LLGLLTLVLV TFCIIRRRPP TYQPL                             335

SEQ ID NO: 83           moltype = AA   length = 335
FEATURE                 Location/Qualifiers
source                  1..335
                        mol_type = protein
                        organism = Mus musculus
SEQUENCE: 83
MRLPVCLILL GPLIAQGTEE DCPHKKAVTL LPSFTMTPTA TESTASPTTS HRPTTTSHGN   60
VTVHTSSGPT TVTHNPATTT SHGNATISHA TVSPTTNGTA TSPRSSTVGP HPGPPPPSPS  120
PRSKGALGNY TWANGSQPCV QLQAQIQIRI LYPIQGGRKV KLKWGLKRAW GISVLNPNKT  180
KVQGGCDGTH PHLSLSFPYG QLTFGFKQDL HQSPSTVYLD YMAVEYNVSF PQAAWWTFMA  240
QNSSLRELQA PLGQSFCCGN ASIVLSPAVH LDLLSLRLQA AQLPDKGHFG PCFSCNRDQS  300
LLLPLIIGLV LLGLLTLVLI AFCITRRRQS TYQPL                             335

SEQ ID NO: 84           moltype = AA   length = 354
```

```
FEATURE                 Location/Qualifiers
source                  1..354
                        mol_type = protein
                        organism = Macaca mulatta
SEQUENCE: 84
MRLAVLFLGA LLGLLAAQGT GNDCPHKKSA TLLPSFTVTP TATESTGTTS HRTTKSHKTT    60
THRTTTTGTT SHRPTTATHN PTTTSHRNAT VHPTSNSTAT SQGPSTATHR PATTSHGNAT   120
VHPTSNSTAT SPGLTSSAHP GPPPPSPSPS PASKETIGDY MWTNGSQPCV HLQAQIQIRV   180
MYTTQGGGEA WGISVLNPNK TKVQGSCEGA HPHLLLSFPY GHLSFGFMQD LQQRVVYLSY   240
MAVEYNVSFP HAAQWTFSAQ NASLRDLQAP LGQSFSCSNS SIILSPAVHL DLLSLRLQAA   300
QLPHTGVFGQ SFSCPSDRSI LLPLIIGLVL LGLLALVLIA FCIVRRRPSA YQAL         354

SEQ ID NO: 85           moltype = AA   length = 330
FEATURE                 Location/Qualifiers
source                  1..330
                        mol_type = protein
                        organism = Rattus norvegicus
SEQUENCE: 85
MRFPVCLTLL VLLVAQGTGK DCPHKKAATL LPSFTETPTT TGSTASPTTT HRPTTTSHRP    60
TTTSHRPTTT SHRPTTTSHR PTTTSHRPTT TSHGNATVSP TTNSPGFSTV GPHPGPPPPS   120
PSPSPSSTGA LGNYTWTNGS QPCVQLQAQI QIRILYLTQG GKKAWGLSVL NPNKTKVQGG   180
CDSAHPHLAL SFPYGQLTFG FKQDRHQSHS TVYLNYMAVE YNVSFPQAAQ WTFSAQNSSL   240
QELQAPLGQS FCCGNTSIVL SPAIHLDLLS LRLQAAQLPD KGHFGPCFSC ASDQSLLLPL   300
IIGLVLLGLL TLVLIAFCVT RRRQSTYQPL                                   330

SEQ ID NO: 86           moltype = AA   length = 329
FEATURE                 Location/Qualifiers
source                  1..329
                        mol_type = protein
                        organism = Canis lupus
SEQUENCE: 86
MRPAVFFLGA LVGLLAAQGT RSDCPHKKSA TLLPSFTVTP TATESTGSPG TTSHSTTTAE    60
TTSHAPNTTT HQAPTTPGHR NTTIHPTTSN STSNTTGTTG TGKPHTSTSY TQPGPGPRPP   120
PPSPGPGPQD AIGDYTWTTG SQPCARLQAR IQIGVVYPTG AGGQAWGISV LNPNSTKPWG   180
DCDGARPHLL LSFPFGQLSF GFTQEPQQGS VYLDYLALQY NVSFPQAAQW TFSGQNASLR   240
ALQAPLGQSF SCRNASILLT PALRLDLLHL KLQAAQLPPS GAFGPSFSCP SEHFNLLLPI   300
VGVISLGLLA LALVTFCIIR RRPPTYQPL                                    329

SEQ ID NO: 87           moltype = AA   length = 322
FEATURE                 Location/Qualifiers
source                  1..322
                        mol_type = protein
                        organism = Equus caballus
SEQUENCE: 87
MRLAVLFSGA LLGLLAAQET GNDCPHKKSA TLLPSFTVTP TATESTASPG TTSHQTTQSH    60
RTTTTGTTSD HPTTATHNPT TTSHGNTTVH PTTSNSTVTS PGSASSSPHP RPPPPSPSPS   120
PGSKEAIGDY IWTNGSQPCV RLQAQIQIRV LYPTLGGGKA WGISVLNPNK TKAQGGCAHP   180
HLLLSFPYGQ LSFGFKQEPL QSTVYLNYIA VEYNVSFPQA AQWTFLVQNS SLRDLQAPLG   240
QRFSCRNASI ALSPAFHLDL LSLKLQAAQL TPTGAFGPSF SCPSDQSILL PLIIGLILLG   300
LFALVLITFC VIRRRPPTYQ AL                                           322

SEQ ID NO: 88           moltype = AA   length = 305
FEATURE                 Location/Qualifiers
source                  1..305
                        mol_type = protein
                        organism = Oryctolagus cuniculus
SEQUENCE: 88
MRLPVLFLAL LGLHAASSGT TSHRTTKNPH TTSHSTATPG TTSHRPTTAT PTTGHGNVTV    60
HPTTSNTTSN TTTTTGTSPG FSTSTPHPGP PPPPSPSPG SREAVGNYTW TNGSQPCVQL   120
QAQIQIRVLY PTQGGGQAWG MSVLNPNRTK AQGGCEGPRP HLLLSFPYGQ LSFGFKQDPG   180
QGQSAVYLSY LAVEYNVSFP QAARWTFSAQ NASLRDLQAP LGQSFSCRNA SIAVSPALHL   240
DLLSLRVQAA QLPRTGIFGP SFSCPADHPS ILVPLIIGLI LVGLLALVLV AFCIARRRPS   300
AYQAL                                                              305

SEQ ID NO: 89           moltype = AA   length = 291
FEATURE                 Location/Qualifiers
source                  1..291
                        mol_type = protein
                        organism = Sus scrofa
SEQUENCE: 89
MTLAVLFLGA LLGLLAESTT SHRTTTPRTT TTGTTSHGPT TVTHNPATTT SHGNATVHPT    60
SSSTATSPGS STRPPHPGPP PPSPSPSPGS QEAIGDYTWT NGSQPCVQLQ AQIQIRVLYP   120
TQGGGEAWGI SVLNPNKTKA LGGCEGAHPH VRLSFPYGQL TFGFKQQPQE STVYLNYMAV   180
EYNVSFPQAA QWTFVQNSS LRDLQTPVGR SYSCRNASII LSTAFHLDLL SLKLQAAQLP   240
PTGNFGPSFS CPSDQTILLP LIIGLIFLGL LILVLVTFCI IRRRPAYQP L             291

SEQ ID NO: 90           moltype = AA   length = 354
FEATURE                 Location/Qualifiers
source                  1..354
```

```
                          mol_type = protein
                          organism = Papio anubis
SEQUENCE: 90
MRLAVLFSGA  LLGLLAAQGT  GNDCPHKKSA  TLLPSFTVTP  TATESTGTTS  HRTTKSHKTT   60
THRTTTTGTT  SHRPTTATHN  PNTTSHRNAT  VHPTSNSTAT  SQGPSTATHR  PATTSHGNAT  120
VHPTSNSTAT  SPGLTSSAHP  GPPPPSPSPS  PASKETIGDY  MWTNGSQPCV  HLQAQIQIRV  180
MYTTQGGGEA  WGISVLNPNK  TKVQGSCEGA  HPHLLLSFPY  GHLSFGFMQD  LQQRVVYLSY  240
MAVEYNVSFP  HAAQWTFSAQ  NASLRDLQAP  LGQSFSCSNS  SIILSPAVHL  DLLSLRLQAA  300
QLPHTGVFGQ  SFSCPSDRSI  LLPLIIGLVL  LGLLALVLIA  FCIVRRRPSA  YQAL        354

SEQ ID NO: 91             moltype = AA  length = 323
FEATURE                   Location/Qualifiers
source                    1..323
                          mol_type = protein
                          organism = Monodelphis domestica
SEQUENCE: 91
MRLSLLLSGI  LLGLLAEQGA  GDKCPQEKSV  TLVPSFTVTT  IATERSTTSP  ETTTSSGSTA   60
TTYRTSTAAT  TPHSNSTATS  YSTTSEGTAV  THGTTTSPRN  TSTTSTSQSV  PVPPSPQPTS  120
SPSGAVGDYI  GANGSQLCVH  LRAQIQMRVL  YQASGGGKLW  GIFVLNPNRT  MAQGNCEANH  180
SSLILSFPNG  KLIFGFKQDS  IKKIVYLSHL  ATEFNVSFPS  ATRWIFSVEN  SSLQDLQTPL  240
GHSFSCRNRS  IALSPDIHLD  LLSLQLQAAQ  LSSSGAFGAA  FSCSADLNIL  VPLVVGLVLL  300
TLLILVLSAF  CISRRRPPAY  QPL                                             323

SEQ ID NO: 92             moltype = AA  length = 263
FEATURE                   Location/Qualifiers
source                    1..263
                          mol_type = protein
                          organism = Ornithorhynchus anatinus
SEQUENCE: 92
MGLTLPLPAQ  GSQCRANCPH  KKSATLVPSF  TVTPTATSGP  TTTAHQTTTD  HGTTTSHETT   60
TSQGTSTHGT  STPHTTTTGH  GTTTGHQNTS  HSTTTSHGTS  TPHKTTTRHP  TTSHGTTTSH  120
GTSTGHWTAR  PTIRPGPPPP  PPSPGKAVGN  YTVFNGSQPC  LRLRAEIRLW  VLYQAQEEGE  180
APPVSGAASF  PPPRPRPVAG  EGDGERSRVT  PVASAMTVEG  GSRAGFAMLG  AEVRSRAPSL  240
GRAGKTRLRI  HQPVVVLQHT  YYV                                             263

SEQ ID NO: 93             moltype = AA  length = 280
FEATURE                   Location/Qualifiers
source                    1..280
                          mol_type = protein
                          organism = Homo sapiens
SEQUENCE: 93
MDLQGRGVPS  IDRLRVLLML  FHTMAQIMAE  QEVENLSGLS  TNPEKDIFVV  RENGTTCLMA   60
EFAAKFIVPY  DVWASNYVDL  ITEQADIALT  RGAEVKGRCG  HSQSELQVFW  VDRAYALKML  120
FVKESHNMSK  GPEATWRLSK  VQFVYDSSEK  THFKDAVSAG  KHTANSHHLS  ALVTPAGKSY  180
ECQAQQTISL  ASSDPQKTVT  MILSAVHIQP  FDIISDFVFS  EEHKCPVDER  EQLEETLPLI  240
LGLILGLVIM  VTLAIYHVHH  KMTANQVQIP  RDRSQYKHMG                          280

SEQ ID NO: 94             moltype = AA  length = 280
FEATURE                   Location/Qualifiers
source                    1..280
                          mol_type = protein
                          organism = Pan troglodytes
SEQUENCE: 94
MDLRGRAVPS  IDRLRVLLML  FHTMAQIMAE  QEVENLSGLS  TNPEKDIFVV  RENGTTCLMA   60
EFAAKFIVPY  DVWASNYVDL  ITEQADIALT  RGAEVKGRCG  HSESELQVFW  VDRAYALKML  120
FVKESHNMSK  GPEATWRLSK  VQFVYDSSEK  THFKDAVSAG  KHTANSHHLS  ALVTPAGKSY  180
ECQAQQTISL  ASSDLQKTVT  MILSAVHIQP  FDIISDFVFS  EEHKCPVDER  EQLEETLPLI  240
LGLILGLVIM  VTLAIYHVHH  KMTANQVQIP  RDRSQYKHMG                          280

SEQ ID NO: 95             moltype = AA  length = 280
FEATURE                   Location/Qualifiers
source                    1..280
                          mol_type = protein
                          organism = Macaca mulatta
SEQUENCE: 95
MDLQGRAVPS  VDRLRVLLML  FHTMAQIMAE  QEVENLSGLS  TNPEKDIFVV  RENGTTCLMA   60
EFAAKFIVPY  DVWASNYVDL  ITEQADIALT  RGAEVKGRCG  HSESELQVFW  VDRAYALKML  120
FVKESHNTSK  GPEATWRLSK  VQFVYDSSEK  THFKDAVSAG  KHTANSHHLS  ALVTPAGKSY  180
ECQAQQTISL  ASSDPQKMVT  MILSAVHIQP  FDIISDFVFS  EEHKCPVDER  EQLEETLPLI  240
LGLILGLVIV  VTLTIYHVHH  KMTANQVQIP  RDRSQYKHMG                          280

SEQ ID NO: 96             moltype = AA  length = 280
FEATURE                   Location/Qualifiers
source                    1..280
                          mol_type = protein
                          organism = Canis lupus
SEQUENCE: 96
MDLRGRAFPS  VYRLRVLLML  FYTMARITAE  QEVENLSGLS  TNPEKDIFVV  RENGTTCLMA   60
EFAAKFIVPY  DVWASNYVDL  ITEQADISLT  RGAEVKGHCG  HNESELQVFW  VDRAYALKML  120
```

```
FVKESRNASK GPEATWRLSK VQFVYDSSEK THFKDAVSAG KHTANSHRLS ALVTPAGKSY    180
ECQAQQSISL ASSDPQKTVT MILSAVHIQP FDIISDFVFS EEHKCPVDER EQLEETLPLI    240
LGLILGLVIV VTLAIYHIHH KMTANQVQIP RDRSQYKHMG                          280

SEQ ID NO: 97              moltype = AA   length = 280
FEATURE                    Location/Qualifiers
source                     1..280
                           mol_type = protein
                           organism = Bos taurus
SEQUENCE: 97
MDLRRRALLG VDGLRVLLML FHTVTRIMAE QEVENLSGLS TNPEKDIFVV RENGTTCLMA     60
EFAAKFIVPY DVWASNYVDL ITEQADISLT RGAEVKGHCG HDESELQVFW VDRAYALKML    120
FLKESHNTPK GPEATWKLSK VQFVYDSSEK THFKDAVSAG KHTANSHHLS ALVTPAGKSY    180
ECQAQQTISL ASSDPQKTVT MILSAVHIQP FDIISDFVFS EEHKCPVDER EQLEETLPLI    240
LGLILGLVIV VTLVIYHIHH KMTANQVQIP RDRSQYKHMG                          280

SEQ ID NO: 98              moltype = AA   length = 280
FEATURE                    Location/Qualifiers
source                     1..280
                           mol_type = protein
                           organism = Mus musculus
SEQUENCE: 98
MDLRVRTLLG GDRLRILLMF FHVMVQTVAE QEVENLSGLS TNPEKDIFVV RENGTTCLMA     60
EFAAKFIVPY DVWASNYVDL ITEQAEISLT RGAEVKGHCG HNESELEVFW VDHAYTLRML    120
FVKESHNTSK GPEATWNLNK VHFVYDSSEK THFKAPVKVN KYIASSHHLS ALVTPAGMSY    180
ECQAQQTISL ASSDPQKTVT MILSAVHIQP FDIISDFVFS EEHKCPVDEQ EQLEETLPLI    240
LGLILGLVIV ITLVIYHIHH KMTANQVQIP RDRSQYKHMG                          280

SEQ ID NO: 99              moltype = AA   length = 280
FEATURE                    Location/Qualifiers
source                     1..280
                           mol_type = protein
                           organism = Rattus norvegicus
SEQUENCE: 99
MDLRGRALLG GDRLRILLMF FHAMAQTVAE QEVENLSGLS TNPEKDIFVV RENGTTCLMA     60
EFAAKFIVPY DVWASNYVDL ITEQADISLT RGAEVKGRCG HNESELQVFW VDRAYTLKML    120
FVKESHNTSK GLEATWKLSK VQFVYDSSEK THFKDAVSAG KHTANSHHLS ALVTPAGMSY    180
ECQAQQTISL ASSDPQKTVT MILSAVHIQP FDIISDFVFS EEHKCPVDER EQLEETLPLI    240
LGLILGLVIV ITLVIYHIHH KMTANQVQIP RDRSQYKHMG                          280

SEQ ID NO: 100             moltype = AA   length = 299
FEATURE                    Location/Qualifiers
source                     1..299
                           mol_type = protein
                           organism = Gallus gallus
SEQUENCE: 100
MAAGRLPGLL FLLHAAARLA AEQEVENLSG LSPNPEKDIF VVRENRTTCL MAEFAAKFVV     60
PYDVWASNYV DLITEQADIP LSRGAEMKGK CGTNESELEI SWLERAYTLK LFFLKVRGCP    120
RRLGRGRCAA ALRGPDQPCP PQEGHNTSRG PEAFWRLSRI QFSYDTSERT YFKDAVSPGK    180
HTASSHRLSA LVTPAGKSYE CQAQQTISLI SSDHQKSVQL LLSEVRIQPF DITADFVFSE    240
EHKCPVDQRE QLEETLPLIL GLILGLVIVI TLCVYHIHHK LTANQVQIPR DRSQYKHMG     299

SEQ ID NO: 101             moltype = AA   length = 276
FEATURE                    Location/Qualifiers
source                     1..276
                           mol_type = protein
                           organism = Xenopus tropicalis
SEQUENCE: 101
MDYRACTSAL RMPVLLLLLC TFSCNLAEQE VENLSGLSSN PDKNIFAIRE NGTTCLMAEF     60
SARILVPYEV PSSNEVDWDL EEASIQLPRD TEIRGKCWNN ESELHLSWLD KAYTLKLFFS    120
KEGQDASKSR SWKMSKIQFL YDPSEHTIFK SGARPGRHTA NSHHLSLMVT PAGMSYECEA    180
TQRISLTSTD HQKIVVLYLS EVHLQPFDIK SDFVYSEEYK CPTDQRKQLE ETLPLILGLT    240
LGVAILIIVA VYHIHHKMTA NQVQIPRDRS LYKHMG                              276

SEQ ID NO: 102             moltype = AA   length = 338
FEATURE                    Location/Qualifiers
source                     1..338
                           mol_type = protein
                           organism = Rattus norvegicus
SEQUENCE: 102
MVGRVQPDRK QLPLVLLRLL CLLPTGLPVR SVDFNRGTDN ITVRQGDTAI LRCVVEDKNS     60
KVAWLNRSGI IFAGHDKWSL DPRVELEKRH ALEYSLRIQK VDVYDEGSYT CSVQTQHEPK    120
TSQVYLIVQV PPKISNISSD VTVNEGSNVT LVCMANGRPE PVITWRHLTP LGREFEGEEE    180
YLEILGITRE QSGKYECKAA NEVSSADVKQ VKVTVNYPPT ITESKSNEAT TGRQASLKCE    240
ASAVPAPDFE WYRDDTRINS ANGLEIKSTE GQSSLTVTNV TEEHYGNYTC VAANKLGVTN    300
ASLVLFRPGS VRGINGSISL AVPLWLLAAS LFCLLSKC                            338

SEQ ID NO: 103             moltype = AA   length = 338
FEATURE                    Location/Qualifiers
```

```
source                      1..338
                            mol_type = protein
                            organism = Equus caballus
SEQUENCE: 103
MVGRVQPDRK QLPLVLLRLL CLLPTGLPVR SVDFNRGTDN ITVRQGDTAI LRCVVEDKNS    60
KVAWLNRSGI IFAGHDKWSL DPRVELEKRH SLEYSLRIQK VDVYDEGSYT CSVQTQHEPK   120
TSQVYLIVQV PPKISNISSD VTVNEGSNVT LVCMANGRPE PVITWRHLTP TGREFEGEEE   180
YLEILGITRE QSGKYECKAA NEVSSADVKQ VKVTVNYPPT ITESKSNEAT TGRQASLKCE   240
ASAVPAPDFE WYRDDTRITS ANGLEIKSTE GQSSLTVANV TEEHYGNYTC VAANNLGVTN   300
ASLVLFRPGS VRGINGSISL AVPLWLLAAS LLCLLSKC                          338

SEQ ID NO: 104              moltype = AA  length = 338
FEATURE                     Location/Qualifiers
source                      1..338
                            mol_type = protein
                            organism = Sus scrofa
SEQUENCE: 104
MVARVQPDRK QLPLVLLRLL CLLPTGLPVR SVDFNRGTDN ITVRQGDTAI LRCVVEDKNS    60
KVAWLNRSGI IFAGHDKWSL DPRVELEKRH SLEYSLRIQK VDVYDEGSYT CSVQTQHEPK   120
TSQVYLIVQV PPKISNISSD VTVNEGSNVT LVCMANGRPE PVITWRHLTP TGRELEGEEE   180
YLEILGITRE QSGKYECKAA NEVSSADVKQ VKVTVNYPPT ITESKSNEAT TGRKASLKCE   240
ASAVPAPDFE WYRDDTRINS ANGLEIKSTE GQSSLTVTNV TEEHYGNYTC VAANNLGVTN   300
ASLVLFRPGS VRGINGSISL AVPLWLLAAS LLCLLSKC                          338

SEQ ID NO: 105              moltype = AA  length = 338
FEATURE                     Location/Qualifiers
source                      1..338
                            mol_type = protein
                            organism = Bos taurus
SEQUENCE: 105
MVARVQPDRK QLPLVLLRLL CLLPTGLPVR SVDFNRGTDN ITVRQGDTAI LRCVVEDKNS    60
KVAWLNRSGI IFAGHDKWSL DPRVELEKRH SLEYSLRIQK VDVYDEGSYT CSVQTQHEPK   120
TSQVYLIVQV PPKISNISSD VTVNEGSNVT LVCMANGRPE PVITWRHLTP TGREFEGEEE   180
YLEILGITRE QSGKYECKAA NEVSSADVKQ VKVTVNYPPT ITESKSNEAT TGRKASLKCE   240
ASAVPAPDFE WYRDDTRINS ANGLEIKSTE GQSSLTVTNV TEEHYGNYTC VAANNLGMTN   300
ASLVLFRPGS VRGINGSISL AVPLWLLAAS LLCLLSKC                          338

SEQ ID NO: 106              moltype = AA  length = 417
FEATURE                     Location/Qualifiers
source                      1..417
                            mol_type = protein
                            note = str. PEST
                            organism = Anopheles gambiae
SEQUENCE: 106
MSFAGEAASQ ILNKAEPLFI SRSEAFKFAV GDTITLPCEV ASPGTYVLAW KRGIAILTAG    60
SVKVTPDPRV RLVNGYSLQI RDAVPQDAGD YICQIAMLDP REITHSVEIL VPPKITHVTS   120
GGHLQVRKGS PVRLECSATG NPMPNITWTR KNNLLPNGEE QFTNPVYVIE NMDRHKGGTY   180
ICTANNGVGQ VATSQIILHV LYPPEISVEN PTVYSGEGQE AMLVCIVHGE SQPEVLWHKD   240
TMQIDQTERH VIENRGARHT LIIRKVHPQD FGNYSCIADN QLGKTRKTVT LTGKPKTAVF   300
RSVPNSQWKD KYNISWIVDS HSPIEEFKLY YRQMTFSIGQ LQPLQTDWRD IVLPAFPYSH   360
HYTQGMSYLI RGLEPDQQYE ARVQSRNRYG WSDFSESFLF TTSNTGKWMG QCCTNPG     417

SEQ ID NO: 107              moltype = AA  length = 334
FEATURE                     Location/Qualifiers
source                      1..334
                            mol_type = protein
                            organism = Xenopus tropicalis
SEQUENCE: 107
MRPCLLHSIW MLGFVLCLLS LQGLPVRSGD FNRSTDNITV RQGDTAILRC FVEDRSSRVA    60
WLNRSGIIFA GDDKWSLDPR VELEKRSLLE YSLRIQKVDV SDEGPYTCSV QTKQHTKTTQ   120
VYLIVQVPPK ISNISADITV NEGSNVTLMC IAYGRPEPMI TWRHLTPTAR DFEGEEEFLE   180
IQGITREQSG RYECKAANEV ASADVKQVRV TVNYPPIITE SKSNEATTGK QAILRCEASA   240
VPAPDFEWYK DDTRINSAQG LEIRNTGSRS VLMVANVTEE HYGNYTCVAA NKLGITNTSL   300
YLYIGPGTPI DSATSLAASL WLMANLLFCL FCTC                              334

SEQ ID NO: 108              moltype = AA  length = 338
FEATURE                     Location/Qualifiers
source                      1..338
                            mol_type = protein
                            organism = Canis lupus
SEQUENCE: 108
MLGARRPPRS QLPLVLLRLL CLLPTGLPVR SVDFNRGTDN ITVRQGDTAI LRCVVEDKNS    60
KVAWLNRSGI IFAGHDKWSL DPRVELEKRH SLEYSLRIQK VDVYDEGSYT CSVQTQHEPK   120
TSQVYLIVQV PPKISNISSD VTVNEGSNVT LVCMANGRPE PVITWRHLTP TGREFEGEEE   180
YLEILGITRE QSGKYECKAA NEVSSADVRQ VKVTVNYPPT ITESKSNEAT TGRKASLKCE   240
ASAVPAPDFE WYRDDTRINS ANGLEIKSTE GQSSLTVTNV TEEHYGNYTC VAANNLGVTN   300
ASLVLFRPGS VRGINGSISL AVPLWLLAAS LLCLLSKC                          338

SEQ ID NO: 109              moltype = AA  length = 338
```

```
FEATURE                 Location/Qualifiers
source                  1..338
                        mol_type = protein
                        organism = Monodelphis domestica
SEQUENCE: 109
MVGRVHPDRK QLPLVLLRLL CLLPTGLPVR GVDFTRGTDN ITVRQGDTAI LRCYVEDKSS   60
KVAWLNRSGI IFAGHDKWSL DPRVELEKRT ALEYSLRIQK VDVYDEGSYT CSVQTQHQPK  120
TSQVYLIVQV PPKISNISSD VTVNEGSNVT LVCMANGRPE PVITWRHLTP TGREFEGEEE  180
YLEILGITRE QSGKYECKAA NEVSSADVKQ VKVTVNYPPT ITESKSNEAT TGRQASLKCE  240
ASAVPAPDFE WYRDDTRINS ANGLEIKSIE GQSLLMVTNV TEEHYGNYTC VAANKLGVTN  300
ASLILFRPGS VRGINGSISL AVPLWLLAAS LFCLLSKC                         338

SEQ ID NO: 110          moltype = AA  length = 338
FEATURE                 Location/Qualifiers
source                  1..338
                        mol_type = protein
                        organism = Gallus gallus
SEQUENCE: 110
MVARAQPDRK QLPLVLLRLL CLLPTGLPVR SVDFTRGTDN ITVRQGDTAI LRCFVEDRSS   60
KVAWLNRSGI IFAGEDKWSL DPRVELEKRS PLEYSLRIQK VDVYDEGSYT CSVQTQHHPK  120
TSQVYLIVQV PPKISNISSD ITVNEGSNVT LVCMANGRPE PVITWRHLTP TGKEFEGEEE  180
YLEILGITRE QSGKYECKAA NEVASADVKQ VRVTVNYPPT ITESKSNEAA TGRQALLRCE  240
ASAVPTPDFE WYRDDTRINS ANGLEIKSTG SQSLLMVANV TEEHYGNYTC VAANKLGVTN  300
ASLYLYRPGT GRVDNGSVSL AVPLWLLAAS LLCLLSKC                         338

SEQ ID NO: 111          moltype = AA  length = 335
FEATURE                 Location/Qualifiers
source                  1..335
                        mol_type = protein
                        organism = Taeniopygia guttata
SEQUENCE: 111
MRTYWLHSIW VLGFFLSLFS LQGLPVRSVD FTRGTDNITV RQGDTAILRC YVEDRSSKVA   60
WLNRSGIIFA GEDKWSLDPR VELEKRNPLE YSLRIQKVDV YDEGSYTCSV QTQHHPKTSQ  120
VYLIVQVPPK ISNISSDITV NEGSNVTLVC MANGRPETWR HLTPTGK EFEGEEEYLE    180
ILGITREQSG KYECKAANEV ASADVKQVRV TVNYPPTITE SKSNEAATGR QALLRCEASA  240
VPTPDFEWYR DDTRINSANG LEIKSTGSQS LLMVANVTEE HYGNYTCVAA NKLGVTNASL  300
YLYRPGTGRV DNGSMSLAVP LWLLAASLLC LLSKC                            335

SEQ ID NO: 112          moltype = AA  length = 334
FEATURE                 Location/Qualifiers
source                  1..334
                        mol_type = protein
                        organism = Xenopus tropicalis
SEQUENCE: 112
MRPCLLHSIW MLGFVLCLLS LQGLPVRSGD FNRSTDNITV RQGDTAILRC FVEDRSSRVA   60
WLNRSGIIFA GDDKWSLDPR VELEKRSLLE YSLRIQKVDV SDEGPYTCSV QTKQHTKTTQ  120
VYLIVQVPPK ISNISADITV NEGSNVTLMC IAYGRPEPVI TWRHLTPTAR DPFEGEEEFLE 180
IQGITREQSG RYECKAANEV ASADVKQVRV TVNYPPIITE SKSNEATTGK QAILRCEASA  240
VPAPDFEWYK DDTRINSAQG LEIRNTGSRS VLMVANVTEE HYGNYTCVAA NKLGITNTSL  300
YLYIGPGTPI DSATSLAASL WLMANLLFCL FCTC                             334

SEQ ID NO: 113          moltype = AA  length = 337
FEATURE                 Location/Qualifiers
source                  1..337
                        mol_type = protein
                        organism = Oreochromis niloticus
SEQUENCE: 113
MQVGRKSCWR QLQASFFRLL CLIPTGFPVR SVDMQRATDN ITIRQGDTAI IRCYVDDKVS   60
KVAWLNRSNI IFAGQDKWSL DPRVDLVTKG QLEYSLRIQK VDVYDEGSYT CSIQTKQQPK  120
TSQVYLIVQV PASIYQVSND ITVNEGSNVT LSCLANGRPD PAITWRLLNP SAEPLDGEEY  180
LDIIGIMRTQ AGRYECKASN DVATPDVKYV NVIVNYPPTI KKTQSSETPV GRNGTLRCEV  240
TAVPTPEFEW YRDDKRLANT QSITIQTSGT TTSLTIANIT EEDYGNYTCV ASNRLGVQNA  300
SLFLYRPGTG RDINGSACVS QSLWLLLASF ACLFLKC                          337

SEQ ID NO: 114          moltype = AA  length = 164
FEATURE                 Location/Qualifiers
source                  1..164
                        mol_type = protein
                        organism = Homo sapiens
SEQUENCE: 114
LPSCKEDEYP VGSECCPKCS PGYRVKEACG ELTGTVCEPC PPGTYIAHLN GLSKCLQCQM   60
CDPAMGLRAS RNCSRTENAV CGCSPGHFCI VQDGDHCAAC RAYATSSPGQ RVQKGGTESQ  120
DTLCQNCPPG TFSPNGTLEE CQHQTKCSWL VTKAGAGTSS SHWV                  164

SEQ ID NO: 115          moltype = AA  length = 562
FEATURE                 Location/Qualifiers
source                  1..562
                        mol_type = protein
                        organism = synthetic construct
```

```
SEQUENCE: 115
MAPRSARRPL LLLLLLLLLG LMHCASAAMF MVKNGNGTAC IMANFSAAFS VNYDTKSGPK    60
NMTLDLPSDA TVVLNRSSCG KENTSDPSLV IAFGRGHTLT LNFTRNATRY SVQLMSFVYN   120
LSDTHLFPNA SSKEIKTVES ITDIRADIDK KYRCVSGTQV HMNNVTVTLH DATIQAYLSN   180
SSFSRGETRC EQDRPSPTTA PPAPPSPSPS PVPKSPSVDK YNVSGTNGTC LLASMGLQLN   240
LTYERKDNTT VTRLLNINPN KTSASGSCGA HLVTLELHSE GTTVLLFQFG MNASSSRFFL   300
QGIQLNTILP DARDPAFKAA NGSLRALQAT VGNSYKCNAE EHVRVTKAFS VNIFKVWVQA   360
FKVEGGQFGS VEECLLDENS LEMGAPTLPP AWQPFLKDHR ISTFKNWPFL EGCACTPERM   420
AEAGFIHCPT ENEPDLAQCF FCFKELEGWE PDDDPIEEHK KHSSGCAFLS VKKQFEELTL   480
GEFLKLDRER AKNKIAKETN NKKKEFEETA KKVRRAIEQL AAMDEFTLIP IAVGGALAGL   540
VLIVLIAYLV GRKRSHAGYQ TI                                          562

SEQ ID NO: 116          moltype = AA  length = 558
FEATURE                 Location/Qualifiers
source                  1..558
                        mol_type = protein
                        organism = synthetic construct
SEQUENCE: 116
MAPRSARRPL LLLLLLLLLG LMHCASAMGA PTLPPAWQPF LKDHRISTFK NWPFLEGCAC    60
TPERMAEAGF IHCPTENEPD LAQCFFCFKE LEGWEPDDDP IEEHKHSSG CAFLSVKKQF   120
EELTLGEFLK LDRERAKNKI AKETNNKKKE FEETAKKVRR AIEQLAAMDA MFMVKNGNGT   180
ACIMANFSAA FSVNYDTKSG PKNMTLDLPS DATVVLNRSS CGKENTSDPS LVIAFGRGHT   240
LTLNFTRNAT RYSVQLMSFV YNLSDTHLFP NASSKEIKTV ESITDIRADI DKKYRCVSGT   300
QVHMNNVTVT LHDATIQAYL SNSSFSRGET RCEQDRPSPT TAPPAPPSPS PSPVPKSPSV   360
DKYNVSGTNG TCLLASMGLQ LNLTYERKDN TTVTRLLNIN PNKTSASGSC GAHLVTLELH   420
SEGTTVLLFQ FGMNASSSRF FLQGIQLNTI LPDARDPAFK AANGSLRALQ ATVGNSYKCN   480
AEEHVRVTKA FSVNIFKVWV QAFKVEGGQF GSVEECLLDE NSMLIPIAVG GALAGLVLIV   540
LIAYLVGRKR SHAGYQTI                                                558

SEQ ID NO: 117          moltype = AA  length = 370
FEATURE                 Location/Qualifiers
source                  1..370
                        mol_type = protein
                        organism = synthetic construct
SEQUENCE: 117
MAPRSARRPL LLLLLLLLLG LMHCASAMGA PTLPPAWQPF LKDHRISTFK NWPFLEGCAC    60
TPERMAEAGF IHCPTENEPD LAQCFFCFKE LEGWEPDDDP IEEHKHSSG CAFLSVKKQF   120
EELTLGEFLK LDRERAKNKI AKETNNKKKE FEETAKKVRR AIEQLAAMDA MFMVKNGNGT   180
ACIMANFSAA FSVNYDTKSG PKNMTLDLPS DATVVLNRSS CGKENTSDPS LVIAFGRGHT   240
LTLNFTRNAT RYSVQLMSFV YNLSDTHLFP NASSKEIKTV ESITDIRADI DKKYRCVSGT   300
QVHMNNVTVT LHDATIQAYL SNSSFSRGET RCEQDLIPIA VGGALAGLVL IVLIAYLVGR   360
KRSHAGYQTI                                                         370

SEQ ID NO: 118          moltype = AA  length = 375
FEATURE                 Location/Qualifiers
source                  1..375
                        mol_type = protein
                        organism = synthetic construct
SEQUENCE: 118
MAPRSARRPL LLLLLLLLLG LMHCASAAMF MVKNGNGTAC IMANFSAAFS VNYDTKSGPK    60
NMTLDLPSDA TVVLNRSSCG KENTSDPSLV IAFGRGHTLT LNFTRNATRY SVQLMSFVYN   120
LSDTHLFPNA SSKEIKTVES ITDIRADIDK KYRCVSGTQV HMNNVTVTLH DATIQAYLSN   180
SSFSRGETRC EQDLEMGAPT LPPAWQPFLK DHRISTFKNW PFLEGCACTP ERMAEAGFIH   240
CPTENEPDLA QCFFCFKELE GWEPDDDPIE EHKKHSSGCA FLSVKKQFEE LTLGEFLKLD   300
RERAKNKIAK ETNNKKKEFE ETAKKVRRAI EQLAAMDEFT LIPIAVGGAL AGLVLIVLIA   360
YLVGRKRSHA GYQTI                                                   375

SEQ ID NO: 119          moltype = AA  length = 527
FEATURE                 Location/Qualifiers
source                  1..527
                        mol_type = protein
                        organism = synthetic construct
SEQUENCE: 119
MAPRSARRPL LLLLLLLLLG LMHCASAAMF MVKNGNGTAC IMANFSAAFS VNYDTKSGPK    60
NMTLDLPSDA TVVLNRSSCG KENTSDPSLV IAFGRGHTLT LNFTRNATRY SVQLMSFVYN   120
LSDTHLFPNA SSKEIKTVES ITDIRADIDK KYRCVSGTQV HMNNVTVTLH DATIQAYLSN   180
SSFSRGETRC EQDLEMGAPT LPPAWQPFLK DHRISTFKNW PFLEGCACTP ERMAEAGFIH   240
CPTENEPDLA QCFFCFKELE GWEPDDDPIE EHKKHSSGCA FLSVKKQFEE LTLGEFLKLD   300
RERAKNKIAK ETNNKKKEFE ETAKKVRRAI EQLAAMDEFT CLLASMGLQL NLTYERKDNT   360
TVTRLLNINP NKTSASGSCG AHLVTLELHS EGTTVLLFQF GMNASSSRFF LQGIQLNTIL   420
PDARDPAFKA ANGSLRALQA TVGNSYKCNA EEHVRVTKAF SVNIFKVWVQ AFKVEGGQFG   480
SVEECLLDEN SMLIPIAVGG ALAGLVLIVL IAYLVGRKRS HAGYQTI                527
```

LAMP CONSTRUCTS

CROSS-REFERENCE TO RELATED APPLICATIONS

This application is a continuation of U.S. patent application Ser. No. 17/514,857, filed Oct. 29, 2021, which is a divisional of U.S. patent application Ser. No. 16/607,082, filed Oct. 21, 2019, now U.S. Pat. No. 11,203,629, which is a national stage application of International Patent Application No. PCT/US2018/028753, filed Apr. 22, 2018, which claims priority to U.S. Provisional Application Nos. 62/549,033 filed Aug. 23, 2017, 62/549,119, filed Aug. 23, 2017, and 62/488,741, filed Apr. 22, 2017, each of which is incorporated in their entirety by reference herein.

SEQUENCE LISTING

The present application contains a Sequence Listing which has been submitted electronically in XML format. Said XML copy, created on Aug. 22, 2023, is named "01305-0007-02US-T1-ST26.xml" and is 148,153 bytes in size. The information in the electronic format of the sequence listing is incorporated herein by reference in its entirety.

BACKGROUND OF THE INVENTION

Field of the Invention

The invention relates to improved LAMP Constructs and their use in treating subjects suffering from infectious disease, diabetes, allergies, hyperproliferative disorders and/or cancer. Additionally, improved LAMP constructs described herein can be used to generate antibodies in non-human vertebrates preferably where the genome of the non-human vertebrates comprise at least partially human immunoglobulin regions and/or humanized immunoglobulin regions. Prime boost protocols utilizing the LAMP improved Constructs described herein are also described.

Discussion of the Related Art

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

DNA vaccines are new and promising candidates for the development of both prophylactic and therapeutic vaccines. They are proven to be safe and the lack of immune responses to a vector backbone may be a definitive advantage if repetitive cycles of vaccination are required to achieve clinical benefits. However, one perceived disadvantage of conventional DNA vaccines is their low immunogenicity in humans. A key limiting step in the immunogenicity of epitope-based DNA vaccines may be the access of epitopes to the MHCII presentation pathway to T cells, which is likely a stochastic process in the case of a vaccine without targeting technology.

U.S. Pat. No. 5,633,234 describes chimeric proteins comprising an antigenic domain of modified influenza hemagglutinin (HA) and a cytoplasmic endosomal/lysosomal targeting signal which effectively target antigens to that compartment. The antigenic domain was processed and peptides from it presented on the cell surface in association with major histocompatibility (MHC) class II molecules. The cytoplasmic tail of LAMP-1 was used to form the endosomal/lysosomal targeting domain of the chimeric protein.

U.S. Pat. No. 8,318,173 extended these initial observations to describe chimeric proteins (and the corresponding DNAs that encode these proteins) comprising the HIV-1 Gag protein inserted between the full lumenal domain and a transmembrane domain of LAMP-1. This construct was introduced into dendritic cells which were then reported to target the MHC II pathway.

This approach has proved useful in increasing cellular and humoral responses to several virus antigens, human papillomavirus E7, dengue virus membrane protein, HIV-1 gp160 membrane protein, HIV-1 P55 Gag, West Nile membrane protein, hepatitis C virus NS3 protein and cytomegalovirus pp 65 (see, e.g., Bonini, et al., J. Immunol. 166: 5250-5257, 2001). The enhanced immune response can be attributed to co-localization of LAMP with MHC II and the more efficient processing and delivery of antigenic peptides. In addition, LAMP-targeting is reported to result in the presentation of an increased number of immunogenic epitopes, thus inducing a qualitatively broadened immune response compared to untargeted antigen. For example, Fernandes et al., 2000, Eur. J. Immunol. 30(8): 2333-43, demonstrated an increase in the number of presented peptides of a LAMP-trafficked OVA antigen encoded in a vaccinia vector. Of 12 peptides generated from exogenously supplied OVA, 9 were presented by an OVA/LAMP chimera, as compared to only 2 by the construct without LAMP.

While it has been determined that the cytoplasmic domain of LAMP is necessary (in conjunction with a signal sequence and transmembrane domain), it is not always sufficient for endosomal/lysosomal trafficking of all antigens. Instead, the full lumenal domain of LAMP has been shown to be also required for the trafficking of proteins to the lysosomal vesicular pathway.

However, even with the presence of the complete lumenal domain and the complete transmembrane/cytoplasmic tail of LAMP ("complete LAMP Constructs"), it has increasingly been found that the efficacy of a particular antigen to raise an immune response is highly dependent on the particular sequence used in these constructs. In fact, different antigenic fragments of the same protein when inserted into the complete LAMP constructs have been found to not elicit the same immune response. Sometimes the antigen fragment generates an immune response and other times it does not. These observations make the ability to predict ahead of time which particular antigenic sequence from a protein of interest will raise an immune response difficult with the complete LAMP Constructs.

Moreover, in generating the complete LAMP Constructs, it has been repeatedly observed that the full lumenal domain is required to properly express and process an antigen. For example, in Godinho et al., PLoS ONE 9(6): 9(6): e99887. doi:10.1371/journal.pone.0099887, the authors reported that the complete and intact lumenal domain was the necessary minimal region needed to target an antigen to the lysosomes and that fragments of the lumenal domain did not work. See, id. at page 6.

Specifically, the Godinho authors showed that by completely removing the first luminal domain and some of the second luminal domain (i.e., T1-Lum/gag construct), both protein expression and antibody response is decreased. Similarly, removing 25% of first luminal domain but having an intact second luminal domain (i.e., T2-lum/gag), both protein expression and antibody response comparatively increased but still less than the results obtained with the complete LAMP construct.

Moreover, the authors acknowledged that the ability to raise an immune response is dependent upon the particular antigen and the epitopes used in these complete LAMP Constructs. For example, on page 9, column 2, the authors state "accordingly, previous studies demonstrated that DNA vaccines that generate Gag secreted as VLP, or in a soluble form, induce different levels of T and B cell activation, which were also different from the response induced by cytoplasmic Gag." However, insertion of an antigenic sequence between the full lumenal domain of LAMP and the full transmembrane/cytoplasmic domain of LAMP as has been described in the literature results in such large polynucleotide sequences that it becomes either too costly to produce at commercial levels or impractical from a scientific perspective.

Thus, there is a need to design new and improved LAMP Constructs that can be used as vaccines to effectively treat, for example, allergies, infectious disease, diabetes, hyperproliferative disorders and/or cancer. Moreover, once improved, these new LAMP Constructs can be used to generate antibodies.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

It is an object of this invention to provide novel constructs ("improved LAMP Constructs") comprising specific fragments and/or variants of LAMP domains that effectively present an antigen(s) of interest to the immune system to generate an enhanced immune response. These improved LAMP Constructs effectively direct the antigens to the lysosomal/endosomal compartment where they are processed and presented to major histocompatibility complex (MHC) class II molecules so that helper T cells are preferentially stimulated and/or antibodies are generated.

The improved LAMP Constructs and methods described herein may elicit an immune response in a subject. The immune response may be an immune response to the epitopes of the antigens in the improved LAMP Construct (e.g., vaccine). Vaccines arm the immune system of the subject such that the immune system may detect and destroy that which contains the antigens of the vaccines in the subject. The improved LAMP Constructs and methods described herein may elicit a Th1 immune response in the subject. Th1 immune responses may include secretion of inflammatory cytokines (e.g., IFNγ, TNFα) by a subset of immune cells (e.g., antigen specific T-cells). In some cases, the inflammatory cytokines activate another subtype of immune cells (e.g., cytotoxic T-cells) which may destroy that which contains the antigen in the subject.

In some cases, the epitopes and/or antigens used in the improved LAMP Constructs and methods described herein may be recognized by the immune system of a subject to elicit a Th1 immune response and release Type I cytokines. The Th1 response may be initiated by the interaction between the epitope and the T-cell, more specifically, the major histocompatibility complex (MHC) expressed by the T-cell. For example, high affinity binding of an epitope to an MHC receptor may stimulate a Th1 response. MHC receptors may be at least one of a plurality of types of MHC receptors. The MHC receptors engaged on a T-cell may vary across individuals in a population.

In some cases, the immune response is a Type 1 immune response. In some cases, the immune response is characterized by a ratio of Type I cytokine production to Type II cytokine production that is greater than 1. In some cases, the immune response is characterized by a ratio of Type I cytokine production to Type II cytokine production that is less than 1. In some cases, the immune response is characterized by a ratio of IFNγ production to IL-10 production that is greater than 1. In some cases, the immune response is characterized by a ratio of IFNγ production to IL-10 production that is less than 1.

It is yet another object of this invention to provide improved methods of treatment for cancer and/or hyperproliferative disorders by eliciting an anti-tumor immune response through stimulation of helper T cells.

The improved LAMP Constructs described herein can also be used to treat allergies, such as for example, food allergies (e.g., peanut allergens, such as Ara H1, H2 and/or H3), or environmental allergens, such as for example pollen (tree pollen, such as for example CRY J1 or CRY J2), dog dander, cat saliva, or dust mites. Other diseases and/or disorders that can be treated using the improved LAMP Constructs described herein include, for example, infectious disease and diabetes.

The invention further provides a nucleic acid molecule encoding any of the improved LAMP Constructs described herein. The invention also provides an improved LAMP Construct comprising an antigen to generate antibodies. The improved LAMP Construct can comprise a nucleic acid wherein the nucleic acid molecule is operably linked to an expression control sequence. In one preferred aspect, the improved LAMP Construct is a vaccine vector, suitable for vaccinating a patient. In another aspect, the invention provides a delivery vehicle comprising the improved LAMP Construct for facilitating the introduction of the nucleic acid molecule encoding the antigen into a cell. The delivery vehicle may be lipid-based (e.g., a liposome formulation), viral-based (e.g., comprising viral proteins encapsulating the nucleic acid molecule), or cell-based.

In preferred embodiments, the invention provides an injectable composition comprising an improved LAMP Construct comprising an antigen of interest for eliciting an immune response (e.g., generation of antibodies) in a mammal to an antigen. In preferred embodiments, this vaccine generates a preferential Th1 response to a Th2 response. The improved LAMP Constructs comprise at least one epitope of an antigen.

The invention also provides a cell comprising any of the improved LAMP Constructs described herein which can be used to generate an immune response. In one aspect, the cell is an antigen presenting cell. The antigen presenting cell may be a professional antigen presenting cell (e.g., a dendritic cell, macrophage, B cell, and the like) or an engineered antigen presenting cell (e.g., a non-professional antigen presenting cell engineered to express molecules required for antigen presentation, such as MHC class II molecules). The molecules required for antigen presentation may be derived from other cells, e.g., naturally occurring, or may themselves be engineered (e.g. mutated or modified to express desired properties, such as higher or lower affinity for an antigenic epitope). In one aspect, the antigen presenting cell does not express any co-stimulatory signals and the antigen is an auto-antigen.

The invention additionally provides a kit comprising a plurality of cells comprising any of the improved LAMP Constructs described herein. At least two of the cells express different MHC class II molecules, and each cell comprises the same LAMP Construct. In one aspect, a kit is provided comprising an improved LAMP Construct and a cell for receiving the vector.

The invention also provides a transgenic animal comprising at least one of the cells and/or at least one of the improved LAMP Constructs described herein. The invention also provides a transgenic animal comprising at least one of the cells described herein.

The invention further provides a method for generating an immune response in an animal (e.g., a human or a non-human vertebrate) to an antigen, comprising: administering to the animal a cell as described above, wherein the cell expresses, or can be induced to express, the improved LAMP Construct in the animal. In one aspect, the cell comprises an MHC class II molecule compatible with MHC proteins of the animal, such that the animal does not generate an immune response against the MHC class II molecule. In one preferred aspect, the animal is a human.

In one further aspect, the invention provides a method for eliciting an immune response to an antigen, comprising administering to an animal, such as a human or a non-human vertebrate, any of the improved LAMP Constructs described herein. Preferably, the improved LAMP Construct is infectious for a cell of the animal. For example, the improved LAMP Construct may be a viral vector, such as a vaccinia improved LAMP Construct.

Prime boost protocols are also contemplated. For example, the invention further provides a method for generating an immune response in an animal to an antigen, comprising priming the animal with an improved LAMP Construct comprising an antigen as described herein followed by at least one boosting of the animal with the antigen or a related antigen (e.g., a second antigen derived from the same or highly similar protein sequence). Mixtures of antigens can be used in either or both the priming and the boosting step. Use of an improved LAMP Construct for the prime step followed by an antigen boost step has been shown to significantly produce higher titers, indicating the power of LAMP in enhancing antibody response.

In a further aspect, a cell is obtained from a patient, the improved LAMP Construct described herein is introduced into the cell and the cell or progeny of the cell is reintroduced into the patient. In one aspect, the cell is a stem cell-capable of differentiating into an antigen presenting cell. Treatments of human patients as well as veterinary use are specifically contemplated.

The present invention also comprises methods of generating antibodies in a non-human vertebrate wherein the non-human vertebrate is injected with an improved LAMP Construct comprising an antigen of interest as described herein. The antigen of interest is then efficiently presented to the immune system with the help of LAMP in the non-human vertebrate to raise antibodies against the antigen.

Specifically, by combining presentation of the antigen of interest with LAMP, the antigen is then effectively transported to the cytoplasmic endosomal/lysosomal compartments, where the antigen can be processed and peptides from it presented on the cell surface in association with major histocompatibility (MHC) class II molecules.

These generated antibodies can be isolated from the blood of the vertebrate (as polyclonals) and then further isolated to generate monoclonal antibodies using standard techniques.

In preferred embodiments, the genome of the non-human vertebrate comprises an introduced partially human immunoglobulin region, said introduced region comprising human immunoglobulin variable region locus coding sequences and non-coding sequences based on the endogenous immunoglobulin variable region locus of the non-human vertebrate. Preferably, non-human vertebrate's genome has at least part or all of the endogenous immunoglobulin region removed.

In further preferred embodiments, the production of human monoclonal antibodies in the non-human vertebrate requires that the host have at least one locus that will express human heavy chain immunoglobulin proteins and one locus that will express human light chain immunoglobulin proteins.

In some aspects, the partially human immunoglobulin variable region locus comprises human $V_H$ coding sequences and non-coding $V_H$ sequences based on the endogenous $V_H$ region of the non-human vertebrate. In these aspects, the partially human immunoglobulin variable region locus further comprises human D and J gene coding sequences and non-coding D and J gene sequences based on the endogenous genome of the non-human vertebrate host.

In other aspects, the immunoglobulin region comprises an introduced region comprising human $V_L$ coding sequences and non-coding $V_L$ sequences based on the endogenous $V_L$ region of the non-human vertebrate. More preferably, the introduced partially human immunoglobulin region comprising human $V_L$ coding sequences further comprises human J gene coding sequences and non-coding J gene sequences based on the endogenous genome of the non-human vertebrate host.

In certain aspects, the vertebrate is a mammal, and preferably the mammal is a rodent, e.g., a mouse or rat. In other aspects, the vertebrate is avian, e.g., a chicken. Other non-human vertebrates include rabbits, llamas, camels, a cow, a guinea pig, a hamster, a dog, a cat, a horse, a non-human primate, a simian (e.g. a monkey or ape), a monkey (e.g. marmoset, baboon, rhesus macaque), or an ape (e.g. gorilla, chimpanzee, orangutan, gibbon).

In further embodiments, the partially human immunoglobulin region comprises human $V_H$ gene coding regions, and further comprises i) human D and J gene coding sequences and ii) non-coding D and J gene and pre-DJ sequences based on the endogenous genome of the non-human vertebrate host. In other aspects, the $V_H$ gene coding regions derive (at least partially) from other sources—e.g., they could be rationally or otherwise designed sequences, sequences that are a combination of human and other designed sequences, or sequences from other species, such as nonhuman primates.

In yet another specific aspect, the partially human immunoglobulin region comprises human $V_L$ gene coding regions, and further comprises i) human J gene coding sequences and ii) non-coding J gene sequences based on the endogenous genome of the non-human vertebrate host. In a specific aspect, the partially human immunoglobulin region comprises human $V_H$ coding regions, human D and J gene coding sequences, and non-coding D and J gene and pre-DJ sequences based on the endogenous genome of the non-human vertebrate host.

The methods described herein can be used in the production and/or optimization of antibodies, including fully human antibodies, humanized antibodies, chimeric antibodies, for diagnostic and therapeutic uses. Hybridomas producing such antibodies are also a further object of the invention.

These and other aspects, objects and features are described in more detail below.

BRIEF DESCRIPTION OF THE FIGURES

The objects and features of the invention can be better understood with reference to the following detailed description and accompanying drawings.

FIG. 3 provides alignment of LAMP-1 proteins found in other species as compared to human LAMP-1 (SEQ ID NO:1). The equivalent domains of these other species can be used to generate the improved LAMP Constructs described herein and are readily identifiable by comparing the domains identified for human LAMP-1 in FIG. 2 and FIG. 3 to the alignments shown in FIG. 3.

FIG. 4 provides alignment of LAMP-2 proteins found in other species as compared to human LAMP-2 (SEQ ID NO:2). The equivalent domains of these other species can be used to generate the improved LAMP Constructs described herein and are readily identifiable by comparing the domains identified for human LAMP-2 in FIG. 2 and FIG. 4 to the alignments shown in FIG. 4.

FIG. 5 provides alignment of LAMP-3 proteins found in other species as compared to human LAMP-3 (SEQ ID NO:3). The equivalent domains of these other species can be used to generate the improved LAMP Constructs described herein and are readily identifiable by comparing the domains identified for human LAMP-3 in FIG. 2 and FIG. 5 to the alignments shown in FIG. 5.

FIG. 6 provides alignment of LIMP-2 proteins found in other species as compared to human LIMP-2 (SEQ ID NO:4). The equivalent domains of these other species can be used to generate the improved LAMP Constructs described herein and are readily identifiable by comparing the domains identified for human LIMP-2 in FIG. 2 and FIG. 6 to the alignments shown in FIG. 6.

FIG. 7 provides alignment of LIMBIC proteins found in other species as compared to human LIMBIC (SEQ ID NO:67). The equivalent domains of these other species can be used to generate the improved LAMP Constructs described herein and are readily identifiable by comparing the domains identified for human LIMBIC in FIG. 2 and FIG. 7 to the alignments shown in FIG. 7.

FIG. 8 provides alignment of Endolyn proteins found in other species as compared to human Endolyn (SEQ ID NO:5). The equivalent domains of these other species can be used to generate the improved LAMP Constructs described herein and are readily identifiable by comparing the domains identified for human Endolyn in FIG. 2 and FIG. 8 to the alignments shown in FIG. 8.

FIG. 9 provides alignment of Macrosailin proteins found in other species as compared to human Macrosailin (SEQ ID NO:80). The equivalent domains of these other species can be used to generate the improved LAMP Constructs described herein and are readily identifiable by comparing the domains identified for human Macrosailin in FIG. 2 and FIG. 9 to the alignments shown in FIG. 9.

FIG. 10 provides alignment of LAMP-5 proteins found in other species as compared to human LAMP-5 (SEQ ID NO:93). The equivalent domains of these other species can be used to generate the improved LAMP Constructs described herein and are readily identifiable by comparing the domains identified for human LAMP-5 in FIG. 2 and FIG. 10 to the alignments shown in FIG. 10.

FIG. 11 shows results obtained when mice were immunized with HVEM-LAMP, HVEM, or LAMP on day 0, 7, and 14. On day 28, mice were bled and serum samples were isolated. HVEM specific IgG was examined by ELISA. Data represent geometric mean of antibody titers±geometric SD, n=6. **p value<0.01

FIG. 12 shows results obtained when mice were immunized with HVEM-LAMP, HVEM, or LAMP on day 0, 7, and 14. On day 35, mice were boosted with 5 μg HVEM protein in the presence of alum adjuvant. Mice were bled on day 49 and serum samples were isolated. HVEM specific IgG was examined by ELISA. Data represent geometric mean of antibody titers±geometric SD, n=6. *p value<0.001; **p value<0.0001.

FIG. 19 provides the amino acid sequence of each LAMP construct tested. The signal sequence of each construct is depicted as lower case and underlined letters; the Survivin sequence is depicted in capitalized, white letters, shaded in black; the luminal domain is depicted in italics and capitalized letters and the transmembrane/cytolosolic domain is depicted in capitalized letter and shaded in grey, and in ILC-4, the second homology domain is bolded. Additional amino acids (LE and EF) may be included as part of the cloning linkers.

DETAILED DESCRIPTION

Figure 1:
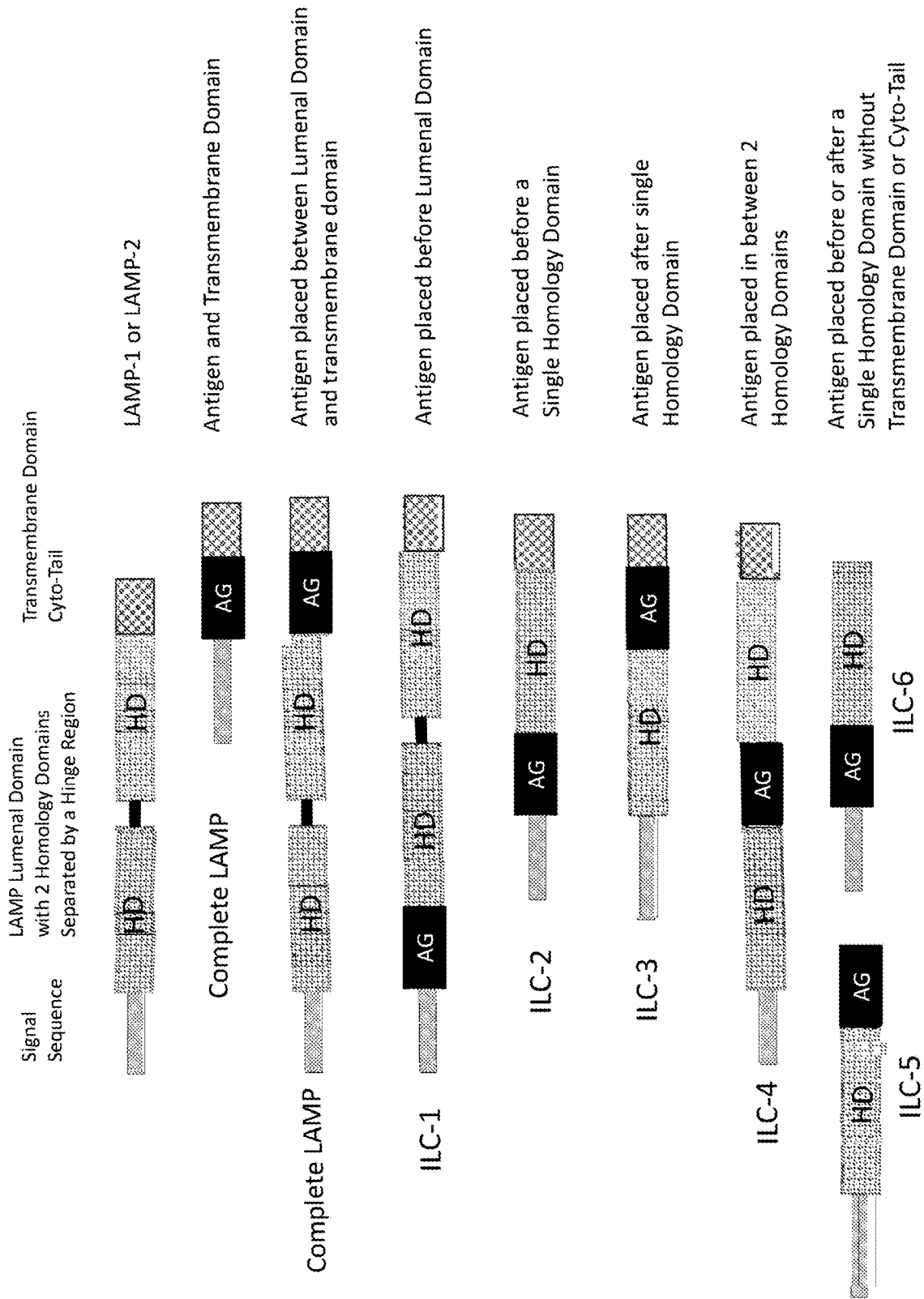
FIG. 1 illustrates the general scheme of different types of improved LAMP Constructs (identified as ILC-1, ILC-2, ILC-3, ILC-4, ILC-5 and ILC-6) that can be used as described herein.

The invention provides improved LAMP Constructs and nucleic acids encoding these which can be used to generate vaccines and/or used to raise antibodies. The improved LAMP Constructs can be used to modulate or enhance an immune response. In one preferred aspect, the invention provides a method for treating a patient with an allergy, infectious disease, diabetes, cancer or a hyperproliferative disorder by providing an improved LAMP Construct described herein. The improved LAMP Constructs can also be used to raise antibodies in non-human vertebrates, and in preferably, non-human mammals.

Definitions

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the improved LAMP Constructs and methods include the recited elements, but do not exclude other elements. "Consisting essentially of", when used to define improved LAMP Constructs and methods, shall mean excluding other elements of any essential significance to the combination. Thus, an improved LAMP Construct consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the improved LAMP Constructs of this invention. Embodiments defined by each of these transition terms are within the scope of this invention.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term 'about' means within an acceptable error range for the particular value, such as ±1-20%, preferably ±1-10% and more preferably ±1-5%.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

As used herein, "the lysosomal/endosomal compartment" refers to membrane-bound acidic vacuoles containing LAMP molecules in the membrane, hydrolytic enzymes that function in antigen processing, and MHC class II molecules for antigen recognition and presentation. This compartment functions as a site for degradation of foreign materials internalized from the cell surface by any of a variety of mechanisms including endocytosis, phagocytosis and pinocytosis, and of intracellular material delivered to this compartment by specialized autolytic phenomena (de Duve, Eur. J. Biochem. 137: 391, 1983). The term "endosome" as used herein and in the claims encompasses a lysosome.

As used herein, a "lysosome-related organelle" refers to any organelle which comprises lysosymes and includes, but is not limited to, MIIC, CIIV, melanosomes, secretory granules, lytic granules, platelet-dense granules, basophil granules, Birbeck granules, phagolysosomes, secretory lysosomes, and the like. Preferably, such an organelle lacks mannose 6-phosphate receptors and comprises LAMP, but may or may not comprise an MHC class II molecule. For reviews, see, e.g., Blott and Griffiths, Nature Reviews, Molecular Cell Biology, 2002; Dell'Angelica, et al., The FASEB Journal 14: 1265-1278, 2000.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

As used herein, the term "peptide" refers to a compound of two or more subunit amino acids, amino acid analogs, or peptidomimetics. The subunits may be linked by peptide bonds or by other bonds (e.g., as esters, ethers, and the like).

As used herein, the term "amino acid" refers to either natural and/or unnatural or synthetic amino acids, including glycine and both D or L optical isomers, and amino acid analogs and peptidomimetics. A peptide of three or more amino acids is commonly called an oligopeptide if the peptide chain is short. If the peptide chain is long (e.g., greater than about 10 amino acids), the peptide is commonly called a polypeptide or a protein. While the term "protein" encompasses the term "polypeptide", a "polypeptide" may be a less than full-length protein.

As used herein a "LAMP polypeptide" refers to the mammalian lysosomal associated membrane proteins human LAMP-1, human LAMP-2, human LAMP-3, human LIMP-2, human Endolyn, human LIMBIC, human LAMP-5, or human Macrosailin as described herein, as well as orthologs (such as, for example, the LAMP proteins shown in FIGS. 3-10), and allelic variants.

As used herein, "expression" refers to the process by which polynucleotides are transcribed into mRNA and/or translated into peptides, polypeptides, or proteins. If the polynucleotide is derived from genomic DNA, expression may include splicing of the mRNA transcribed from the genomic DNA.

As used herein, "under transcriptional control" or "operably linked" refers to expression (e.g., transcription or translation) of a polynucleotide sequence which is controlled by an appropriate juxtaposition of an expression control element and a coding sequence. In one aspect, a DNA sequence is "operatively linked" to an expression control sequence when the expression control sequence controls and regulates the transcription of that DNA sequence.

As used herein, "coding sequence" is a sequence which is transcribed and translated into a polypeptide when placed under the control of appropriate expression control sequences. The boundaries of a coding sequence are determined by a start codon at the 5' (amino) terminus and a translation stop codon at the 3' (carboxyl) terminus. A coding sequence can include, but is not limited to, a prokaryotic sequence, cDNA from eukaryotic mRNA, a genomic DNA sequence from eukaryotic (e.g., mammalian) DNA, and even synthetic DNA sequences. A polyadenylation signal and transcription termination sequence will usually be located 3' to the coding sequence.

As used herein, two coding sequences "correspond" to each other if the sequences or their complementary sequences encode the same amino acid sequences.

As used herein, "signal sequence" denotes the endoplasmic reticulum translocation sequence. This sequence encodes a signal peptide that communicates to a cell to direct a polypeptide to which it is linked (e.g., via a chemical bond) to an endoplasmic reticulum vesicular compartment, to enter an exocytic/endocytic organelle, to be delivered either to a cellular vesicular compartment, the cell surface or to secrete the polypeptide. This signal sequence is sometimes clipped off by the cell in the maturation of a protein. Signal sequences can be found associated with a variety of proteins native to prokaryotes and eukaryotes.

As used herein, "trafficking" denotes movement or progression of the polypeptide encoded by the improved LAMP Construct through cellular organelles or compartments in the pathway from the rough endoplasmic reticulum to the endosomal/lysosomal compartment or related organelles where antigen processing and binding to MHC II occurs.

As used herein, an "improved LAMP Construct" and an "improved LAMP Construct comprising an antigen" and an "improved LAMP Construct comprising an antigen of interest" are used interchangeably. The different arrangements of the improved LAMP Constructs are illustrated in FIG. 1 as ILC1-ILC6. Moreover, the use of an "improved LAMP Construct" encompasses both the polynucleotide sequence of the improved LAMP Construct as well as the protein encoded by the polynucleotide sequence of the improved LAMP Construct.

As used herein, an "improved LAMP Construct delivery vehicle" is defined as any molecule or group of molecules or macromolecules that can carry an improved LAMP Construct into a host cell (e.g., such as genes or gene fragments, antisense molecules, ribozymes, aptamers, and the like) and which occurs in association with an improved LAMP Construct as described herein.

As used herein, "improved LAMP Construct delivery," or "improved LAMP Construct transfer," refers to the introduction of the improved LAMP Construct into a host cell, irrespective of the method used for the introduction. The introduced improved LAMP Constructs may be stably or transiently maintained in the host cell. Stable maintenance typically requires that the introduced improved LAMP Construct either contains an origin of replication compatible with the host cell or integrates into a replicon of the host cell such as an extrachromosomal replicon (e.g., a plasmid) or a nuclear or mitochondrial chromosome.

As used herein, a "viral improved LAMP Construct" refers to a virus or viral particle that comprises the improved LAMP Construct to be delivered into a host cell, either in vivo, ex vivo or in vitro. Examples of viral improved LAMP Constructs include, but are not limited to, adenovirus vectors, adeno-associated virus vectors, retroviral vectors, and the like. In aspects where gene transfer is mediated by an adenoviral vector, an improved LAMP Construct includes the adenovirus genome or part thereof, and a selected, non-adenoviral gene, in association with adenoviral capsid proteins.

As used herein, "adenoviral-mediated gene transfer" or "adenoviral transduction" refers to the process by which an improved LAMP Construct is transferred into a host cell by virtue of the adenovirus entering the cell. Preferably, the improved LAMP Construct is able to replicate and/or integrate and be transcribed within the cell.

As used herein, "adenovirus particles" are individual adenovirus virions comprised of an external capsid and an improved LAMP Construct, where the capsid is further comprised of adenovirus envelope proteins. The adenovirus envelope proteins may be modified to comprise a fusion polypeptide which contains a polypeptide ligand covalently attached to the viral protein, e.g., for targeting the adenoviral particle to a particular cell and/or tissue type.

As used herein, the term "administering" or "immunizing" or "injecting" an improved LAMP Construct refers to transducing, transfecting, microinjecting, electroporating, or shooting the cell with the improved LAMP Construct. In some aspects, improved LAMP Constructs are introduced into a target cell by contacting the target cell with a delivery cell (e.g., by cell fusion or by lysing the delivery cell when it is in proximity to the target cell).

As used herein, the phrase "prime boost" describes the use of an improved LAMP Construct described herein used to prime a T-cell response followed by the use of a second improved LAMP Construct comprising an antigen, a DNA vaccine comprising an antigen or a recombinant antigen to boost the response. These heterologous prime-boost immunizations elicit immune responses of greater height and breadth than can be achieved by priming and boosting with the same vector. The priming with an improved LAMP Construct comprising an antigen initiates memory cells; the boost step expands the memory response. Preferably, use of the two different agents do not raise responses against each other and thus do not interfere with each other's activity. Mixtures of antigens are specifically contemplated in the prime and/or boost step. Boosting can occur one or multiple times.

As used herein, "hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

As used herein, a polynucleotide or polynucleotide region (or a polypeptide or polypeptide region) which has a certain percentage (for example, at least about 50%, at least about 60%, at least about 70%, at least about 80%, at least about 85%, at least about 90%, at least about 95%, at least about 99%) of "sequence identity" to another sequence means that, when maximally aligned, using software programs routine in the art, that percentage of bases (or amino acids) are the same in comparing the two sequences.

Two sequences are "substantially homologous" or "substantially similar" when at least about 50%, at least about 60%, at least about 70%, at least about 75%, and preferably at least about 80%, and most preferably at least about 90 or 95% of the nucleotides match over the defined length of the DNA sequences. Similarly, two polypeptide sequences are "substantially homologous" or "substantially similar" when at least about 50%, at least about 60%, at least about 66%, at least about 70%, at least about 75%, and preferably at least about 80%, and most preferably at least about 90 or 95% of the amino acid residues of the polypeptide match over a defined length of the polypeptide sequence. Sequences that are substantially homologous can be identified by comparing the sequences using standard software available in sequence data banks. Substantially homologous nucleic acid sequences also can be identified in a Southern hybridization experiment under, for example, stringent conditions as defined for that particular system. Defining appropriate hybridization conditions is within the skill of the art. For example, stringent conditions can be: hybridization at 5×SSC and 50% formamide at 42° C., and washing at 0.1×SSC and 0.1% sodium dodecyl sulfate at 60° C. Further examples of stringent hybridization conditions include: incubation temperatures of about 25 degrees C. to about 37 degrees C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40 degrees C. to about 50 degrees C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55 degrees C. to about 68 degrees C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. Similarity can be verified by sequencing, but preferably, is also or alternatively, verified by function (e.g., ability to traffic to an endosomal compartment, and the like), using assays suitable for the particular domain in question.

The terms "percent (%) sequence similarity", "percent (%) sequence identity", and the like, generally refer to the degree of identity or correspondence between different nucleotide sequences of nucleic acid molecules or amino acid sequences of polypeptides that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wisconsin), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al, J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al, Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb.

Another non-limiting example of a mathematical algorithm utilized for the comparison of sequences is the algorithm of Myers and Miller, CABIOS 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, MA; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

Another non-limiting example of how percent identity can be determined is by using software programs such as those described in Current Protocols In Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

Statistical analysis of the properties described herein may be carried out by standard tests, for example, t-tests, ANOVA, or Chi squared tests. Typically, statistical significance will be measured to a level of p=0.05 (5%), more preferably p=0.01, p=0.001, p=0.0001, p=0.000001

"Conservatively modified variants" of domain sequences also can be provided. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed-base and/or deoxyinosine residues (Batzer, et al., 1991, Nucleic Acid Res. 19: 5081; Ohtsuka, et al., 1985, J. Biol. Chem. 260: 2605-2608; Rossolini et al., 1994, Mol. Cell. Probes 8: 91-98).

The term "biologically active fragment", "biologically active form", "biologically active equivalent" of and "functional derivative" of a wild-type protein, possesses a biological activity that is at least substantially equal (e.g., not significantly different from) the biological activity of the wild type protein as measured using an assay suitable for detecting the activity.

As used herein, "in vivo" nucleic acid delivery, nucleic acid transfer, nucleic acid therapy" and the like, refer to the introduction of an improved LAMP Construct directly into the body of an organism, such as a human or non-human mammal, whereby the improved LAMP Construct is introduced to a cell of such organism in vivo.

As used herein, the term "in situ" refers to a type of in vivo nucleic acid delivery in which the improved LAMP Construct is brought into proximity with a target cell (e.g., the nucleic acid is not administered systemically). For example, in situ delivery methods include, but are not limited to, injecting an improved LAMP Construct directly at a site (e.g., into a tissue, such as a tumor or heart muscle), contacting the improved LAMP Construct with cell(s) or tissue through an open surgical field, or delivering the improved LAMP Constructs to a site using a medical access device such as a catheter.

As used herein, the term "isolated" or "purified" means separated (or substantially free) from constituents, cellular and otherwise, in which the polynucleotide, peptide, polypeptide, protein, antibody, or fragments thereof, are normally associated with in nature. For example, with respect to an improved LAMP Construct, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart. By substantially free or substantially purified, it is meant at least 50% of the population, preferably at least 70%, more preferably at least 80%, and even more preferably at least 90%, are free of the components with which they are associated in nature.

As used herein, a "target cell" or "recipient cell" refers to an individual cell or cell which is desired to be, or has been, a recipient of the improved LAMP Constructs described herein. The term is also intended to include progeny of a single cell, and the progeny may not necessarily be completely identical (in morphology or in genomic or total DNA complement) to the original parent cell due to natural, accidental, or deliberate mutation. A target cell may be in contact with other cells (e.g., as in a tissue) or may be found circulating within the body of an organism.

As used herein, a "subject" is a vertebrate, preferably a mammal, more preferably a human. Mammals include, but are not limited to, murines, simians, humans, farm animals, sport animals, and pets. In other preferred embodiments, the "subject" is a rodent (e.g. a rat, a mouse, a rabbit, a llama, camels, a cow, a guinea pig, a hamster, a dog, a cat, a horse, a non-human primate, a simian (e.g. a monkey or ape), a monkey (e.g. marmoset, baboon, rhesus macaque), or an ape (e.g. gorilla, chimpanzee, orangutan, gibbon). In other embodiments, non-human mammals, especially mammals that are conventionally used as models for demonstrating therapeutic efficacy in humans (e.g. murine, primate, porcine, canine, or rabbit animals) may be employed.

The terms "cancer," "neoplasm," and "tumor," are used interchangeably and in either the singular or plural form, refer to cells that have undergone a malignant transformation that makes them pathological to the host organism. Primary cancer cells transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass, e.g., by procedures such as CAT scan, MR imaging, X-ray, ultrasound or palpation, and/or which is detectable because of the expression of one or more cancer-specific antigens in a sample obtainable from a patient.

In preferred embodiments, the cancer (including all stages of progression, including hyperplasia) is an adenocarcinoma, sarcoma, skin cancer, melanoma, bladder cancer, brain cancer, breast cancer, uterine cancer, ovarian cancer, prostate cancer, lung cancer (including, but not limited to NSCLC, SCLC, squamous cell cancer), colorectal cancer, anal cancer, rectal cancer, cervical cancer, liver cancer, head and neck cancer, oral cancer, salivary gland cancer, esophageal cancer, pancreas cancer, pancreatic ductal adenocarcinoma (PDA), renal cancer, stomach cancer, kidney cancer, multiple myeloma or cerebral cancer.

The improved LAMP Constructs described herein can also be used to treat allergies, such as for example, food allergies (e.g., peanut allergens, such as Ara H1, H2 and/or H3), or environmental allergens, such as for example pollen (tree pollen, such as for example CRY J1 or CRY J2), dog dander, cat saliva, or dust mites. Other diseases and/or disorders include, for example, infectious disease and diabetes.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Compositions comprising the improved LAMP Constructs also can include stabilizers and preservatives. For examples of carriers, stabilizers and adjuvants, see Martin Remington's Pharm. Sci., 15th Ed. (Mack Publ. Co., Easton (1975)).

A cell has been "transformed", "transduced", or "transfected" by the improved LAMP Constructs when such nucleic acids have been introduced inside the cell. Transforming DNA may or may not be integrated (covalently linked) with chromosomal DNA making up the genome of the cell. In prokaryotes, yeast, and mammalian cells for example, the improved LAMP Constructs may be maintained on an episomal element, such as a plasmid. In a eukaryotic cell, a stably transformed cell is one in which the improved LAMP Constructs have become integrated into a chromosome so that it is inherited by daughter cells through chromosome replication. This stability is demonstrated by the ability of the eukaryotic cell to establish cell lines or clones comprised of a population of daughter cells containing the improved LAMP Constructs. A "clone" is a population of cells derived from a single cell or common ancestor by mitosis. A "cell line" is a clone of a primary cell that is capable of stable growth in vitro for many generations (e.g., at least about 10).

As used herein, an "effective amount" is an amount sufficient to affect beneficial or desired results, e.g., such as an effective amount of the improved LAMP Construct transfer and/or expression, and/or the attainment of a desired therapeutic endpoint. An effective amount can be administered in one or more administrations, applications or dosages. In one aspect, an effective amount of an improved LAMP Construct is an amount sufficient to transform/transduce/transfect at least one cell in a population of cells comprising at least two cells.

As used herein, a "therapeutically effective amount" is used herein to mean an amount sufficient to prevent, correct and/or normalize an abnormal physiological response. In one aspect, a "therapeutically effective amount" is an amount sufficient to reduce by at least about 30 percent, more preferably by at least 50 percent, most preferably by at least 90 percent, a clinically significant feature of pathology, such as for example, allergic response, size of a tumor mass, antibody production, cytokine production, fever or white cell count, etc.

An "antibody" is any immunoglobulin, including antibodies and fragments thereof, that binds a specific antigen. The term encompasses polyclonal, monoclonal, and chimeric antibodies (e.g., bispecific antibodies). An "antibody combining site" is that structural portion of an antibody molecule comprised of heavy and light chain variable and hypervariable regions that specifically binds antigen. Exemplary antibody molecules are intact immunoglobulin molecules, substantially intact immunoglobulin molecules, and those portions of an immunoglobulin molecule that contains the paratope, including Fab, Fab', F(ab')$_2$ and F(v) portions, which portions are preferred for use in the therapeutic methods described herein. Thus, the term antibody encompasses not only whole antibody molecules, but also antibody fragments as well as variants (including derivatives such as fusion proteins) of antibodies and antibody fragments. Examples of molecules which are described by the term "antibody" in this application include, but are not limited to: single chain Fvs (scFvs), Fab fragments, Fab' fragments, F(ab')$_2$, disulfide linked Fvs (sdFvs), Fvs, and fragments comprising or alternatively consisting of, either a $V_L$ or a $V_H$ domain. The term "single chain Fv" or "scFv" as used herein refers to a polypeptide comprising a $V_L$ domain of an antibody linked to a $V_H$ domain of an antibody. See Carter (2006) Nature Rev. Immunol. 6:243.

Additionally, antibodies of the invention include, but are not limited to, monoclonal, multi-specific, bi-specific, human, humanized, mouse, or chimeric antibodies, single chain antibodies, camelid antibodies, Fab fragments, F(ab') fragments, anti-idiotypic (anti-Id) antibodies (including, e.g., anti-Id antibodies to antibodies of the invention), domain antibodies and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably, the antibodies are human antibodies. As used herein, "human" antibodies include antibodies having the amino acid sequence of a human immunoglobulin and include antibodies isolated from human immunoglobulin libraries and xenomice or other organisms that have been genetically engineered to produce human antibodies. The improved LAMP Constructs described herein can be used in combination with known techniques for generating human antibodies and human monoclonal antibodies as described in the exemplified protocols, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; and Lonberg and Huszar, Int. Rev. Immunol. 13:65-93 (1995).

Human antibodies or "humanized" chimeric monoclonal antibodies can be produced using the improved LAMP Constructs in combination with techniques described herein or otherwise known in the art. For example, standard methods for producing chimeric antibodies are known in the art. See, for review the following references: Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

The antibodies of the present invention may be monovalent, bivalent, trivalent or multivalent. For example, monovalent scFvs can be multimerized either chemically or by association with another protein or substance. A scFv that is fused to a hexahistidine tag or a Flag tag can be multimerized using Ni-NTA agarose (Qiagen) or using anti-Flag antibodies (Stratagene, Inc.). Additionally, the improved LAMP Constructs can be used to generate monospecific, bispecific, trispecific or of greater multispecificity for the encoded antigen(s) contained in the improved LAMP Construct. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et. al., J. Immunol. 148:1547-1553 (1992).

An "epitope" is a structure, usually made up of a short peptide sequence or oligosaccharide, that is specifically recognized or specifically bound by a component of the immune system. T-cell epitopes have generally been shown to be linear oligopeptides. Two epitopes correspond to each other if they can be specifically bound by the same antibody. Two epitopes correspond to each other if both are capable of binding to the same B cell receptor or to the same T cell receptor, and binding of one antibody to its epitope substantially prevents binding by the other epitope (e.g., less than about 30%, preferably, less than about 20%, and more preferably, less than about 10%, 5%, 1%, or about 0.1% of the other epitope binds). In the present invention, multiple epitopes can make up an antigen.

The term "antigen" or "antigen of interest" as used herein covers any polypeptide sequence encoded by a polynucleotide sequence cloned into the improved LAMP Construct which is used to elicit an innate or adaptive immune response. An "antigen" encompasses both a single antigen as well as multiple antigenic sequences (derived from the same or different proteins) cloned into the improved LAMP Construct.

The term "antigen presenting cell" as used herein includes any cell which presents on its surface an antigen in association with a major histocompatibility complex molecule, or portion thereof, or, alternatively, one or more non-classical MHC molecules, or a portion thereof. Examples of suitable APCs are discussed in detail below and include, but are not limited to, whole cells such as macrophages, dendritic cells, B cells, hybrid APCs, and foster antigen presenting cells.

As used herein an "engineered antigen-presenting cell" refers to an antigen-presenting cell that has a non-natural molecular moiety on its surface. For example, such a cell may not naturally have a costimulator on its surface or may have an additional artificial costimulator in addition to a natural costimulator on its surface, or may express a non-natural class II molecule on its surface. In preferred embodiments, the engineered antigen-presenting cell has the antigen expressed from the improved LAMP Construct on its surface.

As used herein, "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates.

As used herein, "partially human" refers to a nucleic acid having sequences from both a human and a non-human vertebrate. In the context of partially human sequences, the partially human nucleic acids have sequences of human immunoglobulin coding regions and sequences based on the non-coding sequences of the endogenous immunoglobulin region of the non-human vertebrate. The term "based on" when used with reference to endogenous non-coding sequences from a non-human vertebrate refers to sequences that correspond to the non-coding sequence and share a relatively high degree of homology with the non-coding sequences of the endogenous loci of the host vertebrate, e.g., the non-human vertebrate from which the ES cell is derived. Preferably, the non-coding sequences share at least an 80%, more preferably 90% homology with the corresponding non-coding sequences found in the endogenous loci of the non-human vertebrate host cell into which a partially human molecule comprising the non-coding sequences has been introduced.

The term "immunoglobulin variable region" as used herein refers to a nucleotide sequence that encodes all or a portion of a variable region of an antibody molecule or all or a portion of a regulatory nucleotide sequence that controls expression of an antibody molecule. Immunoglobulin regions for heavy chains may include but are not limited to all or a portion of the V, D, J, and switch regions, including introns. Immunoglobulin region for light chains may include but are not limited to the V and J regions, their upstream flanking sequences, introns, associated with or adjacent to the light chain constant region gene.

By "transgenic animal" is meant a non-human animal, usually a mammal, having an exogenous nucleic acid sequence present as an extrachromosomal element in a portion of its cells or stably integrated into its germ line DNA (i.e., in the genomic sequence of most or all of its cells). In generating a transgenic animal comprising human sequences, a partially human nucleic acid is introduced into the germ line of such transgenic animals by genetic manipulation of, for example, embryos or embryonic stem cells of the host animal according to methods well known in the art.

A "vector" includes plasmids and viruses and any DNA or RNA molecule, whether self-replicating or not, which can be used to transform or transfect a cell.

As used herein, a "genetic modification" refers to any addition, deletion or disruption to a cell's normal nucleotides. Art recognized methods include viral mediated gene transfer, liposome mediated transfer, transformation, transfection and transduction, e.g., viral-mediated gene transfer such as the use of the improved LAMP Constructs based on DNA viruses such as adenovirus, adeno-associated virus and herpes virus, as well as retroviral based vectors.

The practice of the present invention employs, unless otherwise indicated, conventional molecular biology, microbiology, and recombinant DNA techniques within the skill of the art. Such techniques are explained fully in the literature. See, e.g., Maniatis, Fritsch & Sambrook, In Molecular Cloning: A Laboratory Manual (1982); DNA Cloning: A Practical Approach, Volumes I and II (D. N. Glover, ed., 1985); Oligonucleotide Synthesis (M. J. Gait, ed., 1984); Nucleic Acid Hybridization (B. D. Hames & S. J. Higgins, eds., 1985); Transcription and Translation (B. D. Hames & S. I. Higgins, eds., 1984); Animal Cell Culture (R. I. Freshney, ed., 1986); Immobilized Cells and Enzymes (IRL Press, 1986); B. Perbal, A Practical Guide to Molecular Cloning (1984).

Figure 2B:
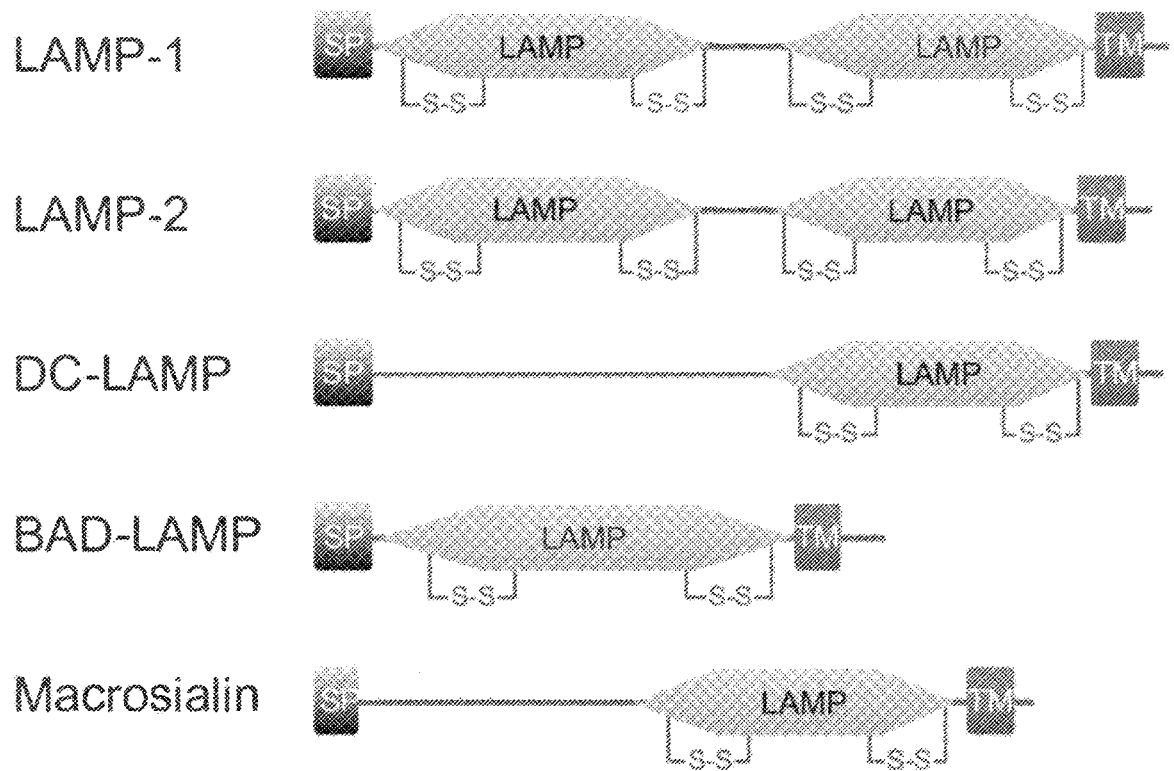
FIG. 2A illustrates the domains of the LAMP proteins defined herein while FIG. 2B defines the specific amino acid boundaries of these domains for human LAMP-1 (SEQ ID NO:1), human LAMP-2 (SEQ ID NO:2), human LAMP-3 (SEQ ID NO:3), human LIMP-2 (SEQ ID NO:4), human Endolyn (SEQ ID NO:5), human Macrosailin (SEQ ID NO:80), human LAMP-5 (SEQ ID NO:93) and human LIMBIC (SEQ ID NO:67). As described herein the LAMP lumenal domains, homology domains, transmembrane domains, the cytoplasmic tail and the signal sequences can be used to generate the improved LAMP Constructs ILC-1, ILC-2, ILC-3, ILC-4, ILC-5 and ILC-6 as described herein.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention LAMP Constructs LAMP-1, as deduced from a cDNA clone (Chen, et al., J. Biol. Chem. 263: 8754, 1988) consists of a polypeptide core of about 382 amino acids with a large (346-residue) lumenal amino-terminal domain followed by a 24-residue hydrophobic transmembrane region and short (12-residue) carboxyl-terminal cytoplasmic tail. See, FIGS. 2A and 2B. The lumenal domain is highly glycosylated, being substituted with about 20 asparagine linked complex-type oligosaccharides and consists of two approximately 160-residue "homology domains" that are separated by a proline/serine-rich hinge region. Each of these "homology domains" contains 4 uniformly spaced cysteine residues, disulfide bonded to form four 36-38-residue loops symmetrically placed within the two halves of the lumenal domain (Arterburn, et al., J. Biol. Chem. 265: 7419, 1990; see, also Chen, et al., J. Biol. Chem. 25: 263(18): 8754-8, 1988). FIG. 2A schematically shows the conserved domains between LAMP-1, LAMP-2, LAMP-3, Endolyn, LIMBIC, LAMPS, or Macrosailin.

Previously reported LAMP constructs comprise the following elements in this specific arrangement:
  (a) a full lumenal domain of LAMP-1 protein, the antigen and then the full transmembrane/cytoplasmic tail of LAMP-1 protein; or
  (b) the antigen and the full transmembrane/cytoplasmic tail of a LAMP-1 protein. In example (a), the antigenic sequence is inserted in between the full lumenal domain of a LAMP-1 protein and the LAMP-1 full transmembrane domain/cytoplasmic tail. Both constructs have been shown to successfully target an antigenic sequence to the lysosome/endosome and will be referred to as "complete LAMP Constructs" as shown in FIG. 1 as compared to the improved LAMP Constructs ILC1-ILC6 described herein. The improved LAMP Constructs described herein do not include the complete LAMP Constructs described in the prior art.

Although it has been widely reported in the literature that fragments smaller than the full lumenal domain of LAMP-1 were not effective in generating a robust immune response (see, e.g. Godinho et al.) the inventors unexpectedly discovered that specific fragments, in certain arrangements, did in fact effectively present antigens to the immune system, generating a robust immune response, including the generation of a different repitoire of antibodies. For example, the inventors have identified that the minimal LAMP lumenal domain fragment that is effective for generating a robust immune response is not the full lumenal domain (as widely reported in the literature) but rather a single Homology Domain of the Lumenal Domain of a LAMP Protein.

For example, constructs can comprise, not the full lumenal domain, but instead a single Homology Domain of the Lumenal Domain of a LAMP Protein. As used herein, the "Homology Domain" comprises at least the 4 uniformly spaced cysteine residues shown in FIGS. 3-10. These cysteine resides are labeled 1, 2, 3, and 4 (and in LIMP-2 and Macrosailin—five cysteines are identified, LIMBIC—six cysteines are identified and Endolyn—eight cysteines are identified) in each Homology Domain as shown in FIGS. 3-10 and are defined herein as the "Cysteine Conserved Fragment." Additional amino acids can be included to either the N-terminus end and/or the C-terminus end of the Cysteine Conserved Fragment to generate, up to and including a full Homology Domain of a LAMP protein. These additional added amino acids can be derived from the Homology Domain from which the Cysteine Conserved Fragment is derived or from other LAMP Protein Homology Domains. Thus, as used herein, a LAMP Homology Domain comprises and/or consists of one Cysteine Conserved Fragment. At least two LAMP Homology Domains make up the Lumenal Domain of LAMP-1, LAMP-2, LAMP-3, or Endolyn.

Specifically, in one preferred embodiment, the improved LAMP Construct comprises at least one antigen of interest fused to the N-terminus of the lumenal domain of a LAMP protein, at least one homology domain of a LAMP protein, or at least one Cysteine Conserved Fragment of a LAMP protein. See, for example ILC-2 and ILC-6 of FIG. 1. In preferred embodiments, these constructs also comprise a transmembrane domain of a LAMP protein, and/or the cytosolic tail of a LAMP protein. In other preferred embodiments, when an antigen contains a transmembrane domain, the transmembrane domain of a LAMP protein and/or the cytosolic tail of a LAMP protein is unnecessary. In preferred embodiments, two homology domains are included in the improved LAMP Construct (e.g., ILC-1 of FIG. 1). In further preferred embodiments, the two homology domains are derived from a LAMP-1, LAMP-2, LAMP-3, or an Endolyn protein. Alternatively, the two homology domains are derived from different LAMP proteins. In these constructs comprising two homology domains, a LAMP hinge domain may also be included. The improved LAMP Constructs described in this paragraph are unexpected in view of the prior art as the antigen has always been placed in between the full lumenal LAMP-1 domain and the full LAMP-1 transmembrane/cytoplasmic tail, as fragments of the lumenal domain have not been reported to be effective in generating a robust immune response.

In another preferred embodiment, the improved LAMP Construct comprises at least one antigen of interest fused to the C-terminus of a single homology domain of a LAMP protein or a single Cysteine Conserved Fragment of a LAMP protein. See, for example, ILC-3 and ILC-5 of FIG. 1. In preferred embodiments, these constructs also comprise a transmembrane domain of a LAMP protein, and/or the cytosolic tail of a LAMP protein. In other preferred embodiments, when an antigen contains a transmembrane domain, the transmembrane domain of a LAMP protein and/or the cytosolic tail of a LAMP protein is unnecessary. The improved LAMP Constructs described in this paragraph are unexpected in view of the prior art as described above.

In another preferred embodiment, the improved LAMP Construct comprises at least one antigen of interest fused in between a first homology domain of a LAMP protein and a second homology domain of a LAMP protein (or at least between two Cysteine Conserved Fragments). See, for example, ILC-4 of FIG. 1. In preferred embodiments, these constructs also comprise a transmembrane domain of a LAMP protein, and/or the cytosolic tail of a LAMP protein. In preferred embodiments, the two homology domains are derived from LAMP-1, LAMP-2, LAMP-3, or an Endolyn protein. In these constructs, the antigen may be placed in the LAMP hinge region. Alternatively, two homology domains from two different LAMP proteins may be used. This arrangement of at least one antigen of interest fused in between two LAMP homology domains (including Cysteine Conserved Fragments) is unexpected in view of the prior art as described above.

Each of the improved LAMP Constructs defined above can be generated using the domains defined in the Figures. For example, it is specifically contemplated that the domains included in the improved LAMP Construct illustrated in FIG. 1, for example, can originate from sequences derived from orthologous sequences. See, FIGS. 3-10 for example. It is expressly contemplated that the equivalent domains defined in FIGS. 2A and 2B be used to generate the improved LAMP Constructs illustrated in FIG. 1 for orthologous sequences. Moreover, the orthologous sequences shown in FIGS. 3-10 are representative of the sequences that can be used to generate the domains. It is well within the skill in the art to identify other orthologous sequences and/or isotypes and comparing them to the alignments shown in FIGS. 3-10. Thus, by identifying the equivalent boundaries defined in FIGS. 2A and 2B for a human LAMP protein with the alignments shown in FIGS. 3-10, one can generate the improved LAMP Constructs illustrated in FIG. 1.

As would be well understood by the skilled artisan, the boundaries of each domain are an approximation and may be adjusted at least 1, 2, 3, 4, 5, 6, 7, 8, 9, or 10 amino acids based on cloning considerations and restriction enzyme placement. Therefore, when a particular domain (e.g., a LAMP Homology Domain) is included in the improved LAMP Construct, the amino acids beginning and ending of the domain may be adjust by at least 1, 2, 3, 4, 5, 6, 7, 8, 9, or 10 amino acids as those boundaries defined in FIG. 2B.

Each of the improved LAMP Constructs described above can additionally comprise a signal sequence and/or additional amino acids in between each domain for cloning purposes as is well known in the art. Additionally, the LAMP homologous domains, the LAMP lumenal domain, the LAMP transmembrane domain, and/or the LAMP cytosolic tail domain can originate from the same LAMP protein (e.g., human LAMP-1) or different LAMP proteins (e.g., lumenal domain from human LAMP-1 and transmembrane domain from human LAMP-2, and/or mixing of orthologous domains in the same gene family (e.g., LAMP-1) or different gene family (LAMP-1 and LAMP-2).

Polypeptide variants of the described LAMP Constructs are contemplated. For example, polypeptides at least about 60%, at least about 70%, at least about 75%, at least about 80%, at least about 85%, at least about 90%, at least about 95%, 96%, 97%, 98% or 99% identity to any of the improved LAMP Constructs described herein as well as polynucleotides encoding these variants. Variants of the improved LAMP Constructs retain the ability to function by targeting the antigenic sequence to the lysosome. For example, a modified lumenal sequence must retain the ability to traffic both membrane and non-membrane antigenic materials to an endosomal compartment with at least about 50%, at least about 60%, at least 70%, at least about 80%, at least about 90%, or at least about 100% efficacy compared to the original domain sequence, i.e., an efficacy that results in sufficient antigen presentation by a cell comprising the chimeric sequence for it to mount an immune response. In one aspect, sequences containing a suitable trafficking signal may be identified by constructing an improved LAMP Construct containing the well-characterized antigenic domain of ovalbumin, a transmembrane domain, and the cytoplasmic domain of a protein containing a putative lysosomal/endosomal targeting signal. Efficiency of targeting can be measured by determining the ability of antigen presenting cells, expressing the improved LAMP Construct, to stimulate HA epitope-specific, MHC class II restricted T-cells (see, e.g., Example 5 of U.S. Pat. No. 5,633,234).

Polynucleotides encoding any of the described improved LAMP Constructs are preferred embodiments of the invention, along with polynucleotides at least about 60%, at least about 70%, at least about 75%, at least about 80%, at least about 85%, at least about 90%, at least about 95%, 96%, 97%, 98% or 99% identity to any of the improved LAMP Construct polynucleotides described herein. Variants of the improved LAMP Constructs retain the ability to function by targeting the antigenic sequence to the lysosome. For example, a modified lumenal sequence must retain the ability to traffic both membrane and non-membrane antigenic materials to an endosomal compartment with at least about 50%, at least about 60%, at least 70%, at least about 80%, at least about 90%, or at least about 100% efficacy compared to the original domain sequence, i.e., an efficacy that results in sufficient antigen presentation by a cell comprising the chimeric sequence for it to mount an immune response. In one aspect, sequences containing a suitable trafficking signal may be identified by constructing an improved LAMP Construct containing the well-characterized antigenic domain of ovalbumin, a transmembrane domain, and the cytoplasmic domain of a protein containing a putative lysosomal/endosomal targeting signal. Efficiency of targeting can be measured by determining the ability of antigen presenting cells, expressing the improved LAMP Construct, to stimulate HA epitope-specific, MHC class II restricted T-cells (see, e.g., Example 5 of U.S. Pat. No. 5,633,234).

Assembly of Sequences Encoding Improved LAMP Constructs

Procedures for constructing improved LAMP Constructs comprising the antigen of interest are well known in the art (see e.g., Williams, et al., J. Cell Biol. 111: 955, 1990). DNA sequences encoding the desired segments can be obtained from readily available recombinant DNA materials such as those available from the American Type Culture Collection, 12301 Parklawn Drive, Rockville, Md. 20852, U.S.A., or from DNA libraries that contain the desired DNA.

For example, the DNA segments corresponding to the desired domain sequences can be assembled with appropriate control and signal sequences using routine procedures of recombinant DNA methodology. See, e.g., as described in U.S. Pat. No. 4,593,002, and Langford, et al., Molec. Cell. Biol. 6: 3191, 1986.

A DNA sequence encoding a protein or polypeptide can be synthesized chemically or isolated by one of several approaches. The DNA sequence to be synthesized can be designed with the appropriate codons for the desired amino acid sequence. In general, one will select preferred codons for the intended host in which the sequence will be used for expression. The complete sequence may be assembled from overlapping oligonucleotides prepared by standard methods and assembled into a complete coding sequence. See, e.g., Edge, Nature 292: 756, 1981; Nambair, et al. Science 223: 1299, 1984; Jay, et al., J. Biol. Chem. 259: 6311, 1984.

In one aspect, one or more of the nucleic acids encoding the domain sequences of the improved LAMP Construct are isolated individually using the polymerase chain reaction (M. A. Innis, et al., In PCR Protocols: A Guide to Methods and Applications, Academic Press, 1990). The domains are preferably isolated from publicly available clones known to contain them, but they may also be isolated from genomic DNA or cDNA libraries. Preferably, isolated fragments are bordered by compatible restriction endonuclease sites which allow an improved LAMP Construct encoding the antigen sequence to be constructed. This technique is well known to those of skill in the art. Domain sequences may be fused directly to each other (e.g., with no intervening sequences), or inserted into one another (e.g., where domain sequences are discontinuous), or may be separated by intervening sequences (e.g., such as linker sequences).

The basic strategies for preparing oligonucleotide primers, probes and DNA libraries, as well as their screening by nucleic acid hybridization, are well known to those of ordinary skill in the art. See, e.g., Sambrook, et al., 1989, supra; Perbal, 1984, supra. The construction of an appropriate genomic DNA or cDNA library is within the skill of the art. See, e.g., Perbal, 1984, supra. Alternatively, suitable DNA libraries or publicly available clones are available from suppliers of biological research materials, such as Clonetech and Stratagene, as well as from public depositories such as the American Type Culture Collection.

Selection may be accomplished by expressing sequences from an expression library of DNA and detecting the expressed peptides immunologically. Clones which express peptides that bind to MHC II molecules and to the desired antibodies/T cell receptors are selected. These selection procedures are well known to those of ordinary skill in the art (see, e.g., Sambrook, et al., 1989, supra).

Once a clone containing the coding sequence for the desired polypeptide sequence has been prepared or isolated, the sequence can be cloned into any suitable vector, preferably comprising an origin of replication for maintaining the sequence in a host cell.

Nucleic Acid Delivery Vehicles

In one aspect, a vaccine composition comprising an improved LAMP Construct is introduced into a cell. The cell may be a host cell for replicating the nucleic acid or for expressing the improved LAMP Construct. Preferably, the host cell for expressing the improved LAMP Construct is an antigen presenting cell (described further below).

In preferred embodiments, the improved LAMP Construct further comprises a polynucleotide sequence for insertion into a target cell and an expression control sequence operably linked thereto to control expression of the polynucleotide sequence (e.g., transcription and/or translation) in the cell. Examples include plasmids, phages, autonomously replicating sequences (ARS), centromeres, and other sequences which are able to replicate or be replicated in vitro or in a host cell (e.g., such as a bacterial, yeast, or insect cell) and/or target cell (e.g., such as a mammalian cell, preferably an antigen presenting cell) and/or to convey the sequences encoding the improved LAMP Construct to a desired location within the target cell.

Recombinant expression vectors may be derived from micro-organisms which readily infect animals, including man, horses, cows, pigs, llamas, giraffes, dogs, cats or chickens. Preferred vectors include those which have already been used as live vaccines, such as vaccinia. These recombinants can be directly inoculated into a host, conferring immunity not only to the microbial vector, but also to express foreign antigens. Preferred vectors contemplated herein as live recombinant vaccines include RNA viruses, adenovirus, herpesviruses, poliovirus, and vaccinia and other pox viruses, as taught in Flexner, Adv. Pharmacol. 21: 51, 1990, for example.

Expression control sequences include, but are not limited to, promoter sequences to bind RNA polymerase, enhancer sequences or negative regulatory elements to bind to transcriptional activators and repressors, respectively, and/or translation initiation sequences for ribosome binding. For example, a bacterial expression vector can include a promoter such as the lac promoter and for transcription initiation, the Shine-Dalgarno sequence and the start codon AUG (Sambrook, et al., 1989, supra). Similarly, a eukaryotic expression vector preferably includes a heterologous, homologous, or chimeric promoter for RNA polymerase II, a downstream polyadenylation signal, the start codon AUG, and a termination codon for detachment of a ribosome.

Expression control sequences may be obtained from naturally occurring genes or may be designed. Designed expression control sequences include, but are not limited to, mutated and/or chimeric expression control sequences or synthetic or cloned consensus sequences. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.).

In order to optimize expression and/or transcription, it may be necessary to remove, add or alter 5' and/or 3' untranslated portions of the vectors to eliminate extra, or alternative translation initiation codons or other sequences that may interfere with, or reduce, expression, either at the level of transcription or translation. Alternatively, consensus ribosome binding sites can be inserted immediately 5' of the start codon to enhance expression. A wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma, adenovirus, herpes virus and other sequences known to control the expression of genes of mammalian cells, and various combinations thereof.

In one aspect, the improved LAMP Construct comprises an origin of replication for replicating the vector. Preferably, the origin functions in at least one type of host cell which can be used to generate sufficient numbers of copies of the sequence for use in delivery to a target cell. Suitable origins therefore include, but are not limited to, those which function in bacterial cells (e.g., such as *Escherichia* sp., *Salmonella* sp., *Proteus* sp., *Clostridium* sp., *Klebsiella* sp., *Bacillus* sp., *Streptomyces* sp., and *Pseudomonas* sp.), yeast (e.g., such as Saccharamyces sp. or *Pichia* sp.), insect cells, and mammalian cells. In one preferred aspect, an origin of replication is provided which functions in the target cell into which the nucleic acid delivery vehicle is introduced (e.g., a mammalian cell, such as a human cell). In another aspect, at least two origins of replication are provided, one that functions in a host cell and one that functions in a target cell.

The improved LAMP Construct may alternatively, or additionally, comprise sequences to facilitate integration of at least a portion of the nucleic acid deliver vector into a target cell chromosome. For example, the improved LAMP Construct may comprise regions of homology to target cell chromosomal DNA. In one aspect, the delivery vector comprises two or more recombination sites which flank a nucleic acid sequence encoding the improved LAMP Construct.

The vector may additionally comprise a detectable and/or selectable marker to verify that the vector has been successfully introduced in a target cell and/or can be expressed by the target cell. These markers can encode an activity, such as, but not limited to, production of RNA, peptide, or protein, or can provide a binding site for RNA, peptides, proteins, inorganic and organic compounds or compositions and the like.

Examples of detectable/selectable markers genes include, but are not limited to: DNA segments that encode products which provide resistance against otherwise toxic compounds (e.g., antibiotics); DNA segments that encode products which are otherwise lacking in the recipient cell (e.g., tRNA genes, auxotrophic markers); DNA segments that encode products which suppress the activity of a gene product; DNA segments that encode products which can be readily identified (e.g., phenotypic markers such as beta-galactosidase, a fluorescent protein (GFP, CFP, YFG, BFP, RFP, EGFP, EYFP, EBFP, dsRed, mutated, modified, or enhanced forms thereof, and the like), and cell surface proteins); DNA segments that bind products which are otherwise detrimental to cell survival and/or function; DNA segments that otherwise inhibit the activity of other nucleic acid segments (e.g., antisense oligonucleotides); DNA segments that bind products that modify a substrate (e.g., restriction endonucleases); DNA segments that can be used to isolate or identify a desired molecule (e.g., segments encoding specific protein binding sites); primer sequences; DNA segments, which when absent, directly or indirectly confer resistance or sensitivity to particular compounds; and/or DNA segments that encode products which are toxic in recipient cells.

The marker gene can be used as a marker for conformation of successful gene transfer and/or to isolate cells expressing transferred genes and/or to recover transferred genes from a cell. For example, in one aspect, the marker gene is used to isolate and purify antigen presenting cells expressing the improved LAMP Constructs.

Substantially similar genes may be provided, e.g., genes with greater than about 50%, greater than about 70%, greater than 80%, greater than about 90%, and preferably, greater than about 95% identity to a known gene. Substantially similar domain sequences may initially be identified by selecting a sequence which specifically hybridizes to a domain sequence of interest under stringent hybridization conditions. Performing assays to determine the suitability of homologous, variant, or modified domain sequences is merely a matter of screening for sequences which express the appropriate activity. Such screening is routine in the art.

The improved LAMP Construct may be provided as naked nucleic acids or in a delivery vehicle associated with one or more molecules for facilitating entry of a nucleic acid into a cell. Suitable delivery vehicles include, but are not limited to: liposomal formulations, polypeptides, polysaccharides, lipopolysaccharides, viral formulations (e.g., including viruses, viral particles, artificial viral envelopes and the like), cell delivery vehicles, and the like.

Lipid-Based Formulations

Delivery vehicles designed to facilitate intracellular delivery of the improved LAMP Constructs must interact with both non-polar and polar environments (in or on, for example, the plasma membrane, tissue fluids, compartments within the cell, and the like). Therefore, preferably, delivery vehicles are designed to contain both polar and non-polar domains or a translocating sequence for translocating an improved LAMP Construct into a cell.

Compounds having polar and non-polar domains are termed amphiphiles. Cationic amphiphiles have polar groups that are capable of being positively charged at, or around, physiological pH for interacting with negatively charged polynucleotides such as DNA.

The improved LAMP Constructs described herein can be provided in formulations comprising lipid monolayers or bilayers to facilitate transfer of the vectors across a cell membrane. Liposomes or any form of lipid membrane, such as planar lipid membranes or the cell membrane of an intact cell, e.g., a red blood cell, can be used. Liposomal formulations can be administered by any means, including administration intravenously or orally.

Liposomes and liposomal formulations can be prepared according to standard methods and are well known in the art, see, e.g., Remington's; Akimaru, 1995, Cytokines Mol. Ther. 1: 197-210; Alving, 1995, Immunol. Rev. 145: 5-31; Szoka, 1980, Ann. Rev. Biophys. Bioeng. 9: 467; U.S. Pat. Nos. 4,235,871; 4,501,728; and 4,837,028. In one aspect, the liposome comprises a targeting molecule for targeting a liposome:improved LAMP Construct complex to a particular cell type. In a particularly preferred aspect, a targeting molecule comprises a binding partner (e.g., a ligand or receptor) for a biomolecule (e.g., a receptor or ligand) on the surface of a blood vessel or a cell found in a target tissue.

Liposome charge is an important determinant in liposome clearance from the blood, with negatively charged liposomes being taken up more rapidly by the reticuloendothelial system (Juliano, 1975, Biochem. Biophys. Res. Commun. 63: 651) and thus having shorter half-lives in the bloodstream. Incorporating phosphatidylethanolamine derivatives enhances the circulation time by preventing liposomal aggregation. For example, incorporation of N-(omega-carboxy)acylamidophosphatidylethanolamines into large unilamellar vesicles of L-alpha-distearoylphosphatidylcholine dramatically increases the in vivo liposomal circulation lifetime (see, e.g., Ahl, 1997, Biochim. Biophys. Acta 1329: 370-382). Liposomes with prolonged circulation half-lives are typically desirable for therapeutic and diagnostic uses. For a general discussion of pharmacokinetics, see, e.g., Remington's, Chapters 37-39, Lee, et al., In Pharmacokinetic Analysis: A Practical Approach (Technomic Publishing AG, Basel, Switzerland 1996).

Typically, liposomes are prepared with about 5 to 15 mole percent negatively charged phospholipids, such as phosphatidylglycerol, phosphatidylserine or phosphatidyl-inositol. Added negatively charged phospholipids, such as phosphatidylglycerol, also serve to prevent spontaneous liposome aggregation, and thus minimize the risk of undersized liposomal aggregate formation. Membrane-rigidifying agents, such as sphingomyelin or a saturated neutral phospholipid, at a concentration of at least about 50 mole percent, and 5 to 15 mole percent of monosialylganglioside can also impart desirably liposome properties, such as rigidity (see, e.g., U.S. Pat. No. 4,837,028).

Additionally, the liposome suspension can include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

The improved LAMP Constructs of the invention can include multilamellar vesicles of heterogeneous sizes. For example, vesicle-forming lipids can be dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture which is in a more easily hydrated powderlike form. This film is covered with an aqueous solution of the peptide or polypeptide complex and allowed to hydrate, typically over a 15 to 60 minute period with agitation. The size distribution of the resulting multilamellar vesicles can be shifted toward smaller sizes by hydrating the lipids under more vigorous agitation conditions or by adding solubilizing detergents such as deoxycholate. The hydration medium preferably comprises the nucleic acid at a concentration which is desired in the interior volume of the liposomes in the final liposome suspension.

Following liposome preparation, the liposomes can be sized to achieve a desired size range and relatively narrow distribution of liposome sizes. One preferred size range is about 0.2 to 0.4 microns, which allows the liposome suspension to be sterilized by filtration through a conventional filter, typically a 0.22 micron filter. Filter sterilization can be carried out on a high throughput basis if the liposomes have been sized down to about 0.2 to 0.4 microns. Several techniques are available for sizing liposome to a desired size (see, e.g., U.S. Pat. No. 4,737,323).

Suitable lipids include, but are not limited to, DOTMA (Felgner, et al., 1987, Proc. Natl. Acad. Sci. USA 84: 7413-7417), DOGS or Transfectain™ (Behr, et al., 1989, Proc. Natl. Acad. Sci. USA 86: 6982-6986), DNERIE or DORIE (Felgner, et al., Methods 5: 67-75), DC-CHOL (Gao and Huang, 1991, BBRC 179: 280-285), DOTAP™ (McLachlan, et al., 1995, Gene Therapy 2: 674-622), Lipofectamine™. and glycerolipid compounds (see, e.g., EP901463 and WO98/37916).

Other molecules suitable for complexing with the improved LAMP Constructs include cationic molecules, such as, polyamidoamine (Haensler and Szoka, 1993, Bioconjugate Chem. 4: 372-379), dendritic polysine (WO 95/24221), polyethylene irinine or polypropylene h-nine (WO 96/02655), polylysine (U.S. Pat. No. 5,595,897; FR 2 719 316), chitosan (U.S. Pat. No. 5,744,166), DNA-gelatin coarcervates (see, e.g., U.S. Pat. Nos. 6,207,195; 6,025,337; 5,972,707) or DEAE dextran (Lopata, et al., 1984, Nucleic Acid Res. 12: 5707-5717).

Viral-Based Gene Delivery Vehicles

In one aspect, the improved LAMP Construct delivery vehicle comprises a virus or viral particle. In this aspect, preferably, the improved LAMP Construct comprises a viral vector. Viral vectors, such as retroviruses, adenoviruses, adeno-associated viruses and herpes viruses, are often made up of two components, a modified viral genome and a coat structure surrounding it (see, e.g., Smith et al., 1995, Ann. Rev. Microbiol. 49: 807-838), although sometimes viral vectors are introduced in naked form or coated with proteins other than viral proteins. Most current vectors have coat structures similar to a wild-type virus. This structure packages and protects the viral nucleic acid and provides the means to bind and enter target cells.

Preferably, viral vectors comprising the improved LAMP Constructs described herein are modified from wild-type viral genomes to disable the growth of the virus in a target cell while enabling the virus to grow in a host cell (e.g., such as a packaging or helper cell) used to prepare infectious particles. Vector nucleic acids generally essential cis-acting viral sequences for replication and packaging in a helper line and expression control sequences for regulating the expression of a polynucleotide being delivered to a target cell. Other viral functions are expressed in trans in specific packaging or helper cell lines as are known in the art.

Preferred improved LAMP Constructs are viral vectors derived from a virus selected from the group consisting of herpes viruses, cytomegaloviruses, foamy viruses, lentiviruses, Semliki forrest virus, AAV (adeno-associated virus), poxviruses, adenovirases and retroviruses. Such viral vectors are well known in the art.

In one preferred aspect, a viral vector used is an adenoviral vector. The adenoviral genome consists of a linear double-stranded DNA molecule of approximately 36 kb carrying more than about thirty genes necessary to complete the viral replication cycle. The early genes are divided into 4 regions (E1 to E4) that are essential for viral replication with the exception of the E3 region, which is believed to modulate the anti-viral host immune response. The E1 region (EIA and EIB) encodes proteins responsible for the regulation of transcription of the viral genome. Expression of the E2 region genes (E2A and E2B) leads to the synthesis of the polypeptides needed for viral replication. The proteins encoded by the E3 region prevent cytolysis by cytotoxic T cells and tumor necrosis factor (Wold and Gooding, 1991, Virology 184: 1-8). The proteins encoded by the E4 region are involved in DNA replication, late gene expression and splicing and host cell shut off (Halbert, et al., 1985, J. Virol. 56: 250-257). The late genes generally encode structural proteins contributing to the viral capsid. In addition, the adenoviral genome carries at cis-acting 5' and 3' ITRs (Inverted Terminal Repeat) and packaging sequences essential for DNA replication. The ITRs harbor origins of DNA replication while the encapsidation region is required for the packaging of adenoviral DNA into infectious particles.

Adenoviral vectors can be engineered to be conditionally replicative (CRAd vectors) in order to replicate selectively in specific cells (e.g., such as proliferative cells) as described in Heise and Kim (2000, J. Clin. Invest. 105: 847-851). In another aspect, an adenoviral vector is replication-defective for the E1 function (e.g., by total or partial deletion or mutagenesis of E1). The adenoviral backbone of the vector may comprise additional modifications (deletions, insertions or mutations in one or more viral genes). An example of an E2 modification is illustrated by the thermosensitive mutation localized on the DBP (DNA Binding Protein) encoding gene (Ensinger et al., 1972, J. Virol. 10: 328-339). The adenoviral sequence may also be deleted of all or part of the E4 region (see, e.g., EP 974 668; Christ, et al., 2000, Human Gene Ther. 11: 415-427; Lusky, et al., 1999, J. Virol. 73: 8308-8319). Additional deletions within the non-essential E3 region may allow the size of the polynucleotide being delivered to be increased (Yeh, et al., 1997, FASEB Journal 11: 615 623). However, it may be advantageous to retain all or part of the E3 sequences coding for polypeptides (e.g., such as gp19k) allowing the virus to escape the immune system (Gooding, et al., 1990, Critical Review of Immunology 10: 53-71) or inflammatory reactions (EP 00440267.3).

Second generation vectors retaining the ITRs and packaging sequences and comprising substantial genetic modifications to abolish the residual synthesis of the viral antigens also may be used in order to improve long-term expression of the expressed gene in the transduced cells (see, e.g., WO 94/28152; Lusky, et al., 1998, J. Virol 72: 2022-2032).

The improved LAMP Constructs being introduced into the cell may be inserted in any location of the viral genome, with the exception of the cis-acting sequences. Preferably, it is inserted in replacement of a deleted region (E1, E3 and/or E4), preferably, within a deleted E1 region.

Adenoviruses can be derived from any human or animal source, in particular canine (e.g. CAV-1 or CAV-2 Genbank ref. CAVIGENOM and CAV77082, respectively), avian (Genbank ref. AAVEDSDNA), bovine (such as BAV3; Reddy, et al., 1998, J. Virol. 72: 1394 1402), murine (Genbank ref. ADRMUSMAVI), ovine, feline, porcine or simian sources or alternatively, may be a hybrid virus. Any serotype can be employed. However, the human adenoviruses of the C sub-group are preferred, especially adenoviruses 2 (Ad2) and 5 (Ad5). Such viruses are available, for example, from the ATCC.

Adenoviral particles or empty adenoviral capsids also can be used to transfer improved LAMP Constructs by a virus-mediated cointernalization process as described in U.S. Pat. No. 5,928,944. This process can be accomplished in the presence of cationic agent(s) such as polycarbenes or lipid vesicles comprising one or more lipid layers.

Adenoviral particles may be prepared and propagated according to any conventional technique in the field of the art (e.g., WO 96/17070) using a complementation cell line or a helper virus, which supplies in trans the missing viral genes necessary for viral replication. The cell lines 293 (Graham et al., 1977, J. Gen. Virol. 36: 59-72) and PERC6 (Fallaux et al., 1998, Human Gene Therapy 9: 1909-1917) are commonly used to complement E1 deletions. Other cell lines have been engineered to complement defective vectors (Yeh, et al., 1996, J. Virol. 70: 559-565; Kroughak and Graham, 1995, Human Gene Ther. 6: 1575-1586; Wang, et al., 1995, Gene Ther. 2: 775-783; Lusky, et al., 1998, J. Virol. 72: 2022-203; EP 919627 and WO 97/04119). The adenoviral particles can be recovered from the culture supernatant but also from the cells after lysis and optionally further purified according to standard techniques (e.g., chromatography, ultracentrifugation, as described in WO 96/27677, WO 98/00524 WO 98/26048 and WO 00/50573).

Cell-type specific targeting may be achieved with vectors derived from adenoviruses having a broad host range by the modification of viral surface proteins. For example, the specificity of infection of adenoviruses is determined by the attachment to cellular receptors present at the surface of permissive cells. In this regard, the fiber and penton present at the surface of the adenoviral capsid play a critical role in cellular attachment (Defer, et al., 1990, J. Virol. 64: 3661-3673). Thus, cell targeting of adenoviruses can be carried out by genetic modification of the viral gene encoding fiber and/or penton, to generate modified fiber and/or penton capable of specific interaction with unique cell surface receptors. Examples of such modifications are described in Wickarn, et al., 1997, J. Virol. 71: 8221-8229; Arriberg, et al., 1997, Virol. Chem 268: 6866-6869; Roux, et al., 1989, Proc. Natl. Acad. Sci. USA 86: 9079-9083; Miller and Vile, 1995, FASEB J. 9: 190-199; WO 93/09221, and in WO 95/28494.

In a particularly preferred aspect, adeno-associated viral sequences are used as vectors. Vectors derived from the human parvovirus AAV-2 (adeno-associated virus type 2) are among the most promising gene delivery vehicles currently being developed. Several of the features of this system for packaging a single-stranded DNA suggest it as a possible alternative to naked DNA for delivery. A primary attractive feature, in contrast to other viral vectors such as vaccinia or adenovirus, is that AAV vectors do not express any viral genes. The only viral DNA sequences included in the vaccine construct are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ to $10^{11}$ particles or copies of DNA in contrast to naked DNA doses of 50 ug or about 1015 copies.

In one aspect, AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay). AAV titer may be determined by quantitative PCR with virus DNA samples prepared after digestion with proteinase K. Preferably, vector titers produced by such a method are approximately $5 \times 10^{12}$ to $1 \times 10^{13}$ DNase resistant particles per ml.

In other aspects, retroviral vectors are used. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (WO 95/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323). Preferably, the improved LAMP Construct is inserted downstream of the encapsidation sequence, preferably in opposite direction relative to the retroviral genome. Cell specific targeting may be achieved by the conjugation of antibodies or antibody fragments to the retroviral envelope protein as is known in the art.

Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, BioTechniques 7: 980; Danos and Mulligan, 1988, Proc. Natl. Acad. Sci. USA 85: 6460; Markowitz, et al., 1988, Virol. 167: 400). The product of the env gene is responsible for the binding of the viral particle to the viral receptors present on the surface of the target cell and, therefore determines the host range of the retroviral particle. in the context of the invention, it is advantageous to use a packaging cell line, such as the PA317 cells (ATCC CRL 9078) or 293EI6 (WO97/35996) containing an amphotropic envelope protein, to allow infection of human and other species' target cells. The retroviral particles are preferably recovered from the culture supernatant and may optionally be further purified according to standard techniques (e.g. chromatography, ultracentrifugation).

Other suitable viruses include poxviruses. The genome of several members of poxyiridae has been mapped and sequenced. A poxyiral vector may be obtained from any member of the poxyiridae, in particular canarypox, fowlpox and vaccinia virus. Suitable vaccinia viruses include, but are not limited to, the Copenhagen strain (Goebel, et al., 1990, Virol. 179: 247-266; Johnson, et al., 1993, Virol. 196: 381-401), the Wyeth strain and the modified Ankara (MVA) strain (Antoine, et al., 1998, Virol. 244: 365-396). The general conditions for constructing a vaccinia virus vector are known in the art (see, e.g., EP 83 286 and EP 206 920; Mayr et al., 1975, Infection 3: 6-14; Sutter and Moss, 1992, Proc. Natl. Acad. Sci. USA 89: 10847-10851). Preferably, the polynucleotide of interest is inserted within a non-essential locus such as the noncoding intergenic regions or any gene for which inactivation or deletion does not significantly impair viral growth and replication.

Poxyiral particles are prepared as described in the art (Piccini, et al., 1987, Methods of Enzymology 153: 545-563; U.S. Pat. Nos. 4,769,330; 4,772,848; 4,603,112; 5,100,587 and 5,179,993). Generally, a donor plasmid is constructed, amplified by growth in *E. coli* and isolated by conventional procedures. Then, it is introduced into a suitable cell culture (e.g. chicken embryo fibroblasts) together with a poxvirus genome, to produce, by homologous recombination, poxyiral particles. These can be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or ultracentrifugation on cesium chloride or sucrose gradients).

The use of vaccinia as a live virus vaccine in the global campaign to eradicate smallpox made vaccinia an obvious choice for development as a live recombinant vaccine vector. Live recombinant vaccinia viruses expressing close to 100 different foreign proteins have been reported, and a number of these are effective experimental vaccines (reviewed by Moss and Flexner, 1987). Vaccinia is particularly versatile as an expression vector because of its large genomic size, capability of accepting at least 25,000 base pairs of foreign DNA, and its ability to infect most eukaryotic cell types, including insect cells (ibid.). Unlike other DNA viruses, poxviruses replicate exclusively in the cytoplasm of infected cells, reducing the possibility of genetic exchange of recombinant viral DNA with the host chromosome. Recombinant vaccinia vectors have been shown to properly process and express proteins from a variety of sources including man, other mammals, parasites, RNA and DNA viruses, bacteria and bacteriophage.

The expression of DNA encoding a foreign protein is controlled by host virus regulatory elements, including upstream promoter sequences and, where necessary, RNA processing signals. Insertion of foreign DNA into nonessential regions of the vaccinia virus genome has been carried out by homologous recombination (Panicali, et al., Proc. Nat'l. Acad. Sci, USA, 79: 4927, 1982; Mackett, et al., Proc. Nat'l. Acad. Sci. USA, 79: 7415, 1982).

Expression of antigens by the improved LAMP Construct may occur because of transcriptional regulatory elements at or near the site of insertion or by more precise genetic engineering. Plasmid vectors that greatly facilitate insertion and expression of foreign genes have been constructed (Mackett, et al., J. Virol, 49: 857, 1982). These vectors contain an expression site, composed of a vaccinia transcriptional promoter and one or more unique restriction endonuclease sites for insertion of the foreign coding sequence flanked by DNA from a nonessential region of the vaccinia genome. The choice of promoter determines both the time (e.g., early or late) and level of expression, whereas the flanking DNA sequence determines the site of homologous recombination.

Only about one in a thousand virus particles produced by this procedure is a recombinant. Although recombinant virus plaques can be identified by DNA hybridization, efficient selection procedures have been developed. By using segments of nonessential vaccinia virus thymidine kinase (TK) gene as flanking sequences, the foreign gene recombines into the TK locus and by insertion inactivates the TK gene. Selection of TK virus is achieved by carrying out the virus plaque assay in TK cells in the presents of 5-bromodeoxyuridine. Phosphorylation of the nucleoside analogue and consequent lethal incorporation into viral DNA occurs only in cells infected with TK+ parental virus. Depending on the efficiency of the transfection and recombination, up to 80 of the plaques are desired recombinants, and the rest are spontaneous TK mutants.

Plasmid vectors that contain the E. coli beta-galactosidase gene, as well as an expression site for a second gene, permit an alternative method of distinguishing recombinant from parental virus (Chakrabarti, et al., Mol. Cell. Biol., 5: 3403, 1985). Plaques formed by such recombinants can be positively identified by the blue color that forms upon addition of an appropriate indicator. By combining both TK selection and beta-galactosidase expression, recombinant virus is readily and quickly isolated. The recombinants are then amplified by propagation in suitable cell lines and expression of the inserted gene is checked by appropriate enzymological, immunological or physical procedures.

An upper limit to the amount of genetic information that can be added to the vaccinia virus genome is not yet known. However, the addition of nearly 25,000 base pairs of foreign DNA had no apparent deleterious effect on virus yield (Smith, et al., Gene, 25:21, 1983). Were it necessary, large segments of the vaccinia virus genome could be deleted to provide additional capacity (Moss, et al., J. Virol. 40: 387, 1981).

Viral capsid molecules may include targeting moieties to facilitate targeting and/or entry into cells. Suitable targeting molecules, include, but are not limited to: chemical conjugates, lipids, glycolipids, hormones, sugars, polymers (e.g. PEG, polylysine, PEI and the like), peptides, polypeptides (see, e.g., WO 94/40958), vitamins, antigens, lectins, antibodies and fragments thereof. Preferably, such targeting molecules recognize and bind to cell-specific markers, tissue-specific markers, cellular receptors, viral antigens, antigenic epitopes or tumor-associated markers.

Compositions comprising an improved LAMP Construct based on viral particles may be formulated in the form of doses of between 10 and $10^{14}$ i.u. (infectious units), and preferably, between 10 and $10^{11}$ i.u. The titer may be determined by conventional techniques. The doses of LAMP Constructs are preferably comprised between 0.01 and 10 mg/kg, more especially between 0.1 and 2 mg/kg.

Self-Replicating RNA

Self-replicating RNA virus vectors can also be constructed using the improved LAMP Constructs as described herein. For example, alphaviruses, flavivuses, measle virus and rhabdoviruses can be used to generate self-replicating RNA virus vaccines. Preferred strains of self-replicating RNA viruses include, but are not limited to rabies virus (RABV), vesicular stomatisitis virus (VSV), West Nile virus, Kunjin virus, Semliki Forest virus (SFV), Sindbis virus (SIN) and/or Venezuelan equine encephalitis virus (VEE).

Self-replicating RNA viruses express the native antigen upon delivery into tissue, thus mimicking live attenuated vaccines without having the risk of reversion to pathogenicity. They also stimulate the innate immune system, thus potentiating responses. See, e.g., Ljungberg, K. "*Self-replicating alphavirus RNA vaccines,*" Expert Rev Vaccines (2):177-94 (2015); Lundstrom, K., "*Oncolytic Alphaviruses in Cancer Immunotherapy*", Vaccines 5:9 (2017); Lundstrom, K. "Replicon RNA Viral Vectors as Vaccines," Vaccines 4:39 (2016) (hereby incorporated by reference in their entirety). Use of self-replicating vaccines comprising the improved LAMP Constructs described herein can also be used in prime-boost protocols.

Moreover, self-replicating RNA viruses can also be encapsulated by liposomes, as described herein, to improve delivery and targeting. Immunization with self-replicating RNA viruses comprising the improved LAMP Constructs described herein may provide higher transient expression levels of antigens resulting in generation of neutralizing antibody responses and protection against lethal challenges under safe conditions.

Cell-Based Delivery Vehicles

The improved LAMP Constructs according to the invention can be delivered to target cells by means of other cells ("delivery cells) which comprise the constructs. Methods for introducing constructs into cells are known in the art and include microinjection of DNA into the nucleus of a cell (Capechi, et al., 1980, Cell 22: 479-488); transfection with $CaPo_4$ (Chen and Okayama, 1987, Mol. Cell Biol. 7: 2745 2752), electroporation (Chu, et al., 1987, Nucleic Acid Res. 15: 1311-1326); lipofection/liposome fusion (Feigner, et al., 1987, Proc. Natl. Acad. Sci. USA 84: 7413-7417) and particle bombardment (Yang, et al., 1990, Proc. Natl. Acad. Sci. USA 87: 9568-9572). Suitable cells include autologous and non-autologous cells, and may include xenogenic cells. Delivery cells may be induced to deliver their contents to the target cells by inducing their death (e.g., by providing inducible suicide genes to these cells).

Accessory Molecules

The compositions comprising the improved LAMP Constructs according to the invention may comprise one or more accessory molecules for facilitating the introduction of an improved LAMP Construct into a cell and/or for enhancing a particular therapeutic effect and/or enhancing antibody production.

In addition, the composition comprising the improved LAMP Construct according to the present invention may include one or more stabilizing substance(s), such as lipids, nuclease inhibitors, hydrogels, hyaluronidase (WO 98/53853), collagenase, polymers, chelating agents (EP 890362), in order to inhibit degradation within the animal/human body and/or improve transfection/infection of the vector into a target cell. Such substances may be used alone or in combination (e.g., cationic and neutral lipids).

It has also been shown that adenovirus proteins are capable of destabilizing endosomes and enhancing the uptake of DNA into cells. The mixture of adenoviruses to solutions containing a lipid-complexed DNA vector or the binding of DNA to polylysine covalently attached to adenoviruses using protein cross-linking agents may substantially improve the uptake and expression of an improved LAMP Construct (see, e.g., Curiel, et al., 1992, Am. I. Respir. Cell. Mol. Biol. 6: 247-252).

Host Cells

Improved LAMP Constructs according to the invention can be expressed in a variety of host cells, including, but not limited to: prokaryotic cells (e.g., *E. coli, Staphylococcus* sp., *Bacillus* sp.); yeast cells (e.g., *Saccharomyces* sp.); insect cells; nematode cells; plant cells; amphibian cells (e.g., *Xenopus*); avian cells; and mammalian cells (e.g., human cells, mouse cells, mammalian cell lines, primary cultured mammalian cells, such as from dissected tissues).

The molecules can be expressed in host cells isolated from an organism, host cells which are part of an organism, or host cells which are introduced into an organism. In one aspect, improved LAMP Constructs are expressed in host cells in vitro, e.g., in culture. In another aspect, improved LAMP Constructs are expressed in a transgenic organism (e.g., a transgenic mouse, rat, rabbit, pig, primate, etc.) that comprises somatic and/or germline cells comprising nucleic acids encoding the improved LAMP Constructs. Methods for constructing transgenic animals are well known in the art and are routine.

Improved LAMP Constructs also can be introduced into cells in vitro, and the cells (e.g., such as stem cells, hematopoietic cells, lymphocytes, and the like) can be introduced into the host organism. The cells may be heterologous or autologous with respect to the host organism. For example, cells can be obtained from the host organism, improved LAMP Constructs introduced into the cells in vitro, and then reintroduced into the host organism.

Antigen Presenting Cells

In a preferred aspect of the invention, an improved LAMP Construct as described herein is introduced into a natural or engineered antigen presenting cell.

The term "antigen presenting cell" (APC) as used herein intends any cell which presents on its surface an antigen in association with a major histocompatibility complex molecule, preferably a class II molecule, or portion thereof. Examples of suitable APCs are discussed in detail below and include, but are not limited to, whole cells such as macrophages, dendritic cells, B cells, hybrid APCs, and foster antigen presenting cells. Methods of making hybrid APCs are described and known in the art.

Dendritic cells (DCs) are potent antigen-presenting cells. It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC" defined above) class I or II protein on the surface of APCs. This interaction is necessary, but not sufficient, for T cell activation to occur. In fact, without the second type of signals, the first type of signals can result in T cell anergy. The second type of signals, called co-stimulatory signals, is neither antigen-specific nor MHC-restricted, and can lead to a full proliferation response of T cells and induction of T cell effector functions in the presence of the first type of signals.

Several molecules have been shown to enhance co-stimulatory activity. These include, but are not limited to, heat stable antigen (HSA), chondroitin sulfate-modified MHC invariant chain (Ii-CS), intracellular adhesion molecule I (ICAM-1), and B7 co-stimulatory molecule on the surface of APCs and its counter-receptor CD28 or CTLA-4 on T cells.

Other important co-stimulatory molecules are CD40, CD54, CD80, CD86. As used herein, the term "co-stimulatory molecule" encompasses any single molecule or combination of molecules which, when acting together with a peptide/MHC complex bound by a TCR on the surface of a T cell, provides a co-stimulatory effect which achieves activation of the T cell that binds the peptide. The term thus encompasses B7, or other co-stimulatory molecule(s) on an APC, fragments thereof (alone, complexed with another molecule(s), or as part of a fusion protein) which, together with peptide/MHC complex, binds to a cognate ligand and result in activation of the T cell when the TCR on the surface of the T cell specifically binds the peptide. Co-stimulatory molecules are commercially available from a variety of sources, including, for example, Beckman Coulter.

In one aspect of the invention, the method described in Romani et al., J. Immunol. Methods 196: 135-151, 1996, and Bender et al, J. Immunol. Methods 196: 121-135, 1996, are used to generate both immature and mature dendritic cells from the peripheral blood mononuclear cells (PBMCs) of a mammal, such as a murine, simian or human. Briefly, isolated PBMCs are pre-treated to deplete T- and B-cells by means of an immunomagnetic technique. Lymphocyte-depleted PBMC are then cultured for in RPMI medium 9 e.g., about 7 days), supplemented with human plasma (preferably autologous plasma) and GM-CSF/IL-4, to generate dendritic cells. Dendritic cells are nonadherent when compared to their monocyte progenitors. Thus, on approximately day 7, non-adherent cells are harvested for further processing.

The dendritic cells derived from PBMC in the presence of GM-CSF and IL-4 are immature, in that they can lost the nonadherence property and revert back to macrophage cell fate if the cytokine stimuli are removed from the culture. The dendritic cells in an immature state are very effective in processing native protein antigens for the MHC class II restricted pathway (Romani, et al., J. Exp. Med. 169:1169, 1989). Further maturation of cultured dendritic cells is accomplished by culturing for 3 days in a macrophage-conditioned medium (CM), which contains the necessary maturation factors. Mature dendritic cells are less able to capture new proteins for presentation but are much better at stimulating resting T cells (both CD4 and CD8) to grow and differentiate.

Mature dendritic cells can be identified by their change in morphology, such as the formation of more motile cytoplasmic processes; by their nonadherence; by the presence of at least one of the following markers: CD83, CD68, HLA-DR or CD86; or by the loss of Fc receptors such as CD 115 (reviewed in Steinman, Annu. Rev. Immunol. 9: 271, 1991). Mature dendritic cells can be collected and analyzed using typical cytofluorography and cell sorting techniques and devices, such as FACScan and FACStar. Primary antibodies used for flow cytometry are those specific to cell surface antigens of mature dendritic cells and are commercially available. Secondary antibodies can be biotinylated Igs followed by FITC- or PE-conjugated streptavidin.

Alternatively, others have reported that a method for upregulating (activating) dendritic cells and converting monocytes to an activated dendritic cell phenotype. This method involves the addition of calcium ionophore to the culture media convert monocytes into activated dendritic cells. Adding the calcium 21 ionophore A23187, for example, at the beginning of a 24-48 hour culture period resulted in uniform activation and dendritic cell phenotypic conversion of the pooled "monocyte plus DC" fractions: characteristically, the activated population becomes uniformly CD 14 (Leu M3) negative, and upregulates HLA-DR, HLA-DQ, ICAM-1,137.1, and 137.2. Furthermore, this activated bulk population functions as well on a small numbers basis as a further purified. Specific combination(s) of cytokines have been used successfully to amplify (or partially substitute) for the activation/conversion achieved with calcium ionophore: these cytokines include but are not limited to G-CSF, GM-CSF, IL-2, and IL-4. Each cytokine when given alone is inadequate for optimal upregulation.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/nonadherence steps (Freudenthal et al. PNAS 87: 7698-7702, 1990); Percoll gradient separations (Mehta-Damani, et al., J. Immunol. 153: 996-1003, 1994); and fluorescence activated cell sorting techniques (Thomas et al., J. Immunol. 151: 6840-52, 1993).

There are many other methods routine in the art for isolating professional antigen presenting cells (or their precursors) and that such methods and others which may be developed are not limiting and are encompassed within the scope of the invention.

In one embodiment, the APCs and therefore the cells presenting one or more antigens are autologous. In another embodiment, the APCs presenting the antigen are allogeneic, i.e., derived from a different subject.

As discussed herein, improved LAMP Constructs can be introduced into APCs using the methods described above or others known in the art, including, but not limited to, transfection, electroporation, fusion, microinjection, viral-based delivery, or cell based delivery. Arthur et al., Cancer Gene Therapy 4(1): 17-25, 1997, reports a comparison of gene transfer methods in human dendritic cells.

Known, partial and putative human leukocyte antigen (HLA), the genetic designation for the human MHC, amino acid and nucleotide sequences, including the consensus sequence, are published (see, e.g., Zemmour and Parham, Immunogenetics 33: 310-320, 1991), and cell lines expressing HLA variants are known and generally available as well, many from the American Type Culture Collection ("ATCC"). Therefore, using PCR, MHC class II-encoding nucleotide sequences are readily operatively linked to an expression vector of this invention that is then used to transform an appropriate cell for expression therein.

Professional APCs can be used, such as macrophages, B cells, monocytes, dendritic cells, and Langerhans cells. These are collected from the blood or tissue of 1) an autologous donor; 2) a heterologous donor having a different HLA specificity then the host to be treated; or 3) from a xenogeneic donor of a different species using standard procedures (Coligan, et. al., Current Protocols in Immunology, sections 3 and 14, 1994). The cells may be isolated from a normal host or a patient having an infectious disease, cancer, autoimmune disease, or allergy.

Professional APCs may be obtained from the peripheral blood using leukopheresis and "FICOLL/HYPAQUE" density gradient centrifugation (stepwise centrifugation through Ficoll and discontinuous Percoll density gradients). Procedures are utilized which avoid the exposure of the APCs to antigens which could be internalized by the APCs, leading to activation of T cells not specific for the antigens of interest.

Cells which are not naturally antigen presenting can be engineered to be antigen presenting by introducing sequences encoding appropriate molecules. For example, nucleic acid sequences encoding MHC class II molecules, accessory molecules, co-stimulatory molecules and antigen processing assisting molecules can be introduced after direct synthesis, cloning, purification of DNA from cells containing such genes, and the like. One expedient means to obtain genes for encoding the molecules used in the improved LAMP Constructs and methods described herein is by polymerase chain reaction (PCR) amplification on selected nucleic acid templates with selected oligonucleotide primer pairs. For example, epithelial cells, endothelial cells, tumor cells, fibroblasts, activated T cells, eosinophils, keratinocytes, astrocytes, microglial cells, thymic cortical epithelial cells, Schwann cells, retinal pigment epithelial cells, myoblasts, vascular smooth muscle cells, chondrocytes, enterocytes, thyrocytes and kidney tubule cells can be used. These may be primary cells recently explanted from a host and not extensively passaged in cell culture to form an established cell line, or established cell lines that are relatively homogeneous and capable of proliferating for many generations or indefinitely.

Cells that are not professional APCs are isolated from any tissue of an autologous donor; a heterologous donor or a xenogeneic donor, where they reside using a variety of known separation methods (Darling, Animal Cells: Culture and Media. J. Wiley, New York, 1994; Freshney, Culture of Animal Cells. Alan R. Liss, Inc., New York, 1987). Non-autologous cells, e.g., heterologous or xenogeneic cells, can be engineered ex vivo to express HLA class I and class II molecules that match known human HLA specificities. These cells can then be introduced into a human subject matching the HLA specificity of the engineered cells. The cells are further engineered ex vivo to express one or more LAMP Constructs according to the invention.

The engineered cells are maintained in cell culture by standard cell culture methods (Darling, Animal Cells: Culture and Media". J. Wiley, New York, 1994; Freshney, Culture of Animal Cells". Alan R. Liss, Inc., New York, 1987). Cell lines for use in the present invention are obtained from a variety of sources (e.g., ATCC Catalogue of Cell Lines & Hybidomas, American Type Culture Collection, 8th edition, 1995), or are produced using standard methods (Freshney, Culture of Immortalized Cells, Wiley-Liss, New York, 1996). Non-transformed cell lines are preferred for use in human subjects.

In one aspect, CD34+precursors that are differentiating under the influence of GM-CSF into dendritic cells are obtained from the body of a subject and nucleic acids encoding LAMP Constructs according to the invention are introduced into the cells, which are then injected into the subject. Utilizing the improved LAMP Constructs as described herein will enhance the association of peptides derived from a particular antigen with MHC class II molecules on the transduced antigen presenting cells, resulting in significantly more potent systemic T cell dependent immune responses and/or antibody production. While the antigen presenting cells transfected in this strategy are preferably autologous cells, any MHC class II cells that effectively present antigen in the host may be used as described above.

Peptide Vaccines

Also within the scope of this invention are peptide vaccines encoded by the improved LAMP Construct Preferably, the antigen is processed within the compartment/organelle (or subsequent compartment/organelle to which it is delivered) to generate an epitope bound to an MHC class II molecule capable of modulating an immune response.

The peptide vaccines encoded by the improved LAMP Constructs may also may be bound in a membranous structure to facilitate its administration to the body of an organism. For example, the peptide vaccine encoded by the improved LAMP Construct may be incorporated into liposomes, as described in U.S. Pat. No. 4,448,765.

When a protein or polypeptide is to be used as an immunogen, it may be produced by expression of any one or more of the improved LAMP Constructs described herein in a recombinant cell or it may be prepared by chemical synthesis. For example, the Merrifield technique (Journal of American Chemical Society, vol. 85, pp. 2149-2154, 1968), can be used.

Methods of Producing Antibodies using LAMP Constructs

The improved LAMP Constructs as polynucleotides, the encoded proteins of the improved LAMP Constructs, and/or cells (such as antigen presenting cells which express the improved LAMP Constructs described herein) can be used to generate antibodies by methods well known by the skilled artisan, such as, for example, methods described in the art. See, for instance, Sutcliffe et al., supra; Wilson et al., supra; Chow et al., Proc. Natl. Acad. Sci. USA 82:910-914 (1985); and Bittle et al., J. Gen. Virol. 66:2347-2354 (1985). If in vivo immunization is used, animals may be immunized with a protein encoded by the improved LAMP Construct and/or a polynucleotide comprising the improved LAMP Construct comprising an antigen as described herein. Priming with improved LAMP Constructs as polynucleotides, the encoded proteins of the improved LAMP Constructs, and/or cells (such as antigen presenting cells which express the improved LAMP Constructs described herein) followed by boosting with an antigen is a preferred embodiment of the invention. In further preferred embodiments, priming with an improved LAMP Construct as described herein followed by boosting with an antigen is specifically contemplated and can be used to generate an even more robust immune response, especially in view of antibody repertoire diversity and titer.

The improved LAMP Construct comprising the antigen may be injected into the non-human vertebrate to raise antibodies. Preparation and injection of LAMP Constructs into non-human vertebrates can be accomplished according to principles of immunization of animals that are well known to those skilled in the art.

The use of an improved LAMP Construct to effectively present the antigen involves, in one aspect, the antigen being processed by LAMP in Antigen Presenting Cells after endocytosis and fusion of the endosome with a lysosome. The endosome then merges with an exocytic vesicle from the Golgi apparatus containing class II MHC molecules, to which the resultant peptides bind. The MHC-peptide complex then trafficks to the plasma membrane where the antigen is available for display to CD4+ T cells.

Animals such as rabbits, rats, mice, llamas, camels, and/or cows can be immunized with the improved LAMP Construct comprising an antigen and/or a polynucleotide encoding the improved LAMP Construct comprising an antigen. Additional animals suitable for immunization include, non-human mammals, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon, rhesus macaque), an ape (e.g. gorilla, chimpanzee, orangutan, gibbon).

For instance, intraperitoneal and/or intradermal injection of emulsions containing about 100 micrograms of an improved LAMP Construct comprising an antigen or carrier protein and Freund's adjuvant or any other adjuvant known for stimulating an immune response may be used. Several booster injections (such as with the recombinant antigen protein) may be needed, for instance, at intervals of about two weeks, to provide a useful titer of an anti-antigen antibody which can be detected, for example, by ELISA assay using free antigen adsorbed, directly or indirectly (e.g., via a biotinylated AviTag), to a solid surface. The titer of anti-antigen antibodies in serum from an immunized animal may be increased by selection of anti-antibodies, for instance, by adsorption to the antigen on a solid support and elution of the selected antibodies according to methods well known in the art.

Alternatively, a polynucleotide encoding the improved LAMP Construct comprising an antigen can also be directly introduced into animals. See, for example, U.S. Pat. Nos. 5,676,954; 6,875,748; 5,661,133; Sahin et al., Nat Rev Drug Discov, 2014 October; 13(10):759-80; Kariko et al., Mol Ther, 2008 November; 16(11):1833-40; Kariko et al., Nucleic Acid Res, 2011, November; 39(21):e142; U.S. Pat. No. 6,511,832. In one example, an improved LAMP Construct comprising an antigen is directly injected into a non-human vertebrate. Injection into the animals can occur via intramuscular, intradermal, intranasal, subcutaneous, intravenous, intratracheal, and intrathecal deliveries. Follow-on boosting with a recombinant antigen can also be include in generating the antibodies.

Additionally, antibodies generated by the disclosed methods can be affinity matured using display technology, such as for example, phage display, yeast display or ribosome display. In one example, single chain antibody molecules ("scFvs") displayed on the surface of phage particles are screened to identify those scFvs that immunospecifically bind to the antigen and/or the starting protein. The present invention encompasses both scFvs and portions thereof that are identified to immunospecifically bind to the antigen and/or the starting protein. Such scFvs can routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule.

Recombinant expression of the raised antibodies (including scFvs and other molecules comprising, or alternatively consisting of, antibody fragments or variants thereof (e.g., a heavy or light chain of an antibody of the invention or a portion thereof or a single chain antibody of the invention)) using the improved LAMP Construct comprising an antigen and/or a polynucleotide encoding the improved LAMP Construct comprising an antigen of the invention, requires construction of an expression vector(s) containing a polynucleotide that encodes the antibody or fragment or variant thereof. Once a polynucleotide encoding an antibody molecule (e.g., a whole antibody, a heavy or light chain of an antibody, or variant or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing an antibody by expressing a polynucleotide containing an antibody encoding nucleotide sequence are described herein. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination and are described herein. The invention, thus, provides replicable vectors comprising a nucleotide sequence encoding the anti-antigen antibody obtained and isolated as described herein (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy chain, the entire light chain, or both the entire heavy and light chains.

The expression vector(s) can be transferred to a host cell by conventional techniques and the transfected cells are then cultured by conventional techniques to produce either the anti-antigen antibody. Thus, the invention includes host cells containing polynucleotide(s) encoding the anti-antigen antibody (e.g., whole antibody, a heavy or light chain thereof, or portion thereof, or a single chain antibody of the invention, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express anti-antigen antibody. Such host-expression systems represent vehicles by which the coding sequences of interest may be produced and subsequently purified, but also represent cells which may, when transformed or transfected, with the appropriate nucleotide coding sequences, express the anti-antigen antibody. These include, but are not limited to, microorganisms such as bacteria (e.g., *E. coli, B. subtilis*) transformed with recombinant bacteriophage DNA, plasmid DNA or cosmid DNA expression vectors containing sequences; yeast (e.g., *Saccharomyces, Pichia*) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, are used for the expression of the anti-antigen antibody. For example, mammalian cells such as Chinese hamster ovary cells (CHO), in conjunction with a vector such as the major intermediate early gene promoter element from human cytomegalovirus is an effective expression system (Foecking et al., Gene 45:101 (1986); Cockett et al., Bio/Technology 8:2 (1990)).

In bacterial systems, a number of expression vectors may be advantageously selected depending upon the intended use. For example, when a large quantity of a protein is to be produced (for either antibody production or encoded polypeptides of the improved LAMP Construct), vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or Factor Xa protease cleavage sites so that the cloned target gene product can be released from the GST moiety.

In an insect system, *Autographa californica* nuclear polyhedrosis virus (AcNPV) may be used as a vector to express an anti-antigen antibody or the encoded polypeptides of the improved LAMP Construct. The virus grows in *Spodoptera frugiperda* cells. Coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized express an anti-antigen antibody or the encoded polypeptides of the improved LAMP Construct. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the anti-antigen antibody or the encoded polypeptides of the improved LAMP Construct in infected hosts (e.g., see Logan & Shenk, Proc. Natl. Acad. Sci. USA 8 1:355-359 (1984)).

Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed, to this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, NSO, MDCK, 293, 3T3, W138, and in particular, breast cancer cell lines such as, for example, BT483, Hs578T, HTB2, BT20 and T47D, and normal mammary gland cell line such as, for example, CRL7030 and HsS78Bst.

For long-term, high-yield production of recombinant proteins, stable expression is preferred. For example, cell lines which stably express the express an anti-antigen antibody or the encoded polypeptides of the improved LAMP Construct may be engineered. Rather than using expression vectors which contain viral origins of replication, host cells can be transformed with a polynucleotide controlled by appropriate expression control elements (e.g., promoter, enhancer, sequences, transcription terminators, polyadenylation sites, etc.), and a selectable marker. Following the introduction of the foreign polynucleotide, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the anti-antigen antibody or the encoded polypeptides of the improved LAMP Construct.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Goldspiel et al., Clinical Pharmacy, 12: 488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH 11(5):155-2 15 (May; 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example; in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., J. Mol. Biol. 150:1 (1981).

The expression levels of either an anti-antigen antibody or the encoded polypeptides of the improved LAMP Construct can be increased by vector amplification (for a review, see Bebbington and Hentschel, *The Use Of Vectors Based On Gene Amplification For The Expression Of Cloned Genes In Mammalian Cells In DNA Cloning*, Vol. 3. (Academic Press, New York, 1987)). When a marker in the vector system expressing an anti-antigen antibody or the encoded polypeptides of the improved LAMP Construct is amplifiable, an increase in the level of inhibitor present in the host cell culture will increase the number of copies of the marker gene. Since the amplified region is associated with the coding sequence, production of the anti-antigen antibody express or the encoded polypeptides of the improved LAMP Construct will also increase (Crouse et al., Mol. Cell. Biol. 3:257 (1983)).

Other elements that can be included in vector sequences include heterologous signal peptides (secretion signals), membrane anchoring sequences, introns, alternative splice sites, translation start and stop signals, inteins, biotinylation sites and other sites promoting post-translational modifications, purification tags, sequences encoding fusions to other proteins or peptides, separate coding regions separated by internal ribosome reentry sites, sequences encoding "marker" proteins that, for example, confer selectability (e.g., antibiotic resistance) or sortability (e.g., fluorescence), modified nucleotides, and other known polynucleotide cis-acting features not limited to these examples.

The host cell may be co-transfected with two expression vectors of the invention, for example, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA or synthetic DNA sequences.

Once an anti-antigen antibody or the encoded polypeptides of the improved LAMP Construct has been produced by recombinant expression, it may be purified by any method known in the art for purification of a protein, for example, by chromatography (e.g., ion exchange, affinity (particularly by Protein A affinity and immunoaffinity for the specific antigen), and sizing column chromatography), centrifugation, differential solubility, or by any other standard technique for the purification of proteins. Further, an anti-antigen antibody or the encoded polypeptides of the improved LAMP Construct may be fused to heterologous polypeptide sequences described herein or otherwise known in the art to facilitate purification.

In one example, the anti-antigen antibody or the encoded polypeptides of the improved LAMP Construct may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876, 969, issued Mar. 2,1999, EP Patent 0 413 622, and U.S. Pat. No. 5,766,883, issued Jun. 16,1998), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fe fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the anti-antigen antibody or the encoded polypeptides of the improved LAMP Construct described herein can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Administration

Vaccine material according to this invention may contain the immune stimulatory improved LAMP Constructs described herein or may be recombinant microorganisms, or antigen presenting cells which express the immune stimulatory improved LAMP Constructs. Preparation of improved LAMP Constructs containing vaccine material according to this invention and administration of such improved LAMP Constructs for immunization of individuals are accomplished according to principles of immunization that are well known to those skilled in the art.

Large quantities of these materials may be obtained by culturing recombinant or transformed cells containing replicons that express the improved LAMP Constructs described herein. Culturing methods are well-known to those skilled in the art and are taught in one or more of the documents cited above. The improved LAMP Construct vaccines are generally produced by culture of recombinant or transformed cells and formulated in a pharmacologically acceptable solution or suspension, which is usually a physiologically-compatible aqueous solution, or in coated tablets, tablets, capsules, suppositories or ampules, as described in the art, for example in U.S. Pat. No. 4,446,128, incorporated herein by reference. Administration may be any suitable route, including oral, rectal, intranasal or by injection where injection may be, for example, transdermal, subcutaneous, intramuscular or intravenous.

The improved LAMP Constructs are administered to a mammal in an amount sufficient to induce an immune response in the mammal. A minimum preferred amount for administration is the amount required to elicit antibody formation to a concentration at least 4 times that which existed prior to administration. A typical initial dose for administration would be 10-5000 micrograms when administered intravenously, intramuscularly or subcutaneously, or $10^5$ to $10^{11}$ plaque forming units of a recombinant vector, although this amount may be adjusted by a clinician doing the administration as commonly occurs in the administration of vaccines and other agents which induce immune responses. A single administration may usually be sufficient to induce immunity, but multiple administrations may be carried out to assure or boost the response.

The improved LAMP Construct vaccines may be tested initially in a non-human mammal (e.g., a mouse or primate). For example, assays of the immune responses of inoculated mice can be used to demonstrate greater antibody, T cell proliferation, and cytotoxic T cell responses to the improved LAMP Constructs than to wild type antigen. Improved LAMP Constructs can be evaluated in Rhesus monkeys to determine whether the vaccine formulation that is highly effective in mice will also elicit an appropriate monkey immune response. In one aspect, each monkey receives a total of 5 mg DNA per immunization, delivered IM and divided between 2 sites, with immunizations at day 0 and at weeks 4, 8, and 20, with an additional doses optional. Antibody responses, ADCC, CD4+ and CD8+ T-cell cytokine production, CD4+ and CD8+ T-cell antigen-specific cytokine staining can be measured to monitor immune responses to the vaccine.

Further description of suitable methods of formulation and administration according to this invention may be found in U.S. Pat. No. 4,454,116 (constructs), U.S. Pat. No. 4,681,762 (recombinant bacteria), and U.S. Pat. Nos. 4,592,002 and 4,920,209 (recombinant viruses).

Cancer Immunotherapy: Candidates for Prevention and Treatment

Candidates for cancer immunotherapy would be any patient with a cancer treated with either an improved LAMP Construct as described herein. Examples include patients with documented Epstein-Barr virus associated lymphomas, patients with HPV associated cervical carcinomas, patients with chronic HCV, or patients with a defined re-arrangement or mutation in an oncogene or tumor suppressor gene.

In preferred embodiments, cancers that can be treated using the vaccines described herein include, but are not limited to all stages of progression, including hyperplasia of an adenocarcinoma, sarcoma, skin cancer, melanoma, bladder cancer, brain cancer, breast cancer, uterine cancer, ovarian cancer, prostate cancer, lung cancer (including, but not limited to NSCLC, SCLC, squamous cell cancer), colorectal cancer, anal cancer, rectal cancer, cervical cancer, liver cancer, head and neck cancer, oral cancer, salivary gland cancer, esophageal cancer, pancreas cancer, pancreatic ductal adenocarcinoma (PDA), renal cancer, stomach cancer, kidney cancer, multiple myeloma or cerebral cancer.

It is envisioned that therapy with a vaccine composition comprising the improved LAMP Constructs could be utilized at any period during the course of the individual's cancer, once it is identified. It is also possible that in high risk patients, vaccination in order to prevent the subsequent emergence of a cancer.

Procedure for Therapy

In one embodiment, the improved LAMP Constructs could be injected into the patient at any suitable time during the course of their malignancy. For example, the improved LAMP Constructs would be injected at a stage when the tumor burden was low. In an alternative embodiment in which the improved LAMP Construct is introduced into the individual's antigen presenting cells, precursors to the antigen presenting cells or mature antigen presenting cells are drawn either from the individual's bone marrow or peripheral blood by vena puncture. These cells are established in culture followed by transduction with the improved LAMP Construct. Once transduction had occurred, these antigen presenting cells are injected back into the patient.

In a particularly preferred embodiment, the invention provides a method of treatment for a cancer patient having low tumor burden, such as early in the disease, after resection of a neoplastic tumor, or when the burden of tumor cells is otherwise reduced. In this method, a cell population containing autologous stem cells capable of differentiation into antigen presenting cells which will express MHC class II molecules is obtained from the patient. These cells are cultured and transformed by introducing an improved LAMP Construct to deliver the antigen to be associated with an MHC class II molecule either within the compartment/organelle or within another compartment/organelle to which the antigen is delivered.

The transfected stem cell population is then reintroduced into the patient, where the stem cells differentiate into antigen presenting cells which express MHC class II molecules complexed with $T_h$ epitopes from the antigen. The immune response to the antigen will be enhanced by enhanced stimulation of the helper T cell population.

More generally, in one embodiment, this invention provides a vaccine composition comprising the improved LAMP Construct for modulating an immune response in a mammal to an antigen (i.e., stimulating, enhancing, or reducing such a response).

Kits

The invention further comprises kits to facilitate performing the methods described herein. In one aspect, a kit comprises an improved LAMP Construct as described herein and a cell for receiving the improved LAMP Construct. The kit may additionally comprise one or more nucleic acids for engineering the cell into a professional APC. In one aspect, however, the cell is a professional APC. The cell may or may not express co-stimulatory molecules. In a preferred aspect, when the cell does not express co-stimulatory molecules, the antigen encoded by the improved LAMP Construct is an autoantigen. In another aspect, a panel of cells is provided expressing different MHC molecules (e.g., known to be expressed in human beings). In a further aspect, the kit comprises reagents to facilitate entry of the improved LAMP Constructs into a cell (e.g., lipid-based formulations, viral packaging materials, cells, and the like). In still a further aspect, one or more T cell lines specific for the antigen encoded by the improved LAMP Construct is provided, to verify the ability of the improved LAMP Construct to elicit, modulate, or enhance an immune response.

EXAMPLES

The invention will now be further illustrated with reference to the following examples. It will be appreciated that what follows is by way of example only and that modifications to detail may be made while still falling within the scope of the invention.

Example 1—Construction of LAMP Constructs

The improved LAMP Constructs illustrated in FIG. 1 can be constructed using standard molecular biology techniques well known to the skilled artisan. For example, plasmids comprising the polynucleotides can be designed to generate the different structures ILC-1 to ILC-6 shown in FIG. 1. The LAMP domains illustrated in FIG. 1 can be derived from the amino acid sequences shown in FIGS. 3-10. Preferably the LAMP domains are derived from the human LAMP proteins shown in FIGS. 3-10. It is envisioned that the corresponding domains can also be cloned from the orthologous sequences by identifying the equivalent domains when compared to the human sequence. An antigen of interest (including one or more antigens of interest) can be cloned into the described LAMP Constructs either individually or in combination.

Example 2—Immune Response Evaluation of Mice to LAMP Constructs

The ability of the improved LAMP Constructs as described in Example 1 can be tested for their ability to modulate an immune response. For example, Female BALB/c mice can be immunized i.d with 50 ug of the improved LAMP Constructs and 5 ug of GMCSF in 100 ul PBS using nanopass on day 0, 14 and 28. Experiment will then be terminated 4 weeks after the last dose.

Splenocytes (3×105/well) are stimulated with antigenic protein (10 ug/ml) in T cell media (RPMI with 10% heat inactivated FBS, 1% penicillin/streptomycin, and 1×2-ME), supernatants are collected 72 h after. Supernatants are diluted (400 ul supernatant+200 ul T cell media) and cytokines are evaluated by ELISA. IL-10 or IL-4 production can be measured via ELISPOT assay.

Example 3—Improved Antigen Presentation using LAMP Constructs

Survivin is the smallest member of the Inhibitor of Apoptosis (IAP) family of proteins, involved in inhibition of apoptosis and regulation of cell cycle. These functional attributes make Survivin a unique protein exhibiting divergent functions i.e. regulating cell proliferation and cell death. Expression of Survivin in tumors correlates with not only inhibition of apoptosis and a decreased rate of cell death, but also resistance to chemotherapy and aggressiveness of tumors [1-6]. Therefore, Survivin is an important target for cancer vaccines and therapeutics [7-9]. Survivin has also been found to be prominently expressed on both human and embryonic stem cells and many somatic stem cell types indicating its yet unexplored role in stem cell generation and maintenance.

Cancer is a heterogeneous group of diseases where abnormal cell growth with potential to invade other body parts takes control of normal homeostasis and becomes fatal if not timely and rightly treated. Immunotherapy specifically targets tumor cells thereby avoiding collateral damage to non-tumor cells and inducing anti-tumor response. This anti-tumor response also has the potential to eradicate tumor at distant sites in the body which may not be possible by surgical resection. Induction or enhancement of anti-tumor immune response is a formidable challenge in cancer because tumor cells use multiple evasion strategies and avoid being detected or eliminated by immune cells.

The aim of this project is to evaluate in vivo immune response of all new generation of LAMP Constructs injected by I.D. in BALB/c mice. Specifically, mice were immunized with 50 μg of the tested constructs defined in the legend of FIG. 1 by intradermal injection. No adjuvants were added at this experiment. Six mice per group were administrated with vaccines every 7 days with total three dose in one month. Immune response was monitored 14 days after the last immunization.

The tested LAMP constructs were generated as described herein and the sequence of each tested construct is shown in FIG. 19. Survivin protein was purchased from MyBiosource (San Diego, CA). Survivin peptides were from GenScript (Piscataway, NJ). Anti-survivin and m-IgGk-BP-HRP were bought from Santa Cruz Biotechnology (Dallas, TX), and mouse Monoclonal anti-LAMP-1/CD107a were from Ori-Gene Technologies (Rockville, MD). ELISPOT antibody pairs for IFNγ were from Biolegend. Fluorescently coupled CD3, CD4, CD8, CD44, CD62L, IFNγ, TNFα, granzyme B, CD69 monoclonal antibodies and Zombie aqua fixable viability kit were purchased from BioLegend (San Diego, CA). Goat anti-mouse IgG2a-HRP and goat anti-mouse IgG-HRP were purchased from Southern Biotechnologies (Birmingham, AL). Streptavidin-HRP was purchased from Thermo Fisher (Waltham, MA). SureBlue TMB microwell peroxidase substrate and TMB stop solution were purchased from KPL (Gaithersburg, MD).

50 µg of each construct was used in a total volume of 100 ul per mouse per dose for Pharmajet. Mice were immunized with the vaccine by i.d. delivery on days 0, 7, and 14. Mice were bled on days 28 for serum collection. Serum was collected and stored in −30° C. Spleens were collected on day 28 at the termination of experiment and processed for ELISPOT and FACS to evaluate survivin specific T cell responses.

Measurement of plasma survivin-specific total IgG by ELISA. The murine antibody response to survivin was assessed by indirect ELISA. ELISA plates (MaxiSorp) were coated with 2 µg/ml survivin (1-142) protein in carbonate-bicarbonate buffer overnight and then blocked with 2% BSA in PBS. Plasma samples were diluted 1:100 in blocking buffer. Samples were detected with goat anti-mouse IgG-HRP (Southern Biotech, Birmingham, AL). Reaction was developed with SureBlue TMB Substrate and stopped with TMB Stop Solution from KPL (Gaithersburg, MD). Plates were read (OD450) by using Epoch ELISA reader (BioTek, Winooski, VT).

Evaluation of antigen-specific T cell response. To assess antigen-specific T cell response in the vaccinated mice, splenocytes from vaccinated mice were evaluated for antigen-specific IFNγ production by Enzyme-linked immunospot (ELISPOT). For ELISPOT assays, 96-well nitrocellulose plates (Millipore), were coated overnight at 4° C. with 100 µl/well of capture monoclonal antibody in PBS. The plates were washed three times with 200 µl/well PBS and blocked with 200 µl/well T cell media for at least 2 hrs at room temperature. Splenocytes were plated at $3\times10^5$ cells/well and co-cultured with 2 µg/ml pooled peptides of Survivin (Table 1) or concavalin A (0.125 µg/ml) or medium alone in a total volume of 200 µl/well T cell media (RPMI-1640 with L-Glutamine and HEPES (ATCC), 1% penicillin, 1% streptomycin, and $5\times10^{-5}$M β-ME) at $3\times10^5$ cells/well for 48 h at 37° C. in 5% $CO_2$. The plates were washed two times with 200 µl/well PBS and two times with 200 µl/well PBS-T (0.05% Tween/PBS). Diluted detection antibodies (50 µl/well in PBS-T/0.5% BSA) were added and plates were incubated for 2 hrs with shaking at room temperature. Plates were washed four times with PBS. Streptavidin-alkaline phosphatase diluted in PBS (50 µl/well) were added and incubated for 2 h. Plates were washed with PBS four times and developed with 50 l/well of 3-Amino-9-Ethylcarbazole (AEC, BD Bioscience) substrate for 10 min. Color development was stopped by washing under running tap water. After drying 72 h at room temperature in dark, colored spots were counted using an AID ELISPOT High-Resolution Reader System and AID ELISPOT Software version 3.5 (Autoimmun Diagnostika GmbH).

TABLE 1

| Pooled peptides from Genscript | |
|---|---|
| Pooled P1 | Sur1-15, Sur11-25, Sur 21-35, Sur31-45, sur 41-55 |
| Pooled P2 | Sur51-65, sur61-75, sur71-85, sur81-95 |
| Pooled P3 | Sur91-105, sur 101-115, sur111-125, sur121-135, sur131-142 |
| Pooled P4 | Sur31-45, sur41-55 and sur51-65 |

Western blots. 293T cells were transfected with the tested constructs using lipofectamine 2000 reagents (Invitrogen). Transfected cells were washed with PBS and suspended in 200 µl of RIPA lysis buffer with halt proteinase inhibitors (Thermo Scientific, Waltham, MA). Lysates were centrifuges (700 g for 15 minutes at 4° C.), followed by measurement of protein concentration in the clarified supernatants using Pierce BCA protein Assay kit (ThermoFisher Scientific, Waltham, MA). 10 µg of protein was electrophoresed in pre-cast (4-20%) SDS-PAGE gels (BioRad, Hercules, California), and transferred onto nitrocellulose membranes (BioRad) and immunoblotted with mAbs to hLAMP. Membranes were blocked with Detection™ block buffer (KPL) and probed with rabbit anti-human LAMP (Sino Biological Inc., Beijing, China) or anti-survivin antibody and goat anti-rabbit-HRP antibody, and then developed with TMB (KPL).

Flow cytometry. Cells were first labelled with Zombie aqua fixable viability dye in PBS (1:500 dilution), followed by surface antibodies (1:100 dilution) in staining buffer (4% FBS, 2% rat serum, 2% mouse serum in PBS). For intracellular staining cells were stained with Zombie aqua, followed by surface staining, fixation with 4% paraformaldehyde, and stained with intracellular antibody in permeabilization buffer (PBS with 1% FCS 0.1% saponin). Samples were analyzed on a CytoFlex flow cytometer (Beckman Coulter) and analyzed using Kaluza software (Beckman Coulter).

Statistics. Two-Way ANOVA test was performed using GraphPad Prism 6.0 software or R file to evaluate the statistical significance. Each mouse's RPMI result was deducted from the results of the antigen activation.

Study Design.

| 18-ONC-019 Survivin Pharmajet validation in Balb/c mice (serum) | | | | | | | | | | | | |
|---|---|---|---|---|---|---|---|---|---|---|---|---|
| T/W Group | Treatment | Concentration | Dose | Route | # Mice | Vol. | Mice ID | Eartag | IN D-0 | PJ = yes D-7 | DNA = yes D-14 | D-28 |
| A | Control Vector | 2.52 mg/ml | 50 ug | Pharamajet | 6 | 100 ul | 7896-7901 | Eartag/ Pre few per group pool | Feb. 16, 2018 | Feb. 26, 2018 $1^{st}$ Immunization | Mar. 5, 2018 2nd Immunization | Mar. 12, 2018 $3^{rd}$ Immunization | Mar. 26, 2018 Harvest spleen and serum |
| B | Survivin + LAMP | 3.4 mg/ml | 50 ug | Pharamajet | 6 | 100 ul | 7902-7907 | | | | | |
| C | Survivin preluminal LAMP | 5.88 mg/ml | 50 ug | Pharamajet | 6 | 100 ul | 7908-7913 | | | | | |
| D | LAMP-luminal-D1-survivin | 2 mg/ml | 50 ug | Pharamajet | 6 | 100 ul | 7914-7919 | | | | | |

| | 18-ONC-019 Survivin Pharmajet validation in Balb/c mice (serum) | | | | | | | | | | | |
|---|---|---|---|---|---|---|---|---|---|---|---|---|
| T/W Group | Treatment | Concentration | Dose | Route | # Mice | Vol. | Mice ID | Eartag | IN D-0 | PJ = yes D-7 | DNA = yes D-14 | D-28 |
| E | Survivin-LAMP-luminal domain1 | 2 mg/ml | 50 ug | Pharamajet | 6 | 100 ul | 7997-8002 | | | | | |
| F | LAMP-hinge-survivin | 2 mg/ml | 50 ug | Pharamajet | 6 | 100 ul | 8003-8008 | | | | | |

Figure 13:
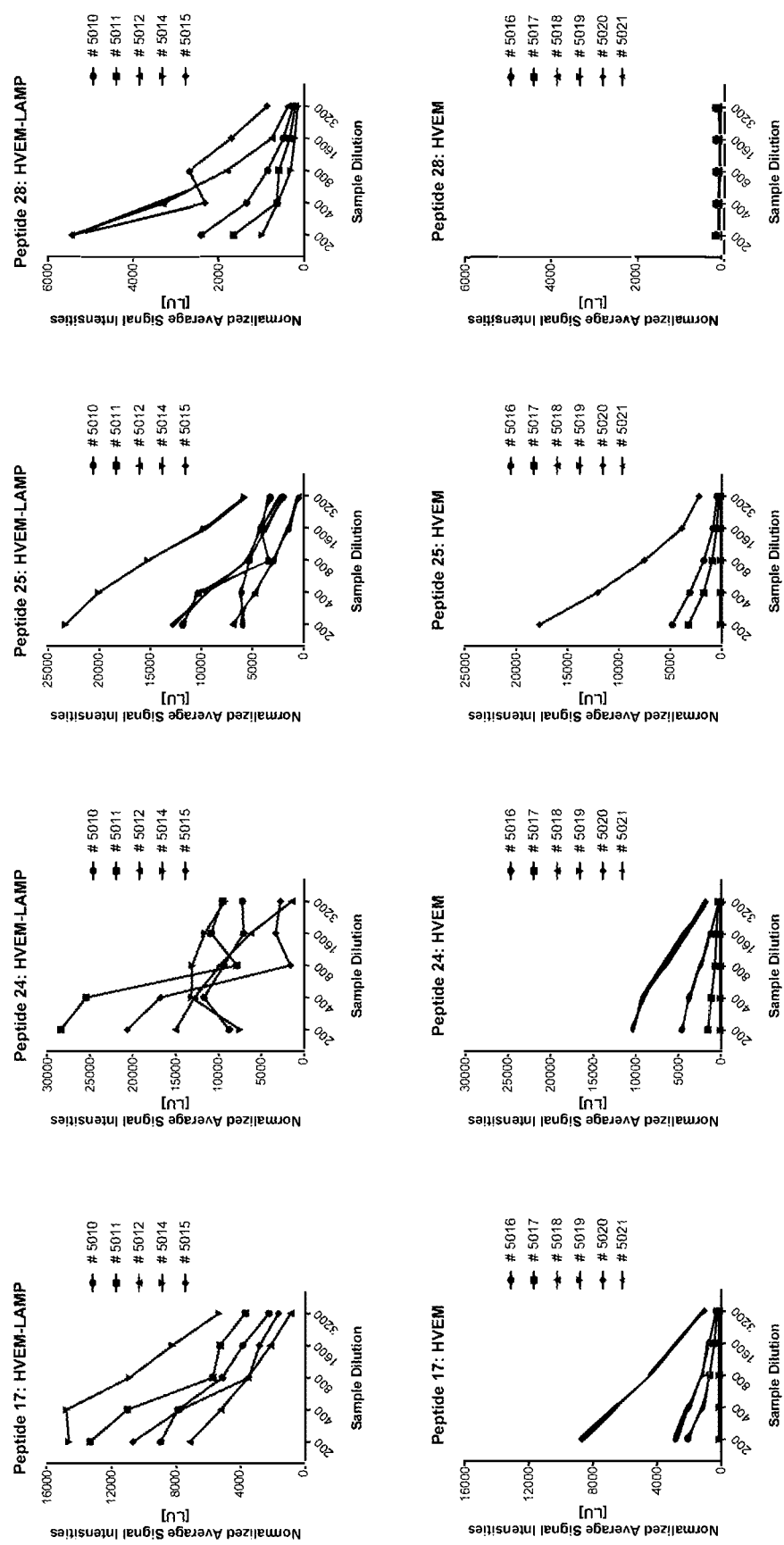
FIG. 13 shows that LAMP alters the binding affinity of epitopes in CRD3/4 of HVEM.
Figure 14:
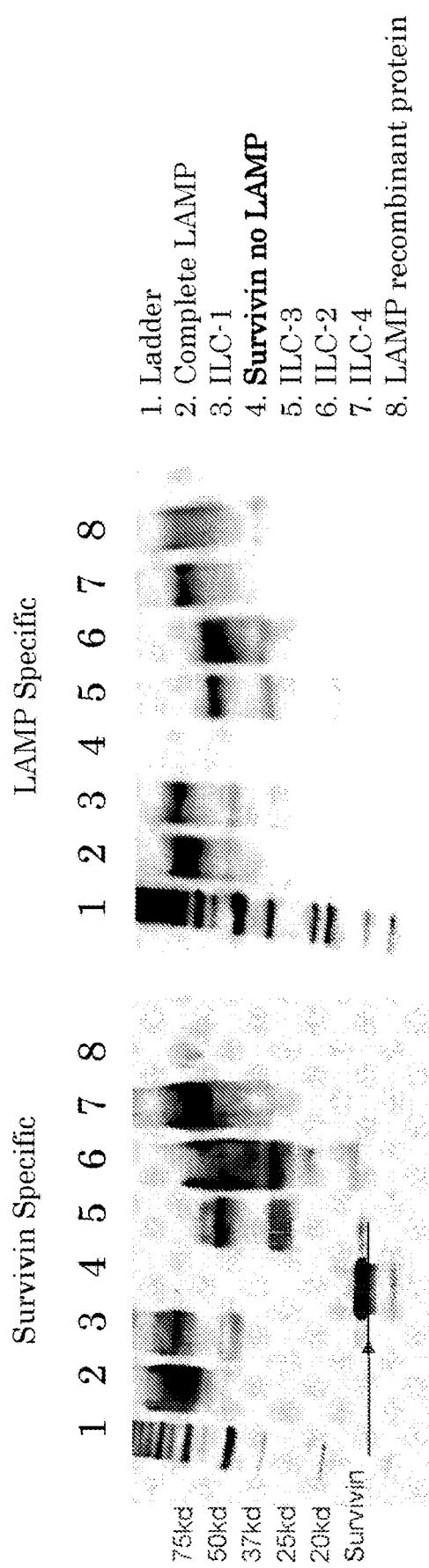
FIG. 14 confirms protein expression of tested improved LAMP Constructs. In each of FIGS. 14-17, the labels "complete LAMP Construct", ILC-1, ILC-2, ILC-3 and ILC-4 correspond to the constructs as depicted in FIG. 1.

FIG. 14: Validation of the plasmids: 293T cells were transfected with the plasmids for 3 days. Transfected cells were lysed, and then electrophoresed in pre-cast SDS-PAGE gel. The proteins were transferred to nitrocellulose membranes and immunoblotted with mAbs to human LAMP (OriGene, #TA337108) or survivin Santa Cruz #17779). Molecular weight of LAMP=100 KD, Survivin=16KD. FIG. 13 shows that all tested LAMP constructs produced appropriately sized protein.

Figure 15:
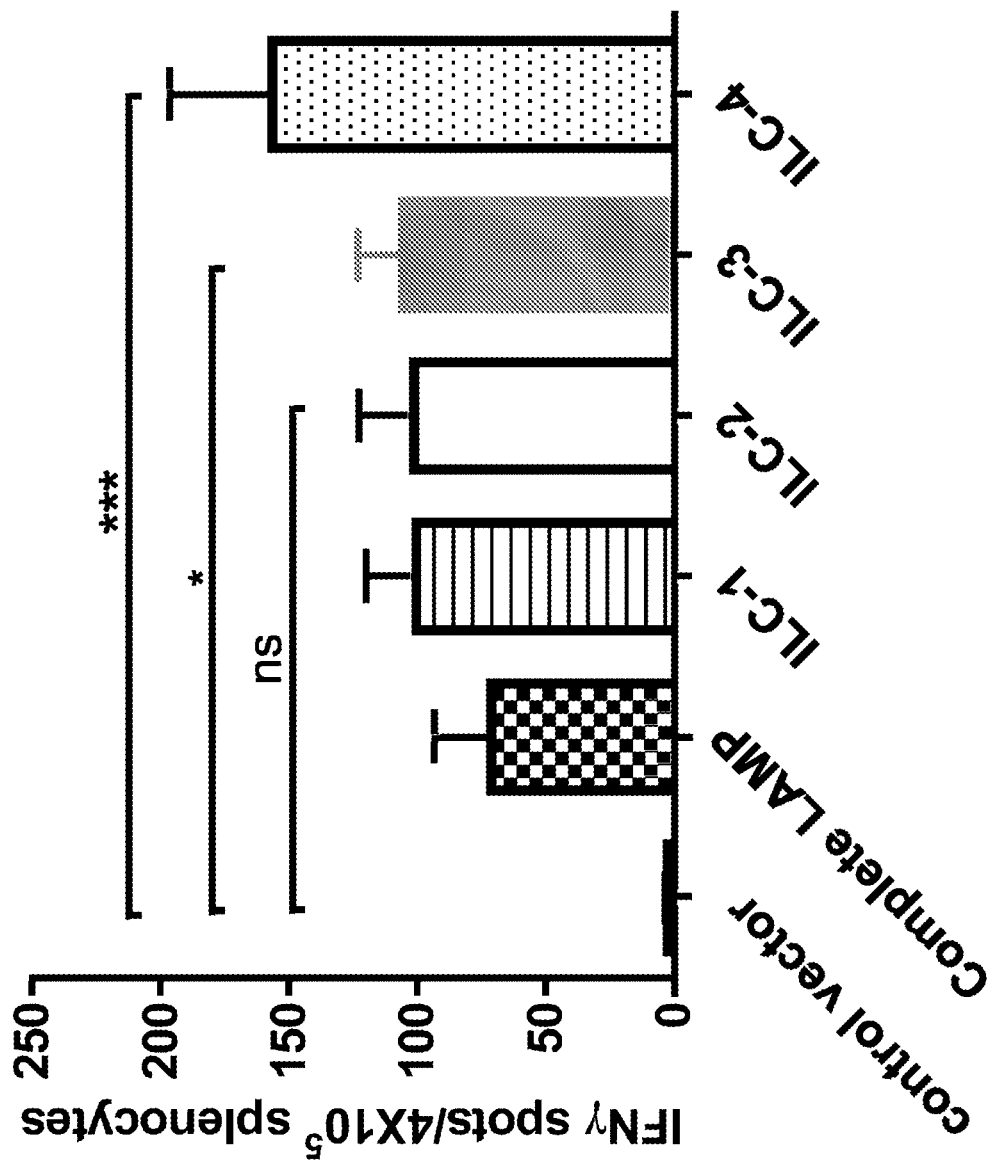
FIG. 15 shows that the improved LAMP Constructs induce Th1 effector T cells producing INFγ.
Figure 16:
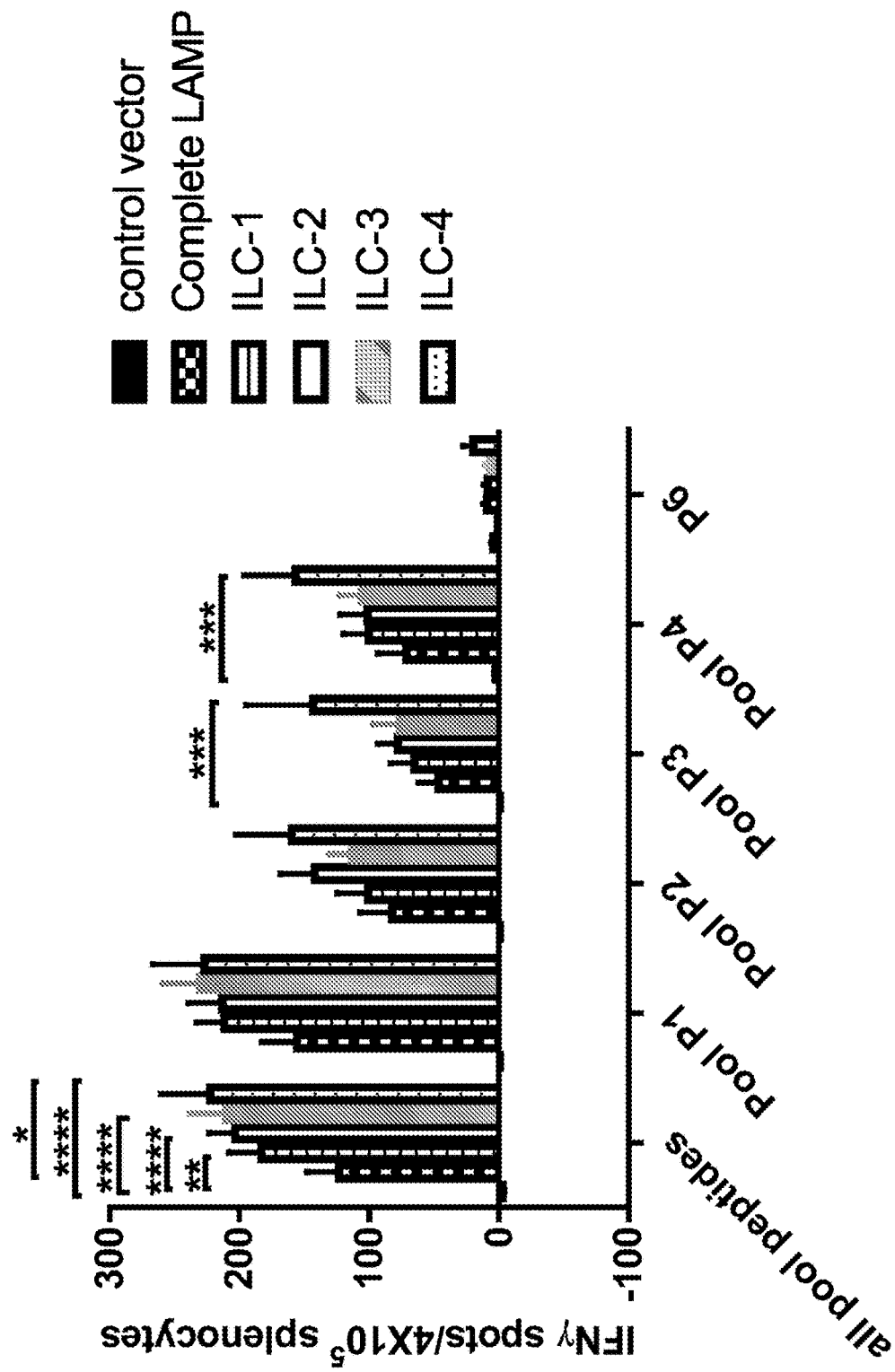
FIG. 16 shows a particular improved LAMP construct (e.g., ILC-4 as shown in FIG. 1) elicited a significantly higher T cell response against all survivin peptide pools.

FIGS. 15 and 16: Tested LAMP Constructs induce $T_h1$ effector T cells producing IFNγ. Female BALB/c mice were immunized i.d with 50 μg of the indicated constructs in 100 μl PBS via Pharmajet device on day 0, 7 and 14. Experiment was terminated 14 days after the last dose. Splenocytes ($3\times10^5$/well) were stimulated with survivin pooled peptides (4 μg/ml) in T cell media (RPMI with 10% heat inactivated FBS, 1% penicillin/streptomycin, and 1× β-ME), for 48 h. A. IFNγ production by spots. B. IFNγ production induced by all pooled peptides (bar figure from A). n=6 per group. Two way ANOVA (R file) was used for statistical analysis. FIG. 14 shows that all tested LAMP constructs induced a robust T cell response as shown by IFNγ production.

We unexpectedly found that after 3 dose of the improved LAMP Constructs (one week apart), a robust $T_h1$ type response elicited by tested LAMP Constructs, especially ILC-4 where the hinge sequence was replaced by survivin gene. More interestingly, improved LAMP Construct ILC-4 appears to recognize the survivin epitopes from N-terminal to C-terminal, and induce T cell response against human survivin peptide sequence which is 100% identical to the mouse. We also found longer (72 hrs) stimulation of frozen-thawed splenocyte cells with survivin peptides, ILC-4 showed significant higher IFNγ production than the first generation of LAMP-survivin (see FIG. 19). Specifically, FIG. 16 shows that the all improved LAMP Constructs tested showed higher T cell response with ILC-4 having the best activity as this constructed elicited a significantly higher T cell response against all survivin peptides pools. Moreover, contrary to what was known in the art, removal of the second homology domain of the luminal domain created an improved LAMP construct that elicited a more robust immune response as compared to the complete LAMP construct (see, results for ILC-2 and ILC-3). Frozen splenocytes (4×105/well) were stimulated with pooled peptides 4 (4 μg/ml) in T cell media (RPMI with 10% heat inactivated FBS, 1% penicillin/streptomycin, and 1× β-ME), for 48 h. n=6 per group. Two way ANOVA was used for statistical analysis. *p<0.05, p<0.01, *p<0.005, **p<0.0001

Figure 17:
FIG. 17 shows that CD4 T cells are the major source of IFNγ producing cells and that the improved LAMP Constructs demonstrate an increase in the CD4 effector memory cell population over the Complete LAMP construct.

FIG. 17. CD4 T cells are the major source of IFNγ producing cells. Female BALB/c mice were immunized i.d with 50 μg of the indicated vaccines in 100 μl PBS via Pharmajet device on day 0, 7 and 14. Experiment was terminated 14 days after the last dose. Splenocytes ($1\times10^6$/well) were stimulated with pooled peptides 1 (4 μg/ml) in T cell media (RPMI with 10% heat inactivated FBS, 1% penicillin/streptomycin, and 1× β-ME) over night, followed by adding monesin and brefeldin A and culturing for additional 5h. Cells were harvested and stained by Zombie, surface marker, and intracellular staining according to ITI staining protocol. Cells are gated on memory CD4 T cells (CD4+CD44+CD62L-) or CD8 T cells (CD8+CD44+CD62L-). Data is representative of one mouse in each group. While there is an increase in CD8 effector memory cells in vaccinated mice with the various constructs, IFNγ production is more pronounced in the CD4 T cell population.

Figure 18:
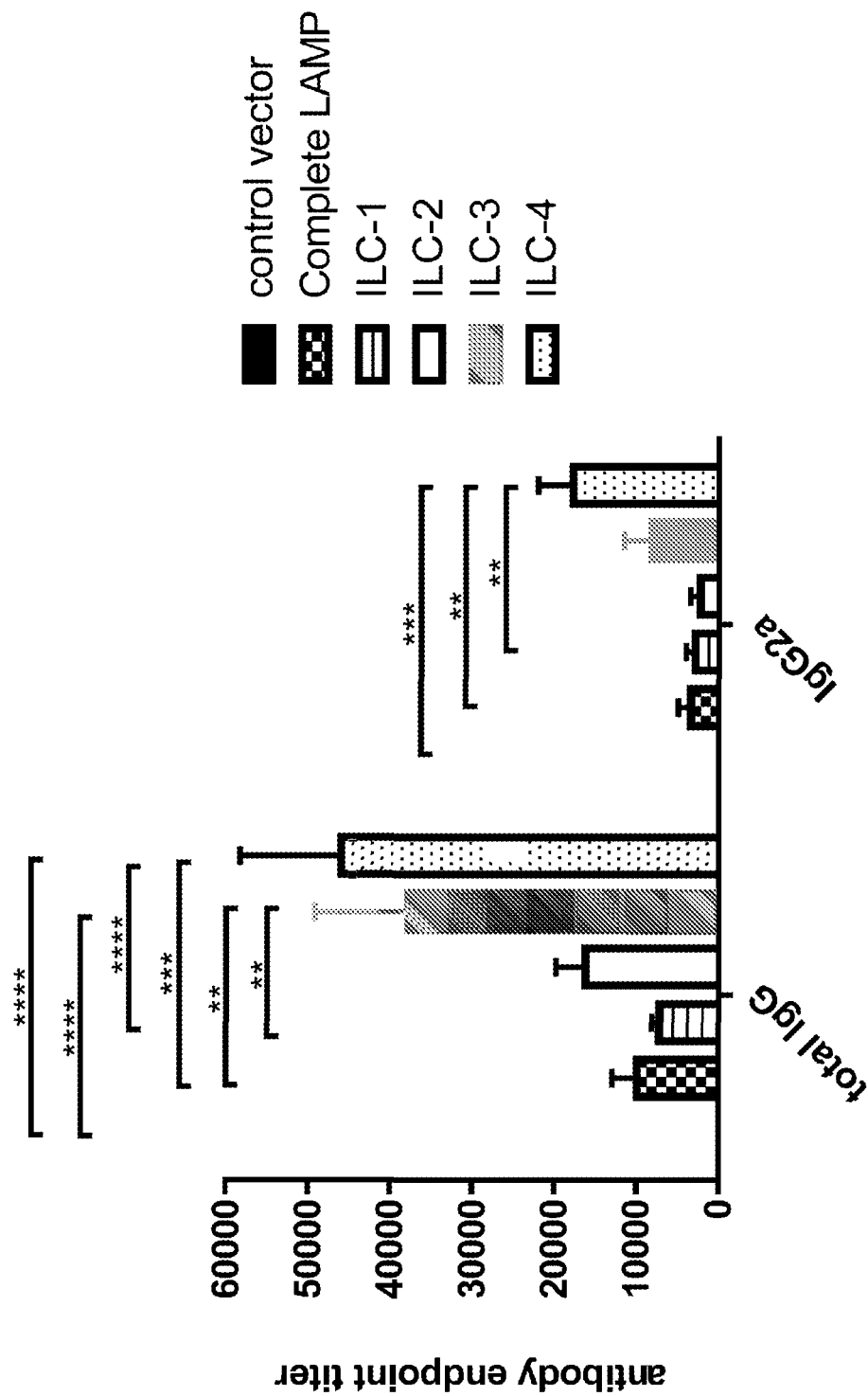
FIG. 18 shows that the improved LAMP Constructs produced stronger Survivin-specific total IgG response in BALB/c mice.

FIG. 18: Improved LAMP Constructs produced stronger survivin-specific total IgG response in BALB/c mice. Female BALB/c mice were immunized i.d with 50 μg of the indicated vaccines in 100 μl PBS via Pharmajet device on day 0, 7 and 14. Experiment was terminated 14 days after the last dose. Mice were bleed on days 28. Serum was separated and stored in −30° C. Total IgG and IgG2a were determined in serum by ELISA. Briefly, ELISA plates were coated with 2 μg/ml survivin (1-142aa), blocked with PBS/2% BSA, serum (1:100 dilution in blocking buffer) were evaluated by HRP-conjugated goat anti mouse IgG (1:6000) and IgG2a (1:11000). n=6 mice per group. p<0.01, *p<0.005, ****p<0.0001. Importantly and contrary to what was known in the art, FIG. 18 shows that fragments of the luminal domain worked better than use of the complete luminal domain (i.e., compare complete LAMP construct with constructs ILC-2 and IL-3). Moreover and unexpectedly, insertion of the antigen between the two homology domains of the luminal domain generated the strongest antibody response (see, ILC-4).

References relied on in this section.
1. Kami K, Doi R, Koizumi M, Toyoda E, Mori T, Ito D, et al. Survivin expression is a prognostic marker in pancreatic cancer patients. Surgery. 2004; 136(2):443-8. doi: 10.1016/j.surg.2004.05.023. PubMed PMID: 15300213.
2. Zhang S Q, Qiang S Y, Yang W B, Jiang J T, J1 Z Z. [Expression of survivin in different stages of carcinogenesis and progression of breast cancer]. Ai Zheng. 2004; 23(6):697-700. PubMed PMID: 15191674.
3. Zhang X, Zhong L, Hu K, Li Q. [Expression of survivin and its correlation with apoptosis in non-small cell lung cancer]. Zhongguo Fei Ai Za Zhi. 2004; 7(2):138-41. doi: 10.3779/j.issn.1009-3419.2004.02.14. PubMed PMID: 21215009.
4. Kishi H, Igawa M, Kikuno N, Yoshino T, Urakami S, Shiina H. Expression of the survivin gene in prostate cancer: correlation with clinicopathological characteristics, proliferative activity and apoptosis. J Urol. 2004; 171(5):1855-60. doi: 10.1097/01.ju.0000120317.88372.03. PubMed PMID: 15076293.
5. Asanuma K, Tsuji N, Endoh T, Yagihashi A, Watanabe N. Survivin enhances Fas ligand expression via up-regula- 6. Miyachi K, Sasaki K, Onodera S, Taguchi T, Nagamachi M, Kaneko H, et al. Correlation between survivin mRNA expression and lymph node metastasis in gastric cancer. Gastric Cancer. 2003; 6(4):217-24. doi: 10.1007/s10120-003-0255-2. PubMed PMID: 14716515.
7. Badana A K, Chintala M, Gavara M M, Naik S, Kumari S, Kappala V R, et al. Lipid rafts disruption induces apoptosis by attenuating expression of LRP6 and survivin in triple negative breast cancer. Biomed Pharmacother. 2017; 97:359-68. doi: 10.1016/j.biopha.2017.10.045. PubMed PMID: 29091885.
8. Cai J P, Wang Y D, Zhang X, Xue H Z. [Expression of P16 and survivin in liver cancer and their clinical significance]. Zhonghua Gan Zang Bing Za Zhi. 2017; 25(10):778-80. doi: 10.3760/cma.j.issn.1007-3418.2017.10.013. PubMed PMID: 29108210.
9. Cho H J, Kim H R, Park Y S, Kim Y H, Kim D K, Park S I. Prognostic value of survivin expression in stage III non-small cell lung cancer patients treated with platinum-based therapy. Surg Oncol. 2015; 24(4):329-34. doi: 10.1016/j.suronc.2015.09.001. PubMed PMID: 26690822.
10. Godinho R M, Matassoli F L, Lucas C G, Rigato P O, Goncalves J L, Sato M N, et al. Regulation of HIV-Gag expression and targeting to the endolysosomal/secretory pathway by the luminal domain of lysosomal-associated membrane protein (LAMP-1) enhance Gag-specific immune response. PLoS One. 2014; 9(6):e99887. doi: 10.1371/journal.pone.0099887. PubMed PMID: 24932692; PubMed Central PMCID: PMCPMC4059647.

Example 4: Therapeutic Treatment of LAMP Constructs

Female BALB/c mice can be inoculated s.c with syngeneic 7000 4T1 mammary carcinoma cells on day 0. Vaccine 50 ug and 5 ug of GMCSF in 100 ul PBS is given i.d using nanopass once the tumors are palpable. Primary tumors are measured with a caliper and tumor volume is calculated using the formula p/6 (length×width)3/2. Average tumor volume as a function of days after tumor inoculation can be measured. A Kaplan-Meier plot can be used to show overall survival at the point of termination.

Example 5—Prime/Boost Protocol

Herpesvirus entry mediator (HVEM), also known as tumor necrosis factor receptor superfamily member 14 (TNFRSF14) or CD270, is a human cell surface receptor of the TNF-receptor superfamily. In recent years, HVEM has been found highly expressed on hematopoietic cells and a variety of parenchymal cells, such as breast, melanoma, colorectal, and ovarian cancer cells, as well as gut epithelium. HVEM is a bidirectional protein, either inhibiting or stimulating T cells, through binding to BTLA or LIGHT (TNFSF14).

We generated a DNA vaccine encoding HVEM-LAMP to generate an antibody which could block the inhibitory function of HVEM for tumor therapeutic applications. We hypothesized that LAMP will promote the antibody response by enhancing the affinity of HVEM specific antibodies and/or expanding the repertoire of B cell epitopes in the HVEM protein. In this study, we compared the immunogenicity of HVEM encoding plasmid with and without LAMP. The HVEM sequence:

HVEM amino acids 39-202
(SEQ ID NO: 114)
LPSCKEDEYPVGSECCPKCSPGYRVKEACGELTGTVCEPCPPGTYIA

HLNGLSKCLQCQMCDPAMGLRASRNCSRTENAVCGCSPGHFCIVQDG

DHCAACRAYATSSPGQRVQKGGTESQDTLCQNCPPGTFSPNGTLEEC

QHQTKCSWLVTKAGAGTSSSHWV

Plasmids encoding HVEM-LAMP and HVEM and recombinant HVEM protein were designed by ITI and produced by NTC (Lincoln, NE). Polynucleotides encoding the following HVEM sequence was cloned into the improved LAMP Constructs described herein:

Goat anti-mouse IgG-HRP was purchased from Southern Biotechnologies (Birmingham, AL). SureBlue TMB microwell peroxidase substrate and TMB stop solution were purchased from KPL (Gaithersburg, MD). ELISPOT plates were ordered from EMD Millipore (Billerica, MA, Cat. No. MAIPS4510). IFN-γ antibody pair used in ELISPOT was purchased from BioLegend (San Diego, CA) and clones AN18 and R46A2 were used as coating and detection, respectively. Streptavidin-HRP and AEC substrate were purchased from BD Biosciences (San Jose, CA).

Six to eight week old female Balb/c mice were purchased from Harlan Laboratories (Frederick, MA) and maintained at animal facility in Immunomic Therapeutics, Inc. (Rockville, MA). Mice (n=6) were treated with 10 g/dose of HVEM-LAMP, HVEM, or LAMP vector control by Ichor electroporation IM delivery at days 0, 7, and 14. On day 35, mice were boosted with 5 μg HVEM protein in the presence of Alum by i.p. injection. On day 28 and 49, mice were bled and sera were isolated for antibody detection. Mice were sacrificed on day 56 and splenocytes were tested for IFN-γ production by ELISPOT.

ELISA procedure was followed by Su et al., J of Immunol Res; (10):1-15 (2016). Plates were coated with 5 μg/ml HVEM protein. Data were analyzed by using Microsoft Excel and Prism 6 software.

The primary aim of this study was to compare the antibody profiles between HVEM-LAMP and HVEM. On day 28, HVEM-LAMP vaccinated mice produced significant higher level of HVEM specific IgG antibody than that of the HVEM group (FIG. 11). After a protein boost, the HVEM specific antibody was increased about 1000-fold in HVEM immunized mice and the mean titer was changed from 100 to 108000. This result indicates that the immune memory was induced by the HVEM DNA plasmid. Although HVEM DNA alone only induced a minimal antibody response, protein boost rapidly recalled the immune memory. On the other hand, HVEM-LAMP group again exhibited a significant higher titer than the HVEM and LAMP groups, the mean titer is 5 folds of the HVEM group, indicating the power of LAMP in enhancing antibody response (FIG. 12).

Additionally serum samples (Day 49) from HVEM+LAMP or HVEM alone immunized/HVEM protein boosted mice were pooled and tested for peptide mapping. Twelve peptides were found to be bound to the pooled serum (mouse IgG reaction) and seven of the twelve peptides showed strong binding affinity. HVEM+LAMP alters the binding affinity of peptides 17. 24, 25, and 28 as compared to HVEM alone as shown in FIG. 13. These changes may have physiological effects in protecting tumor growth.

In conclusion, data from this study suggest that two constructs were expressed in vivo and LAMP significantly improved the humoral immune response.

Example 6: Production of an Antibody from a Polypeptide

Anti-antigen antibodies can be prepared by a variety of standard methods of raising antibodies using animal injection. (See, Current Protocols, Chapter 2.) For example, cells expressing an improved LAMP Construct comprising an antigen described herein is administered to a non-human vertebrate to induce the production of sera containing polyclonal antibodies. In a preferred method, a preparation of the LAMP/antigen protein is prepared and purified to render it substantially free of natural contaminants. Such a preparation is then introduced into the non-human vertebrate to produce polyclonal antisera of greater specific activity.

In the most preferred method, the anti-antigen antibodies of the present invention are monoclonal antibodies (or protein binding fragments thereof). Such monoclonal antibodies can be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing a non-human vertebrate animal (preferably a rabbit, mouse, cow, camel, llama) with an improved LAMP Construct comprising an antigen, the encoded polypeptide of an improved LAMP Construct comprising an antigen or, more preferably, with an improved LAMP Construct-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such non-human vertebrate host (e.g, mice) are extracted and fused with a suitable myeloma cell line. Any suitable myeloma cell line may be employed in accordance with the present invention; however, it is preferable to employ the parent myeloma cell line (SP20), available from the ATCC™. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the antigen.

It will be appreciated that Fab and F(ab')2 and other fragments of the anti-antigen antibodies may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 7: Use of Polynucleotides to Generate Polyclonal and Monoclonal Antibodies Methods of directly injecting polynucleotides into animals are well described in the art. See, for example, U.S. Pat. Nos. 5,676,954; 6,875,748; 5,661,133. For example, a polynucleotide encoding an improved LAMP Construct comprising an antigen can be injected into the quadriceps muscles of restrained awake mice (female 6-12 week old BALB/c or Nude, nu/nu, from Harlan Sprague Dawley, Indianapolis, Ind.). In one embodiment, 50 µg of a polynucleotide in 50 µl solution using a disposable sterile, plastic insulin syringe and 28G ½ needle (Becton-Dickinson, Franklin Lakes, N.J., Cat. No. 329430) fitted with a plastic collar cut from a micropipette tip can be used to inject the mice, as described in Hartikka, J., et al., Hum. Gene Ther. 7:1205-1217 (1996)).

Alternatively, 6-week old Sprague Dawley female mice (body weight 20-25 grams) can be given 5000 ppm ZnOSO4 in their drinking water beginning 24 hours prior to injection. This amount of zinc has been shown to be able to activate the metallothionein promoter. Each mouse is then injected intravenously through a tail vein puncture with a 25 gauge needle with 30 µg of a polynucleotide encoding an improved LAMP Construct comprising an antigen complexed with 150 µg liposome (Lipofection™) in a total volume of 30 µl. Animal care should be maintained throughout the study and should be performed in compliance with the "Guide for the Use and Care of Laboratory Animals", Institute of Laboratory Animal Resources, Commission on Life Sciences, National Research Council, National Academy Press.

After the injected polynucleotide encoding the improved LAMP Construct comprising an antigen is delivered into the cells in the animal, the antigen is delivered to the endosome/lysosome, processed and presented to the immune system. The improved LAMP Construct comprising an antigen can then stimulate the production of antibodies specific to the antigen. These antibodies can be isolated and used as a polyclonal mixture or further isolated into single species or monoclonals. The process of the immune response and production of antibodies against foreign antigens in vivo are well known in the art.

In a third animal model, Balb/c 3T3 A31 cells are transfected by electroporation with a polynucleotide encoding an improved LAMP Construct comprising an antigen. G418 resistant clones expressing LAMP Construct comprising an antigen are identified by their ability to bind human RBC. To generate polyclonal antibodies, Balb/c mice are immunized twice intraperitoneally, at an interval of 14 days, with $10^7$ cells comprising the improved LAMP Construct comprising an antigen. After a final boost, the immune serum is collected, IgG is purified by protein G Sepharose and passed over an antigen column prepared by coupling 1.0 mg purified antigen to cyanogen bromide activated Sepharose CL-4B. Bound IgG can be eluted with 0.1 M glycine buffer pH 2.5 and neutralized with 0.1 volumes of 0.1 M Tris pH 8.0. To generate a monoclonal antibody (mAb), Balb/c mice are immunized with LAMP Construct comprising an antigen and hybridomas are generated by fusing immune spleen cells with the SP2 myeloma following standard methods (28). A positive well reacting specifically with an antigen can be identified by enzyme-linked immunosorbent assays as described in the art. The hybridoma is cloned three times by limiting dilution to produce an antibody.

Example 8: Immunization of an improved LAMP Construct Comprising an Antigen

Methods of raising antibodies in mammals are well known in the art. In one example, polyclonal antiserum against LAMP Construct comprising an antigen is raised by immunization of pathogen free rabbits with a total of 500 µg an improved LAMP Construct comprising an antigen over a period of two months. For example, the improved LAMP Construct comprising an antigen can be dissolved in PBS and emulsified with an equal volume of Freund's adjuvant. After the final booster, the serum of the rabbits can be separated to determine the titer of the polyclonal antiserum.

In an additional animal model, groups of 5 mice (C57BL/6J; Jackson Labs) can be subcutaneously immunized with 5 µg of endotoxin-free LAMP Construct comprising an antigen emulsified in alum. Three weeks later, mice are bled and the presence of anti-antigen specific antibodies can be determined by titering the seras by ELISA (direct binding of antibodies in sera to wild type BPTI or APP-KI coated, directly or indirectly (via a biotinylated tag and streptavidin), on the wells).

To obtain monoclonal antibodies, 4-6 week old Balb/c mice can be immunized with an improved LAMP Construct comprising an antigen (for example 4 times with 2 week intervals with 10-100 µg/injection dissolved in Freunds complete adjuvant for the first injection, and Freund's incomplete adjuvant for subsequent immunizations). Splenocytes are isolated and fused with a fusion cell line such as Sp2/0 myeloma cells, followed by limiting dilution. Growing clones are screened using for example an enzyme-linked immunosorbant assay (ELISA). 96 cells plates are coated with an improved LAMP Construct comprising an antigen or with a control protein. The culture supernatant is added, followed by washing and addition of a labeled anti-mouse antibody for detection. After limited dilution cloning of the anti-antigen antibody producing stable hybridomas are obtained. From each cell, supernatant is collected and by affinity chromatography using protein A sepharose columns monoclonal antibodies can be purified.

Variations, modifications, and other implementations of what is described herein will occur to those of ordinary skill in the art without departing from the spirit and scope of the invention and the claims. All of the patents, patent applications, international applications, and references identified are expressly incorporated herein by reference in their entireties.

What is claimed is:

1. A polynucleotide encoding a lysosomal associated membrane protein (LAMP) construct,
   wherein the LAMP construct comprises two homology domains of a luminal domain of a LAMP protein, and an antigenic domain heterologous to the LAMP protein, wherein the LAMP construct further comprises a transmembrane domain of a LAMP protein, and wherein the antigenic domain is placed between the two homology domains.

2. The polynucleotide of claim 1, wherein the LAMP construct further comprises a signal sequence.

3. The polynucleotide of claim 2, wherein the signal sequence is derived from a LAMP protein.

4. The polynucleotide of claim 1, wherein the antigenic domain is separated from one or both of the homology domains by a linker.

5. The polynucleotide of claim 4, wherein the linker comprises an amino acid sequence of GPGPG or PMGLP.

6. The polynucleotide of claim 1, wherein the LAMP construct further comprises a cytoplasmic tail of a LAMP protein.

7. The polynucleotide of claim 1, wherein the LAMP protein is selected from the group consisting of LAMP-1, LAMP-2, LAMP-3, LIMP-2, Macrosailin, Endolyn, LAMP-5 and LIMBIC.

8. The polynucleotide of claim 1, wherein the LAMP protein comprises an amino acid sequence selected from the group consisting of SEQ ID NOS:1-113.

9. The polynucleotide of claim 1, wherein the LAMP Protein comprises an amino acid sequence at least 70%, at least 75%, at least 80%, at least 85%, at least 90%, at least 95%, 96%, 97%, 98% or 99% identical to the amino acid sequence of any one of SEQ ID NO:1-113.

10. A polynucleotide encoding a lysosomal associated membrane protein (LAMP) construct,
    wherein the LAMP construct comprises two homology domains of a luminal domain of human LAMP-1 protein, and an antigenic domain heterologous to the human LAMP-1 protein, wherein the LAMP construct further comprises a transmembrane domain of a LAMP protein, and
    wherein the antigenic domain is placed between the two homology domains.

11. The polynucleotide of claim 10, wherein the two homology domains comprise human LAMP-1 Homology Domain 1 and human LAMP-1 Homology Domain 2.

12. The polynucleotide of claim 11,
    wherein the human LAMP-1 Homology Domain 1 comprises:
    (a) the amino acid sequence of residues 29 to 194 of SEQ ID NO: 1, or
    (b) a variant of (a) wherein said variant comprises an amino acid sequence at least 95% identical to the amino acid sequence of (a); and/or
    wherein the human LAMP-1 Homology Domain 2 comprises:
    (c) an amino acid sequence of residues 228 to 381 or residues 228 to 382 of SEQ ID NO: 1, or
    (d) a variant of (c) wherein said variant comprises an amino acid sequence at least 95% 97% identical to the amino acid sequence of (c).

13. The polynucleotide of claim 11, wherein the human LAMP-1 Homology Domain 1 comprises an amino acid sequence at least about 95% identical to the amino acid sequence of residues 29-194 of SEQ ID NO: 1, and wherein the human LAMP-1 Homology Domain 2 comprises the amino acid sequence of residues 228-381 of SEQ ID NO: 1.

14. The polynucleotide of claim 13, wherein the human LAMP-1 Homology Domain 1 comprises an amino acid sequence at least about 97% identical to the amino acid sequence of residues 29-194 of SEQ ID NO: 1.

15. The polynucleotide of claim 10, wherein the Transmembrane Domain comprises residues 383-405 of SEQ ID NO: 1.

16. The polynucleotide of claim 10, wherein the LAMP construct further comprises a cytoplasmic tail of a LAMP protein.

17. The polynucleotide of claim 16, wherein the Cytoplasmic Tail comprises residues 406 to 417 of SEQ ID NO: 1.

18. The polynucleotide of claim 1, wherein the polynucleotide is a viral vector.

19. The polynucleotide of claim 1, wherein the polynucleotide is a self-replicating RNA viral vector.

20. An isolated host cell comprising the polynucleotide of claim 1.

21. An isolated antigen presenting cell comprising the polynucleotide of claim 1.

22. The isolated antigen presenting cell of claim 21, wherein the cell is a dendritic cell.

23. The polynucleotide of claim 10, wherein the polynucleotide is a viral vector.

24. The polynucleotide of claim 10, wherein the polynucleotide is a self-replicating RNA viral vector.

25. An isolated host cell comprising the polynucleotide of claim 10.

26. An isolated antigen presenting cell comprising the polynucleotide of claim 10.

27. The isolated antigen presenting cell of claim 26, wherein the cell is a dendritic cell.

28. A method of treating a disease or a disorder, wherein the method comprises administering to a subject in need thereof the polynucleotide of claim 1 in an amount sufficient to reduce or treat the diseases or disorders.

* * * * *